US008168395B2

(12) United States Patent
Li et al.

(10) Patent No.: US 8,168,395 B2
(45) Date of Patent: May 1, 2012

(54) TASTE RECEPTORS OF THE T1R FAMILY FROM DOMESTIC DOG

(75) Inventors: Xia Li, Havertown, PA (US); Weihua Li, Broomall, PA (US); Joseph G. Brand, Wayne, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 78 days.

(21) Appl. No.: 12/428,730

(22) Filed: Apr. 23, 2009

(65) Prior Publication Data

US 2009/0233379 A1 Sep. 17, 2009

Related U.S. Application Data

(62) Division of application No. 11/578,472, filed as application No. PCT/US2005/012765 on Apr. 14, 2005, now Pat. No. 7,541,158.

(60) Provisional application No. 60/562,208, filed on Apr. 14, 2004.

(51) Int. Cl.

| | |
|---|---|
| ***C07K 14/705*** | (2006.01) |
| ***C07K 19/00*** | (2006.01) |
| ***G01N 33/567*** | (2006.01) |
| *C12N 15/62* | (2006.01) |

(52) U.S. Cl. .......... 435/7.1; 435/7.2; 435/69.7; 436/501

(58) Field of Classification Search ........................ None
See application file for complete search history.

(56) References Cited

U.S. PATENT DOCUMENTS

| | | | |
|---|---|---|---|
| 4,399,216 | A | 8/1983 | Axel et al. |
| 4,879,236 | A | 11/1989 | Smith et al. |
| 5,585,277 | A | 12/1996 | Bowie et al. |
| 7,368,285 | B2 | 5/2008 | Zoller et al. |
| 7,541,158 | B2 | 6/2009 | Li et al. |

FOREIGN PATENT DOCUMENTS

| | | | |
|---|---|---|---|
| EP | 0 367 566 | A1 | 3/1997 |
| WO | WO 91/09955 | A1 | 7/1991 |
| WO | WO 91/18982 | A1 | 12/1991 |
| WO | WO 92/20808 | A1 | 11/1992 |
| WO | WO 94/12650 | A2 | 6/1994 |
| WO | WO 97/09433 | A1 | 3/1997 |
| WO | WO 01/72842 | A2 | 10/2001 |
| WO | WO 02/064631 | A2 | 8/2002 |
| WO | WO 2005/116069 | | 12/2005 |

OTHER PUBLICATIONS

Anderson, W. F., "Human Gene Therapy", Nature, Apr. 30, 1998, supplement to vol. 392, No. 6679, pp. 25-30.
Andersson, B. et al., "The Sweet Taste Fibres of the Dog", Acta physiol scan, Nov. 1950, 21(2-3), 105-119.
Bartoshuk, L. M. et al., "Taste of Water in the Cat: Effects on Sucrose Preference", Science, Feb. 19, 1971, 171(972), 699-701.
Beauchamp, G. K. et al., "Flavor Preferences in Cats (*Felis catus* and *Panthera* sp.)", J. Comp. Physiol. Psychol., Oct. 1977, 91(5), 1118-1127.
Bidlack, J. M. et al., "Assay of G Protein-Coupled Receptor Activation of G Proteins in Native Cell Membranes Using [$^{35}$S]GTPγS Binding", Methods Mol Biol., 2004, 237, 135-143.
Boudreau, J. C. et al., "Neurophysiology of geniculate ganglion (facial nerve) taste systems: species comparisons", Chem. Senses, 1985, 10, 89-127.
Bradshaw, J. W. S., "Sensory and experimental factors in the design of foods for domestic dogs and cats", Proc. Nutrition Soc., Mar. 1991, 50(1), 99-106.
Cane, D. E. et al., "Harnessing the Biosynthetic Code: Combinations, Permutations, and Mutations", Science, Oct. 2, 1998, 282(5386), 63-68.
Elbashir, S. M. et al., "RNA interference is mediated by 21-and 22-nucleotide RNAs", Genes & Development, Jan. 15, 2001, 15(2), 188-200.
Friedmann, T., "Progress Toward Human Gene Therapy", Science, Jun. 16, 1989, 244(4910), 1275-1281.
Galés, C. et al., "Real-time monitoring of receptor and G-protein interactions in living cells", Nat Methods, Mar. 2005, 2(3), 177-184.
Grace, J. et al., "The Influence of Previous Experience on the Taste Behavior of Dogs Toward Sucrose and Saccharin",, Physiology and Behavior, Jul. 1969, 4, 553-558.
Kitagawa, M. et al., "Molecular Genetic Identification Of A Candidate Receptor Gene for Sweet Taste", Bioch. Bioph. Res. Comm., Apr. 27, 2001, 283(1), 236-242.
Kurihara, K. et al., "Introductory Remarks on Umami Taste", Ann. N. Y. Acad. Sci., Nov. 30, 1998, 855, 393-397.
Li, X. et al., "Human receptors for sweet and umami taste", Proc Natl Acad Sci USA, Apr. 2, 2002, 99(7), 4692-4696.
Li, X. et al., "Genetic, Physical, And Comparative Map Of The Subtelomeric Region of Mouse Chromosome 4", Mamm. Genome, Jan. 2002, 13(1), 5-19.
Li, X. et al., "High-Resolution Genetic Mapping of the Saccharin Preference Locus (Sac) And the Putative Sweet Taste Receptor (T1R1) Gene (Gpr70) To Mouse Distal Chromosome 4", Mamm. Genome, Jan. 2001, 12(1), 13-16.
Li, X. et al., "Pseudogenization of a sweet-receptor gene accounts for cats' indifference toward sugar", PLOS Genetics, Jul. 2005, 11, 27-35.
Margolskee, R. F., "Molecular mechanisms of bitter and sweet taste transduction", J. Biol. Chem., Jan. 4, 2002, 277(1), 1-4.

(Continued)

*Primary Examiner* — John Ulm
(74) *Attorney, Agent, or Firm* — Woodcock Washburn LLP

(57) ABSTRACT

The present invention relates to the discovery of several genes of the domestic dog (*Canine familiaris*) associated with taste perception. The invention provides, inter alia, the nucleotide sequence of the canine Tas1r1, Tas1r2, and Tas1r3 receptor genes, the amino acid sequences of the polypeptides encoded thereby, and antibodies to the polypeptides. The present invention also relates to methods for screening for compounds that modify the genes' function or activity, the compounds identified by such screens, and mimetics of the identified compounds. The invention further provides methods for modifying the taste preferences, ingestive responses, or general behavior of a mammal such as a dog by administering compounds that affect the function or activity of the gene or the polypeptide encoded thereby.

20 Claims, 20 Drawing Sheets

OTHER PUBLICATIONS

Miller, A. D., "Human gene therapy comes of age", Nature, Jun. 11, 1992, 357(6378), 455-460.

Ming, D. et al. "Characterization and solubilization of bitter-responsive receptors that couple to gustducin", Proc. Natl. Acad. Sci. USA, Jul. 21, 1998, 95(15), 8933-8938.

Montmayeur, J. P. et al., "Receptors For Bitter And Sweet Taste",Curr. Opin. Neurobiol., Aug. 2002, 12(4), 366-371.

Nelson, G. et al., "An amino-acid taste receptor", Nature, Mar. 14, 2002, 416(6877), 199-202.

Nelson, G. et al., "Mammalian Sweet Taste Receptors", Cell, Aug. 10, 2001, 106(3), 381-390.

Ruiz-Avila, L. et al., "An In Vitro Assay Useful to Determine the Potency of Several Bitter Compounds", Chem. Senses, Aug. 2000, 25(4), 361-368.

Verma, I. M., "Gene Therapy", Scientific American, Nov. 1990, 263(5) 68-72, 81-84.

Wahlestedt et al., "Potent and nontoxic antisense oligonucleotides containing locked nucleic acids", Proc. Natl. Acad. Sci. USA, May 9, 2000, 97(10), 5633-5638.

Xu, H et al., "Different functional roles of T1R subunits in the heteromeric taste receptors", Proc Natl Acad Sci USA, Sep. 28, 2004, 101(39), 14258-14263.

Yan, W. et al., "Bitter taste transduced by PLC-beta(2)-dependent rise in IP(3) and alpha-gustducin-dependent fall in cyclic nucleotides", Am J Physiol Cell Physiol, Apr. 2001, 280(4), C742-751.

FIG. 1A

```
SEQ ID NO:13  mouseTas1r1   ATGCTTTTCTGGGCAGCTCACCTGCTGCTCAGCCTGCAGCTGGCCGTTGCTTACTGCTGG 60
SEQ ID NO:14  ratTas1r1     ATGCTCTTCTGGGCTGCTCACCTGCTGCTCAGCCTGCAGTTGGTC------TACTGCTGG 54
SEQ ID NO:133 catTas1r1     ATGTCACTCCCGGCGGCTCACCTGGT---CGGCCTGCAGCTCTCCCTCTCCTGCTGCTGG 57
SEQ ID NO:2   dogTas1r1     ATGTCACTCCTGGCAGCTCACCTGGT---CAGCTTGCAGCTCTCCCTCTCCTGCTGCTGG 57
SEQ ID NO:15 humanTAS1R1   ATGCTGCTCTGCACGGCTCGCCTGGT---CGGCCTGCAGCTTCTCATTTCCTGCTGCTGG 57
SEQ ID NO:10  mouseTas1r2   ATGGGACCCCAGGCGAGGACACT------CCATTTGCTGTTTCTC-----CTGCTGCATG 49
SEQ ID NO:11  ratTas1r2     ATGGGTCCCCAGGCAAGGACACT------CTGCTTGCTGTCTCTC-----CTGCTGCATG 49
SEQ ID NO:12  humanTAS1R2   ATGGGGCCCAGGGCAAAGACCAT------CTGCTCCCTGTTCTTC-----CTCCTATGGG 49
SEQ ID NO:5   dogTas1r2     ATGGGACCCCGGGCCAAGGCGGT------CTGCTCCCTATTCATC-----CTGCTGCAGG 49
SEQ ID NO:135 catTas1r2     ATGGGACCCCGGGCCAGGGAAGT------CTGCTGCTTCATCATC-----CTGCCGCGGC 49
SEQ ID NO:16  mouseTas1r3   ATGCCAGCTTTGGCTATCATGGGTCTCA------------GCCTGG-CTGCTTTCCTGGA 47
SEQ ID NO:17  ratTas1r3     ATGCCGGGTTTGGCTATCTTGGGCCTCA------------GTCTGG-CTGCTTTCCTGGA 47
SEQ ID NO:8   dogTas1r3     ATGGCAGGCCTGATGCTCCTGAGCCTCA-------------------TGGCTCTCTTGGG 41
SEQ ID NO:137 catTas1r3     ATGCCCGGCCTCGCTCTCCTGGGCCTCACGGCTCTCCTGGGCCTCA-CGGCTCTCTTGGA 59
SEQ ID NO:18  humanTAS1R3   ATGCTGGGCCCTGCTGTCCTGGGCCTCA------------GCCTCT-GGGCTCTCCTGCA 47
                            ***                                                 *

              mouseTas1r1   GCTTTCAGCTGCCA--AAGGACAGAATCCTCTCCAG-GTTTCAGCCTCCCTGGGGACTTC 117
              ratTas1r1     GCTTTCAGCTGCCA--AAGGACAGAGTCCTCTCCAG-GCTTCAGCCTTCCTGGGGACTTC 111
              catTas1r1     GCTCTCAGCTGCCA--CAGCACAGAGACGTCTGCCG-ACTTCAGCCTCCCTGGGGATTAC 114
              dogTas1r1     GCCCTCAGCTGCCA--CAACACAGAGTCATCTCCTG-ATTTCAGCCTCCCTGGGGATTAC 114
              humanTAS1R1   GCCTTTGCCTGCCA--TAGCACGGAGTCTTCTCCTG-ACTTCACCCTCCCCGGAGATTAC 114
              mouseTas1r2   CTCTGCCTAAGCCAGTCATGCTGGTAGGGAACTCCG-ACTTTCACCTGGCTGGGGACTAC 108
              ratTas1r2     TTCTGCCTAAGCCAGGCAAGCTGGTAGAGAACTCTG-ACTTCCACCTGGCCGGGGACTAC 108
              humanTAS1R2   TCCTGGCTGAGCC---------GGCTGAGAACTCGG-ACTTCTACCTGCCTGGGGATTAC 99
              dogTas1r2     TCCTGGCTGAACC---------GGCTGAGAACTCAG-ACTTCTACCTGCCTGGAGATTAC 99
              catTas1r2     TCCTGGCTGAGCC---------GGCTGAGAACTCAG-ACTTCTACTTGGCTGGGGATTAC 99
              mouseTas1r3   GCTTGGGATGGGGG--CCTCTTTGTGTCTGTCACAGCAATTCAAGGCACAAGGGGACTAC 105
              ratTas1r3     GCTTGGGATGGGGT--CCTCTTTGTGTCTGTCACAGCAATTCAAGGCACAAGGGGACTAT 105
              dogTas1r3     CCTTGGAGCAGGCG--CCCCATTGTGCTTATCCCGGCAGCTCAGGATGCAAGGGGACTAT 99
              catTas1r3     CCACGGGGAGGGCG--CAACGTCCTGCTTGTCACAGCAGCTCAGGATGCAGGGGGACTAT 117
              humanTAS1R3   CCCTGGGACGGGGG--CCCCATTGTGCCTGTCACAGCAACTTAGGATGAAGGGGGACTAC 105
                                                                 * *    *          ** ** *

              mouseTas1r1   CTCCTGGCAGGCCTGTTCTCCCTCCATGCTGACTGTCTGCAGGTGAGACAC---AGACCT 174
              ratTas1r1     CTCCTTGCAGGTCTGTTCTCCCTCCATGGTGACTGTCTGCAGGTGAGACAC---AGACCT 168
              catTas1r1     CTCCTCGCAGGTCTGTTCCCTCTGCACTCTGACTGTCCGGGCGTGAGGCAC---CGGCCC 171
              dogTas1r1     CTACTTGCAGGTCTGTTCCCTCTGCACTCTGACTGTCCCGGGGTGAGACGC---AGGCCC 171
              humanTAS1R1   CTCCTGGCAGGCCTGTTCCCTCTCCATTCTGGCTGTCTGCAGGTGAGGCAC---AGACCC 171
              mouseTas1r2   CTCCTGGGTGGCCTCTTTACCCTCCATGCCAACGTGAAGAGCGTCTCTCACCTCAGCTAC 168
              ratTas1r2     CTCCTGGGTGGCCTCTTTACCCTCCATGCCAACGTGAAGAGCATCTCCCACCTCAGCTAC 168
              humanTAS1R2   CTCCTGGGTGGCCTCTTCTCCCTCCATGCCAACATGAAGGGCATTGTTCACCTTAACTTC 159
              dogTas1r2     CTCCTGGGTGGCCTCTTCACCCTCCATGCCAACGTGAAGGGCACCGTCCACCTCAGCTTC 159
              catTas1r2     TTCCTCGGCGGCCTCTTCACCCTCCATGCCAACGTGAAGGGCATCGTCCACCTCAACCTC 159
              mouseTas1r3   ATACTGGGCGGGCTATTTCCCCTGGGCTCAACCG---AGGAGGCCACTCTCAACCAGAGA 162
              ratTas1r3     ATATTGGGTGGACTATTTCCCCTGGGCACAACTG---AGGAGGCCACTCTCAACCAGAGA 162
              dogTas1r3     GTGCTGGGCGGGCTCTTCCCCCTGGGCACAGCTG---AGGACACAGGTCTCAGTGACAGG 156
              catTas1r3     GTGCTGGGTGGGCTCTTCCCTCTGGGCTCTGCCG---AGGGTACAGGTCTTGGCGACGGG 174
              humanTAS1R3   GTGCTGGGGGGGCTGTTCCCCCTGGGCGAGGCCG---AGGAGGCTGGCCTCCGCAGCCGG 162
                              *   *  *   ** **  **   *  **                  *

              mouseTas1r1   CTGGTGACAAGTTGTGACAGGTCTGACAGCTTCAACGGCCATGGCTATCACCTCTTCCAA 234
              ratTas1r1     CTGGTGACAAGTTGTGACAGGCCCGACAGCTTCAACGGCCATGGCTACCACCTCTTCCAA 228
              catTas1r1     ACGGTGACCCTCTGTGACAGGCCCGACAGCTTCAACGGTCACGGCTACCACCTCTTCCAG 231
              dogTas1r1     ATGGTGACCCTCTGTGACAGGTCCAACAGCTTCAATGGCCATGGCTACCACCTCTTTCAG 231
              humanTAS1R1   GAGGTGACCCTGTGTGACAGGTCTTGTAGCTTCAATGAGCATGGCTACCACCTCTTCCAG 231
              mouseTas1r2   CTGCAGGTGCCCAAGTGCAATGAGTACAACATGAAGGTCTTGGGCTACAACCTCATGCAG 228
              ratTas1r2     CTGCAGGTGCCCAAGTGCAATGAGTTCACCATGAAGGTGTTGGGCTACAACCTCATGCAG 228
              humanTAS1R2   CTGCAGGTGCCCATGTGCAAGGAGTATGAAGTGAAGGTGATAGGCTACAACCTCATGCAG 219
              dogTas1r2     CTGCAGGTGCCCCAGTGCAAGAAGTATGAAATGAAGGTGTTGGGCTACAACCTGATGCAG 219
              catTas1r2     CTGCAGGTGCCCCAGTGCAAGGAGTATGAAATAAAGGTGTTGGGCTACGATCTCATGCAG 219
              mouseTas1r3   ACACAACCCAACAGCATCCCGTGCAACAGGTTCTCACCCCTTGGTTTGTTCCTGGCCATG 222
              ratTas1r3     ACACAGCCCAACGGCATCCTATGTACCAGGTTCTCGCCCCTTGGTTTGTTCCTGGCCATG 222
              dogTas1r3     ACACAGCCCAATGCCACTGTGTGCACCAGGTTCTCGTCCCTCGGCCTGCTCTGGGCGCTG 216
              catTas1r3     CTGCAGCCCAATGCCACCGTGTGCACCAGGTTCTCGTCTCTGGGCCTGCTCTGGGCGCTG 234
              humanTAS1R3   ACACGGCCCAGCAGCCCTGTGTGCACCAGGTTCTCCTCAAACGGCCTGCTCTGGGCACTG 222
                                        •                       **
                                        •
```

FIG. 1B

```
                                               •
mouseTas1r1     GCCATGCGGTTCACCGTTGAGGAGATAAACAACTCCACAGCTCTGCTTCCCAACATCACC 294
ratTas1r1       GCCATGCGGTTCACTGTTGAGGAGATAAACAACTCCTCGGCCCTGCTTCCCAACATCACC 288
catTas1r1       GCCATGCGGTTTGGCATCGAGGAGATAAACAACTCCACGGCCCTCCTGCCGAACGTCACC 291
dogTas1r1       GCCATGCGGTTTGGCATTGAGGAGATCAACAACTCCACAACACTGCTGCCTAATGTCACC 291
humanTAS1R1     GCTATGCGGCTTGGGGTTGAGGAGATAAACAACTCCACGGCCCTGCTGCCCAACATCACC 291
mouseTas1r2     GCCATGCGATTCGCCGTGGAGGAAATCAACAACTGTAGCTCTCTGCTGCCCGGCGTGCTG 288
ratTas1r2       GCCATGCGTTTCGCTGTGGAGGAGATCAACAACTGTAGCTCCCTGCTACCCGGCGTGCTG 288
humanTAS1R2     GCCATGCGCTTCGCGGTGGAGGAGATCAACAATGACAGCAGCCTGCTGCCTGGTGTGCTG 279
dogTas1r2       GCCATGCGCTTTGCGGTGGAAGAGATTAACAACCGCAGCGACCTGCTGCCCGGCGTGCTG 279
catTas1r2       GCCATGTGCTTTGCAGGGGAGGAGATCAATAGCCAGAGCAGCCTGCTGCCTGGCGTGCTG 279
mouseTas1r3     GCTATGAAGATGGCTGTGGAGGAGATCAACAATGGATCTGCCTTGCTCCCTGGGCTGCGG 282
ratTas1r3       GCTATGAAGATGGCTGTAGAGGAGATCAACAATGGATCTGCCTTGCTCCCTGGGCTGCGA 282
dogTas1r3       GCCATGAAGATGGCGGTGGAGGAGGTCAACAACAGGTCCACGCTGCTGCCAGGACTGCGC 276
catTas1r3       GCCGTGAAGATGGCGGTGGAGGAGATCAACAACGGGTCGGCCCTGCTGCCCGGGCTGCAC 294
humanTAS1R3     GCCATGAAAATGGCCGTGGAGGAGATCAACAACAAGTCGGATCTGCTGCCCGGGCTGCGC 282
                **  **    *       ** **  * ** *            * ** **     *

mouseTas1r1     CTGGGGTATGAACTGTATGACGTGTGCTCAGAGTCT---TCCAATGTCTATGCCACCCTG 351
ratTas1r1       CTGGGGTATGAGCTGTACGACGTGTGCTCAGAATCT---GCCAATGTGTATGCCACCCTG 345
catTas1r1       CTGGGATACCAGCTGTACGACGTGTGCTCGGAGTCT---GCCAACGTGTATGCCACACTA 348
dogTas1r1       CTGGGGTACCAGCTGTATGACGTGTGCTCAGAGTCA---GCCAATGTGTACGCCACACTC 348
humanTAS1R1     CTGGGGTACCAGCTGTATGATGTGTGTTCTGACTCT---GCCAATGTGTATGCCACGCTG 348
mouseTas1r2     CTCGGCTACGAGATGGTGGATGTCTGCTACCTCTCC---AACAATATCCAGCCTGGGCTC 345
ratTas1r2       CTCGGCTACGAGATGGTGGATGTCTGTTACCTCTCC---AACAATATCCACCCTGGGCTC 345
humanTAS1R2     CTGGGCTATGAGATCGTGGATGTGTGCTACATCTCC---AACAATGTCCAGCCGGTGCTC 336
dogTas1r2       CTGGGCTATGAGATAGTGGATGTCTGCTACATCTCC---AACAACGTCCAGCCCGTGCTC 336
catTas1r2       CTGGGCTACAAAATGGTGGATGTCAGCTACATCTCC---AACAATGTCCAGCCCGTGCTC 336
mouseTas1r3     CTGGGCTATGACCTATTTGACACATGCTCCGAGCCAGTGGTCACCATGAAATCCAGTCTC 342
ratTas1r3       CTGGGCTATGACCTGTTTGACACATGCTCAGAGCCAGTGGTCACCATGAAGCCCAGCCTC 342
dogTas1r3       CTGGGCTACGACCTCTTTGACACATGTTCGGAGCCTGTGGTGGCCATGAAGCCCAGCCTC 336
catTas1r3       CTGGGCTATGACCTCTTTGACACGTGTTCAGAGCCCATGGTGGCCATGAAGCCCAGCCTC 354
humanTAS1R3     CTGGGCTACGACCTCTTTGATACGTGCTCGGAGCCTGTGGTGGCCATGAAGCCCAGCCTC 342
                ** ** **  *  *    **     * *      *           *  *  *    **

mouseTas1r1     AGGGTGCTCGCCCAGCAAGGGACAGGCCACCTAGAGATGCAGAGAGATCTTCGCAACCAC 411
ratTas1r1       AGGGTGCTTGCCCTGCAAGGGCCCCGCCACATAGAGATACAGAAAGACCTTCGCAACCAC 405
catTas1r1       AACGTGCTCTCCCTGCTGGGGACACATCACGTAGAGATCCGAGCAGACCCTTCCCACTAT 408
dogTas1r1       AACGTACTCTCCACGCTGGGGACACATCACATAGAGATCCAAGCAGACCCTTCCCACTAT 408
humanTAS1R1     AGAGTGCTCTCCCTGCCAGGGCAACACCACATAGAGCTCCAAGGAGACCTTCTCCACTAT 408
mouseTas1r2     TACTTCCTGTC---ACAGATAGATGACTTCCTGCCCATCCTCAAAGACTACAGCCAGTAC 402
ratTas1r2       TACTTCCTGGC---ACAGGACGACGACCTCCTGCCCATCCTCAAAGACTACAGCCAGTAC 402
humanTAS1R2     TACTTCCTGGC---ACACGAGGACAACCTCCTTCCCATCCAAGAGGACTACAGTAACTAC 393
dogTas1r2       TACTTCTTGGC---ACGGGAGGACTACTCCCTGCCCATCCAGGAGGACTACAGCCACTAC 393
catTas1r2       CACTTCCCGGC---AAAGGAGGACTGTTCCTTGCCCATCCAGGAGGACTACAGCCACTGT 393
mouseTas1r3     ATGTTCCTGGCCAAGGTGGGCAGTCAAAGCATTGCTGCCTACTGCAACTACACACAGTAC 402
ratTas1r3       ATGTTCATGGCCAAGGTGGGAAGTCAAAGCATTGCTGCCTACTGCAACTACACACAGTAC 402
dogTas1r3       ATGTTCATGGCCAAAGCGGGCAGCTGCGACATCGCCGCCTACTGCAACTACACGCAGTAC 396
catTas1r3       GTGTTCATGGCCAAAGCAGGCAGCTGCAGCATTGCCGCCTACTGCAATTACACACAGTAC 414
humanTAS1R3     ATGTTCCTGGCCAAGGCAGGCAGCCGCGACATCGCCGCCTACTGCAACTACACGCAGTAC 402
                    *     *                  * *              *        *

mouseTas1r1     TCCTCCAAGGTGGTGGCACTCATTGGCCTGATAACACTGACCACGCTGTCACCACTGCT 471
ratTas1r1       TCCTCCAAGGTGGTGGCCTTCATCGGCCTGACAACACTGACCACGCTGTCACTACCGCT 465
catTas1r1       TCGCCTGCCGCCCTGGCTGTCATTGGGCCTGACACCACCAACCACGCAGCCACCACTGCA 468
dogTas1r1       TCCCCGGCCGCCCTGGCGGTGATTGGACCTGACACCACCAACCATGCTGCCACCGCTGCA 468
humanTAS1R1     TCCCCTACGGTGCTGGCAGTGATTGGGCCTGACAGCACCAACCGTGCTGCCACCACAGCC 468
mouseTas1r2     AGGCCCCAAGTGGTGGCCGTCATTGGCCCAGACAACTCTGAGTCCGCCATCACCGTGTCC 462
ratTas1r2       ATGCCCCACGTGGTGGCTGTCATTGGCCCCGACAACTCTGAGTCCGCCATTACCGTGTCC 462
humanTAS1R2     ATTTCCCGTGTGGTGGCTGTCATTGGCCCTGACAACTCCGAGTCTGTCATGACTGTGGCC 453
dogTas1r2       GTGCCCCGTGTGTTGGCGGTCATTGGCCCTGACAACTCCGAGTCCACTACTACTGTGGCC 453
catTas1r2       GTGCCCCGTGTGGTGGCTGTCATTGGTCCTGGCAACTCTGAGTCCACTGTGACTGTGGCC 453
mouseTas1r3     CAACCCCGTGTGCTGGCTGTCATCGGCCCCCACTCATCAGAGCTTGCCCTCATTACAGGC 462
ratTas1r3       CAACCCCGTGTGCTGGCTGTCATTGGTCCCCACTCATCAGAGCTTGCCCTCATTACAGGC 462
dogTas1r3       CAGCCCCGTGTGCTGGCAGTCATTGGGCCACACTCATCTGAGCTCGCCCTCATCACCGGC 456
catTas1r3       CAGCCCCGCGTGCTGGCCGTCATCGGGCCCCACTCGTCTGAGCTCGCCCTCGTCACCGGC 474
humanTAS1R3     CAGCCCCGTGTGCTGGCTGTCATCGGGCCCCACTCGTCAGAGCTCGCCATGGTCACCGGC 462
                    *    *   ****  * ** ** **        *  *
```

FIG. 1C

```
mouseTas1r1     GCCCTGCTGAGCCCTTTTCTGATGCCCCTGGTCAGCTATGAGGCGAGCAGCGTGATCCTC 531
ratTas1r1       GCCTTGCTGGGTCCTTTCCTGATGCCCCTGGTCAGCTATGAGGCAAGCAGCGTGGTACTC 525
catTas1r1       GCCCTGCTGAGCCCCTTCCTGGTGCCCCTGATCAGCTACGAGGCCAGCAGCGTGACGCTC 528
dogTas1r1       GCCCTGCTGAGCCCGTTTCTGGTGCCTGTGATCAGCTACGAGGCCAGCAGTGTGATGCTT 528
humanTAS1R1     GCCCTGCTGAGCCCTTTCCTGGTGCCCATGATTAGCTATGCGGCCAGCAGCGAGACGCTC 528
mouseTas1r2     AACATTCTCTCCTACTTCCTCGTGCCACAGGTCACATATAGCGCCATCACCGACAAGCTG 522
ratTas1r2       AACATTCTCTCTCATTTCCTCATCCCACAGATCACATACAGCGCCATCTCCGACAAGCTG 522
humanTAS1R2     AACTTCCTCTCCCTATTTCTCCTTCCACAGATCACCTACAGCGCCATCAGCGATGAGCTG 513
dogTas1r2       CATTTCCTCTCACTCTTCCTCCTTCCACAGATCACCTACAGCGCCATCAGTGACGATCTG 513
catTas1r2       CGCTTCCTCTCTCTCTTCCTCCTTCCACAGATCACCTACAGCGCCATCAGTGACGAGCTA 513
mouseTas1r3     AAGTTCTTCAGCTTCTTCCTCATGCCACAGGTCAGCTATAGTGCCAGCATGGATCGGCTA 522
ratTas1r3       AAGTTCTTCAGCTTCTTCCTCATGCCACAGGTCAGCTATAGTGCCAGCATGGATCGGCTA 522
dogTas1r3       AAGTTCTTCAGCTTCTTCCTCATGCCTCAGGTCAGCTACGGGGCCAGCACCGACCGGCTG 516
catTas1r3       AAGTTCTTCAGCTTCTTCCTTGTGCCTCAGGTCAGCTACGGCGCCAGCACCGACCGGCTG 534
humanTAS1R3     AAGTTCTTCAGCTTCTTCCTCATGCCCCAGGTCAGCTACGGTGCTAGCATGGAGCTGCTG 522
                    *  *       ** **  * **   * * *  **    ** * *   *     **

mouseTas1r1     AGTGGGAAGCGCAAGTTCCCGTCCTTCTTGCGCACCATCCCCAGCGATAAGTACCAGGTG 591
ratTas1r1       AGTGCCAAGCGCAAGTTCCCGTCTTTCCTTCGTACCGTCCCCAGTGACCGGCACCAGGTG 585
catTas1r1       GGAGTGAAGCGGCATTACCCCTCGTTTCTGCGCACCATCCCCAGCGACAAGCACCAGGTG 588
dogTas1r1       GGAGTGAAGCGGTATTACCCCTCGTTTCTGCGCACTATCCCCAGCGATAAGTACCAGGTG 588
humanTAS1R1     AGCGTGAAGCGGCAGTATCCCTCTTTCCTGCGCACCATCCCCAATGACAAGTACCAGGTG 588
mouseTas1r2     CGAGACAAGCGGCGCTTCCCTGCCATGCTGCGCACTGTGCCCAGCGCCACCCACCACATC 582
ratTas1r2       CGGGACAAGCGGCACTTCCCTAGCATGCTACGCACAGTGCCCAGCGCCACCCACCACATC 582
humanTAS1R2     CGAGACAAGGTGCGCTTCCCGGCTTTGCTGCGTACCACACCCAGCGCCGACCACCACGTC 573
dogTas1r2       CGGGACAAGCAGCACTTCCCGGCCCTGCTGCGCACAGTGGCGGGCGCGGACCACCAGATC 573
catTas1r2       CGGGACAAGCAGCGCTTCCCGGCCCTTCTGCCCACAGCGCCGGGCGCCGATCACCAGATC 573
mouseTas1r3     AGTGACCGGGAAACGTTTCCATCCTTCTTCCGCACAGTGCCCAGTGACCGGGTGCAGCTG 582
ratTas1r3       AGTGACCGGGAAACATTTCCATCCTTCTTCCGCACAGTGCCCAGTGACCGGGTGCAGCTG 582
dogTas1r3       AGCAACCGGGAGACGTTCCCATCCTTCTTCCGCACGGTGTCCAGCGACCGCGTACAGGCA 576
catTas1r3       AGCAACCGGGAGATCTTCCCGTCCTTCTTCCGCACGGTGCCCAGCGACCAGGTGCAGGTG 594
humanTAS1R3     AGCGCCCGGGAGACCTTCCCCTCCTTCTTCCGCACCGTGCCCAGCGACCGTGTGCAGCTG 582
                 *      *      *  **     *  * *  **     *    *        **

mouseTas1r1     GAAGTCATAGTGCGGCTGCTGCAGAGCTTCGGCTGGGTCTGGATCTCGCTCGTTGGCAGC 651
ratTas1r1       GAGGTCATGGTGCAGCTGCTGCAGAGTTTTGGGTGGGTGTGGATCTCGCTCATTGGCAGC 645
catTas1r1       GAGGCCATGGTGCTGCTGCTGCAGAGCTTCGGGTGGGTCTGGATCTCGGTGGTCGGCAGC 648
dogTas1r1       GAGATCATGGTGCTACTGCTGCAGAGGTTTGGGTGGGTCTGGATCTCATTGGTGGGCAGC 648
humanTAS1R1     GAGACCATGGTGCTGCTGCTGCAGAAGTTCGGGTGGACCTGGATCTCTCTGGTTGGCAGC 648
mouseTas1r2     GAGGCCATGGTGCAACTGATGGTTCACTTCCAGTGGAACTGGATCGTGGTGCTGGTGAGC 642
ratTas1r2       GAGGCCATGGTGCAGCTGATGGTTCACTTCCAATGGAACTGGATTGTGGTGCTGGTGAGC 642
humanTAS1R2     GAGGCCATGGTGCAGCTGATGCTGCACTTCCGCTGGAACTGGATCATTGTGCTGGTGAGC 633
dogTas1r2       GAGGCCATGGTGCAGCTCCTGCTCCACTTCAACTGGAACTGGATCATCGTGCTAGTGAGC 633
catTas1r2       GAGGCCATGGTGCAGCTGATGTTGTACTTCCGCCGGAACTGGATCATCGCGCTGGTGAGC 633
mouseTas1r3     CAGGCAGTTGTGACTCTGTTGCAGAACTTCAGCTGGAACTGGGTGGCCGCCTTAGGGAGT 642
ratTas1r3       CAGGCCGTTGTGACACTGTTGCAGAATTTCAGCTGGAACTGGGTGGCTGCCTTAGGTAGT 642
dogTas1r3       GTGGCCATGGTGGAGCTGCTGCAGGAGCTTGGCTGGAACTGGGTGGCTGCAGTGGGCAGC 636
catTas1r3       GCGGCCATGGTGGAGCTGCTGGAGGAGCTCGGCTGGAACTGGGTGGCGGCGGTGGGTAGT 654
humanTAS1R3     ACGGCCGCCGCGGAGCTGCTGCAGGAGTTCGGCTGGAACTGGGTGGCCGCCCTGGGCAGC 642
                         * *   **  **       *     **   *** *        * *  **

mouseTas1r1     TATGGTGACTACGGGCAGCTGGGCGTACAGGCGCTGGAGGAGC---TGGCCACTCCACGG 708
ratTas1r1       TACGGTGATTACGGGCAGCTGGGTGTGCAGGCGCTGGAGGAGC---TGGCCGTGCCCCGG 702
catTas1r1       GACGGCGACTACGGGCAGCTGGGGGTGCAGGCGCTGGAGGAGC---AGGCCACCCAGCAG 705
dogTas1r1       GACGGCGACTATGGGCAGCTGGGGGTGCAGGCACTGGAGGAGC---AGGCCACCCAGCAG 705
humanTAS1R1     AGTGACGACTATGGGCAGCTAGGGGTGCAGGCACTGGAGAACC---AGGCCACTGGTCAG 705
mouseTas1r2     GATGACGATTATGGCCGAGAGAACAGCCACCTGCTGAGCCAGCGTCTGACCAACACTGGC 702
ratTas1r2       GACGACGATTACGGCCGCGAGAACAGCCACCTGTTGAGCCAGCGTCTGACCAAAACGAGC 702
humanTAS1R2     AGCGACACCTATGGCCGCGACAATGGCCAGCTGCTTGGCGAGCGCGTGGCCCG---GCGC 690
dogTas1r2       AGCGACGACTACGGCCGCTACAACAGCCAGCTGCTCAACGATCGCCTGGCCA---CCGGC 690
catTas1r2       AGCGGCGACTGCGGCCGCGACGACAGCCAGCTGCTCAGCGATCGCCCGGCCGG---CGGC 690
mouseTas1r3     GATGATGACTATGGCCGGGAAGGTCTGAGCATCTTTTCTAGTC---TGGCCAATGCACGA 699
ratTas1r3       GATGATGACTATGGCCGGGAAGGTCTGAGCATCTTTTCTGGTC---TGGCCAACTCACGA 699
dogTas1r3       GATGACGAGTATGGCCGGCAGGGCCTGAGCCTCTTCTCCAGCC---TGGCCAATGCCAGG 693
catTas1r3       GACGACGAGTATGGCCGGCAGGGCCTGAGCCTCTTCTCCGGCC---TGGCCAGCGCCAGG 711
humanTAS1R3     GACGACGAGTACGGCCGGCAGGGCCTGAGCATCTTCTCGGCCC---TGGCCGCGGCACGC 699
                   *     *  ** *                  *       *    * **
```

FIG. 1D

```
mouseTas1r1     GGCATCTGCGTCGCCTTCAAGGACGTGGTGCCTCT-CTCCGCCCAGGCGGGTGACCC-764
ratTas1r1       GGCATCTGCGTCGCCTTCAAGGACATCGTGCCTTT-CTCTGCCCGGGTGGGTGACCC-758
catTas1r1       GGCATCTGCGTTGCCTTCAAGGACATCATCCCCTT-CTCTGCCCGGCCGGGCGACGA-761
dogTas1r1       GGCATCTGCATTGCCTTCAAGGACATCATACCCTT-CTCTGCCCAGCCGGGTAATGA-761
humanTAS1R1     GGGATCTGCATTGCTTTCAAGGACATCATGCCCTT-CTCTGCCCAGGTGGGCGATGA-761
mouseTas1r2     GATATCTGCATTGCCTTCCAGGAGGTTCTGCCTGTACCAGAACCCAACCAGGCCGTGAGG 762
ratTas1r2       GACATCTGCATTGCCTTCCAGGAGGTTCTGCCCATACCTGAGTCCAGCCAGGTCATGAGG 762
humanTAS1R2     GACATCTGCATCGCCTTCCAGGAGACGCTGCCCACACTGCAGCCCAACCAGAACATGACG 750
dogTas1r2       GACATCTGCATCGCCTTCCAGGAGACGCTGCCCATGCCGCAGCCCGACCAGGTGGTGACG 750
catTas1r2       GACACCTGCATCGCCTTCCGGGAGACGCTGCCCATGCCCCAGCCCAACCAGGCGGTGACG 750
mouseTas1r3     GGTATCTGCATCGCACATGAGGGCCTGGTGCCACAA-CATGACACTAGTGGCCAACAGTT 758
ratTas1r3       GGTATCTGCATTGCACACGAGGGCCTGGTGCCACAA-CATGACACTAGTGGCCAACAATT 758
dogTas1r3       GGCATCTGTATTGCGCATGAGGGCCTGGTGCCATTG-CCGCACACGAGTAGCCTGCGGCT 752
catTas1r3       GGCATCTGCATCGCGCATGAGGGCCTGGTGCCACTG-CCGC---CAGGCAGCCTGCGGCT 767
humanTAS1R3     GGCATCTGCATCGCGCACGAGGGCCTGGTGCCGCTG-CCCCGTGCCGATGACTCGCGGCT 758
                *  * ***  * **      **      * **            *

mouseTas1r1     ---AAGGA-----------TGCAGCGCATGATGCTGCGTCTGGCTCGAGCCAGGACCACC 810
ratTas1r1       ---GAGGA-----------TGCAGAGCATGATGCAGCATCTGGCTCAGGCCAGGACCACC 804
catTas1r1       ---GAGGA-----------TGCAGAGCATCATGCACCACCTGGCCCGAGCGAGGACCACC 807
dogTas1r1       ---GAGGA-----------TGCAGAGCATGATGTACCACCTGGACCGAGCAAGGACCACT 807
humanTAS1R1     ---GAGGA-----------TGCAGTGCCTCATGCGCCACCTGGCCCAGGCCGGGGCCACC 807
mouseTas1r2     CCTGAGGAGCAGGACCAACTGGACAACATCCTGGACAAGCTGCGGCGG---ACCTCGGCG 819
ratTas1r2       TCCGAGGAGCAGAGACAACTGGACAACATCCTGGACAAGCTGCGGCGG---ACCTCGGCG 819
humanTAS1R2     TCAGAGGAGCGCCAGCGCCTGGTGACCATTGTGGACAAGCTGCAGCAG---AGCACAGCG 807
dogTas1r2       GAGTGGGAGCGCCAGCGCCTGGAGGCCATCGTGGGCAAGCTGCAGCAG---AGCTCGGCG 807
catTas1r2       CAGTGGGAGCGCCGGCGCCTGAAGGCCATCGTGGACGAGCAGCAGCGGCAGAGCTCTGCG 810
mouseTas1r3     GGGCAAGG-----------TGCTGGATGTACTACGCCAAGTGAACCAA---AGTAAAGTA 804
ratTas1r3       GGGCAAGG-----------TGGTGGATGTGCTACGCCAAGTGAACCAA---AGCAAAGTA 804
dogTas1r3       GGGCACTG-----------TCCAGGGCCTACTGCACCAGGTAAACCAG---AGCAGCGTG 798
catTas1r3       GGGCGCCC-----------TACAGGGCCTGCTGCGCCAGGTGAACCAG---AGCAGCGTG 813
humanTAS1R3     GGGGAAGG-----------TGCAGGACGTCCTGCACCAGGTGAACCAG---AGCAGCGTG 804
                                   *        *  *             *

mouseTas1r1     GTGGTCGTGGTCTT-CTCTAACCGGCACCTGGCTGGAGTG-TTCTTCAGGTCTGTGGTG 867
ratTas1r1       GTGGTTGTGGTCTT-CTCTAACCGGCACCTGGCTAGAGTG-TTCTTCAGGTCCGTGGTG 861
catTas1r1       GTTGTGGTCGTTTT-CTCCAGCAGGCAGCTGGCCAGGGTG-TTCTTTGAGTCGGTGGTG 864
dogTas1r1       GTTGTGGTCGTTTT-CTCCAGCAGGCAGCTGGCCAGGGTG-TTCTTCGAGTCCGTGGTC 864
humanTAS1R1     GTCGTGGTTGTTTT-TTCCAGCCGGCAGTTGGCCAGGGTG-TTTTTCGAGTCCGTGGTG 864
mouseTas1r2     CGTGTGGTGGTGATATTCTCGCCAGAGCTGAGCCTGCACAACTTCTTCCGCGAGGTGCTG 879
ratTas1r2       CGCGTCGTGGTGGTGTTCTCGCCCGAGCTGAGCCTGTATAGCTTCTTTCACGAGGTGCTC 879
humanTAS1R2     CGCGTCGTGGTCGTGTTCTCGCCCGACCTGACCCTGTACCACTTCTTCAATGAGGTGCTG 867
dogTas1r2       CGCGTCGTGGTGCTGTTCTCGCCAGACCTGATCCTGCACAACTTCTTCCGCGAGGTGCTC 867
catTas1r2       CGCGTCGTGGTCCTGCTGTCGCCAAAGCTGGTCCTGCACAACTTCTTCCGCGAGGTGCTC 870
mouseTas1r3     CAAGTGGTGGTGCTGTTTGCCTCTGCCCGTGCTGTCTACTCCCTTTTTAGTTACAGCATC 864
ratTas1r3       CAGGTGGTGGTGCTGTTTGCATCTGCCCGTGCTGTCTACTCCCTTTTTAGCTACAGCATC 864
dogTas1r3       CAGGTGGTGGTGCTTTTCTCTTCCACTCGTGCTGCCCGCACCCTCTTCAGCTACAGCATC 858
catTas1r3       CAGGTGGTGGTGCTGTTCTCCTCCGCCCACGCGGCCCGCACCCTCTTCAGCTACAGCATC 873
humanTAS1R3     CAGGTGGTGCTGCTGTTCGCCTCCGTGCACGCCGCCCACGCCCTCTTCAACTACAGCATC 864
                   ** **  *  *  *                          * **           *

mouseTas1r1     CTGGCCAACCTGACTGGCAAAGTGTGGATCGCCTCCGAAGACTGGGCCATCTCCACGTAC 927
ratTas1r1       CTGGCCAACCTGACTGGCAAAGTGTGGGTCGCCTCAGAAGACTGGGCCATCTCCACGTAC 921
catTas1r1       CTGGCCAACCTGACTGCCAAGGTGTGGATCGCCTCAGAAGACTGGGCCATCTCTAGACAC 924
dogTas1r1       CTGGCCAAGCTGACTGCCAAGGTGTGGATCGCTTCAGAAGACTGGGCCATCTCCAGACAT 924
humanTAS1R1     CTGACCAACCTGACTGGCAAGGTGTGGGTCGCCTCAGAAGCCTGGGCCCTCTCCAGGCAC 924
mouseTas1r2     CGCTGGAACTTCACAGGCTTTGTGTGGATTGCCTCTGAGTCCTGGGCCATCGACCCTGTT 939
ratTas1r2       CGCTGGAACTTCACGGGTTTTGTGTGGATCGCCTCTGAGTCCTGGGCTATCGACCCAGTT 939
humanTAS1R2     CGCCAGAACTTCACGGGCGCCGTGTGGATCGCCTCCGAGTCCTGGGCCATCGACCCGGTC 927
dogTas1r2       CGCCAGAACTTCACGGGCGCCGTGTGGATCGCCTCCGAGTCCTGGGCCATCGACCCGGTT 927
catTas1r2       CGCCAGAACCTCACGGGCGTCGTGCGGATCGCCTCCGAGTCCTGGGCCATCGACCCGGTC 930
mouseTas1r3     CATCATGGCCTCTCACCCAAGGTATGGGTGGCCAGTGAGTCTTGG-CTGACATCTGACCT 923
ratTas1r3       CTTCATGACCTCTCACCCAAGGTATGGGTGGCCAGTGAGTCCTGG-CTGACCTCTGACCT 923
dogTas1r3       CACTGCAGGCTCTCGCCCAAGGTTTGGGTGGCCAGTGAGGCCTGG-CTGACCTCGGACCT 917
catTas1r3       CGCTGCAAGCTCTCACCCAAGGTGTGGGTGGCCAGCGAGGCCTGG-CTGACCTCAGACCT 932
humanTAS1R3     AGCAGCAGGCTCTCGCCCAAGGTGTGGGTGGCCAGCGAGGCCTGG-CTGACCTCTGACCT 923
                          *  *       **  ** * **    **    *** *   *
```

FIG. 1E

```
mouseTas1r1    ATCACCAAT---GTGCCCGGGATCCAGGGCATTGGGACGGTGCTGGGGGTGGCCATCCAG 984
ratTas1r1      ATCACCAGC---GTGACTGGGATCCAAGGCATTGGGACGGTGCTCGGTGTGGCCGTCCAG 978
catTas1r1      ATCAGCAAT---GTGCCCGGGATCCAGGGCATTGGCACGGTGCTGGGTGTGGCCATCCAG 981
dogTas1r1      ATTAGCAGC---CTGCCCAGGATCTGGGGCATTGGCACAGTGTTGGGCGTGGCCATCCAG 981
humanTAS1R1    ATCACTGGG---GTGCCCGGGATCCAGCGCATTGGGATGGTGCTGGGCGTGGCCATCCAG 981
mouseTas1r2    CTACACAAC---CTCACAGAGCTGCGCCACACGGGCACTTTCCTGGGCGTCACCATCCAG 996
ratTas1r2      CTGCATAAC---CTCACGGAGCTGCGCCACACGGGTACTTTTCTGGGCGTCACCATCCAG 996
humanTAS1R2    CTGCACAAC---CTCACGGAGCTGGGCCACTTGGGCACCTTCCTGGGCATCACCATCCAG 984
dogTas1r2      CTGCACAAC---CTCACCGAGCTGCGCCAAACCGGCACCTTCCTGGGCGTCACCACCCAG 984
catTas1r2      CTGCACGACAGGCCCAC-GCGCTGCACAGCCTCCTGGGCTGCACCCAGACCAGCAGCTCC 989
mouseTas1r3    GGTCATGAC—ACTTCCCAATATTGCCCGTGTGGGCACTGTGCTTGGGTTTTTGCAGCGG 981
ratTas1r3      GGTCATGAC—ACTTCCCAATATTGCCCGTGTGGGCACTGTTCTTGGGTTTCTGCAGCGC 981
dogTas1r3      GGTCATGAC—GCTGCCTGGCATGGCTGAGGTGGGCACCGTGCTTGGCTTTCTGCAGCAG 975
catTas1r3      GGTCATGAC—GCTGCCCGGCATGCCTGGGGTGGGCACCGTGCTGGGCTTCCTGCAGCAG 990
humanTAS1R3    GGTCATGGG—GCTGCCCGGCATGGCCCAGATGGGCACGGTGCTTGGCTTCCTCCAGAGG 981
                                    *

mouseTas1r1    CAGAGACAAGTCCCTGGCCTGAAGGAGTTTGAAGAGTCCTATGT----CCAGGCAGTGAT 1040
ratTas1r1      CAGAGACAAGTCCCTGGGCTGAAGGAGTTTGAGGAGTCTTATGT----CAGGGCTGTAAC 1034
catTas1r1      CAGAGGCTTGTCCCTGGCCTGAAGGAGTTTGAAGAGGCCTATGT----CCAGGCAGATAA 1037
dogTas1r1      CAGAAGCTTGTCCCTGGTCTGAAGGAGTTTGAAGAGGCCTACGT----CCGGGCAAAGAA 1037
humanTAS1R1    AAGAGGGCTGTCCCTGGCCTGAAGGCGTTTGAAGAAGCCTATGC----CCGGGCAGACAA 1037
mouseTas1r2    AGGGTGTCCATCCCTGGCTTCAGCCAGTTCCGAGTGCGCCACGA----CAAGCC------ 1046
ratTas1r2      AGGGTGTCCATCCCTGGCTTCAGTCAGTTCCGAGTGCGCCGTGA----CAAGCC------ 1046
humanTAS1R2    AGCGTGCCCATCCCGGGCTTCAGTGAGTTCCGCGAGTGGGGCCC----ACAGGC------ 1034
dogTas1r2      AGTGTGCCCATCCCGGGCTTCAGCGAGTTCCGCATACGCCGCAC----CCCGGT------ 1034
catTas1r2      GGGTCGTCTATCCCTGGCA—GGTGAGGCCCCAC----CCACGG----AGAGTC------ 1033
mouseTas1r3    GGTGCCCTACTGCCTGAATTTTCCCATTATGTGGAGACTCACCTTGCCCTGGCCGCTGAC 1041
ratTas1r3      GGTGCCCTACTGCCTGAATTTTCCCATTATGTGGAGACTCGCCTTGCCCTAGCTGCTGAC 1041
dogTas1r3      GGCGCCCCAATACCCGAGTTCCCATCCTATGTGCAGACCTGCCTGGCCCTGGCTGCTGAC 1035
catTas1r3      GGCGCCCCGATGCCGGAGTTCCCATCCTACGTGCGGACCCGCCTGGCCCTGGCCGCTGAC 1050
humanTAS1R3    GGTGCCCAGCTGCACGAGTTCCCCCAGTACGTGAAGACGCACCTGGCCCTGGCCACCGAC 1041
                          *  *   *                                *

mouseTas1r1    GGGTGCTCCCAGAACTTGCCCAGAGG---------GGTCCTGGTGCGGCACTAACCAGCT 1091
ratTas1r1      AGCTGCTCCCAGCGCTTGCCCGGAGG---------GGTCCTGGTGCAGCACTAACCAGCT 1085
catTas1r1      GGGGGCCCCTGGGCCTTGCTCCAGGA---------CCTCCGAGTGCAGCAGCAACCAGCT 1088
dogTas1r1      GGCAGCCCATAGGCCTTGCTCCAGGG---------ACTCCTGGTGCAGCAGCAACCAACT 1088
humanTAS1R1    GAAGGCCCCTAGGCCTTGCCACAAGG---------GCTCCTGGTGCAGCAGCAATCAGCT 1088
mouseTas1r2    AGAGTATCCCATGCCTAACGAGACCA---------GCCTGAGGACTACCTGTAACCAGGA 1097
ratTas1r2      AGGGTATCCCGTGCCTAACACGACCA---------ACCTGCGGACGACCTGCAACCAGGA 1097
humanTAS1R2    TGGGCCGCCACCCCTCAGCAGGACCA---------GCCAGAGCTATACCTGCAACCAGGA 1085
dogTas1r2      CAGGCTGCCTGAGCCCAACAGGACCA---------GCCTGGAGGCCACCTGCAACCAGGA 1085
catTas1r2      GGGGCCACACACGCA-GGCGCCGCCA---------CAGCCCTGAGTGGTTGCCATGGAGA 1083
mouseTas1r3    CCAGCATTCTGTGCCTCACTGAATGCGGAGT---TGGATCTGGAGGAACATGTGATGGGG 1098
ratTas1r3      CCAACATTCTGTGCCTCCCTGAAAGCTGAGT---TGGATCTGGAGGAGCGCGTGATGGGG 1098
dogTas1r3      CCTGCCTTTTGCGCCTCACTGGATGCAGAGCAGCCGGGCCTGGAAGAGCACGTGGTGGGG 1095
catTas1r3      CCTGCCTTCTGCGCCTCGCTGGACGCTGAACAGCCAGGCCTGGAGGAGCACGTGGTGGGG 1110
humanTAS1R3    CCGGCCTTCTGCTCTGCCCTGGGCGAGAGGGAGCAGGGTCTGGAGGAGGACGTGGTGGGC 1101
                                   *

mouseTas1r1    GTGCAGGGAGTGTCACGCTTTCACGACATGGAACATGCCC-------------------- 1131
ratTas1r1      GTGCCGGGAGTGCCACACGTTCACGACTCGTAACATGCCC-------------------- 1125
catTas1r1      CTGTAGAGAGTGTCGGGCTTTCACGGCAGAGCAGATGCCC-------------------- 1128
dogTas1r1      CTGCAGAGAGTGCCAAGCTTTCACAGTACAGCAGATGCCC-------------------- 1128
humanTAS1R1    CTGCAGAGAATGCCAAGCTTTCATGGCACACACGATGCCC-------------------- 1128
mouseTas1r2    CTGTGACGCCTGCATGAACATCACCGAGTCCTTTAACAAC-------------------- 1137
ratTas1r2      CTGTGACGCCTGCTTGAACACCACCAAGTCCTTCAACAAC-------------------- 1137
humanTAS1R2    GTGCGACAACTGCCTGAACGCCACCTTGTCCTTCAACACC-------------------- 1125
dogTas1r2      GTGCGACACCTGCCAGGACACCACCGCGTCCTTCAACAGC-------------------- 1125
catTas1r2      CCACTGC-CCTGCTCTAGCGTCCCCCTCTCTGGCCGGGTC-------------------- 1122
mouseTas1r3    CAACGCTGTCCACGGTGTGACGACATCATGCTGCAGAACCTATCATCTGGGCTGTTGCAG 1158
ratTas1r3      CCACGCTGTTCACAATGTGACTACATCATGCTACAGAACCTGTCATCTGGGCTGATGCAG 1158
dogTas1r3      CCCCGCTGTCCCCAGTGTGACCACGTCACTCTGGA--------------GGCTA------ 1135
catTas1r3      CCACGCTGCCCCCAATGTGACCACGTCACGCTAGAGAACC-------------------- 1150
humanTAS1R3    CAGCGCTGCCCGCAGTGTGACTGCATCACGCTGCAGAACG-------------------- 1141
```

FIG. 1F

```
mouseTas1r1     ---GAGCTTGGAGCCTTCTCCATGAGCGCTGCCTACAATGTGTATGAGGCTGTGTATGCT 1188
ratTas1r1       ---ACGCTTGGAGCCTTCTCCATGAGTGCCGCCTACAGAGTGTATGAGGCTGTGTACGCT 1182
catTas1r1       ---ACGCTCGGGGCATTCTCCATGAGCTCTGCTTATAACGCCTACCGGGCAGTCTACGCA 1185
dogTas1r1       ---ACACTCGGAGCATTCTCCATGAGCTCTGCCTACAATGCCTACCGGGCTGTCTACGCA 1185
humanTAS1R1     ---AAGCTCAAAGCCTTCTCCATGAGTTCTGCCTACAACGCATACCGGGCTGTGTATGCG 1185
mouseTas1r2     ---GTTCTCATGCTTTCGGGGGAGCGTGTGGTCTACAGTGTGTACTCGGCCGTCTACGCG 1194
ratTas1r2       ---ATCCTTATACTTTCGGGGGAGCGCGTGGTCTACAGCGTGTACTCGGCAGTTTACGCG 1194
humanTAS1R2     ---ATTCTCAGGCTCTCTGGGGAGCGTGTCGTCTACAGCGTGTACTCTGCGGTCTATGCT 1182
dogTas1r2       ---ATCCTCATGCTCTCCGGCGAGCGCGTGGTCTACAACGTGTACTCGGCTGTCTACGCC 1182
catTas1r2       ---CTGGGCAAACTGGCGGGAGAGGCCAGGGGACGTACCCTGTCCCCAGACACATAA--- 1176
mouseTas1r3     AACCTATCAGCTGGGCAATTGCACCACCAAATATTTGCAACCTATGCAGCTGTGTACAGT 1218
ratTas1r3       AACCTATCAGCTGGGCAGTTGCACCACCAAATATTTGCAACCTATGCAGCTGTGTACAGT 1218
dogTas1r3       ----TGTCTGCAGGGCTGCTGCACCACCAGACCTTCGCGGCCTACGCAGCCGTGTATGGC 1191
catTas1r3       ----TATCTGCGGGGCTGCTGCACCACCAGACCTTCGCTGCCTACGCGGCTGTGTATGGC 1206
humanTAS1R3     ----TGAGCGCAGGGCTAAATCACCACCAGACGTTCTCTGTCTACGCAGCTGTGTATAGC 1197
                                                           *     *     **

mouseTas1r1     GTGGCCCACGGCCTCCACCAGCTCCTGGGATGTACCTCTGGGACCTGTGCCA---GAGGC 1245
ratTas1r1       GTGGCCCACGGCCTCCACCAGCTCCTGGGATGTACTTCTGAGATCTGTTCCA---GAGGC 1239
catTas1r1       GTGGCCCATGGCCTCCACCAGCTCCTGGGCTGTGCCTCTGGAGCCTGTTCCA---GGGAC 1242
dogTas1r1       GCAGCCCATGGCCTCCACCAGCTCCTGGGCTGTGCCTCTGGAGCCTGTTCCA---GGGAC 1242
humanTAS1R1     GTGGCCCATGGCCTCCACCAGCTCCTGGGCTGTGCCTCTGGAGCTTGTTCCA---GGGGC 1242
mouseTas1r2     GTAGCCCACACCCTCCACAGACTCCTCCACTGCAACCAGGTCCGCTGCACCA---AGCAA 1251
ratTas1r2       GTGGCCCATGCCCTCCACAGACTCCTCGGCTGTAACCGGGTCCGCTGCACCA---AGCAA 1251
humanTAS1R2     GTGGCCCATGCCCTGCACAGCCTCCTCGGCTGTGACAAAAGCACCTGCACCA---AGAGG 1239
dogTas1r2       GTGGCCCATGCATTACACAGCCTTCTGGGCTGCACCCAGGCCTGCTCCA-A---GG-AG 1237
catTas1r2       ------------------------------------------------------------
mouseTas1r3     GTGGCTCAAGCCCTTCACAACACCCTACAGTGCAATGTCTCACATTGCCACGTATCAGAA 1278
ratTas1r3       GTGGCTCAGGCCCTTCACAACACCCTGCAGTGCAATGTCTCACATTGCCACACATCAGAG 1278
dogTas1r3       GTGGCCCAGGCCCTCCACAACACACTGCTCTGCAATGCCTCAGGCTGCCCCCCACGGGAG 1251
catTas1r3       GTGGCCCAAGCCCTTCACAACACACTGCGCTGCAATGCCTCGGGCTGCCCCAGGCGGGAG 1266
humanTAS1R3     GTGGCCCAGGCCCTGCACAACACTCTTCAGTGCAACGCCTCAGGCTGCCCCGCGCAGGAC 1257

mouseTas1r1     CCAGTCTACCCCTGGCAGCTTCTTCAGCAGATCTACAAGGTGAATTTCCTTCTACATAAG 1305
ratTas1r1       CCAGTCTACCCCTGGCAGCTTCTTCAGCAGATCTACAAGGTGAATTTTCTTCTACATGAG 1299
catTas1r1       CGAGTCTACCCCTGGCAGCTTCTGGAGCAGATCCGCAAGGTGAATTTCCTCCTACACAAG 1302
dogTas1r1       CGAGTCTACCCCTGGCAGCTTCTAGAGCAGATCCGCAAGGTGAATTTCCTTCTACACGAG 1302
humanTAS1R1     CGAGTCTACCCCTGGCAGCTTTTGGAGCAGATCCACAAGGTGCATTTCCTTCTACACAAG 1302
mouseTas1r2     ATCGTCTATCCATGGCAGCTACTCAGGGAGATCTGGCATGTCAACTTCACGCTCCTGGGC 1311
ratTas1r2       AAGGTCTACCCGTGGCAGCTACTCAGGGAGATCTGGCACGTCAACTTCACGCTCCTGGGT 1311
humanTAS1R2     GTGGTCTACCCCTGGCAGCTGCTTGAGGAGATCTGGAAGGTCAACTTCACTCTCCTGGAC 1299
dogTas1r2       GTGGTCTACCCCTGGCAGCTCCTTAAGGAAATCTGGAAGGTCAACTTCACCCTTCTGGGC 1297
catTas1r2       ------------------------------------------------------------
mouseTas1r3     CATGTTCTACCCTGGCAGCTCCTGGAGAACATGTACAATATGAGTTTCCATGCTCGAGAC 1338
ratTas1r3       CCTGTTCAACCCTGGCAGCTCCTGGAGAACATGTACAATATGAGTTTCCGTGCTCGAGAC 1338
dogTas1r3       CCAGTGCGGCCCTGGCAGCTCCTAGAAAACATGTACAACTTGACCTTCCGTGTGCGCGGC 1311
catTas1r3       CCTGTGCGGCCCTGGCAGCTCCTAGAGAACATGTACAACGTGAGCTTCCGTGCTCGCGGC 1326
humanTAS1R3     CCCGTGAAGCCCTGGCAGCTCCTGGAGAACATGTACAACCTGACCTTCCACGTGGGCGGG 1317

mouseTas1r1     AAGACTGTAGCATTCGATGACAAGGGGGACCCTCTAGGTTATTATGACATCATCGCCTGG 1365
ratTas1r1       AATACTGTGGCATTTGATGACAACGGGGACACTCTAGGTTACTACGACATCATCGCCTGG 1359
catTas1r1       GACACCGTGAGGTTTAATGACAACGGGGACCCTCTCAGTGGCTACGACATAATTGCCTGG 1362
dogTas1r1       GACACTGTGATATTTAATGACAACGGGGACCCTCTCAGTGGCTATGACATAATTGCCTGG 1362
humanTAS1R1     GACACTGTGGCGTTTAATGACAACAGAGATCCCCTCAGTAGCTATAACATAATTGCCTGG 1362
mouseTas1r2     AACCAGCTCTTCTTCGACGAACAAGGGGACATGCCGATGCTCCTGGACATCATCCAGTGG 1371
ratTas1r2       AACCGGCTCTTCTTTGACCAACAAGGGGACATGCCGATGCTCTTGGACATCATCCAGTGG 1371
humanTAS1R2     CACCAAATCTTCTTCGACCCGCAAGGGGACGTGGCTCTGCACTTGGAGATTGTCCAGTGG 1359
dogTas1r2       CACAATGTCTTTTTTGGGCAGCAAGGGGACGTGCTCATGCCCATGGAGGTCATCCAGTGG 1355
catTas1r2       ------------------------------------------------------------
mouseTas1r3     TTGACACTACAGTTTGATGCTGAAGGGAATGTAGACATGGAATATGACCTGAAGATGTGG 1398
ratTas1r3       TTGACACTGCAGTTTGATGCCAAAGGGAGTGTAGACATGGAATATGACCTGAAGATGTGG 1398
dogTas1r3       TTAGCACTGCAGTTCGATGCCAGGGGGAACGTGAATATGGATTATGACCTGAAACTGTGG 1371
catTas1r3       CTGGCACTGCAGTTCGACGCCAGCGGGAACGTGAACGTGGATTACGACCTGAAACTGTGG 1386
humanTAS1R3     CTGCCGCTGCGGTTCGACAGCAGCGGAAACGTGGACATGGAGTACGACCTGAAGCTGTGG 1377
```

FIG. 1G

```
mouseTas1r1    GACTGGAATGGACCTGAATGGACCTTTGAGGTCATTGGTTCTGCCTCACTGTCTCCAGTT 1425
ratTas1r1      GACTGGAATGGACCTGAATGGACCTTTGAGATCATTGGCTCTGCCTCACTGTCTCCAGTT 1419
catTas1r1      GACTGGAGTGGCCCCAAGTGGAACTTCAGGGTCATTGGCTCCTCCATGTGGCCTCCAGTT 1422
dogTas1r1      GACTGGAGTGGTCCCAAGTGGACCTTCAGGGTCATCGGCTCCTCCACGTGGCCTCCAGTT 1422
humanTAS1R1    GACTGGAATGGACCCAAGTGGACCTTCACGGTCCTCGGTTCCTCCACATGGTCTCCAGTT 1422
mouseTas1r2    CAATGGGGCCTGAGCCAGAACCCCTTCCAAAGCATCGCCTCCTACTCCCCCACCGAGACG 1431
ratTas1r2      CAGTGGGACCTGAGCCAGAATCCCTTCCAAAGCATCGCCTCCTATTCTCCCACCAGCAAG 1431
humanTAS1R2    CAATGGGACCGGAGCCAGAATCCCTTCCAGAGCGTCGCCTCCTACTACCCCCTGCAGCGA 1419
dogTas1r2      CAGTGGGACCTGAGCCAGAACCCTTTCCAGAGCATCGCCTCCTACTACCCCAAGCTGCGG 1415
catTas1r2      ------------------------------------------------------------
mouseTas1r3    GTGTGGCAGAGCCCTACACCTGTATTACATACTGTGGGCACCTTCAACGGCACCCTTCAG 1458
ratTas1r3      GTGTGGCAGAGCCCTACACCTGTACTACATACTGTAGGCACCTTCAACGGCACCCTTCAG 1458
dogTas1r3      GTGTGGCGGACCTGAAGCCCGAGTTGCGCACCGTAGGTGCCTTCAACGGCCGCCTGAAG 1431
catTas1r3      GTGTGGCAGGACCCGACGCCCGAGCTGCGCACCGTAGGCACCTTCAAGGGCCGCCTGGAG 1446
humanTAS1R3    GTGTGGCAGGGCTCAGTGCCCAGGCTCCACGACGTGGGCAGGTTCAACGGCAGCCTCAGG 1437

mouseTas1r1    CATCTAGACATAAATAAGACAAAAATCCAGTGGCACGGGAAGAACAATCAGGTGCCTGTG 1485
ratTas1r1      CATCTGGACATAAATAAGACAAAAATCCAGTGGCACGGGAAGAACAATCAGGTGCCTGTG 1479
catTas1r1      CAGCTGGACATAAATAAAACCAAAATCCGGTGGCACGGGAAGGACAACCAGGTGCCAAAG 1482
dogTas1r1      CAGCTGGACATAAATAAAACCAAAATCCGGTGGCACGGAGAGGACAACCAGGTGCCTGAG 1482
humanTAS1R1    CAGCTAAACATAAATGAGACCAAAATCCAGTGGCACGGAAAGGACAACCAGGTGCCTAAG 1482
mouseTas1r2    AGGCTGACCTACATTAG---CAATGTGTCCTGGTACACCCCCAACAACACGGTCCCCATA 1488
ratTas1r2      AGGCTAACCTACATTAA---CAATGTGTCCTGGTACACCCCCAACAACACGGTCCCTGTC 1488
humanTAS1R2    CAGCTGAAGAACATCCA---AGACATCTCCTGGCACACCGTCAACAACACGATCCCTATG 1476
dogTas1r2      CAGCTCAAGGCCATCCA---CAACATCTCCTGGCACACCGCCAACAACACGATCCCCGTG 1472
catTas1r2      ------------------------------------------------------------
mouseTas1r3    CTGCAGCAGTCTA---------AAATGTACTGGC------CAGGCAACCAGGTGCCAGTC 1503
ratTas1r3      CTGCAGCACTCGA---------AAATGTATTGGC------CAGGCAACCAGGTGCCAGTC 1503
dogTas1r3      GTCTGGCACTCCC---------AGATGTCCTGGCACACACCTGGGAACCAGCGGCCCGTG 1482
catTas1r3      CTCTGGCGCTCTC---------AGATGTGCTGGCACACGCCGGGGAAGCAGCAGCCCGTG 1497
humanTAS1R3    ACAGAGCGCCTGA---------AGATCCGCTGGCACACGTCTGACAACCAGAAGCCCGTG 1488

mouseTas1r1    TCAGTGTGTACCAGGGACTGTCTCGAAGGGCACCACAGGTTGGTCATGGGTTCCCACCAC 1545
ratTas1r1      TCAGTGTGTACCACGGACTGTCTGGCAGGGCACCACAGGGTGGTTGTGGGTTCCCACCAC 1539
catTas1r1      TCTGTGTGCTCCAGCGACTGCCTCGAAGGGCACCAGCGAGTGATTTCGGGTTTCTACCAC 1542
dogTas1r1      TCTGTGTGCTCCAGCAACTGTCTTGAAGGGCACCAGCGAGTAGTTGTGGGTTTCTACCAC 1542
humanTAS1R1    TCTGTGTGTTCCAGCGACTGTCTTGAAGGGCACCAGCGAGTGGTTACGGGTTTCCATCAC 1542
mouseTas1r2    TCCATGTGTTCTAAGAGTTGCCAGCCTGGGCAAATGAAAAAACCCATAGGCCTCCACCCG 1548
ratTas1r2      TCCATGTGTTCCAAGAGCTGCCAGCCAGGGCAAATGAAAAAGTCTGTGGGCCTCCACCCT 1548
humanTAS1R2    TCCATGTGTTCCAAGAGGTGCCAGTCAGGGCAAAAGAAGAAGCCTGTGGGCATCCACGTC 1536
dogTas1r2      TCCATGTGTTCCAAGGACTGCCATCCTGGCCAAAGGAAGAAGCCTGTGGGCATCCACTCC 1532
catTas1r2      ------------------------------------------------------------
mouseTas1r3    TCCCAGTGTTCCCGCCAGTGCAAAGATGGCCAGGTTCGCCGAGTAAAGGGCTTTCATTCC 1563
ratTas1r3      TCCCAGTGCTCCCGGCAGTGCAAAGATGGCCAGGTGCGCAGAGTAAAGGGCTTTCATTCC 1563
dogTas1r3      TCCCAGTGCTCCCGGCAGTGCGGGGAGGGCCAGGTGCGCCGTGTGAAGGGCTTCCACTCC 1542
catTas1r3      TCCCAGTGCTCCCGGCAGTGCAAGGAAGGCCAGGTGCGCCGCGTGAAGGGCTTCCACTCT 1557
humanTAS1R3    TCCCGGTGCTCGCGGCAGTGCCAGGAGGGCCAGGTGCGCCGGGTCAAGGGGTTCCACTCC 1548

mouseTas1r1    TGCTGCTTCGAGTGCATGCCCTGTGAAGCTGGGACATTTCTCAACACGAGTGAGCTTCA- 1604
ratTas1r1      TGCTGCTTTGAGTGTGTGCCCTGCGAAGCTGGGACCTTTCTCAACATGAGTGAGCTTCA- 1598
catTas1r1      TGTTGCTTTGAGTGTGTGCCCTGTGAGGCCGGGAGCTTCCTCAACAAGAGCGACCTCCA- 1601
dogTas1r1      TGTTGCTTTGAGTGTGTGCCCTGTGAGGCCGGCACCTTCCTCAACAAGAGTGACCTCCA- 1601
humanTAS1R1    TGCTGCTTTGAGTGTGTGCCCTGTGGGGCTGGGACCTTCCTCAACAAGAGTGACCTCTA- 1601
mouseTas1r2    TGCTGCTTCGAGTGTGTGGACTGTCCGCCGGGCACCTACCTCAACCGATCAGTAGATGAG 1608
ratTas1r2      TGTTGCTTCGAGTGCTTGGATTGTATGCCAGGCACCTACCTCAACCGCTCAGCAGATGAG 1608
humanTAS1R2    TGCTGCTTCGAGTGCATCGACTGCCTTCCCGGCACCTTCCTCAACCACACTGAAGATGAA 1596
dogTas1r2      TGCTGCTTCGAGTGTATTGACTGCCTTCCTGGCACCTTCCTCAACCGAACTGAAGACGAA 1592
catTas1r2      ------------------------------------------------------------
mouseTas1r3    TGCTGCTATGACTGCGTGGACTGCAAGGCGGGCAGCTACCGGAAGCATCCAGATGACTT- 1622
ratTas1r3      TGCTGCTATGACTGTGTGGACTGCAAGGCAGGGAGCTACCGGAAGCATCCAGATGACTT- 1622
dogTas1r3      TGCTGCTATGACTGCGTGGACTGCAAGGCGGGCACCTATCAGCGCAGCCCAGATGACCT- 1601
catTas1r3      TGCTGTTACAACTGCGTGGACTGCAAGGCGGGCAGTTATCAGCGCAACCCAGATGACCT- 1616
humanTAS1R3    TGCTGCTACGACTGTGTGGACTGCGAGGCGGGCAGCTACCGGCAAAACCCAGACGACAT- 1607
```

FIG. 1H

```
mouseTas1r1  --CACCTGCCAGCCTTGTGGAACAGAAGAATGGGCCCCTGAGGGGAGCTCAGCCTGCTTC 1662
ratTas1r1    --CATCTGCCAGCCTTGTGGAACAGAAGAATGGGCACCCAAGGAGAGCACTACTTGCTTC 1656
catTas1r1    --CAGCTGCCAGCCTTGTGGGAAAGAAAAGTGGGCACCCGCGGGAAGTGAAACCTGCTTT 1659
dogTas1r1    --CAGCTGCCAGCCTTGTGGGAAAGAAGAGTGGGCACCTGAGGGAAGTGAATCCTGCTTC 1659
humanTAS1R1  --CAGATGCCAGCCTTGTGGGAAAGAAGAGTGGGCACCTGAGGGAAGCCAGACCTGCTTC 1659
mouseTas1r2  TTTAACTGTCTGTCCTGCCCGGGTTCCATGTGGTCTTACAAGAACAACATCGCTTGCTTC 1668
ratTas1r2    TTTAACTGTCTGTCCTGCCCGGGTTCCATGTGGTCCTACAAGAACGACATCACTTGCTTC 1668
humanTAS1R2  TATGAATGCCAGGCCTGCCCGAATAACGAGTGGTCCTACCAGAGTGAGACCTCCTGCTTC 1656
dogTas1r2    TTTGACTGCCAGCCTTGCCCAAGTTACGAGTGGTCCCATAGGAACGACACCTCCTGCTTC 1652
catTas1r2    ------------------------------------------------------------
mouseTas1r3  --CACCTGTACTCCATGTAACCAGGACCAGTGGTCCCCAGAGAAAAGCACAGCCTGCTTA 1680
ratTas1r3    --CACCTGTACTCCATGTGGCAAGGATCAGTGGTCCCCAGAAAAAAGCACAACCTGCTTA 1680
dogTas1r3    --CCTCTGCACCCAGTGTGACCAGAACCAGTGGTCCCCAGACCGGAGCACACGCTGCTTC 1659
catTas1r3    --CCTCTGCACCCAGTGTGACCAGGACCAGTGGTCCCCAGACCGGAGCACACGCTGCTTC 1674
humanTAS1R3  --CGCCTGCACCTTTTGTGGCCAGGATGAGTGGTCCCCGGAGCGAAGCACACGCTGCTTC 1665

mouseTas1r1  TCACGCACCGTGGAGTTCTTGGGGTGGCATGAACCCATCTCTTTGGTGCTATTAGCAGCT 1722
ratTas1r1    CCACGCACGGTGGAGTTCTTGGCTTGGCATGAACCCATCTCTTTGGTGCTAATAGCAGCT 1716
catTas1r1    CCACGCACCGTGGTGTTTTTGACTTGGCACGAGACCATCTCTTGGGTGCTGCTGGCAGCT 1719
dogTas1r1    CTACGCACTGTGGTGTTTTTGACTTGGCATGAGCCTATCTCTTGGGTGCTGCTGGCAGCT 1719
humanTAS1R1  CCGCGCACTGTGGTGTTTTTGGCTTTGCGTGAGCACACCTCTTGGGTGCTGCTGGCAGCT 1719
mouseTas1r2  AAGCGGCGGCTGGCCTTCCTGGAGTGGCACGAAGTGCCCACTATCGTGGTGACCATCCTG 1728
ratTas1r2    CAGCGGCGGCCTACCTTCCTGGAGTGGCACGAAGTGCCCACCATCGTGGTGGCCATACTG 1728
humanTAS1R2  AAGCGGCAGCTGGTCTTCCTGGAATGGCATGAGGCACCCACCATCGCTGTGGCCCTGCTG 1716
dogTas1r2    AAGCGGCGGCTGGCCTTCCTCGAATGGCACGAGCCCTCCACCATCTTTGTGGTTATGCTG 1712
catTas1r2    ------------------------------------------------------------
mouseTas1r3  CCTCGCAGGCCCAAGTTTCTGGCTTGGGGGGAGCCAGTTGTGCTGTCACTCCTCCTGCTG 1740
ratTas1r3    CCTCGCAGGCCCAAGTTTCTGGCTTGGGGGGAGCCAGCTGTGCTGTCACTTCTCCTGCTG 1740
dogTas1r3    CCCCGCAGGCTCACTTTCCTGGCATGGGGGCAGCCGGCTGTGCTGGTGCTGCTTATACTG 1719
catTas1r3    GCCCGCAAGCCCATGTTCCTGGCATGGGGGGAGCCAGCTGTGCTGCTACTGCTCGCGCTG 1734
humanTAS1R3  CGCCGCAGGTCTCGGTTCCTGGCATGGGGCGAGCCGGCTGTGCTGCTGCTGCTCCTGCTG 1725

mouseTas1r1  AACACGCTATTGCTGCTGCTGCTGATTGGGACTGCTGGCCTGTTTGCCTGGCGTCTTCAC 1782
ratTas1r1    AACACGCTATTGCTGCTGCTGCTGGTTGGGACTGCTGGCCTGTTTGCCTGGCATTTTCAC 1776
catTas1r1    AATACGTTGCTGCTGCTGCTGGTGACTGGGACTGCTGGCCTGTTTGCCTGGCACTTAGAC 1779
dogTas1r1    AATACGCTGCTGTTGCTGCTGGTGGCTGGGACTGCTGGCCTGTTTGCCTGGCACTTAGAC 1779
humanTAS1R1  AACACGCTGCTGCTGCTGCTGCTGCTTGGGACTGCTGGCCTGTTTGCCTGGCACCTAGAC 1779
mouseTas1r2  GCCGCCCTGGGCTTCATCAGTACGCTGGCCATTCTGCTCATCTTCTGGAGACATTTCCAG 1788
ratTas1r2    GCTGCCCTGGGCTTCTTCAGTACACTGGCCATTCTTTTCATCTTCTGGAGACATTTCCAG 1788
humanTAS1R2  GCCGCCCTGGGCTTCCTCAGCACCCTGGCCATCCTGGTGATATTCTGGAGGCACTTCCAG 1776
dogTas1r2    ACCATCCTGGGCTTCCTCAGCACCCTGGCCATCATGGTGATCTTCTGGAGGCACCTCCAC 1772
catTas1r2    ------------------------------------------------------------
mouseTas1r3  CTTTGCCTGGTGCTGGGTCTAGCACTGGCTGCTCTGGGGCTCTCTGTCCACCACTGGGAC 1800
ratTas1r3    CTTTGCCTGGTGCTGGGCCTGACACTGGCTGCCCTGGGGCTCTTTGTCCACTACTGGGAC 1800
dogTas1r3    CTGGCTCTGGCGCTGGGCCTGGTGCTGGTGGCCCTGGGGCTCTTTATTAGGCACCGGGAC 1779
catTas1r3    CTGGCTCTGGCGCTGGGCCTGGCGCTGGCAGCCCTGGGGCTCTTCCTCTGGCACTCGGAC 1794
humanTAS1R3  CTGAGCCTGGCGCTGGGCCTTGTGCTGGCTGCTTTGGGGCTGTTCGTTCACCATCGGGAC 1785

mouseTas1r1  ACGCCTGTTGTGAGGTCAGCTGGGGGTAGGCTGTGCTTCCTCATGCTGGGTTCCTTGGTA 1842
ratTas1r1    ACACCTGTAGTGAGGTCAGCTGGGGGTAGGCTGTGCTTCCTCATGCTGGGTTCCCTGGTG 1836
catTas1r1    ACCCCTGTGGTGAAGTCCGCTGGGGGGCCGACTGTGCTTCTTCATGCTAGGCTCCCTGGCA 1839
dogTas1r1    ACCCCGGTGGTGAGGTCAGCTGGGGGCAGGCTGTGCTTCTTTATGCTGGGCTCCCTGGCA 1839
humanTAS1R1  ACCCCTGTGGTGAGGTCAGCAGGGGGCCGCCTGTGCTTTCTTATGCTGGGCTCCCTGGCA 1839
mouseTas1r2  ACGCCCATGGTGCGCTCGCGGGCGGCCCCCATGTGCTTCCTGATCGTGGTGCCCCTGCTG 1848
ratTas1r2    ACACCCATGGTGCGCTCGCGGCGGTGGCCCCATGTGCTTCCTGATGCTCGTGCCCCTGCTG 1848
humanTAS1R2  ACACCCATAGTTCGCTCGGCTGGGGGCCCCATGTGCTTCCTGATGCTGACACTGCTGCTG 1836
dogTas1r2    ACGCCCGTGGTTCGCTCGGCCGGGGGCCCCATGTGCTTCCTGATGCTGGTGCCGCTGCTG 1832
catTas1r2    ------------------------------------------------------------
mouseTas1r3  AGCCCTCTTGTCCAGGCCTCAGGTGGCTCACAGTTCTGCTTTGGCCTGATCTGCCTAGGC 1860
ratTas1r3    AGCCCTCTTGTTCAGGCCTCAGGTGGGTCACTGTTCTGCTTTGGCCTGATCTGCCTAGGC 1860
dogTas1r3    AGCCCACTGGTTCAGGCCTCAGGGGGGCCACGGGCCTGCTTTGGCTTGGCCTGCCTGGGC 1839
catTas1r3    AGCCCGCTGGTTCAGGCCTCAGGTGGGCCACGGGCCTGCTTTGGCCTGGCTTGCCTGGGC 1854
humanTAS1R3  AGCCCACTGGTTCAGGCCTCGGGGGGGCCCCTGGCCTGCTTTGGCCTGGTGTGCCTGGGC 1845
```

FIG. 1I

```
mouseTas1r1    GCTGGGAGTTGCAGCCTCTACAGCTTCTTCGGGAAGCCCACGGTGCCCGCGTGCTTGCTG 1902
ratTas1r1      GCCGGAAGTTGCAGCTTCTATAGCTTCTTCGGGGAGCCCACGGTGCCCGCGTGCTTGCTG 1896
catTas1r1      GGGGGCAGCTGTGGGCTCTACGGCTTTTTTGGGGAGCCCACGCTGCCCACATGCTTGTTG 1899
dogTas1r1      GGGGGCAGCTGTGGGCTCTATGGCTTTTTTGGGGAGCCCACCCTGGCCACATGCTTGTTG 1899
humanTAS1R1    GCAGGTAGTGGCAGCCTCTATGGCTTCTTTGGGGAACCCACAAGGCCTGCGTGCTTGCTA 1899
mouseTas1r2    CTGGCGTTCGGGATGGTCCCCGTGTATGTGGGCCCCCCCACGGTCTTCTCCTGTTTCTGC 1908
ratTas1r2      CTGGCGTTTGGGATGGTGCCCGTGTATGTGGGGCCCCCCACGGTCTTCTCATGCTTCTGC 1908
humanTAS1R2    GTGGCATACATGGTGGTCCCGGTGTACGTGGGGCCGCCCAAGGTCTCCACCTGCCTCTGC 1896
dogTas1r2      CTGGCGTACGCCATGGTCCCCATGTACATAGGGCAGCCCACGTTCTTCTCGTGCCTCTGG 1892
catTas1r2      ------------------------------------------------------------
mouseTas1r3    CTCTTCTGCCTCAGTGTCCTTCTGTTCCCAGGGCGGCCAAGCTCTGCCAGCTGCCTTGCA 1920
ratTas1r3      CTCTTCTGCCTCAGTGTCCTTCTGTTCCCAGGACGACCACGCTCTGCCAGCTGCCTTGCC 1920
dogTas1r3      CTTGTCTGCCTCAGTGTCCTTCTGTTCCCTGGCCAGCCGGGCCCTGCCAGCTGCCTGGCC 1899
catTas1r3      CTGGTCTGCCTCAGTGTCCTCCTGTTCCCTGGCCAGCCAGGCCCTGCCAGCTGCCTGGCC 1914
humanTAS1R3    CTGGTCTGCCTCAGCGTCCTCCTGTTCCCTGGCCAGCCCAGCCCTGCCCGATGCCTGGCC 1905

mouseTas1r1    CGTCAGCCCCTCTTTTCTCTCGGGTTTGCCATTTTCCTCTCCTGTCTGACAATCCGCTCC 1962
ratTas1r1      CGTCAGCCCCTCTTTTCTCTCGGGTTTGCCATCTTCCTCTCCTGCCTGACAATCCGCTCC 1956
catTas1r1      CGCCAAAGCCTCCTTGCCCTGGGTTTTGCCATCTTCCTGTCCTGCCTGACCATCCGCTCC 1959
dogTas1r1      CGCCAAGGCCTCTTTGCCCTCGGCTTTGCCATCTTCCTGTCCTGCCTGACAATCCGCTCC 1959
humanTAS1R1    CGCCAGGCCCTCTTTGCCCTTGGTTTCACCATCTTCCTGTCCTGCCTGACAGTTCGCTCA 1959
mouseTas1r2    CGCCAGGCTTTCTTCACCGTTTGCTTCTCCGTCTGCCTCTCCTGCATCACGGTGCGCTCC 1968
ratTas1r2      CGACAGGCTTTCTTCACCGTCTGCTTCTCCATCTGCCTATCCTGCATCACCGTGCGCTCC 1968
humanTAS1R2    CGCCAGGCCCTCTTTCCCCTCTGCTTCACAATTTGCATCTCCTGTATCGCCGTGCGTTCT 1956
dogTas1r2      CGCCAGACCTTCTTCACCCTCTGCTTCACCATCTGCATCTCCTGCATCACCGTGCGCTCT 1952
catTas1r2      ------------------------------------------------------------
mouseTas1r3    CAACAACCAATGGCTCACCTCCCTCTCACAGGCTGCCTGAGCACACTCTTCCTGCAAGCA 1980
ratTas1r3      CAACAACCAATGGCTCACCTCCCTCTCACAGGCTGCCTGAGCACACTCTTCCTGCAAGCA 1980
dogTas1r3      CAGCAGCCACTGCTTCACCTTCCACTCACTGGCTGTCTGAGCACACTTTTCCTGCAAGCG 1959
catTas1r3      CAGCAGCCACTGTTCCACCTCCCACTCACTGGCTGCCTGAGCACGTTTTTCCTGCAAGCG 1974
humanTAS1R3    CAGCAGCCCTTGTCCCACCTCCCGCTCACGGGCTGCCTGAGCACACTCTTCCTGCAGGCG 1965

mouseTas1r1    TTCCAACTGGTCATCATCTTCAAGTTTTCTACCAAGGTACCCACATTCTACCACACTTGG 2022
ratTas1r1      TTCCAACTGGTCATCATCTTCAAGTTTTCTACCAAGGTGCCCACATTCTACCGTACCTGG 2016
catTas1r1      TTCCAACTGGTCTTCATCTTCAAGTTTTCTGCCAAGGTACCCACCTTCTACCGTGCCTGG 2019
dogTas1r1      TTCCAACTGGTCTTCATCTTCAAGTTTTCCGCCAAGGTACCCACCTTCTACCAGGCCTGG 2019
humanTAS1R1    TTCCAACTAATCATCATCTTCAAGTTTTCCACCAAGGTACCTACATTCTACCACGCCTGG 2019
mouseTas1r2    TTCCAGATTGTGTGCGTCTTCAAGATGGCCAGACGCCTGCCAAGCGCCTACGGTTTCTGG 2028
ratTas1r2      TTCCAGATCGTGTGTGTCTTCAAGATGGCCAGACGCCTGCCAAGTGCCTACAGTTTTTGG 2028
humanTAS1R2    TTCCAGATCGTCTGCGCCTTCAAGATGGCCAGCCGCTTCCCACGCGCCTACAGCTACTGG 2016
dogTas1r2      TTCCAGATCGTCTGCATCTTCAAGATGGCCAGGCGCCTCCCGCGCGCCTACGGCTACTGG 2012
catTas1r2      ------------------------------------------------------------
mouseTas1r3    GCTGAGACCTTTGTGGAGTCTGAGCTGCCACTGAGCTGGGCAAACTGGCTATGCAGCTAC 2040
ratTas1r3      GCCGAGATCTTTGTGGAGTCTGAGCTGCCACTGAGTTGGGCAAACTGGCTCTGCAGCTAC 2040
dogTas1r3      GCCCAGATATTTGTGGGTTCAGAGCTGCCATCAAGCTGGGCAGATCAGCTGCGTAGGTGC 2019
catTas1r3      GCCGAGATATTTGTGGGGTCGGAGCTGCCACCAAGCTGGGCTGAGAAGATGCGTGGCCGC 2034
humanTAS1R3    GCCGAGATCTTCGTGGAGTCAGAACTGCCTCTGAGCTGGGCAGACCGGCTGAGTGGCTGC 2025

mouseTas1r1    GCCCAAAACCATGGTGCCGGAATATTCGTCATTGTCAGCTCCACGGTCCATTTGTTCCTC 2082
ratTas1r1      GCCCAAAACCATGGTGCAGGTCTATTCGTCATTGTCAGCTCCACGGTCCATTTGCTCATC 2076
catTas1r1      GTCCAAAACCACGGTCCTGGCCTATTTGTGGTGATCAGCTCAATGGCCCAGCTGCTCATC 2079
dogTas1r1      GTCCAAAACCATGGTCCCCGCCTCTTTGTGGTGATCAGCTCCATGGCCCAGCTGCTCATC 2079
humanTAS1R1    GTCCAAAACCACGGTGCTGGCCTGTTTGTGATGATCAGCTCAGCGGCCCAGCTGCTTATC 2079
mouseTas1r2    ATGCGTTACCACGGGCCCTACGTCTTTGTGGCCTTCATCACGGCCGTCAAGGTGGCCCTG 2088
ratTas1r2      ATGCGTTACCACGGGCCCTATGTCTTCGTGGCCTTCATCACGGCCATCAAGGTGGCCCTG 2088
humanTAS1R2    GTCCGCTACCAGGGGCCCTACGTCTCTATGGCATTTATCACGGTACTCAAAATGGTCATT 2076
dogTas1r2      GTGCGCTGCCACGGGCCCTACGTCTTCGTGGCGTCCTTCATGGTGCTCAAGGTGGTCATC 2072
catTas1r2      ------------------------------------------------------------
mouseTas1r3    CTTCGGGGACTCTGGGCCTGGCTAGTGGTACTGTTGGCCACTTTTGTGGAGGCAGCACTA 2100
ratTas1r3      CTTCGGGGCCCCTGGGCTTGGCTGGTGGTACTGCTGGCCACTCTTGTGGAGGCTGCACTA 2100
dogTas1r3      CTGCAGGGGCCCTGGGCCTGGTTGCTGGTGCTGCTTGCTTTGCTGGCGGAAGCGGCATTA 2079
catTas1r3      CTGCGGGGGCCCTGGGCCTGGCTGGTGGTGCTGCTTGCTATGCTGGCAGAAGCCGCATTG 2094
humanTAS1R3    CTGCGGGGGCCCTGGGCCTGGCTGGTGGTGCTGCTGGCCATGCTGGTGGAGGTCGCACTG 2085
```

FIG. 1J

```
mouseTas1r1     TGTCTCACGTGGCTTGCAATGTGGACCCCACGGCCCACCA---GGGAGTACCAGCGCTTC 2139
ratTas1r1       TGTCTCACATGGCTTGTAATGTGGACCCCACGACCCACCA---GGGAATACCAGCGCTTC 2133
catTas1r1       TGTCTAACTTGGCTGGCGGTGTGGACCCCACTGCCCACCA---GGGAGTACCAGCGCTTC 2136
dogTas1r1       TGTGTAACTTGGCTTGCGGTGTGGACCCCGTTGCCCACCA---GGGAGTACCAGCGCTTC 2136
humanTAS1R1     TGTCTAACTTGGCTGGTGGTGTGGACCCCACTGCCTGCTA---GGGAATACCAGCGCTTC 2136
mouseTas1r2     GTGGCAGGCAACATGCTGGCCACCACCATCAACCCCATTGGCCGGACCGACCCCGATGAC 2148
ratTas1r2       GTGGTGGGCAACATGCTGGCCACCACCATCAACCCCATTGGCCGGACCGACCCGGATGAC 2148
humanTAS1R2     GTGGTAATTGGCATGCTGGCCACGGGCCTCAGTCCCACCACCCGTACTGACCCCGATGAC 2136
dogTas1r2       GTGGCAGGCAACGTGCTGGCCACGACCGCCAACCCTACTGCCCGCCCCGACCCCGATGAC 2132
catTas1r2       ------------------------------------------------------------
mouseTas1r3     TGTGCCTGGTATTTGATCGCTTTCCCACCAGAGGTGGTGA-CAGACTGGTCAGTGCTGC 2158
ratTas1r3       TGTGCCTGGTACTTGATGGCTTTCCCTCCAGAGGTGGTGA-CAGATTGGCAGGTGCTGC 2158
dogTas1r3       TGTGCCTGGTACCTGGTGGCCTTTCCACCAGAGGTGGTGA-CAGACTGGTGGGTGCTAC 2137
catTas1r3       TGTGCCTGGTACCTGGTAGCCTTCCCGCCAGAGGTGGTGA-CGGACTGGCGGGTACTGC 2152
humanTAS1R3     TGCACCTGGTACCTGGTGGCCTTCCCGCCGGAGGTGGTGA-CGGACTGGCACATGCTGC 2143

mouseTas1r1     CCCCATCTGGTGATTCTTGAGTGCACAGAGGTCAACTCTGTGGGCTTCCTGGTGGCTTTC 2199
ratTas1r1       CCCCATCTGGTGATTCTCGAGTGCACAGAGGTCAACTCTGTAGGCTTCCTGTTGGCTTTC 2193
catTas1r1       CCTCAGCTGGTGGTGCTTGATTGCACAGAGGCCAACTCACCGGGCTTCATGTTGGCTTTC 2196
dogTas1r1       CCTCAGCTGGTGGTGCTTGACTGCACGGAGGCCAACTCCCCGGGCTTCATGGTGGCCTTT 2196
humanTAS1R1     CCCCATCTGGTGATGCTTGAGTGCACAGAGACCAACTCCCTGGGCTTCATACTGGCCTTC 2196
mouseTas1r2     CCCAATATCATAATCCTCTCCTGCCACCCTAACTACCGCAACGGGCTACTCTTCAACACC 2208
ratTas1r2       CCCAACATCATGATCCTCTCGTGCCACCCTAACTACCGCAACGGGCTACTGTTCAACACC 2208
humanTAS1R2     CCCAAGATCACAATTGTCTCCTGTAACCCCAACTACCGCAACAGCCTGCTGTTCAACACC 2196
dogTas1r2       CCCAATATCATGGTCCTGTCCTGC------AACTACCGCAGGGCGCTGCTGTTCAACACC 2186
catTas1r2       ------------------------------------------------------------
mouseTas1r3     CCACAGA-GGTACTGGAGCACTGCCACGTGCGTTCCTGGGTCAGCCTGGGCTTGGTGCAC 2217
ratTas1r3       CCACGGA-GGTACTGGAACACTGCCGCATGCGTTCCTGGGTCAGCCTGGGCTTGGTGCAC 2217
dogTas1r3       CCACGCA-AGTGCTGGTGCACTGCCGAATGCGCTCCTGGATCAGCTTTGGCCTAGTGCAT 2195
catTas1r3       CCACAGA-GGCGCTGGTGCACTGCCACGTGCACTCCTGGATCAGCTTCGGCCTGGTGCAT 2211
humanTAS1R3     CCACGGA-GGCGCTGGTGCACTGCCGCACACGCTCCTGGGTCAGCTTCGGCCTAGCGCAC 2202

mouseTas1r1     GCACACAACATCCTCCTCTCCATCAGCACCTTTGTCTGCAGCTACCTGGGTAAGGAACTG 2259
ratTas1r1       ACCCACAACATTCTCCTCTCCATCAGTACCTTCGTCTGCAGCTACCTGGGTAAGGAACTG 2253
catTas1r1       GCCTACAATGGCCTCCTGTCCGTCAGCGCCTTTGCCTGCAGCTACCTGGGCAAGGACCTG 2256
dogTas1r1       GCCTACAATGGCCTGCTGTCCGTCAGCGCCTTTGCCTGCAGCTACCTGGGTAAGGACCTG 2256
humanTAS1R1     CTCTACAATGGCCTCCTCTCCATCAGTGCCTTTGCCTGCAGCTACCTGGGTAAGGACTTG 2256
mouseTas1r2     AGCATGGACTTGCTGCTGTCCGTGCTGGGTTTCAGCTTCGCGTACGTGGGCAAGGAACTG 2268
ratTas1r2       AGCATGGACTTGCTGCTGTCTGTGCTGGGTTTCAGCTTCGCTTACATGGGCAAGGAGCTG 2268
humanTAS1R2     AGCCTGGACCTGCTGCTCTCAGTGGTGGGTTTCAGCTTCGCCTACATGGGCAAAGAGCTG 2256
dogTas1r2       AGCCTGGACCTGCTCCTGTCCGTGGCGGGCTTCAGCTTCGCCTACATGGGCAAGGAGCTG 2246
catTas1r2       ------------------------------------------------------------
mouseTas1r3     ATCACCAATGCAATGTTAGCTTTCCTCTGCTTTCTGGGCACTTTCCTGGTACAGAGCCAG 2277
ratTas1r3       ATCACCAATGCAGTGTTAGCTTTCCTCTGCTTTCTGGGCACTTTCCTGGTACAGAGCCAG 2277
dogTas1r3       GCCATCAATGCCATGCTGGCCTTCCTCTGCTTCCTGGGCACGTTCTTGGTGCAGAGCCGG 2255
catTas1r3       GCCACTAACGCCATGCTGGCCTTCCTCTGCTTCCTGGGCACTTTCCTGGTGCAGAGCCGG 2271
humanTAS1R3     GCCACCAATGCCACGCTGGCCTTTCTCTGCTTCCTGGGCACTTTCCTGGTGCGGAGCCAG 2262

mouseTas1r1     CCGGAGAACTATAACGAAGCCAAATGTGTCACCTTCAGCCTGCTCCTCCACTTCGTATCC 2319
ratTas1r1       CCAGAGAACTATAATGAAGCCAAATGTGTCACCTTCAGCCTGCTCCTCAACTTCGTATCC 2313
catTas1r1       CCAGAGAACTACAACGAGGCCAAATGTGTCACTTTTAGTCTGCTGCTCAACTTCGTGTCC 2316
dogTas1r1       CCGGAGAACTACAACGAGGCCAAATGCGTCACCTTCAGTCTGCTCCTCAACTTCGTGTCC 2316
humanTAS1R1     CCAGAGAACTACAACGAGGCCAAATGTGTCACCTTCAGCCTGCTCTTCAACTTCGTGTCC 2316
mouseTas1r2     CCCACCAACTACAACGAAGCCAAGTTCATCACCCTCAGCATGACCTTCTCCTTCACCTCC 2328
ratTas1r2       CCCACCAACTACAACGAAGCCAAGTTCATCACTCTCAGCATGACCTTCTCCTTCACCTCC 2328
humanTAS1R2     CCCACCAACTACAACGAGGCCAAGTTCATCACCCTCAGCATGACCTTCTATTTCACCTCA 2316
dogTas1r2       CCCACCAACTACAACGAGGCCAAGTTCATCACCCTCTGCATGACCTTCTACTTCACCTCC 2306
catTas1r2       ------------------------------------------------------------
mouseTas1r3     CCTGGCCGCTACAACCGTGCCCGTGGTCTCACCTTCGCCATGCTAGCTTATTTCATCACC 2337
ratTas1r3       CCTGGTCGCTATAACCGTGCCCGTGGCCTCACCTTCGCCATGCTAGCTTATTTCATCATC 2337
dogTas1r3       CCAGGCCGCTACAATGGCGCCCGGGGTCTCACTTTTGCCATGCTGGCCTACTTCATCACC 2315
catTas1r3       CCAGGCCGCTACAATGGTGCCCGCGGCCTCACCTTTGCCATGCTGGCCTACTTCATCACC 2331
humanTAS1R3     CCGGGCCGCTACAACCGTGCCCGTGGCCTCACCTTTGCCATGCTGGCCTACTTCATCACC 2322
```

FIG. 1K

```
mouseTas1r1   TGGATCGCTTTCTTCACCATGTCCAGCATTTACCAGGGCAGCTACCTACCCGCGGTCAAT 2379
ratTas1r1     TGGATCGCCTTCTTCACCATGGCCAGCATTTACCAGGGCAGCTACCTGCCTGCGGTCAAT 2373
catTas1r1     TGGATTGCCTTCTTCACCACGGCCAGCGTCTACCAGGGCAAGTACTTGCCCGCGGTCAAC 2376
dogTas1r1     TGGATTGGCTTTTTCACCACAGCCAGCGTCTACCAGGGCAAATACCTGCCCGCGGTCAAC 2376
humanTAS1R1   TGGATCGCCTTCTTCACCACGGCCAGCGTCTACGACGGCAAGTACCTGCCTGCGGCCAAC 2376
mouseTas1r2   TCCATCTCCCTCTGCACGTTCATGTCTGTCCACGATGGCGTGCTGGTCACCATCATGGAT 2388
ratTas1r2     TCCATCTCCCTCTGCACCTTCATGTCTGTGCACGACGGCGTGCTGGTCACCATCATGGAC 2388
humanTAS1R2   TCCGTCTCCCTCTGCACCTTCATGTCTGCCTACAGCGGGGTGCTGGTCACCATCGTGGAC 2376
dogTas1r2     TCCGTCTCCCTCTGCACCTTCATGTCCGTCTATGATGGGGTCCTGGTCACCATCCTGGAC 2366
catTas1r2     ------------------------------------------------------------
mouseTas1r3   TGGGTCTCTTTTGTGCCCCTCCTGGCCAATGTGCAGGTGGCCTACCAGCCAGCTGTGCAG 2397
ratTas1r3     TGGGTCTCTTTTGTGCCCCTCCTGGCTAATGTGCAGGTGGCCTACCAGCCAGCTGTGCAG 2397
dogTas1r3     TGGATCTCCTTTGTCCCTCTCTTTGCCAATGTGCATGTGGCCTACCAGCCCACTGTGCAG 2375
catTas1r3     TGGATCTCCTTTGTGCCCCTCTTTGCCAATGTGCACGTGGCCTACCAGCCTGCCGTGCAG 2391
humanTAS1R3   TGGGTCTCCTTTGTGCCCCTCCTGGCCAATGTGCAGGTGGTCCTCAGGCCCGCCGTGCAG 2382

mouseTas1r1   GTGCTGGCAGGGCTGGCCACTCTGAGTGGCGGCTTCAGCGGCTATTTCCTCCCTAAATGC 2439
ratTas1r1     GTGCTGGCAGGGCTGACCACACTGAGCGGCGGCTTCAGCGGTTACTTCCTCCCCAAGTGC 2433
catTas1r1     GTGCTGGCGGCGCTGAGCAGCCTGAGTGGCGGCTTCAGCGGTTATTTCCTCCCCAAGTGC 2436
dogTas1r1     GTGCTGGCGGCGCTGAGCAGCCTGAGCAGCGGCTTCAGCGGTTACTTCCTCCCCAAGTGC 2436
humanTAS1R1   ATGATGGCTGGGCTGAGCAGCCTGAGCAGCGGCTTCGGTGGGTATTTTCTGCCTAAGTGC 2436
mouseTas1r2   CTCCTGGTCACTGTGCTCAACTTTCTGGCCATCGGCTTGGGGTACTTTGGCCCCAAGTGT 2448
ratTas1r2     CTCCTGGTCACTGTGCTCAACTTCCTGGCCATCGGCTTGGGATACTTTGGCCCCAAGTGT 2448
humanTAS1R2   CTCTTGGTCACTGTGCTCAACCTCCTGGCCATCAGCCTGGGCTACTTCGGCCCCAAGTGC 2436
dogTas1r2     CTCTTGATCACCGTGCTCAACCTTCTGGGCATCAGCTTTGGCTACTTTGGTCCCAAATGC 2426
catTas1r2     ------------------------------------------------------------
mouseTas1r3   ATGGGTGCTATCCTAGTCTGTGCCCTGGGCATCCTGGTCACCTTCCACCTGCCCAAGTGC 2457
ratTas1r3     ATGGGTGCTATCTTATTCTGTGCCCTGGGCATCCTGGCCACCTTCCACCTGCCCAAATGC 2457
dogTas1r3     ATGGCCGCCATCCTCCTCTGTGCCCTGGGCATCCTGGCCACCTTCCACCTGCCCAAGTGC 2435
catTas1r3     ATGGGCACCATCCTCCTCTGTGCCCTGGGTATCCTAGCCACCTTCCACCTGCCCAAGTGC 2451
humanTAS1R3   ATGGGCGCCCTCCTGCTCTGTGTCCTGGGCATCCTGGCTGCCTTCCACCTGCCCAGGTGT 2442

mouseTas1r1   TACGTGATTCTCTGCCGTCCAGAACTCAACAACACAGAACACTTTCAGGCCTCCATCCAG 2499
ratTas1r1     TATGTGATTCTCTGCCGTCCAGAACTCAACAATACAGAACACTTTCAGGCCTCCATCCAG 2493
catTas1r1     TACGTGATCCTGTGCCGCCCAAAATTTAACAGCACACAGCACTTCCAGGCCTCCATCCAG 2496
dogTas1r1     TATGTGATCCTGTGCCGCCCAGATCTCAACAGCACCGAGCACTTCCAGGCCTCCATCCAG 2496
humanTAS1R1   TACGTGATCCTCTGCCGCCCAGACCTCAACAGCACAGAGCACTTCCAGGCCTCCATTCAG 2496
mouseTas1r2   TACATGATCCTTTTCTACCCGGAGCGCAACACTTCAGCTTATTTCAATAGCATGATTCAG 2508
ratTas1r2     TACATGATCCTTTTCTACCCGGAGCGCAACACCTCAGCCTATTTCAATAGCATGATCCAG 2508
humanTAS1R2   TACATGATCCTCTTCTACCCGGAGCGCAACACGCCCGCCTACTTCAACAGCATGATCCAG 2496
dogTas1r2     TACATGGTCCTCTTCTACCCAGAGCGCAACACGCAGGTCTACTTCAGCAGCATGATTCAG 2486
catTas1r2     ------------------------------------------------------------
mouseTas1r3   TATGTGCTTCTTTGGCTGCCAAAGCTCAACACCCAGGAGTTCTTCCTGGGAAGGAATGCC 2517
ratTas1r3     TATGTACTTCTGTGGCTGCCAGAGCTCAACACCCAGGAGTTCTTCCTGGGAAGGAGCCCC 2517
dogTas1r3     TACCTGCTGCTGCAGCAGCTGGAGCTCAACAACCCGGAGTTCTTCCTAGGAGATGATGCC 2495
catTas1r3     TACCTGCTGCTGCAGCGGCCGGAGCTCAACACCCCTGAGTTCTTCCTGGAAGACAATGCC 2511
humanTAS1R3   TACCTGCTCATGCGGCAGCCAGGGCTCAACACCCCCGAGTTCTTCCTGGGAGGGGGCCCT 2502

mouseTas1r1   GACTACACGAGGCGCTGCGGCACTACCTGA------------------------------ 2529
ratTas1r1     GACTACACGAGGCGCTGCGGCACTACC--------------------------------- 2520
catTas1r1     GAGTACACGAGGCGCTGCGGCTCCACCTGA------------------------------ 2526
dogTas1r1     GACTACACGAGGCGCTGCGGCTCCACCTGA------------------------------ 2526
humanTAS1R1   GACTACACGAGGCGCTGCGGCTCCACCTGA------------------------------ 2526
mouseTas1r2   GGCTACACGATGAGGAAGAGCTAG------------------------------------ 2532
ratTas1r2     GGCTACACCATGAGGAAGAGC--------------------------------------- 2529
humanTAS1R2   GGCTACACCATGAGGAGGGACTAG------------------------------------ 2520
dogTas1r2     GGCTACACCATGGGGAAGGACTAG------------------------------------ 2510
catTas1r2     ------------------------------------------------------------
mouseTas1r3   AAGAAAGCAGCAGATGAGAAC-AGTGGCGGTGGTGAGGCAGCTCAGGGACACAATGAATG 2576
ratTas1r3     AAGGAAGCATCAGATGGGAAT-AGTGGTAGTAGTGAGGCAACTCGGGGACACAGTGAATG 2576
dogTas1r3     A---GAGGACAGGGCAGCAGT-GGTAGTGGGGGAAGGAGACTTAGGGCAAAAACAAGTG 2551
catTas1r3     A---GAGCACAGGGCAGCAGTTGGGGGCAGGGGAGGGGAGAATCGGGGCAAAAACAAGTG 2568
humanTAS1R3   GGGGATGCCCAAGGCCAGAAT----GACGGGAACACAGGAAATCAGGGGAAACATGAGTG 2558
```

FIG. 1L

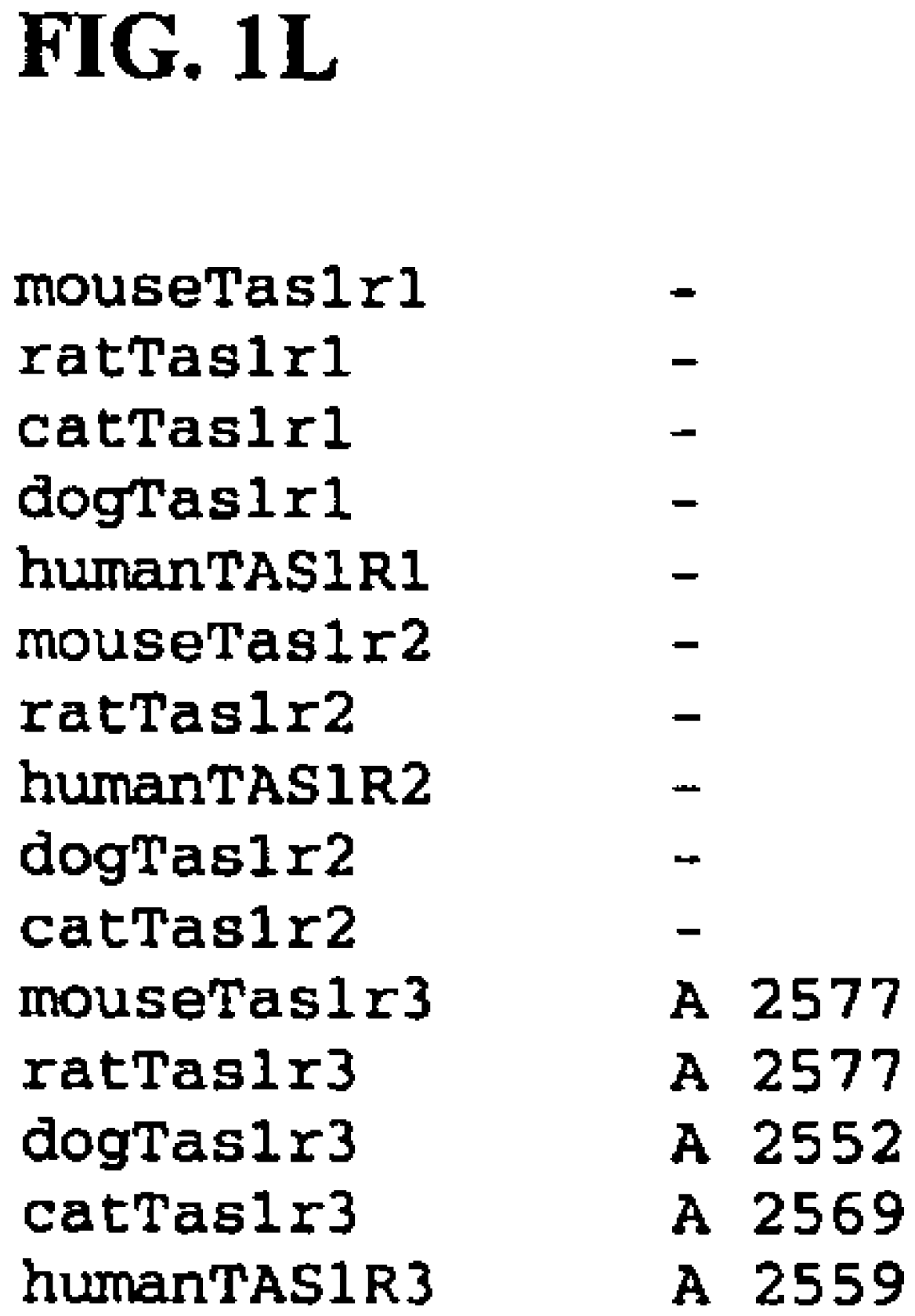

| | |
|---|---|
| mouseTas1r1 | - |
| ratTas1r1 | - |
| catTas1r1 | - |
| dogTas1r1 | - |
| humanTAS1R1 | - |
| mouseTas1r2 | - |
| ratTas1r2 | - |
| humanTAS1R2 | - |
| dogTas1r2 | - |
| catTas1r2 | - |
| mouseTas1r3 | A 2577 |
| ratTas1r3 | A 2577 |
| dogTas1r3 | A 2552 |
| catTas1r3 | A 2569 |
| humanTAS1R3 | A 2559 |

Fig. 2A

```
SEQ ID NO:19  mouseT1R2     MGPQARTLHLLFLLLHALPKPV---MLVGNSDFHLAGDYLLGGLFTLHANVKSVSHLSYL 57
SEQ ID NO:20  ratT1R2       MGPQARTLCLLSLLLHVLPKPG---KLVENSDFHLAGDYLLGGLFTLHANVKSISHLSYL 57
SEQ ID NO:21  humanT1R2     MGPRAKTICSLFFLLWVLAEP------AENSDFYLPGDYLLGGLFSLHANMKGIVHLNFL 54
SEQ ID NO:6   dogT1R2       MGPRAKAVCSLFILLQVLAEP------AENSDFYLPGDYLLGGLFTLHANVKGTVHLSFL 54
SEQ ID NO:136 catT1R2       MGPRAREVCCFIILPRLLAEP------AENSDFYLAGDYFLGGLFTLHANVKGIVHLNLL 54
SEQ ID NO:22  mouseT1R1     MLFWAAHLLLSLQLAVAYCWAFSCQRTESSPGFSLPGDFLLAGLFSLHADCLQVRHR--P 58
SEQ ID NO:23  ratT1R1       MLFWAAHLLLSLQL--VYCWAFSCQRTESSPGFSLPGDFLLAGLFSLHGDCLQVRHR--P 56
SEQ ID NO:3   dogT1R1       MSLLAAHLVS-LQLSLSCCWALSCHNTESSPDFSLPGDYLLAGLFPLHSDCPGVRRR--P 57
SEQ ID NO:134 catT1R1       MSLPAAHLVG-LQLSLSCCWALSCHSTETSADFSLPGDYLLAGLFPLHSDCPGVRHR--P 57
SEQ ID NO:24  humanT1R1     MLLCTARLVG-LQLLISCCWAFACHSTESSPDFTLPGDYLLAGLFPLHSGCLQVRHR--P 57
SEQ ID NO:25  mouseT1R3     MPALAIMGLSLAAFLEL----GMGASLCLSQQFKAQGDYILGGLFPLGSTEEATLNQR-- 54
SEQ ID NO:26  ratT1R3       MPGLAILGLSLAAFLEL----GMGSSLCLSQQFKAQGDYILGGLFPLGTTEEATLNQR-- 54
SEQ ID NO:27  humanT1R3     MLGPAVLGLSLWALLHP----GTGAPLCLSQQLRMKGDYVLGGLFPLGEAEEAGLRSR-- 54
SEQ ID NO:9   dogT1R3       MAGLMLLSLMALLGL------GAGAPLCLSRQLRMQGDYVLGGLFPLGTAEDTGLSDR-- 52
SEQ ID NO:138 catT1R3       MPGLALLGLTALLGLTALLDHGEGATSCLSQQLRMQGDYVLGGLFPLGSAEGTGLGDG-- 58
                            *                            .  :   **:.*.***.*

              mouseT1R2     QVPKCN-EYNMKVLGYNLMQAMRFAVEEINNCSSLLPGVLLGYEMVDVCYL-SNNIQPGL 115
              ratT1R2       QVPKCN-EFTMKVLGYNLMQAMRFAVEEINNCSSLLPGVLLGYEMVDVCYL-SNNIHPGL 115
              humanT1R2     QVPMCK-EYEVKVIGYNLMQAMRFAVEEINNDSSLLPGVLLGYEIVDVCYI-SNNVQPVL 112
              dogT1R2       QVPQCK-KYEMKVLGYNLMQAMRFAVEEINNRSDLLPGVLLGYEIVDVCYI-SNNVQPVL 112
              catT1R2       QVPQCK-EYEIKVLGYDLMQAMCFAGEEINSQSSLLPGVLLGYKMVDVSYI-SNNVQPVL 112
              mouseT1R1     LVTSCDRSDSFNGHGYHLFQAMRFTVEEINNSTALLPNITLGYELYDVCSE-SSNVYATL 117
              ratT1R1       LVTSCDRPDSFNGHGYHLFQAMRFTVEEINNSSALLPNITLGYELYDVCSE-SANVYATL 115
              dogT1R1       MVTLCDRSNSFNGHGYHLFQAMRFGIEEINNSTTLLPNVTLGYQLYDVCSE-SANVYATL 116
              catT1R1       TVTLCDRPDSFNGHGYHLFQAMRFGIEEINNSTALLPNVTLGYQLYDVCSE-SANVYATL 116
              humanT1R1     EVTLCDRSCSFNEHGYHLFQAMRLGVEEINNSTALLPNITLGYQLYDVCSD-SANVYATL 116
              mouseT1R3     TQPNSIPCNRFSPLGLFLAMAMKMAVEEINNGSALLPGLRLGYDLFDTCSEPVVTMKSSL 114
              ratT1R3       TQPNGILCTRFSPLGLFLAMAMKMAVEEINNGSALLPGLRLGYDLFDTCSEPVVTMKPSL 114
              humanT1R3     TRPSSPVCTRFSSNGLLWALAMKMAVEEINNKSDLLPGLRLGYDLFDTCSEPVVAMKPSL 114
              dogT1R3       TQPNATVCTRFSSLGLLWALAMKMAVEEVNNRSTLLPGLRLGYDLFDTCSEPVVAMKPSL 112
              catT1R3       LQPNATVCTRFSSLGLLWALAVKMAVEEINNGSALLPGLHLGYDLFDTCSEPMVAMKPSL 118
                              .       ..  *     *: :  **:*. : ***.: ***.: *..      : . *

              mouseT1R2     YFLSQID-DFLPILKDYSQYRPQVVAVIGPDNSESAITVSNILSYFLVPQVTYSAITDKL 174
              ratT1R2       YFLAQDD-DLLPILKDYSQYMPHVVAVIGPDNSESAITVSNILSHFLIPQITYSAISDKL 174
              humanT1R2     YFLAHED-NLLPIQEDYSNYISRVVAVIGPDNSESVMTVANFLSLFLLPQITYSAISDEL 171
              dogT1R2       YFLARED-YSLPIQEDYSHYVPRVLAVIGPDNSESTTTVAHFLSLFLLPQITYSAISDDL 171
              catT1R2       HFPAKED-CSLPIQEDYSHCVPRVVAVIGPGNSESTVTVARFLSLFLLPQITYSAISDEL 171
              mouseT1R1     RVLAQQGTGHLEMQRDLRNHSSKVVALIGPDNTDHAVTTAALLSPFLMPLVSYEASSVIL 177
              ratT1R1       RVLALQGPRHIEIQKDLRNHSSKVVAFIGPDNTDHAVTTAALLGPFLMPLVSYEASSVVL 175
              dogT1R1       NVLSTLGTHHIEIQADPSHYSPAALAVIGPDTTNHAATAAALLSPFLVPVISYEASSVML 176
              catT1R1       NVLSLLGTHHVEIRADPSHYSPAALAVIGPDTTNHAATTAALLSPFLVPLISYEASSVTL 176
              humanT1R1     RVLSLPGQHHIELQGDLLHYSPTVLAVIGPDSTNRAATTAALLSPFLVPMISYAASSETL 176
              mouseT1R3     MFLAKVGSQSIAAYCNYTQYQPRVLAVIGPHSSELALITGKFFSFFLMPQVSYSASMDRL 174
              ratT1R3       MFMAKVGSQSIAAYCNYTQYQPRVLAVIGPHSSELALITGKFFSFFLMPQVSYSASMDRL 174
              humanT1R3     MFLAKAGSRDIAAYCNYTQYQPRVLAVIGPHSSELAMVTGKFFSFFLMPQVSYGASMELL 174
              dogT1R3       MFMAKAGSCDIAAYCNYTQYQPRVLAVIGPHSSELALITGKFFSFFLMPQVSYGASTDRL 172
              catT1R3       VFMAKAGSCSIAAYCNYTQYQPRVLAVIGPHSSELALVTGKFFSFFLVPQVSYGASTDRL 178
                             . :  .   :    :  :  . .:*.*** .:: .  .. ::. **:* ::* *    *

              mouseT1R2     RDKRRFPAMLRTVPSATHHIEAMVQLMVHFQWNWIVVLVSDDDYGRENSHLLSQRLTNTG 234
              ratT1R2       RDKRHFPSMLRTVPSATHHIEAMVQLMVHFQWNWIVVLVSDDDYGRENSHLLSQRLTKTS 234
              humanT1R2     RDKVRFPALLRTTPSADHHVEAMVQLMLHFRWNWIIVLVSSDTYGRDNGQLLGERVARR- 230
              dogT1R2       RDKQHFPALLRTVAGADHQIEAMVQLLLHFNWNWIIVLVSSDDYGRYNSQLLNDRLATG- 230
              catT1R2       RDKQRFPALLPTAPGADHQIEAMVQLMLYFRRNWIIALVSSGDCGRDDSQLLSDRPAGG- 230
              mouseT1R1     SGKRKFPSFLRTIPSDKYQVEVIVRLLQSFGWVWISLVGSYGDYGQLGVQALEELATPR- 236
              ratT1R1       SAKRKFPSFLRTVPSDRHQVEVMVQLLQSFGWVWISLIGSYGDYGQLGVQALEELAVPR- 234
              dogT1R1       GVKRYYPSFLRTIPSDKYQVEIMVLLLQRFGWVWISLVGSDGDYGQLGVQALEEQATQQ- 235
              catT1R1       GVKRHYPSFLRTIPSDKHQVEAMVLLLQSFGWVWISVVGSDGDYGQLGVQALEEQATQQ- 235
              humanT1R1     SVKRQYPSFLRTIPNDKYQVETMVLLLQKFGWTWISLVGSSDDYGQLGVQALENQATGQ- 235
              mouseT1R3     SDRETFPSFFRTVPSDRVQLQAVVTLLQNFSWNWVAALGSDDDYGREGLSIFSSLANAR- 233
              ratT1R3       SDRETFPSFFRTVPSDRVQLQAVVTLLQNFSWNWVAALGSDDDYGREGLSIFSGLANSR- 233
              humanT1R3     SARETFPSFFRTVPSDRVQLTAAAELLQEFGWNWVAALGSDDEYGRQGLSIFSALAAAR- 233
              dogT1R3       SNRETFPSFFRTVSSDRVQAVAMVELLQELGWNWVAAVGSDDEYGRQGLSLFSSLANAR- 231
              catT1R3       SNREIFPSFFRTVPSDQVQVAAMVELLEELGWNWVAAVGSDDEYGRQGLSLFSGLASAR- 237
                              :  :*::: * ..   :    . *:  :   *:  : * .  *: .   :
```

Fig. 2B

```
mouseT1R2    DICIAFQEVLPVPEPNQAVRPEEQDQLDNILDKLR-RTSARVVVIFSPELSLHNFFREVL 293
ratT1R2      DICIAFQEVLPIPESSQVMRSEEQRQLDNILDKLR-RTSARVVVVFSPELSLYSFFHEVL 293
humanT1R2    DICIAFQETLPTLQPNQNMTSEERQRLVTIVDKLQ-QSTARVVVVFSPDLTLYHFFNEVL 289
dogT1R2      DICIAFQETLPMPQPDQVVTEWERQRLEAIVGKLQ-QSSARVVVLFSPDLILHNFFREVL 289
catT1R2      DTCIAFRETLPMPQPNQAVTQWERRRLKAIVDEQQRQSSARVVVLLSPKLVLHNFFREVL 290
mouseT1R1    GICVAFKDVVPLS------AQAGDPRMQRMMLRLA-RARTTVVVVFSNRHLAGVFFRSVV 289
ratT1R1      GICVAFKDIVPFS------ARVGDPRMQSMMQHLA-QARTTVVVVFSNRHLARVFFRSVV 287
dogT1R1      GICIAFKDIIPFS------AQPGNERMQSMMYHLD-RARTTVVVVFSSRQLARVFFESVV 288
catT1R1      GICVAFKDIIPFS------ARPGDERMQSIMHHLA-RARTTVVVVFSSRQLARVFFESVV 288
humanT1R1    GICIAFKDIMPFS------AQVGDERMQCLMRHLA-QAGATVVVVFSSRQLARVFFESVV 288
mouseT1R3    GICIAHEGLVPQHD----TSGQQLGKVLDVLRQVN-QSKVQVVVLFASARAVYSLFSYSI 288
ratT1R3      GICIAHEGLVPQHD----TSGQQLGKVVDVLRQVN-QSKVQVVVLFASARAVYSLFSYSI 288
humanT1R3    GICIAHEGLVPLPR----ADDSRLGKVQDVLHQVN-QSSVQVVLLFASVHAAHALFNYSI 288
dogT1R3      GICIAHEGLVPLPH----TSSLRLGTVQGLLHQVN-QSSVQVVVLFSSTRAARTLFSYSI 286
catT1R3      GICIAHEGLVPLP-----PGSLRLGALQGLLRQVN-QSSVQVVVLFSSAHAARTLFSYSI 291
             . *:*..  :*                  :  :: .   :: . **::::          :*    :

mouseT1R2    RWNFTGFVWIASESWAIDPVLHNLTELRHTGTFLGVTIQRVSIPGFSQFRVRHDKPEYPM 353
ratT1R2      RWNFTGFVWIASESWAIDPVLHNLTELRHTGTFLGVTIQRVSIPGFSQFRVRRDKPGYPV 353
humanT1R2    RQNFTGAVWIASESWAIDPVLHNLTELGHLGTFLGITIQSVPIPGFSEFREWGPQAGPPP 349
dogT1R2      RQNFTGAVWIASESWAIDPVLHNLTELRQTGTFLGVTTQSVPIPGFSEFRIRRTPVRLPE 349
catT1R2      RQNLTGVVRIASESWAIDPVLH-------------------------------------- 312
mouseT1R1    LANLTGKVWIASEDWAISTYITNVPGIQGIGTVLGVAIQQRQVPGLKEFEESYVQAVMGA 349
ratT1R1      LANLTGKVWVASEDWAISTYITSVTGIQGIGTVLGVAVQQRQVPGLKEFEESYVRAVTAA 347
dogT1R1      LAKLTAKVWIASEDWAISRHISSLPRIWGIGTVLGVAIQQKLVPGLKEFEEAYVRAKKAA 348
catT1R1      LANLTAKVWIASEDWAISRHISNVPGIQGIGTVLGVAIQQRLVPGLKEFEEAYVQADKGA 348
humanT1R1    LTNLTGKVWVASEAWALSRHITGVPGIQRIGMVLGVAIQKRAVPGLKAFEEAYARADKKA 348
mouseT1R3    HHGLSPKVWVASESWLTSDLVMTLPNIARVGTVLGFLQRGALLPEFSHYVETHLALAADP 348
ratT1R3      LHDLSPKVWVASESWLTSDLVMTLPNIARVGTVLGFLQRGALLPEFSHYVETRLALAADP 348
humanT1R3    SSRLSPKVWVASEAWLTSDLVMGLPGMAQMGTVLGFLQRGAQLHEFPQYVKTHLALATDP 348
dogT1R3      HCRLSPKVWVASEAWLTSDLVMTLPGMAEVGTVLGFLQQGAPIPEFPSYVQTCLALAADP 346
catT1R3      RCKLSPKVWVASEAWLTSDLVMTLPGMPGVGTVLGFLQQGAPMPEFPSYVRTRLALAADP 351
                 ::   *  :*** *     .   :

mouseT1R2    PNETSLRTTC-NQDCDACMNITESFNNVLMLSGERVV------------YSVYSAVYAV 399
ratT1R2      PNTTNLRTTC-NQDCDACLNTTKSFNNILILSGERVV------------YSVYSAVYAV 399
humanT1R2    LSRTSQSYTC-NQECDNCLNATLSFNTILRLSGERVV------------YSVYSAVYAV 395
dogT1R2      PNRTSLEATC-NQECDTCQDTTASFNSILMLSGERVV------------YNVYSAVYAV 395
catT1R2      ------------------------------------------------------------
mouseT1R1    PRTCPEGSWCGTNQLCRECHAFTTWNMPELGAFSMSAA------------YNVYEAVYAV 397
ratT1R1      PSACPEGSWCSTNQLCRECHTFTTRNMPTLGAFSMSAA------------YRVYEAVYAV 395
dogT1R1      HRPCSRDSWCSSNQLCRECQAFTVQQMPTLGAFSMSSA------------YNAYRAVYAA 396
catT1R1      PGPCSRTSECSSNQLCRECRAFTAEQMPTLGAFSMSSA------------YNAYRAVYAV 396
humanT1R1    PRPCHKGSWCSSNQLCRECQAFMAHTMPKLKAFSMSSA------------YNAYRAVYAV 396
mouseT1R3    AFCASLN-AELDLEEHVMGQRCPRCDDIMLQNLSSGLLQNLSAGQLHHQIFATYAAVYSV 407
ratT1R3      TFCASLK-AELDLEERVMGPRCSQCDYIMLQNLSSGLMQNLSAGQLHHQIFATYAAVYSV 407
humanT1R3    AFCSALGEREQGLEEDVVGQRCPQCDCITLQNVSAGLN--------HHQTFSVYAAVYSV 400
dogT1R3      AFCASLDAEQPGLEEHVVGPRCPQCDHVTLEAMSAGLL--------HHQTFAAYAAVYGV 398
catT1R3      AFCASLDAEQPGLEEHVVGPRCPQCDHVTLENLSAGLL--------HHQTFAAYAAVYGV 403

mouseT1R2    AHTLHRLLHCNQVRCT-KQIVYPWQLLREIWHVNFTLLGNQLFFDEQGDMPMLLDIIQWQ 458
ratT1R2      AHALHRLLGCNRVRCT-KQKVYPWQLLREIWHVNFTLLGNRLFFDQQGDMPMLLDIIQWQ 458
humanT1R2    AHALHSLLGCDKSTCT-KRVVYPWQLLEEIWKVNFTLLDHQIFFDPQGDVALHLEIVQWQ 454
dogT1R2      AHALHSLLGCTQ-ACS-KEVVYPWQLLKEIWKVNFTLLGHNVFFGQQGDVLMPMEVIQWQ 453
catT1R2      ------------------------------------------------------------
mouseT1R1    AHGLHQLLGCTSGTCA-RGPVYPWQLLQQIYKVNFLLHKKTVAFDDKGDPLGYYDIIAWD 456
ratT1R1      AHGLHQLLGCTSEICS-RGPVYPWQLLQQIYKVNFLLHENTVAFDDNGDTLGYYDIIAWD 454
dogT1R1      AHGLHQLLGCASGACS-RDRVYPWQLLEQIRKVNFLLHEDTVIFNDNGDPLSGYDIIAWD 455
catT1R1      AHGLHQLLGCASGACS-RDRVYPWQLLEQIRKVNFLLHKDTVRFNDNGDPLSGYDIIAWD 455
humanT1R1    AHGLHQLLGCASGACS-RGRVYPWQLLEQIHKVHFLLHKDTVAFNDNRDPLSSYNIIAWD 455
mouseT1R3    AQALHNTLQCNVSHCHVSEHVLPWQLLENMYNMSFHARDLTLQFDAEGNVDMEYDLKMWV 467
ratT1R3      AQALHNTLQCNVSHCHTSEPVQPWQLLENMYNMSFRARDLTLQFDAKGSVDMEYDLKMWV 467
humanT1R3    AQALHNTLQCNASGCPAQDPVKPWQLLENMYNLTFHVGGLPLRFDSSGNVDMEYDLKLWV 460
dogT1R3      AQALHNTLLCNASGCPPREPVRPWQLLENMYNLTFRVRGLALQFDARGNVNMDYDLKLWV 458
catT1R3      AQALHNTLRCNASGCPRREPVRPWQLLENMYNVSFRARGLALQFDASGNVNVDYDLKLWV 463
```

Fig. 2C

```
mouseT1R2   WGLSQNPFQSIASYSPTETRLTY-ISNVSWYTPNNTVPISMCSKSCQPGQMKKPIGLHPC 517
ratT1R2     WDLSQNPFQSIASYSPTSKRLTY-INNVSWYTPNNTVPVSMCSKSCQPGQMKKSVGLHPC 517
humanT1R2   WDRSQNPFQSVASYYPLQRQLKN-IQDISWHTVNNTIPMSMCSKRCQSGQKKKPVGIHVC 513
dogT1R2     WDLSQNPFQSIASYYPKLRQLKA-IHNISWHTANNTIPVSMCSKDCHPGQRKKPVGIHSC 512
catT1R2     ----DRPTRCTAS---------------WAAP----------RPAAPGRLS-------- 334
mouseT1R1   WNGPEWTFEVIGSASLSPVHLDINKTKIQWHGKNNQVPVSVCTRDCLEGHHRLVMGSHHC 516
ratT1R1     WNGPEWTFEIIGSASLSPVHLDINKTKIQWHGKNNQVPVSVCTTDCLAGHHRVVVGSHHC 514
dogT1R1     WSGPKWTFRVIGSSTWPPVQLDINKTKIRWHGEDNQVPESVCSSNCLEGHQRVVVGFYHC 515
catT1R1     WSGPKWNFRVIGSSMWPPVQLDINKTKIRWHGKDNQVPKSVCSSDCLEGHQRVISGFYHC 515
humanT1R1   WNGPKWTFTVLGSSTWSPVQLNINETKIQWHGKDNQVPKSVCSSDCLEGHQRVVTGFHHC 515
mouseT1R3   WQSPTPVLHTVGTFNG---TLQLQQSKMYWPG-NQVPVSQCSRQCKDGQVRRVKGFHSC 522
ratT1R3     WQSPTPVLHTVGTFNG---TLQLQHSKMYWPG-NQVPVSQCSRQCKDGQVRRVKGFHSC 522
humanT1R3   WQGSVPRLHDVGRFNG---SLRTERLKIRWHTSDNQKPVSRCSRQCQEGQVRRVKGFHSC 517
dogT1R3     WRDLKPELRTVGAFNG---RLKVWHSQMSWHTPGNQRPVSQCSRQCGEGQVRRVKGFHSC 515
catT1R3     WQDPTPELRTVGTFKG---RLELWRSQMCWHTPGKQQPVSQCSRQCKEGQVRRVKGFHSC 520
                                         *             .   *:

mouseT1R2   CFECVDCPPGTYLNRSVDEFNCLSCPGSMWSYKNNIACFKRRLAFLEWHEVPTIVVTILA 577
ratT1R2     CFECLDCMPGTYLNRSADEFNCLSCPGSMWSYKNDITCFQRRPTFLEWHEVPTIVVAILA 577
humanT1R2   CFECIDCLPGTFLNHTEDEYECQACPNNEWSYQSETSCFKRQLVFLEWHEAPTIAVALLA 573
dogT1R2     CFECIDCLPGTFLNRTADEFDCQPCPSYEWSHRNDTSCFKRRLAFLEWHEPSTIFVVMLT 572
catT1R2     -------LAG------------EAPPTESRGHT------RRRRHSPEWLP---------- 359
mouseT1R1   CFECMPCEAGTFLNTS-ELHTCQPCGTEEWAPEGSSACFSRTVEFLGWHEPISLVLLAAN 575
ratT1R1     CFECVPCEAGTFLNMS-ELHICQPCGTEEWAPKESTTCFPRTVEFLAWHEPISLVLIAAN 573
dogT1R1     CFECVPCEAGTFLNKS-DLHSCQPCGKEEWAPEGSESCFLRTVVFLTWHEPISWVLLAAN 574
catT1R1     CFECVPCEAGSFLNKS-DLHSCQPCGKEKWAPAGSETCFPRTVVFLTWHETISWVLLAAN 574
humanT1R1   CFECVPCGAGTFLNKS-DLYRCQPCGKEEWAPEGSQTCFPRTVVFLALREHTSWVLLAAN 574
mouseT1R3   CYDCVDCKAGSYRKHP-DDFTCTPCNQDQWSPEKSTACLPRRPKFLAWGEPVVLSLLLLL 581
ratT1R3     CYDCVDCKAGSYRKHP-DDFTCTPCGKDQWSPEKSTTCLPRRPKFLAWGEPAVLSLLLLL 581
humanT1R3   CYDCVDCEAGSYRQNP-DDIACTFCGQDEWSPERSTRCFRRRSRFLAWGEPAVLLLLLLL 576
dogT1R3     CYDCVDCKAGTYQRSP-DDLLCTQCDQNQWSPDRSTRCFPRRLTFLAWGQPAVLVLLILL 574
catT1R3     CYNCVDCKAGSYQRNP-DDLLCTQCDQDQWSPDRSTRCFARKPMFLAWGEPAVLLLLALL 579
                   .*                     .              *

mouseT1R2   ALGFISTLAILLIFWRHFQTPMVRSAGGPMCFLMLVPLLLAFGMVPVYVGPPTVFSCFCR 637
ratT1R2     ALGFFSTLAILFIFWRHFQTPMVRSAGGPMCFLMLVPLLLAFGMVPVYVGPPTVFSCFCR 637
humanT1R2   ALGFLSTLAILVIFWRHFQTPIVRSAGGPMCFLMLTLLLVAYMVVPVYVGPPKVSTCLCR 633
dogT1R2     ILGFLSTLAIMVIFWRHLHTPVVRSAGGPMCFLMLVPLLLAYAMVPMYIGQPTFFSCLWR 632
catT1R2     --------------WRPLPCSSVPLSG---------------------------------- 372
mouseT1R1   TLLLLLLIGTAGLFAWRLHTPVVRSAGGRLCFLMLGSLVAGSCSLYSFFGKPTVPACLLR 635
ratT1R1     TLLLLLLVGTAGLFAWHFHTPVVRSAGGRLCFLMLGSLVAGSCSFYSFFGEPTVPACLLR 633
dogT1R1     TLLLLLVAGTAGLFAWHLDTPVVRSAGGRLCFFMLGSLAGGSCGLYGFFGEPTLATCLLR 634
catT1R1     TLLLLLVTGTAGLFAWHLDTPVVKSAGGRLCFFMLGSLAGGSCGLYGFFGEPTLPTCLLR 634
humanT1R1   TLLLLLLLGTAGLFAWHLDTPVVRSAGGRLCFLMLGSLAAGSGSLYGFFGEPTRPACLLR 634
mouseT1R3   CLVLGLALAALGLSVHHWDSPLVQASGGSQFCFGLICLGLFCLSVLLFPGRPSSASCLAQ 641
ratT1R3     CLVLGLTLAALGLFVHYWDSPLVQASGGSLFCFGLICLGLFCLSVLLFPGRPRSASCLAQ 641
humanT1R3   SLALGLVLAALGLFVHHRDSPLVQASGGPLACFGLVCLGLVCLSVLLFPGQPSPARCLAQ 636
dogT1R3     ALALGLVLVALGLFIRHRDSPLVQASGGPRACFGLACLGLVCLSVLLFPGQPGPASCLAQ 634
catT1R3     ALALGLALAALGLFLWHSDSPLVQASGGPRACFGLACLGLVCLSVLLFPGQPGPASCLAQ 639
                               . *  :*

mouseT1R2   QAFFTVCFSVCLSCITVRSFQIVCVFKMARRLPSAYGFWMRYHGPYVFVAFITAVKVALV 697
ratT1R2     QAFFTVCFSICLSCITVRSFQIVCVFKMARRLPSAYSFWMRYHGPYVFVAFITAIKVALV 697
humanT1R2   QALFPLCFTICISCIAVRSFQIVCAFKMASRFPRAYSYWVRYQGPYVSMAFITVLKMVIV 693
dogT1R2     QTFFTLCFTICISCITVRSFQIVCIFKMARRLPRAYGYWVRCHGPYVFVASFMVLKVVIV 692
catT1R2     --------------------------------------RVLG--------------KL 378
mouseT1R1   QPLFSLGFAIFLSCLTIRSFQLVIIFKFSTKVPTFYHTWAQNHGAGIFVIVSSTVHLFLC 695
ratT1R1     QPLFSLGFAIFLSCLTIRSFQLVIIFKFSTKVPTFYRTWAQNHGAGLFVIVSSTVHLLIC 693
dogT1R1     QGLFALGFAIFLSCLTIRSFQLVFIFKFSAKVPTFYQAWVQNHGPRLFVVISSMAQLLIC 694
catT1R1     QSLLALGFAIFLSCLTIRSFQLVFIFKFSAKVPTFYRAWVQNHGPGLFVVISSMAQLLIC 694
humanT1R1   QALFALGFTIFLSCLTVRSFQLIIIFKFSTKVPTFYHAWVQNHGAGLFVMISSAAQLLIC 694
mouseT1R3   QPMAHLPLTGCLSTLFLQAAETFVESELPLSWANWLCSYLRGLWAWLVVLLATFVEAALC 701
ratT1R3     QPMAHLPLTGCLSTLFLQAAEIFVESELPLSWANWLCSYLRGPWAWLVVLLATLVEAALC 701
humanT1R3   QPLSHLPLTGCLSTLFLQAAEIFVESELPLSWADRLSGCLRGPWAWLVVLLAMLVEVALC 696
dogT1R3     QPLLHLPLTGCLSTLFLQAAQIFVGSELPSSWADQLRRCLQGPWAWLLVLLALLAEAALC 694
catT1R3     QPLFHLPLTGCLSTFFLQAAEIFVGSELPPSWAEKMRGRLRGPWAWLVVLLAMLAEAALC 699
                                                   :
```

Fig. 2D

```
mouseT1R2     AGNMLATTINPIGRTDPDDPNIIILSCHPNYRNGLLFNTSMDLLLSVLGFSFAYVGKELP 757
ratT1R2       VGNMLATTINPIGRTDPDDPNIMILSCHPNYRNGLLFNTSMDLLLSVLGFSFAYMGKELP 757
humanT1R2     VIGMLATGLSPTTRTDPDDPKITIVSCNPNYRNSLLFNTSLDLLLSVVGFSFAYMGKELP 753
dogT1R2       AGNVLATTANPTARPDPDDPNIMVLSCN--YRRALLFNTSLDLLLSVAGFSFAYMGKELP 750
catT1R2       AGEARGRTLSPDT----------------------------------------------- 391
mouseT1R1     LTWLAMWTPRPTREYQR-FPHLVILECTEVNSVGFLVAFAHNILLSISTFVCSYLGKELP 754
ratT1R1       LTWLVMWTPRPTREYQR-FPHLVILECTEVNSVGFLLAFTHNILLSISTFVCSYLGKELP 752
dogT1R1       VTWLAVWTPLPTREYQR-FPQLVVLDCTEANSPGFMVAFAYNGLLSVSAFACSYLGKDLP 753
catT1R1       LTWLAVWTPLPTREYQR-FPQLVVLDCTEANSPGFMLAFAYNGLLSVSAFACSYLGKDLP 753
humanT1R1     LTWLVVWTPLPAREYQR-FPHLVMLECTETNSLGFILAFLYNGLLSISAFACSYLGKDLP 753
mouseT1R3     AWYLIAFPPEVVTDWSV-LPTEVLEHCHVRSWVSLGLVHITNAMLAFLCFLGTFLVQSQP 760
ratT1R3       AWYLMAFPPEVVTDWQV-LPTEVLEHCRMRSWVSLGLVHITNAVLAFLCFLGTFLVQSQP 760
humanT1R3     TWYLVAFPPEVVTDWHM-LPTEALVHCRTRSWVSFGLAHATNATLAFLCFLGTFLVRSQP 755
dogT1R3       AWYLVAFPPEVVTDWWV-LPTQVLVHCRMRSWISFGLVHAINAMLAFLCFLGTFLVQSRP 753
catT1R3       AWYLVAFPPEVVTDWRV-LPTEALVHCHVHSWISFGLVHATNAMLAFLCFLGTFLVQSRP 758

mouseT1R2     TNYNEAKFITLSMTFSFTSSISLCTFMSVHDGVLVTIMDLLVTVLNFLAIGLGYFGPKCY 817
ratT1R2       TNYNEAKFITLSMTFSFTSSISLCTFMSVHDGVLVTIMDLLVTVLNFLAIGLGYFGPKCY 817
humanT1R2     TNYNEAKFITLSMTFYFTSSVSLCTFMSAYSGVLVTIVDLLVTVLNLLAISLGYFGPKCY 813
dogT1R2       TNYNEAKFITLCMTFYFTSSVSLCTFMSVYDGVLVTILDLLITVLNLLGISFGYFGPKCY 810
catT1R2       ------------------------------------------------------------ 391
mouseT1R1     ENYNEAKCVTFSLLLHFVSWIAFFTMSSIYQGSYLPAVNVLAGLATLSGGFSGYFLPKCY 814
ratT1R1       ENYNEAKCVTFSLLLNFVSWIAFFTMASIYQGSYLPAVNVLAGLTTLSGGFSGYFLPKCY 812
dogT1R1       ENYNEAKCVTFSLLLNFVSWIGFFTTASVYQGKYLPAVNVLAALSSLSSGFSGYFLPKCY 813
catT1R1       ENYNEAKCVTFSLLLNFVSWIAFFTTASVYQGKYLPAVNVLAALSSLSGGFSGYFLPKCY 813
humanT1R1     ENYNEAKCVTFSLLFNFVSWIAFFTTASVYDGKYLPAANMMAGLSSLSSGFGGYFLPKCY 813
mouseT1R3     GRYNRARGLTFAMLAYFITWVSFVPLLANVQVAYQPAVQMGAILVCALGILVTFHLPKCY 820
ratT1R3       GRYNRARGLTFAMLAYFIIWVSFVPLLANVQVAYQPAVQMGAILFCALGILATFHLPKCY 820
humanT1R3     GRYNRARGLTFAMLAYFITWVSFVPLLANVQVVLRPAVQMGALLLCVLGILAAFHLPRCY 815
dogT1R3       GRYNGARGLTFAMLAYFITWISFVPLFANVHVAYQPTVQMAAILLCALGILATFHLPKCY 813
catT1R3       GRYNGARGLTFAMLAYFITWISFVPLFANVHVAYQPAVQMGTILLCALGILATFHLPKCY 818

mouseT1R2     MILFYPERNTSAYFNSMIQGYTMRKS---------------------- 843
ratT1R2       MILFYPERNTSAYFNSMIQGYTMRKS---------------------- 843
humanT1R2     MILFYPERNTPAYFNSMIQGYTMRRD---------------------- 839
dogT1R2       MVLFYPERNTQVYFSSMIQGYTMGKD---------------------- 836
catT1R2       ------------------------------------------------ 391
mouseT1R1     VILCRPELNNTEHFQASIQDYTRRCGTT-------------------- 842
ratT1R1       VILCRPELNNTEHFQASIQDYTRRCGTT-------------------- 840
dogT1R1       VILCRPDLNSTEHFQASIQDYTRRCGST-------------------- 841
catT1R1       VILCRPKFNSTQHFQASIQEYTRRCGST-------------------- 841
humanT1R1     VILCRPDLNSTEHFQASIQDYTRRCGST-------------------- 841
mouseT1R3     VLLWLPKLNTQEFFLGRNAKKAADENSGGGEAAQGHNE---------- 858
ratT1R3       VLLWLPELNTQEFFLGRSPKEASDGNSGSSEATRGHSE---------- 858
humanT1R3     LLMRQPGLNTPEFFLGGGPGDAQGQNDGN-TGNQGKHE---------- 852
dogT1R3       LLLQQLELNNPEFFLGDDARGQGSSGSGGKET---------------- 845
catT1R3       LLLQRPELNTPEFFLEDNARAQGSSWGQGRGESGQKQVTPDPVTSPQ 865
```

TASTE RECEPTORS OF THE T1R FAMILY FROM DOMESTIC DOG

CROSS-REFERENCE TO RELATED APPLICATION

This application is a divisional of U.S. application Ser. No. 11/578,472, which is the U.S. National Phase of international patent application PCT/US2005/012765, filed in English on Apr. 14, 2005, designating the United States. PCT/US2005/012765 claims the benefit of U.S. Provisional Application 60/562,208, filed Apr. 14, 2004. The entire contents of each of these applications are incorporated herein by reference.

FIELD OF THE INVENTION

The present invention relates to the field of sensory mechanisms of the domestic dog, *Canis familiaris*. The invention relates, for example, to the discovery of several genes of *Canis familiaris* encoding taste receptors of the T1R family, T1R1 (Tas1r1), T1R2 (Tas1r2), and T1R3 (Tas1r3). The invention further relates to the polypeptides encoded by the canine T1R1, T1R2, and T1R3 genes and to methods and uses of the same.

BACKGROUND OF THE INVENTION

The sense of taste is important for determining food choice, for regulating food intake, and for ensuring efficient use of ingested nutrients. Taste can act as a warning system for the presence of potentially harmful foods, by, for example, the aversive sensations of sourness or bitterness, and as an attractant to potentially nutrient-rich foods, by, for example, the appealing sensations of sweetness, saltiness, and umami.

Taste stimuli are received by taste receptor cells assembled into taste buds that are located in the epithelium of taste papillae of the tongue (Kitagawa et al., *Bioch. Bioph. Res. Comm.,* 283:236-242 (2001)). The stimuli are believed to be transduced by taste receptors at the surface of the taste receptor cells (Id.). The taste receptors encoded by the genes of a given species are reflective of that species' food choices. For example, the "sweet receptors" of an herbivorous species are expected to be different from those of a carnivorous species, since the two consume completely different diets whose foods contain different primary stimuli. Since taste receptor specificity likely reflects food choice, it follows that receptor sequence homology among species may be as predictive or more predictive of food preferences of a given species as phylogenetic relatedness among species.

Evolution has provided that each species' genes code for taste receptors unique to that species' food choices. For example, the "sweet receptors" of an herbivore are expected to be different from those of a carnivore, since the two consume completely different diets whose foods contain different primary stimuli. Even within the Order Carnivora, Feliformia (cat branch) and Caniformia (dog and bear branch) have different diets and show different taste responses to various sweeteners. Since taste receptor specificity must reflect food choice, it may follow that receptor sequence homology among species might be dependent more upon the types of foods consumed by individual species rather than by the phylogenetic relatedness of species. The behavior of carnivores, such as the domestic cat, towards stimuli such as sweet carbohydrates, which it cannot taste (Beauchamp, et al., *J. Comp. Physiol. Psychol.,* 91(5):1118-1127 (1977)), and towards L-amino acids, which it can taste, should be explainable based on the specificity of the taste receptors of carnivores in general. The behavior of the domestic cat (*Felis catus*), a carnivore, towards stimuli such as sweet carbohydrates, which it generally cannot taste, and towards L-amino acids, which it generally can taste, should be explicable by the specificity of taste receptors of other carnivores.

The domestic dog and the domestic cat are two readily accessible and popular members of the Order Carnivora. Neurophysiological studies with dog show that it responds to chemicals representative of each of the five basic taste modalities: sweet, sour, bitter, salty, and umami. However, the spectrum of compounds within each taste group to which the dog responses are different from those to which the human, rodent, and cat respond (Bradshaw, *Proc. Nutrition Soc.,* 50:99-106 (1991)). For example, while the dog responds to a range of mono- and d-saccharides and to some high intensity sweeteners, the cat does not. Particularly active in the dog are D-fructose, 1-D-fructose, and sucrose. (Beauchamp et al., *J. Comp. Physiol. Psychol.,* 91(5):1118-1127 (1977); Boudreau et al., *Chem. Senses,* 10:89-127 (1985); Boudreau (ed.), Neurophysiology and stimulus chemistry of mammalian taste systems. IN FLAVOR CHEMISTRY TRENDS AND DEVELOPMENTS. Washington D.C.: American Chemical Society (1989); Bartoshuk et al., *Science,* 171:699-701 (1971)).

Early studies suggest that domestic dog shows a preference for sucrose and that this behavior is congenital. (Grace & Russek, *Physiology and Behavior,* 4:553-558 (1968)). Additionally, domestic dog is believed to taste saccharin as bitter. (Grace & Russek, *Physiology and Behavior,* 4:553-558 (1968)). Electrophysiological studies showed that dog taste nerve fibers that responded to sucrose exhibited no response to saccharin and that the fibers fired by saccharin respond to the bitter alkaloid, strychnine. (Anderson et al., *Acta physiol scan,* 21:105-119 (1950)). Experiments using amiloride show that the umami component of the canine chorda tympani nerve response is independent of the sodium component. (Kurihara & Kashiwayanagi, *Ann. N.Y. Acad. Sci.,* 855:393-397 (1998)). Direct knowledge of taste receptor genes of the domestic dog will allow insight into an animal's sensory world and may be useful for identifying modulators of the taste receptors encoded thereby to influence an animal's taste preferences.

Molecular receptors for the taste element of sweetness have recently been identified from human, mouse, and rat. Thus far, there are three known members of the T1R taste receptor family: T1R1, T1R2, and T1R3 (Montmayeur & Matsunami, *Curr. Opin. Neurobiol.,* 12(4):366-371 (2002)). The T1R3 receptor gene is located within the Sac locus, the primary genetic locus controlling preference for sweet-tasting stimuli in mice (Li et al., *Mamm. Genome,* 12(1):13-16 (2001); Li et al., *Mamm. Genome,* 13(1):5-19 (2002)). The human syntenic region for the mouse T1R3 gene is on 1p36.33 (1162-1186 kb). The gene for T1R1 is located on human 1p36.23 (6324-6349 kb), which is ~5 Mb from T1R3, and that for T1R2 is located on human 1p36.13 (18483-18729 kb), which is ~12 Mb from T1R1.

Most of the T1Rs are G-protein coupled receptors with long N-terminal extracellular domains believed to be involved in ligand binding (Montmayeur & Matsunami, *Curr. Opin. Neurobiol.,* 12(4):366-371 (2002)). Within the cell, the taste receptors heterodimerize, with T1R3 coupling separately with T1R1 and T1R2. In mouse, the T1R1/T1R3 heterodimer functions as a receptor for selected amino acids. The T1R2/T1R3 heterodimer functions as a receptor for stimuli considered sweet by humans. Current data indicate that the T1R3 component of the T1R heterodimer couples the taste receptor to cellular signal transduction processes, thereby ensuring that the stimulus-binding event is transduced to a neural signal. Thus, knowledge of the T1R receptors will lead to better understanding of species-specific reactions to sapid stimuli.

Currently, mechanisms for identifying novel taste stimuli for the domestic dog are limited, for example, to exhaustive and difficult feeding studies in which a novel ingredient is paired with a control ingredient and intake of the two are compared. Considerable time, effort, and expense can be expended in the discovery of a single stimulus. Furthermore, canine illnesses often are exacerbated by the animal's refusal to eat. Additionally, the molecular features that define acceptable taste stimuli for domestic dog remain largely unknown, making rational computational design approaches for taste stimuli difficult. As a result, knowledge of the canine taste receptor and its ligands may lead to a better understanding of dog taste perception and modulation thereof.

The present invention provides novel canine taste receptors, T1R1, T1R2, and T1R3, (also interchangeably referred to herein as Tas1r1, Tas1r2, and Tas1r3, respectively) methods of use thereof to identify compounds that can stimulate, inhibit, or modify the ingestive responses or general behavior of a dog. The screening methods of the invention allow the rapid screening of binding partners, agonists, antagonists, and modulators of the T1R receptors of the domestic dog. The results of the canine T1R receptor studies reflect the unique taste profile of the domestic dog.

SUMMARY OF THE INVENTION

Certain embodiments of the present invention relate to polynucleotides encoding a T1R receptor, including, but not limited to polynucleotides having the nucleotide sequence of SEQ ID NO:1, SEQ ID NO:2, SEQ ID NO:4, SEQ ID NO:5, SEQ ID NO:7, and SEQ ID NO:8, fragments of the polynucleotide of SEQ ID NO:1, SEQ ID NO:2, SEQ ID NO:4, SEQ ID NO:5, SEQ ID NO:7, and SEQ ID NO:8 encoding a polypeptide having substantially the same biological activity as a polypeptide encoded by the nucleotide sequence of SEQ ID NO:1, SEQ ID NO:2, SEQ ID NO:4, SEQ ID NO:5, SEQ ID NO:7, and SEQ ID NO:8, respectively; variants of the polynucleotide of SEQ ID NO:1, SEQ ID NO:2, SEQ ID NO:4, SEQ ID NO:5, SEQ ID NO:7, or SEQ ID NO:8 having at least 80% homology to the polynucleotide of SEQ ID NO:1, SEQ ID NO:2, SEQ ID NO:4, SEQ ID NO:5, SEQ ID NO:7, or SEQ ID NO:8; polynucleotide variants of SEQ ID NO:1, SEQ ID NO:2, SEQ ID NO:4, SEQ ID NO:5, SEQ ID NO:7, and SEQ ID NO:8 encoding a polypeptide having substantially the same biological activity as a polypeptide encoded by the nucleotide sequence of SEQ ID NO: 1, SEQ ID NO:2, SEQ ID NO:4, SEQ ID NO:5, SEQ ID NO:7, and SEQ ID NO:8, respectively; variants of the polynucleotide of SEQ ID NO:1, SEQ ID NO:2, SEQ ID NO:4, SEQ ID NO:5, SEQ ID NO:7, and SEQ ID NO:8 encoding a polypeptide conferring modified taste perception to one or more taste stimuli relative to a polypeptide encoded by the polynucleotide of SEQ ID NO:1, SEQ ID NO:2, SEQ ID NO:4, SEQ ID NO:5, SEQ ID NO:7, and SEQ ID NO:8, respectively; nucleotide sequences encoding the amino acid sequence of SEQ ID NO:3, SEQ ID NO:6, or SEQ ID NO:9; nucleotide sequences substantially complementary to the nucleotide sequence of SEQ ID NO:1, SEQ ID NO:2, SEQ ID NO:4, SEQ ID NO:5, SEQ ID NO:7, and SEQ ID NO:8; and nucleotide sequences that hybridize to the complement of the polynucleotide having SEQ ID NO: 1, SEQ ID NO:2, SEQ ID NO:4, SEQ ID NO:5, SEQ ID NO:7, and SEQ ID NO:8 under high stringency conditions. The polynucleotides of the invention may be DNA or RNA and may be single- or double-stranded. In some embodiments of the invention, the polynucleotide fragments have at least about 45 nucleotides. The polynucleotide fragments of the invention encode, for example, an extracellular domain of the polypeptide of SEQ ID NO:3, SEQ ID NO:6, or SEQ ID NO:9; a transmembrane domain of the polypeptide of SEQ ID NO:3, SEQ ID NO:6, or SEQ ID NO:9; or an intracellular domain of the polypeptide of SEQ ID NO:3, SEQ ID NO:6, or SEQ ID NO:9.

The invention also encompasses expression vectors containing the polynucleotides of the invention operably linked to a promoter. Another embodiment of the invention provides host cells containing the expression vector. The host cells may be prokaryotic, such as bacterial cells, or eukaryotic, such as yeast or mammalian cells, including human, murine, porcine, bovine, canine, or feline cells. The invention further encompasses cell cultures of the host cells. The invention also encompasses methods of producing a canine T1R receptor by culturing the host cells and recovering receptor therefrom.

Another embodiment of the invention includes T1R receptor polypeptides, including polypeptides encoded by the polynucleotides of the invention. The polypeptides of the invention include, for example, those having the amino acid sequence of SEQ ID NO:3, SEQ ID NO:6, or SEQ ID NO:9, fragments of at least 30 contiguous amino acids of SEQ ID NO:3, SEQ ID NO:6, or SEQ ID NO:9, and variants thereof having substantially the same biological activity as the polypeptide of SEQ ID NO:3, SEQ ID NO:6, or SEQ ID NO:9, respectively. The biological activity of the polypeptides of the invention may be determined, for example, by an in vitro binding assay, such as but not limited to assessing the level of binding of the polypeptide to its respective T1R heterodimerization partner. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, $IP_3$, cAMP, G-protein activation-based assays; or receptor phosphorylation. The variant polypeptides of the invention may have an amino acid sequence having at least one sequence variation of SEQ ID NO:3, SEQ ID NO:6, or SEQ ID NO:9 that confers modified taste perception to one or more taste stimuli relative to a polypeptide of SEQ ID NO:3, SEQ ID NO:6, or SEQ ID NO:9, respectively.

The invention provides methods of identifying a canine T1R receptor variant that confers modified taste perception by expressing a variant of the polynucleotide of SEQ ID NO:1, SEQ ID NO:2, SEQ ID NO:4, SEQ ID NO:5, SEQ ID NO:7, or SEQ ID NO:8 homologous to the polynucleotide of SEQ ID NO:1, SEQ ID NO:2, SEQ ID NO:4, SEQ ID NO:5, SEQ ID NO:7, or SEQ ID NO:8, respectively, and detecting an increase or a decrease in the biological activity of the polypeptide encoded by the variant relative to the biological activity of the polypeptide encoded by SEQ ID NO:1, SEQ ID NO:2, SEQ ID NO:4, SEQ ID NO:5, SEQ ID NO:7, or SEQ ID NO:8, respectively.

The invention further provides kits for the detection of polynucleotides encoding a canine T1R receptor including a polynucleotide that specifically hybridizes to a polynucleotide encoding a polypeptide having an amino acid sequence of SEQ ID NO:3, SEQ ID NO:6, or SEQ ID NO:9, and instructions relating to detection thereof.

Also provided by the invention are antibodies that immunoreact specifically with at least one epitope of a polypeptide of the invention. The invention also includes kits for the detection of polypeptides encoding a canine T1R receptor including antibodies of the invention and instructions relating to detection.

Further provided by the invention are methods for identifying a compound that interacts with a canine T1R receptor by expressing a polynucleotide of the invention in the presence of a test compound, and detecting direct or indirect interaction between a polypeptide produced by the expression step with the compound. Also provided are methods for identifying compounds that interact with a canine T1R receptor by contacting a canine T1R receptor with a test compound, and detecting interaction between the receptor and the compound. The methods for detecting such interaction may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

The invention also provides methods for identifying agonists and antagonists of a canine T1R receptor. For example, the methods of the invention include identification of an agonist of a canine T1R receptor by expressing a polynucleotide of the invention in the presence of a test compound, and detecting increased transcription of said polynucleotide or increased biological activity of a polypeptide produced by the expression step in the presence of the compound relative to the rate of transcription or biological activity of the polypeptide in the absence of the compound. The biological activity detected may be an increase or decrease in the interaction between the T1R receptor and its T1R heterodimerization partner. For example, the T1R heterodimerization partner of a T1R1 or a T1R2 receptor may be T1R3 and vice versa. Also included are methods for identifying agonists of a canine T1R receptor by contacting a polypeptide of the invention with a test compound, and detecting an increase in biological activity of the polypeptide in the presence of the compound relative to biological activity of the polypeptide in the absence of the compound. The methods for identifying agonists of the dog T1R receptors may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

Methods for identifying antagonists of the polypeptides of the invention also are provided. For example, the invention provides methods for identifying antagonists of a canine T1R receptor by expressing a polynucleotide of the invention in the presence of a test compound, and detecting decreased transcription of said polynucleotide or decreased biological activity of a polypeptide produced by the expression step in the presence of the compound relative to the rate of transcription or biological activity of the polypeptide in the absence of the compound. Another example of methods for identifying an antagonist of a canine T1R receptor involves contacting a polypeptide of the invention with a test compound, and detecting a decrease in biological activity of the polypeptide in the presence of the compound relative to biological activity of the polypeptide in the absence of the compound. The methods for identifying the antagonists may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

Also encompassed by the invention are methods for predicting the taste perception of an organism such as a mammal. The methods may involve detection of a nucleotide sequence or amino acid sequence of the invention in a biological sample of the organism. For example, an organism in which a nucleotide sequence of the invention has been identified may perceive saccharin as bitter and/or D-fructose, β-D-fructose, or sucrose as sweet.

Another embodiment of the invention includes compounds and compositions for modifying, for example, stimulating, the taste perception of a mammal, such as a dog. The compounds and compositions may contain at least one of the polynucleotides of the invention, polypeptides of the invention, or compounds identified by the methods of the invention. Examples of the compositions of the invention include veterinary foods and drinks and pharmaceutical compositions. The compositions of the invention may include a pharmaceutically acceptable excipient. The compositions of the invention may be breed-specific. Methods for modifying the taste perception of a mammal (e.g., a dog) by administering to the mammal a polynucleotide of the invention, a polypeptide of the invention, and/or a compound identified according to the methods of the invention also are provided.

The invention further provides transgenic animals comprising a polynucleotide of the invention.

The materials, methods, and examples provided herein are illustrative only and are not intended to be limiting. Other features and advantages of the invention will be apparent from the following detailed description and claims.

BRIEF DESCRIPTION OF THE DRAWINGS

FIGS. 1A-L show the multiple cDNA sequence alignment of the T1R receptors of domestic dog (T1R1, SEQ ID NO:2; T1R2, SEQ ID NO:5; and T1R3, SEQ ID NO:8) with known cDNA nucleotide sequences of receptors of the T1R family from human (T1R1, SEQ ID NO:15; T1R2, SEQ ID NO:12; T1R3, SEQ ID NO:18), cat (T1R1, SEQ ID NO:133; T1R2, SEQ ID NO:135; T1R3, SEQ ID NO:137), mouse (T1R1, SEQ ID NO:13; T1R2, SEQ ID NO:10; T1R3, SEQ ID NO:16), and rat (T1R1, SEQ ID NO:14; T1R2, SEQ ID NO:11; T1R3, SEQ ID NO: 17). An asterisk (*) indicates a conserved nucleotide position among the sequences.

FIGS. 2A-D show the deduced amino acid sequences of the canine T1R taste receptors (T1R1, SEQ ID NO:3; T1R2, SEQ ID NO:6; and T1R3, SEQ ID NO:9) aligned with the amino acid sequences of members of the T1R receptor family from human (T1R1, SEQ ID NO:24; T1R2, SEQ ID NO:21; T1R3, SEQ ID NO:27), cat (T1R1, SEQ ID NO:134; T1R2, SEQ ID NO:136; T1R3, SEQ ID NO:138), rat (T1R1, SEQ ID NO:23; T1R2, SEQ ID NO:20; T1R3, SEQ ID NO:26), and mouse (T1R1, SEQ ID NO:22; T1R2, SEQ ID NO:19; T1R3, SEQ ID NO:25). An asterisk (*) indicates a conserved nucleotide position among the sequences. A colon (:) indicates an observed conserved amino acid substitution. A period (.) indicates an observed semi-conserved amino acid substitution.

FIG. 4A shows that the canine T1R1 receptor (SEQ ID NO:3) is a seven-transmembrane domain receptor. The structure of the canine T1R1 receptor was generated through use of the protein modeling programs available online through the European Bioinformatics Institute and the Sequence Analysis and Consulting Service of the University of California, San Francisco. FIG. 4B illustrates the predicted conformation of dog T1R2 receptor (SEQ ID NO:6) as a seven-transmembrane-domain receptor. FIG. 4C illustrates the predicted conformation of canine T1R3 receptor (SEQ ID NO:9) to be a seven-transmembrane domain structure. The dog T1R receptors T1R1, T1R2, and T1R3 are each predicted to have a seven transmembrane domain-structure, which is typical structure for G protein-coupled receptors involved in taste transduction.

DETAILED DESCRIPTION OF ILLUSTRATIVE EMBODIMENTS

Figure 3:
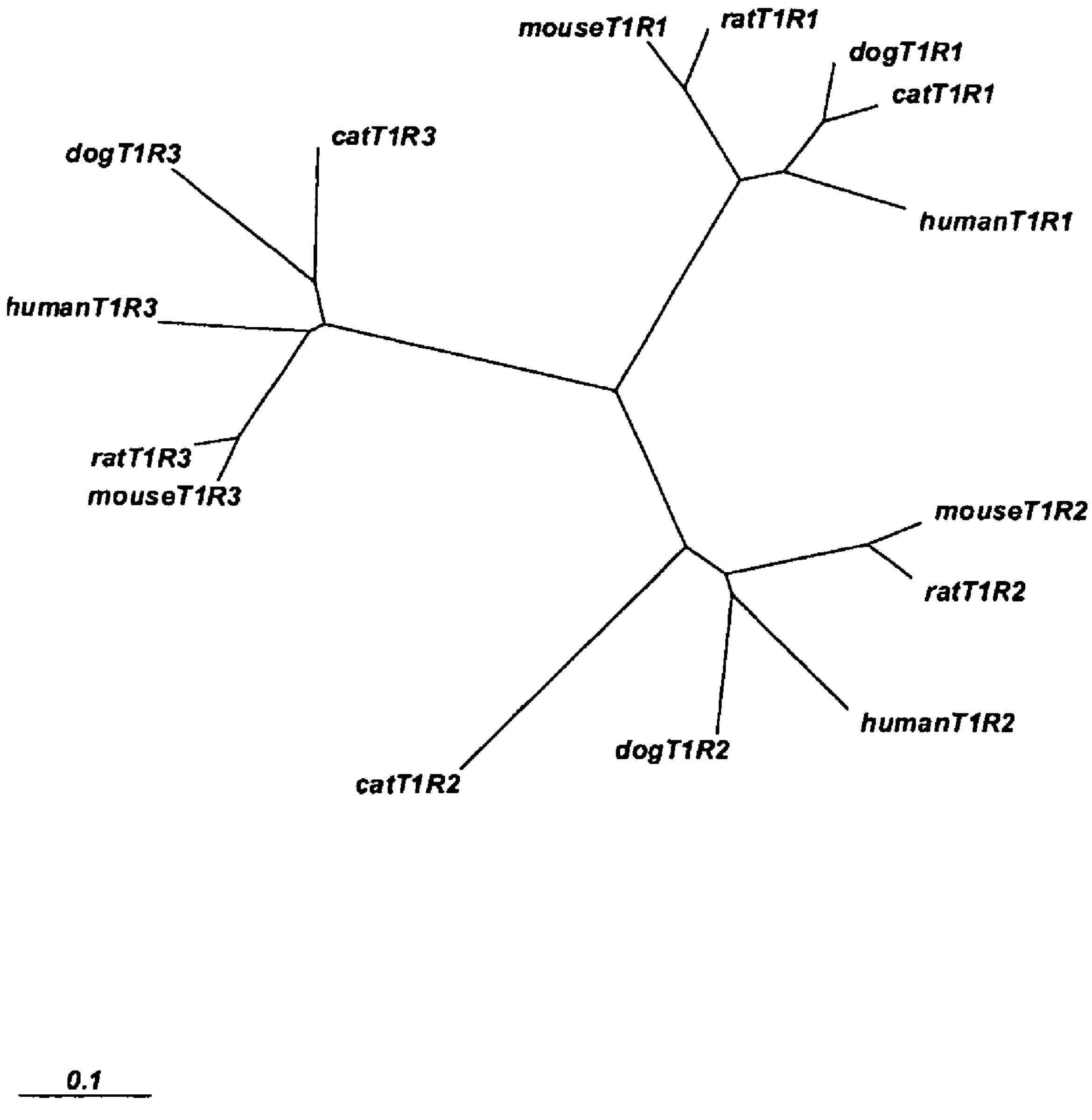
FIG. 3 illustrates a phylogenetic tree showing the relatedness of canine T1R receptor family to the T1R family of receptors including human, cat, rat, and mouse T1R1, T1R2, and T1R3. The T1R receptors of the rat and mouse are closely related, while the T1R receptors of human and dog diverge from rat and mouse. Interestingly, the sweet stimuli to which the rat and mouse respond are very similar, whereas those that stimulate human and those that stimulate dog differ from one another and from those for rat and mouse. For example, humans are unique in their ability to taste most high-intensity sweeteners, while dogs find saccharin bitter.

The reference works, patents, patent applications, and scientific literature that are referred to herein reflect in part the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology are known to those of skill in the art (Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991).

As used herein, "T1R receptor" encompasses the taste receptors of the T1R1, T1R2, and T1R3 types.

As used herein, "taste perception" refers to a response (e.g., biochemical, behavioral) or sensitivity of a T1R receptor of the invention to a taste stimulus. "Taste stimulus" as used herein refers to any compound that elicits, for example at the biochemical level (e.g., activation or inhibition of a taste receptor) or behavioral level (e.g., preference, indifference, or distaste), a taste response which would be perceived by a mammal as at least one of the five taste elements, including sweet, salty, sour, bitter, and umami. "Taste perception" or "taste stimulus," or variants thereof, does not require, though it does include, transmission of a neural signal resulting in in vivo sensation of taste by a mammal. Modification of taste perception includes an alteration of (enhancement of, reduction to, or change to) a biochemical response, an ingestive response, a taste preference, or general behavior of a mammal in response to a compound.

As used herein "polynucleotide" refers to a nucleic acid molecule and includes genomic DNA, cDNA, RNA, mRNA, mixed polymers, recombinant nucleic acids, fragments and variants thereof, and the like. Polynucleotide fragments of the invention comprise at least 10, and preferably at least 12, 14, 16, 18, 20, 25, 30, 35, 40, 45, 50, 75, 80, 90 or 100 consecutive nucleotides of a reference polynucleotide. Polynucleotide fragments of the invention may also comprise at least about 110, 120, 130, 140, 150, 160, 170, 180, 190, 200, 210, 220, 230, 240, 250, 275, 300, 325, 250, 275, 400, 425, 450, 475, 500, 525, 550, 575, 600, 625, 650, 675, 700, 725, 750, 775, 800, 825, 850, 875, 900, 925, 950, 975, or 1000 consecutive nucleotides of a reference polynucleotide. The polynucleotides of the invention include sense and antisense strands. The polynucleotides of the invention may be naturally occurring or non-naturally occurring polynucleotides. A "synthesized polynucleotide" as used herein refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. The polynucleotides of the invention may be single- or double-stranded. The polynucleotides of the invention may be chemically modified and may contain non-natural or derivatized nucleotide bases as will be readily appreciated by those skilled in the art. Such modifications include, for example, labels, methylation, substitution of one or more nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides, etc.), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Recombinant nucleic acid" is a nucleic acid generated by combination of two segments of nucleotide sequence. The combination may be, for example, by chemical means or by genetic engineering.

As used herein, "polynucleotide amplification" refers to a broad range of techniques for increasing the number of copies of specific polynucleotide sequences. Typically, amplification of either or both strand(s) of the target nucleic acid comprises the use of one or more nucleic acid-modifying enzymes, such as a DNA polymerase, ligase, RNA polymerase, or RNA-dependent reverse transcriptase. Examples of polynucleotide amplification include, but are not limited to, polymerase chain reaction (PCR), nucleic acid sequence based amplification (NASB), self-sustained sequence replication (3SR), strand displacement activation (SDA), ligase chain reaction, Qβ replicase system, and the like. A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152, Academic Press, Inc., San Diego, Calif. (Berger), which is incorporated herein by reference in its entirety.

As used herein, the term "oligonucleotide" or "primer" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar, or complementary DNA or RNA in a particular cell or tissue. Oligonucleotides comprise portions of a nucleic acid sequence having at least about 10 nucleotides and as many as about 50 nucleotides, often about 12 or 15 to about 40 or 45 nucleotides. They are chemically synthesized and may be used as probes. "Primer pair" refers to a set of primers including a 5' upstream primer that hybridizes with the 5' end of a target sequence to be amplified and a 3' downstream primer that hybridizes with the complement of the 3' end of the target sequence to be amplified.

As used herein, the term "probe" refers to nucleic acid sequences of variable length, for example between at least about 10 and as many as about 8,500 nucleotides, depending on use. Probes are used in the detection of identical, similar, or complementary target nucleic acid sequences, which target sequences may be single- or double-stranded. Longer probes are usually obtained from a natural or recombinant source, are highly specific, and are much slower to hybridize than oligomers, or shorter probes. They may be single- or double-stranded and are carefully designed to have specificity in PCR, hybridization membrane-based, or ELISA-like technologies. An "overgo probe" is a DNA probe comprising two short, overlapping DNA sequences (e.g., 10-50 nucleotides each) with a complementary overlapping region (e.g., 5-15 nucleotides) that is used in an overgo hybridization strategy. For example, an overgo probe may be two 22mers with an 8 bp complementary overlap, resulting in a 36mer overgo probe. As another example, an overgo probe may be two 24mers with an 8 bp complementary overlap, resulting in a 40mer overgo probe.

As used herein, the phrase "stringent hybridization conditions" or "stringent conditions" refers to conditions under which a probe, primer, or oligonucleotide will hybridize to its target sequence, but to a minimal number of or no other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Stringent temperature conditions will generally include temperatures in excess of 30° C., typically in excess of 37° C., and may be in excess of 45° C. Stringent salt conditions will ordinarily be less than 1.0 M, typically less than 0.5 M, and may be less than 0.2 M. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers, or oligonucleotides (e.g., 10 to 50 nucleotides) and at least about 60° C. for longer probes, primers, or oligonucleotides. Stringent conditions may also be achieved with the addition of destabilizing agents, such as formamide.

As used herein "antisense oligonucleotide" refers to a nucleic acid molecule that is complementary to at least a portion of a target nucleotide sequence of interest and specifically hybridizes to the target nucleotide sequence under physiological conditions. The term "double stranded RNA" or "dsRNA" as used herein refers to a double-stranded RNA molecule capable of RNA interference, including short interfering RNA (siRNA) (see for example, Bass, *Nature,* 411, 428-429 (2001); Elbashir et al., *Nature,* 411, 494-498 (2001)).

As used herein, the term "complementary" refers to Watson-Crick basepairing between nucleotide units of a nucleic acid molecule.

The term "marker gene" or "reporter gene" refers to a gene encoding a product that, when expressed, confers a phenotype at the physical, morphologic, or biochemical level on a transformed cell that is easily identifiable, either directly or indirectly, by standard techniques and includes, but is not limited to, genes encoding proteins that confer resistance to toxins or antibiotics such as ampicillin, neomycin, and methotroxate; genes encoding proteins that complement auxotrophic deficiencies; and genes encoding proteins that supply critical components not available from complex media. Examples of marker genes include green fluorescent protein (GFP), red fluorescent protein (DsRed), cyan fluorescent protein (CFP), yellow fluorescent protein (YFP), cerianthus orange fluorescent protein (cOFP), alkaline phosphatase (AP), β-lactamase, chloramphenicol acetyltransferase (CAT), adenosine deaminase (ADA), aminoglycoside phosphotransferase (neor, G418r) dihydrofolate reductase (DHFR), hygromycin-B-phosphotransferase (HPH), thymidine kinase (TK), lacZ (encoding β-galactosidase), β-lactamase, luciferase (luc), and xanthine guanine phosphoribosyltransferase (XGPRT). As with many of the standard procedures associated with the practice of the invention, skilled artisans will be aware of additional sequences that can serve the function of a marker or reporter. Thus, this list is merely meant to show examples of what can be used and is not meant to limit the invention.

As used herein, the term "promoter" refers to a regulatory element that regulates, controls, or drives expression of a nucleic acid molecule of interest and can be derived from sources such as from adenovirus, SV40, parvoviruses, vaccinia virus, cytomegalovirus, or mammalian genomic DNA. Examples of suitable promoters include, but are not limited to, CMV, MSH2, trp, lac, phage, and TRNA promoters. Suitable promoters that can be used in yeast include, but are not limited to, such constitutive promoters as 3-phosphoglycerate kinase and various other glycolytic enzyme gene promoters such as enolase or glyceraldehyde-3-phosphate dehydrogenase, or such inducible promoters as the alcohol dehydrogenase 2 promoter or metallothionine promoter. Again, as with many of the standard procedures associated with the practice of the invention, skilled artisans will be aware of additional promoters that can serve the function of directing the expression of a marker or reporter. Thus, the list is merely meant to show examples of what can be used and is not meant to limit the invention.

"Operably linked" refers to juxtaposition wherein the components are in a functional relationship. For example, a promoter is operably linked or connected to a coding sequence if it controls the transcription or expression of the sequence.

The terms "polypeptide," "peptide," and "protein" are used interchangeably herein. "Polypeptide" refers to a polymer of amino acids without referring to a specific length. Polypeptides of the invention include peptide fragments, derivatives, and fusion proteins. Peptide fragments preferably have at least about 10, 15, 20, 25, 30, 35, 40, 45, 50, 60, 70, 80, 90, or 100 amino acids. Some peptide fragments of the invention are biologically active. Biological activities include immunogenicity, ligand binding, and activity associated with the reference peptide. Immunogenic peptides and fragments of the invention generate an epitope-specific immune response, wherein "epitope" refers to an immunogenic determinant of a peptide and preferably contains at least three, five, eight, nine, ten, fifteen, twenty, thirty, forty, forty-five, or fifty amino acids. Some immunogenic peptides of the invention generate an immune response specific to that peptide. Polypeptides of the invention include naturally occurring and non-naturally occurring peptides. The term includes modified polypeptides (wherein examples of such modifications include glycosylation, acetylation, phosphorylation, carboxylation, ubiquitination, labeling, etc.), analogs (such as non-naturally occurring amino acids, substituted linkages, etc.), and functional mimetics. A variety of methods for labeling polypeptides are well known in the art and include radioactive isotopes such as $^{32}P$ or $^{35}S$, ligands that bind to labeled antiligands (e.g., antibodies), fluorophores, chemiluminescent agents, enzymes, and antiligands.

As used herein, the term "amino acid" denotes a molecule containing both an amino group and a carboxyl group. In some embodiments, the amino acids are α-, β-, γ- or δ-amino acids, including their stereoisomers and racemates. As used herein the term "L-amino acid" denotes an α-amino acid having the L configuration around the α-carbon, that is, a carboxylic acid of general formula CH(COOH)(NH2)-(side chain), having the L-configuration. The term "D-amino acid" similarly denotes a carboxylic acid of general formula CH(COOH)(NH2)-(side chain), having the D-configuration around the α-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. Amino acid substituents may be attached, for example, through their carbonyl groups through the oxygen or carbonyl carbon thereof, or through their amino groups, or through functionalities residing on their side chain portions.

The amino acid sequences are presented in the amino (N) to carboxy (C) direction, from left to right. The N-terminal α-amino group and the C-terminal β-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commission, or amino acids are represented by their three letters code designations.

As used herein, the term "antibody" is meant to refer to complete, intact antibodies, and Fab, Fab', $F(ab)_2$, $F_v$, and other fragments thereof. Complete, intact antibodies include antibodies such as polyclonal antibodies, monoclonal antibodies, chimeric antibodies, and humanized antibodies, felinized antibodies, and immunologic binding equivalents thereof. The antibodies of the invention may be labeled or unlabeled. Examples of labels of antibodies include, but are not limited to, radionuclides, enzymes, substrates, cofactors, inhibitors, fluorescent agents, chemiluminescent agents, magnetic particles, and the like. Recombinant immunoglobulins are included in the invention.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between two molecules can be detected using a labeled compound. Other methods of detecting binding are well-known to those of skill in the art.

As used herein, the term "contacting" means bringing together, either directly or indirectly, a compound into physical proximity to a molecule of interest. Contacting may occur, for example, in any number of buffers, salts, solutions, or in a cell or cell extract.

As used herein, the terms "modulates" or "modifies" means an increase or decrease in the amount, quality, or effect of a particular activity or protein. "Modulators" refer to any inhibitory or activating molecules identified using in vitro and in vivo assays for, e.g., agonists, antagonists, and their homologs, including fragments, variants, and mimetics, as defined herein, that exert substantially the same biological activity as the molecule. "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred embodiments of the invention, the level of inhibition or upregulation of the expression or biological activity of a molecule or pathway of interest refers to a decrease (inhibition or downregulation) or increase (upregulation) of greater than about 50%, 60%, 70%, 75%, 80%, 85%, 90%, 91%, 92%, 93%, 94%, 95%, 96%, 97%, 98%, or 99%. The inhibition or upregulation may be direct, i.e., operate on the molecule or pathway of interest itself, or indirect, i.e., operate on a molecule or pathway that affects the molecule or pathway of interest.

A "purified" or "substantially purified" polynucleotide or polypeptide is substantially separated from other cellular components that naturally accompany a native (or wild-type) nucleic acid or polypeptide and/or from other impurities (e.g., agarose gel). A purified polypeptide or protein will comprise about 60% to more than 99% w/w of a sample, and may be about 90%, about 95%, about 98%, about 99% or preferably about 100% pure. As used herein, the term "isolated" refers to a molecule that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

"About" as used herein refers to +/−10% of the reference value.

As used herein, "variant" nucleotide or amino acid sequences refer to homologs, including, for example, isoforms, species variants, allelic variants, and fragments of the sequence of interest. "Homologous nucleotide sequence" or "homologous amino acid sequence," or variations thereof, refers to sequences characterized by a homology, at the nucleotide level or amino acid level, of at least about 60%, at least about 70%, at least about 75%, at least about 80%, at least about 81%, at least about 82%, at least about 83%, at least about 84%, at least about 85%, preferably at least about 90%, at least about 95%, at least about 98%, or at least about 99%, and more preferably 100%, to a reference sequence, or portion or fragment thereof encoding or having a functional domain. The reference sequence may include, for example, but is not limited to the nucleic acid sequence of SEQ ID NO:1, SEQ ID NO:2, SEQ ID NO:4, SEQ ID NO:5, SEQ ID NO:7, and SEQ ID NO:8, or portions thereof which encode a functional domain of the encoded polypeptide, SEQ ID NO:3, SEQ ID NO:6, or SEQ ID NO:9, or the polypeptide having amino acid sequence SEQ ID NO:3, SEQ ID NO:6, or SEQ ID NO:9. Functional domains of the T1R receptors of the invention include extracellular domains, transmembrane domains, and intracellular domains. Examples of functional domains of the T1R1 polypeptide of SEQ ID NO:3 include extracellular domains corresponding to residues 1-565, 624-637, 704-725, and 784-786; transmembrane domains corresponding to residues 566-588, 601-623, 638-660, 681-703, 726-748, 761-783, and 787-809; and intracellular domains corresponding to residues 589-600, 661-680, 749-760, and 810-841. Examples of functional domains of the T1R2 receptor of SEQ ID NO:6 include extracellular domains corresponding to residues 1-565, 622-634, 699-723, and 778-782; transmembrane domains corresponding to residues 566-587, 602-621, 635-658, 678-698, 724-744, 758-777, and 783-802; and intracellular domains corresponding to residues 588-601, 659-677, 745-757, and 803-836. Examples of functional domains of the T1R3 polypeptide of SEQ ID NO:9 include the extracellular domains corresponding to residues 1-566, 623-636, 702-725, or 780-793; transmembrane domains corresponding to residues 567-589, 600-622, 637-659, 679-701, 726-748, 761-779, or 794-816; and intracellular domains corresponding to residues 590-599, 660-678, 749-760, or 817-845. Isoforms can be expressed in different tissues of the same organism as a result of, for example, alternative splicing of RNA. Alternatively, isoforms can be encoded by different genes. Homologous nucleotide sequences include nucleotide sequences encoding for a species variant of a protein. Homologous nucleotide sequences also include, but are not limited to, naturally occurring allelic variations and mutations of the nucleotide sequences set forth herein. Study of mutations and polymorphisms of the T1R receptor polynucleotide sequences may explain breed-specific and/or individual taste preferences of a mammal such as a dog. Additionally, sequence variants of the T1R receptors may be associated with specific disease states, such that knowledge of the genes allows diagnosis and treatment of T1R-associated disorders (e.g., obesity, diabetes). Homologous amino acid sequences include those amino acid sequences which encode conservative amino acid substitutions in polypeptides having an amino acid sequence of SEQ ID NO:3, SEQ ID NO:6, or SEQ ID NO:9, as well as in polypeptides identified according to the methods of the invention. Percent homology may be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Smith and Waterman, *Adv. Appl. Math.,* 2: 482-489, 1981). Nucleic acid fragments of the invention preferably have at least about 5, at least about 10, at least about 15, at least about 20, at least about 25, at least about 50, or at least about 100 nucleotides of the reference nucleotide sequence. The nucleic acid fragments of the invention may encode a polypeptide having at least one biological property, or function, that is substantially similar to a biological property of the polypeptide encoded by the full-length nucleic acid sequence.

As is well known in the art, because of the degeneracy of the genetic code, there are numerous DNA and RNA molecules that can code for the same polypeptide as that encoded by a nucleotide sequence of interest. The present invention, therefore, contemplates those other DNA and RNA molecules which, on expression, encode a polypeptide encoded by the nucleic acid molecule of interest. DNA and RNA molecules other than those specifically disclosed herein characterized simply by a change in a codon for a particular amino acid, are within the scope of this invention.

Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the nucleic acid sequence using recombinant DNA techniques. Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis.

A polypeptide variant of the present invention may exhibit substantially the biological activity of a naturally occurring reference polypeptide. "Biological activity" as used herein refers to the level of a particular function (for example, enzymatic activity) of a molecule or pathway of interest in a biological system. "Wild-type biological activity" refers to the normal level of function of a molecule or pathway of interest. "Reduced biological activity" refers to a decreased level of function of a molecule or pathway of interest relative to a reference level of biological activity of that molecule or pathway. For example, reduced biological activity may refer to a decreased level of biological activity relative to the wild-type biological activity of a molecule or pathway of interest. "Increased biological activity" refers to an increased level of function of a molecule or pathway of interest relative to a reference level of biological activity of that molecule or pathway. For example, increased biological activity may refer to an increased level of biological activity relative to the wild-type biological activity of a molecule or pathway of interest.

With respect to the polypeptides of the present invention, "biological activity" is deemed to encompass, among other things, heterodimerization of the polypeptide to its cognate heterodimerization partner, the ability to elicit an adaptive immune response, and the ability to activate or inhibit a specific biochemical or signal transduction pathway. Heterodimerization may be measured by any means known in the art, such as size exclusion chromatography, or an electrophoretic mobility shift assay. Immunogenicity may be measured by means that are well known and practiced in the art. The activation or inhibition of a biochemical or signal transduction pathway may also be determined by any means known in the art. For example, any number of assays that measure the interaction of a G protein-coupled receptor with the G protein, or assays that measure taste transduction may be utilized. See e.g., Ruiz-Avila, L. et al. *Chem. Senses* 25:361-368 (2000); Ming, D. et al. *Proc. Natl. Acad. Sci. USA* 95:8933-8938 (1998); Margolskee, R F *J. Biol. Chem.* 277: 1-4 (2002), Bidlack J *M Methods Mol. Biol.* 237:135-43 (2004); Gale, C, et al. *Nat Methods* 2:177-184 (2005), Nelson G, et al. *Cell* 106: 381-390 (2001), Nelson G, et al. *Nature* 416: 199-202 (2002), Li X, et al. *Proc Natl Acad Sci USA* 99:4692-4696 (2002), Xu, H et al. *Proc Natl Acad Sci USA* 101: 14258-14263 (2004), and Yan W, et al. *Am J Physiol Cell Physiol* 280: C742-751 (2001), each of which is hereby incorporated by reference in its entirety. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, $IP_3$, cAMP, G-protein activation-based assays; or receptor phosphorylation.

"Substantially the same" biological activity refers to a polypeptide fragment, derivative, homolog, analog, or variant retaining at least about 50%, 55%, 60%, 65%, 70%, preferably at least about 75%, 80%, 85%, 90%, more preferably at least about 91%, 92%, 93%, 94%, 95%, and most preferably at least about 96%, 97%, 98%, 99% or greater biological activity of the parent polypeptide. The extent to which a polypeptide fragment, derivative, homolog, analog, or variant retains the biological activity of the parent polypeptide may be assessed by any means available in the art, including, but not limited to, the assays listed or described herein.

Reference to exhibiting "substantially the biological activity of a naturally occurring polypeptide" indicates that variants within the scope of the invention can comprise conservatively substituted sequences, meaning that one or more amino acid residues of a polypeptide are replaced by different residues that do not alter the secondary and/or tertiary structure of the polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges are known in the art (Bowie et al., *Science,* 247: 1306-1310, 1990). Other polypeptide homologs which might retain substantially the biological activities of the reference polypeptide are those where amino acid substitutions have been made in areas outside functional regions of the protein.

A nucleotide and/or amino acid sequence of a nucleic acid molecule or polypeptide employed in the invention or of a compound identified by the screening method of the invention may be used to search a nucleotide and amino acid sequence databank for regions of similarity using Gapped BLAST (Altschul et al., *Nuc. Acids Res.,* 25: 3389, 1997). Briefly, the BLAST algorithm, which stands for Basic Local Alignment Search Tool is suitable for determining sequence similarity (Altschul et al., *J. Mol. Biol.,* 215: 403-410, 1990). Software or performing BLAST analyses is publicly available online through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., *J. Mol. Biol.,* 215: 403-410, 1990). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T, and X determine the sensitivity and speed of the alignment. The BLAST program uses as defaults a word length (W) of 11, the BLOSUM62 scoring matrix (Henikoff et al., *Proc. Natl. Acad. Sci. USA,* 89: 10915-10919, 1992) alignments (B) of 50, expectation (E) of 10, M=5, N=4, and a comparison of both strands. The BLAST algorithm (Karlin et al., *Proc. Natl. Acad. Sci. USA,* 90: 5873-5787, 1993) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA if the smallest sum probability in comparison of the test nucleic acid to the reference nucleic acid is less than about 1, preferably less than about 0.1, more preferably less than about 0.01, and most preferably less than about 0.001.

The term "mimetic" as used herein refers to a compound that is sterically similar to a reference compound. Mimetics are structural and functional equivalents to the reference compounds.

The terms "patient" and "subject" are used interchangeably herein and include, but are not limited to, avians, felines, canines, bovines, ovines, porcines, equines, rodents, simians, and humans. "Host cell" includes, for example, a prokaryotic cell, such as a bacterial cell, or eukaryotic cell, such as a mammalian cell (e.g., human, rodent, canine, feline), a yeast cell, or a plant cell. "Rodents" include, for example, rats and mice.

The term "treatment" as used herein refers to any indicia of success of prevention, treatment, or amelioration of a disease or condition. Treatment includes any objective or subjective parameter, such as, but not limited to, abatement, remission, normalization of receptor activity, reduction in the number or severity of symptoms or side effects, or slowing of the rate of degeneration or decline of the patient. Treatment also includes a prevention of the onset of symptoms in a patient that may be at increased risk for or is suspected of having a disease or condition but does not yet experience or exhibit symptoms thereof.

As used herein, the term "compound" means any identifiable chemical or molecule, including, but not limited to a small molecule, peptide, protein, sugar, nucleotide, or nucleic acid. Such compound can be natural or synthetic.

Polynucleotides

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression of the expression of a T1R receptor in a cultured cell, a tissue, or an animal; for therapeutic purposes; or to provide a model for diseases or conditions characterized by aberrant T1R expression. Specifically excluded from the definition of polynucleotides of the invention are entire isolated, non-recombinant native chromosomes of host cells. Polynucleotides of the invention include the nucleotide sequences of SEQ ID NO: 1, SEQ ID NO:2, SEQ ID NO:4, SEQ ID NO:5, SEQ ID NO:7, and SEQ ID NO:8. It will be appreciated that numerous other polynucleotide sequences exist that also encode the T1R receptors of the invention due to the well-known degeneracy of the universal genetic code.

The invention also provides a purified and isolated polynucleotide comprising a nucleotide sequence that encodes a canine polypeptide, wherein the polynucleotide hybridizes to a polynucleotide having a sequence of SEQ ID NO:1, SEQ ID NO:2, SEQ ID NO:4, SEQ ID NO:5, SEQ ID NO:7, or SEQ ID NO:8, or the non-coding strand complementary thereto, under stringent hybridization conditions.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a T1R polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding a T1R receptor (conventionally followed by second strand synthesis of a complementary strand to provide a double-stranded DNA).

One embodiment of the DNA of the invention comprises a double-stranded molecule along with the complementary molecule (the "non-coding strand" or "complement") having a sequence unambiguously deducible from the coding strand according to Watson-Crick base-pairing rules for DNA.

The present invention includes fragments of nucleotide sequences encoding a T1R receptor comprising at least 10, and preferably at least 12, 14, 16, 18, 20, 25, 30, 35, 40, 45, 50, 75, 80, 90, 100, 110, 120, 130, 140, 150, 160, 170, 180, 190, 200, 210, 220, 230, 240, 250, 275, 300, 325, 250, 275, 400, 425, 450, 475, 500, 525, 550, 575, 600, 625, 650, 675, 700, 725, 750, 775, 800, 825, 850, 875, 900, 925, 950, 975, or 1000 consecutive nucleotides of a polynucleotide encoding a T1R receptor. Fragment polynucleotides of the invention may comprise sequences unique to the T1R-encoding polynucleotide sequence, and therefore hybridize under highly stringent or moderately stringent conditions only (i.e., "specifically") to polynucleotides encoding a T1R receptor (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragments of T1R polynucleotides. One or more polynucleotides can be included in kits that are used to detect the presence of a polynucleotide encoding a T1R receptor, or used to detect variations in a polynucleotide sequence encoding a T1R receptor.

The invention also embraces DNAs encoding T1R polypeptides that hybridize under high stringency conditions to the non-coding strand, or complement, of the polynucleotides.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described, for example, in Ausubel et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described, for example, in Sambrook et al., (Eds.), Molecular Cloning: A Laboratory Manual, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode T1R receptors from different sources (i.e., different tissues or different organisms) through a variety of means well known to the skilled artisan and as disclosed by, for example, Sambrook et al., Molecular cloning: a laboratory manual, Second Edition, Cold Spring Harbor Press, Cold Spring Harbor, N.Y. (1989).

For example, DNA that encodes a T1R receptor may be obtained by screening mRNA, cDNA, or genomic DNA with oligonucleotide probes generated from the T1R gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising a T1R nucleotide sequence can alternatively be synthesized by use of the polymerase chain reaction (PCR) procedure, with the PCR oligonucleotide primers produced from the nucleotide sequences provided herein. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, Methods in Enzymology 152, Academic Press, Inc., San Diego, Calif. (Berger), which is incorporated herein by reference in its entirety.

The polynucleotides of the invention may be used in hybridization techniques known to those skilled in the art, including but not limited to, Northern and Southern blotting and overgo hybridization (see infra). For example, polynucleotide probes of the invention may be used in tissue distribution studies and diagnostic assays.

Automated sequencing methods can be used to obtain or verify the T1R receptor-encoding nucleotide sequence. The nucleotide sequences of the present invention are believed to be accurate. However, as is known in the art, nucleotide sequences obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphism (RFLP) associated with certain disorders, for genetic mapping, and for methods for predicting the taste perception of an organism such as a mammal involving detection of a nucleotide sequence of the invention in a biological sample of the organism. For example, an organism in which a nucleotide sequence of the invention has been identified may perceive saccharin as bitter and/or D-fructose, β-D -fructose, or sucrose as sweet.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding a T1R receptor and/or to express DNA which encodes a T1R receptor. Examples of vectors include, but are not limited to, plasmids, phages, cosmids, episomes, viral particles or viruses, and integratable DNA fragments (i.e., fragments integratable into the host genome by homologous recombination). Examples of viral particles include, but are not limited to, adenoviruses, baculoviruses, parvoviruses, herpesviruses, poxviruses, adeno-associated viruses, Semliki Forest viruses, vaccinia viruses, and retroviruses. Examples of expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™(Invitrogen).

Expression constructs may comprise T1R-encoding polynucleotides operably linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, or promote, homologous recombination in a host cell. Constructs of the invention also may include sequences necessary for replication in a host cell.

Expression constructs may be utilized for production of an encoded protein, but may also be utilized simply to amplify a T1R-encoding polynucleotide sequence. In some embodiments, the vector is an expression vector wherein a polynucleotide of the invention is operably linked to a polynucleotide comprising an expression control sequence. Autonomously replicating recombinant expression constructs such as plasmid and viral DNA vectors incorporating polynucleotides of the invention are also provided. Some expression vectors are replicable DNA constructs in which a DNA sequence encoding a T1R receptor is operably linked or connected to suitable control sequence(s) capable of effecting the expression of the receptor in a suitable host. Amplification vectors do not require expression control domains, but rather need only the ability to replicate in a host, such as conferred by an origin of replication, and a selection gene to facilitate recognition of transformants. The need for control sequences in the expression vector will vary depending upon the host selected and the transformation method chosen. Control sequences include a transcriptional promoter, an optional operator sequence to control transcription, a sequence encoding suitable mRNA ribosomal binding, and sequences which control the termination of transcription and translation.

Vectors of the invention may contain a promoter that is recognized by the host organism. The promoter sequences of the present invention may be prokaryotic, eukaryotic, or viral. Examples of suitable prokaryotic sequences include the $P_R$ and $P_L$ promoters of bacteriophage lambda (The Bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety), the trp, recA, heat shock, and lacz promoters of *E. coli* and the SV40 early promoter (Benoist et al. *Nature,* 1981, 290, 304-310), which is incorporated herein by reference in its entirety. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in vectors of the invention. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding a T1R receptor, resulting in the expression of the mature protein.

Moreover, suitable expression vectors can include an appropriate marker that allows the screening of transformed host cells. The transformation of the selected host is carried out using any one of the various techniques well known to the expert in the art and described in Sambrook et al., supra.

An origin of replication or autonomously replicating sequence (ARS) can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and T1R DNA. An example of a suitable marker is dihydrofolate reductase (DHFR) or thymidine kinase (see, U.S. Pat. No. 4,399,216).

Additional regulatory sequences that may be included in the polynucleotides of the invention include secretion signals which allow the encoded polypeptide to cross and/or lodge in cell membranes, or be secreted from the cell.

Nucleotide sequences encoding a T1R receptor may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al, *Mol. Cell. Biol.,* 1983, 3, 280, Cosman et al., *Mol. Immunol.,* 1986, 23, 935, Cosman et al., *Nature,* 1984, 312, 768, EP-A-0367566, and WO 91/18982, each of which is incorporated herein by reference in its entirety.

Host Cells

According to another aspect of the invention, host cells are provided, including prokaryotic and eukaryotic cells, comprising a polynucleotide of the invention (or vector of the invention) in a manner that permits expression of the encoded T1R polypeptide. Polynucleotides of the invention may be introduced into the host cell as part of a circular plasmid, or as linear DNA comprising an isolated protein-coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cell systems.

The invention provides host cells that are transformed or transfected (stably or transiently) with polynucleotides of the invention or vectors of the invention. As stated above, such host cells are useful for amplifying the polynucleotides and also for expressing a T1R polypeptide or fragment thereof encoded by the polynucleotide.

In still another related embodiment, the invention provides a method for producing a T1R polypeptide (or fragment thereof) comprising the steps of growing a host cell of the invention in a nutrient medium and isolating the polypeptide or variant thereof from the cell or the medium. Because the T1R receptor is a membrane-spanning polypeptide, it will be appreciated that, for some applications, such as certain activity assays, the preferable isolation may involve isolation of cell membranes containing the polypeptide embedded therein, whereas for other applications a more complete isolation may be preferable.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces*, and *Staphylococcus*.

If a eukaryotic expression vector is employed, then the appropriate host cell would be any eukaryotic cell capable of expressing the cloned sequence. Eukaryotic cells may be cells of higher eukaryotes. Suitable eukaryotic cells include, but are not limited to, non-human mammalian tissue culture cells and human tissue culture cells. Host cells include, but are not limited to, insect cells, HeLa cells, Chinese hamster ovary cells (CHO cells), African green monkey kidney cells (COS cells), human HEK-293 cells, and murine 3T3 fibroblasts. Propagation of such cells in cell culture has become a routine procedure (see, TISSUE CULTURE, Academic Press, Kruse and Patterson, eds. (1973), which is incorporated herein by reference in its entirety).

In addition, a yeast host may be employed as a host cell. Yeast cells include, but are not limited to, the genera *Saccharomyces, Pichia*, and *Kluveromyces*. Yeast hosts may be *S. cerevisiae* and *P. pastoris*. Yeast vectors may contain an origin of replication sequence from a 2T yeast plasmid, an autonomous replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In some embodiments, the polypeptides of the invention are expressed using a baculovirus expression system (see, Luckow et al., *Bio/Technology,* 1988, 6, 47; BACULOVIRUS EXPRESSION VECTORS: A LABORATORY MANUAL, O'Reilly et al. (Eds.), W.H. Freeman and Company, New York, 1992; and U.S. Pat. No. 4,879,236, each of which is incorporated herein by reference in its entirety). In addition, the MAXBAC™ complete baculovirus expression system (Invitrogen) can, for example, be used for production in insect cells.

Host cells of the invention are a valuable source of immunogen for development of antibodies specifically immunoreactive with the T1R receptor. Host cells of the invention also are useful in methods for the large-scale production of T1R polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of the canine T1R receptor-encoding nucleotide sequence allows for modification of cells to permit, or increase, expression of endogenous receptor. Cells can be modified (e.g., by homologous recombination) to provide increased expression by replacing, in whole or in part, the naturally occurring T1R promoter with all or part of a heterologous promoter so that the cells express the receptor at higher or lower levels. The heterologous promoter is inserted in such a manner that it is operably linked to endogenous T1R coding sequence. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the T1R coding sequence, amplification of the marker DNA by standard selection methods results in co-amplification of the T1R coding sequences in the cells.

Knock-out and Transplacement Animals

The DNA sequence information provided by the present invention also makes possible the development (e.g., by homologous recombination strategies; see Capecchi, *Science* 244:1288-1292 (1989), which is incorporated herein by reference) of transgenic or gene-targeted animals, including, for example, animals that fail to express functional T1R ("knock-out") or that express a variant thereof ("transplacement"). Such animals (especially small laboratory animals such as rats, rabbits, mice, and cats) are useful as models for studying the in vivo activities of T1R receptors and modulators of T1R receptors.

Antisense and siRNA

Also encompassed by the invention are antisense and short interfering polynucleotides that recognize and hybridize to polynucleotides encoding T1R receptors. Full-length and fragment antisense polynucleotides are provided. Fragment antisense molecules of the invention include those that specifically recognize and hybridize to T1R RNA (as determined by sequence comparison of DNA encoding T1R receptor to DNA encoding other known molecules). Identification of sequences unique to T1R-encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulation of expression of T1R receptor by those cells expressing T1R mRNA.

Antisense nucleic acids (preferably 10 to 30 base-pair oligonucleotides) capable of specifically binding to T1R expression control sequences or T1R RNA are introduced into cells (e.g., by a viral vector or colloidal dispersion system such as a liposome). The antisense nucleic acid binds to the target nucleotide sequence in the cell and prevents transcription and/or translation of the target sequence. Phosphorothioate and methylphosphonate antisense oligonucleotides are specifically contemplated for therapeutic use by the invention. Locked nucleic acids are also specifically contemplated for therapeutic use by the present invention. (See, for example, Wahlestedt et al., *Proc. Natl. Acad. Sci. USA,* 97(10), 5633-5638 (2000), which is incorporated by reference in its entirety.) The antisense oligonucleotides may be further modified by adding poly-L-lysine, transferrin polylysine, or cholesterol moieties at their 5' end. Suppression of T1R expression at either the transcriptional or translational level is useful to generate cellular or animal models for diseases/conditions characterized by aberrant T1R expression.

Antisense oligonucleotides, or fragments of nucleotide sequence of SEQ ID NO:1, SEQ ID NO:2, SEQ ID NO:4, SEQ ID NO:5, SEQ ID NO:7, or SEQ ID NO:8, or sequences complementary or homologous thereto, derived from the nucleotide sequences of the present invention encoding T1R receptors are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides may be directed to regulatory regions of a T1R nucleotide sequence, or mRNA corresponding thereto, including, but not limited to, the initiation codon, TATA box, enhancer sequences, and the like.

Those of skill in the art recognize that the antisense oligonucleotides that inhibit the expression and/or biological activity of a T1R receptor may be predicted using any gene encoding a T1R receptor. Specifically, antisense nucleic acid molecules comprise a sequence preferably complementary to at least about 5, 10, 15, 20, 25, 30, 35, 40, 45, 50, 100, 250 or 500 nucleotides or an entire T1R receptor gene sequence. The antisense oligonucleotides may comprise a sequence complementary to about 15 consecutive nucleotides of the coding strand of the T1R receptor-encoding sequence.

In one embodiment, an antisense nucleic acid molecule is antisense to a "coding region" of the coding strand of a nucleotide sequence encoding a T1R protein. The coding strand may also include regulatory regions of the T1R sequence. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a T1R protein. The term "noncoding region" refers to 5' and 3' sequences which flank the coding region that are not translated into amino acids (i.e., also referred to as 5' and 3' untranslated regions (UTR)).

Antisense oligonucleotides may be directed to regulatory regions of a nucleotide sequence encoding a T1R protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of a T1R mRNA, but also may be an oligonucleotide that is antisense to only a portion of the coding or noncoding region of the mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length.

Another means to inhibit the activity of a T1R receptor according to the invention is via RNA interference (RNAi) (see e.g., Elbashir et al., *Nature,* 411:494-498 (2001); Elbashir et al., *Genes Development,* 15:188-200 (2001)). RNAi is the process of sequence-specific, post-transcriptional gene silencing, initiated by double-stranded RNA (dsRNA) that is homologous in sequence to the silenced gene (e.g., is homologous in sequence to the sequence encoding a T1R receptor, for example but not limited to the sequence as set forth in SEQ ID NO:1, SEQ ID NO:2, SEQ ID NO:4, SEQ ID NO:5, SEQ ID NO:7, or SEQ ID NO:8). siRNA-mediated silencing is thought to occur post-transcriptionally and/or transcriptionally. For example, siRNA duplexes may mediate post-transcriptional gene silencing by reconstitution of siRNA-protein complexes (siRNPs), which guide mRNA recognition and targeted cleavage.

Accordingly, another form of a T1R inhibitory compound of the invention is a short interfering RNA (siRNA) directed against a T1R-encoding sequence. Exemplary siRNAs are siRNA duplexes (for example, 10-25, preferably 20, 21, 22, 23, 24, or 25 residues in length) having a sequence homologous or identical to a fragment of the T1R sequence set forth as SEQ ID NO:1, SEQ ID NO:2, SEQ ID NO:4, SEQ ID NO:5, SEQ ID NO:7, or SEQ ID NO:8 and having a symmetric 2-nucleotide 3'-overhang. The 2-nucleotide 3' overhang may be composed of (2'-deoxy) thymidine because it reduces costs of RNA synthesis and may enhance nuclease resistance of siRNAs in the cell culture medium and within transfected cells. Substitution of uridine by thymidine in the 3' overhang is also well tolerated in mammalian cells, and the sequence of the overhang appears not to contribute to target recognition.

Polypeptides

The invention also provides purified and isolated mammalian T1R receptor polypeptides encoded by a polynucleotide of the invention. Some embodiments include a canine T1R polypeptide comprising the amino acid sequence of SEQ ID NO:3, SEQ ID NO:6, or SEQ ID NO:9, or fragments thereof comprising an epitope specific to the polypeptide. A reference to "epitope specific to" or "polypeptide-specific epitope," or variations thereof, indicates that a portion of the T1R receptor or amino acid sequence is recognizable by an antibody that is specific for the T1R or amino acid sequence.

Included within the scope of the invention are polypeptides encoded by canine allelic variants of T1R. The allelic variants of the T1R receptor of the invention may modify the taste perception of a mammal, such as a dog, to a taste stimulus. Such functional amino acid sequence modifications may account for differences in intraspecies (e.g., breed-specific) taste perception.

Extracellular epitopes are useful for generating and screening for antibodies and other binding compounds that bind to a T1R receptor. Thus, in another embodiment, the invention provides a purified and isolated polypeptide comprising at least one extracellular domain of the T1R receptor. Examples of extracellular domains of the T1R polypeptides of the invention include residues 1-565, 624-637, 704-725, and 784-786 of SEQ ID NO:3; residues 1-565, 622-634, 699-723, and 778-782 of SEQ ID NO:6; and residues 1-566, 623-636, 702-725, or 780-793 of SEQ ID NO:9. Polypeptide fragments of the invention may be continuous portions of the native receptor. However, it will also be appreciated that knowledge of the T1R genes and protein sequences as provided herein permits recombination of various domains that are not contiguous in the native protein.

The invention embraces polypeptides that preferably have at least about 99%, at least about 95%, at least about 90%, at least about 85%, at least about 80%, at least about 75%, at least about 74%, at least about 73%, at least about 72%, at least about 71%, at least about 70%, at least about 65%, at least about 60%, at least about 55%, or at least about 50% identity and/or homology to the polypeptides of the invention.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention.

The invention also embraces variant T1R polypeptides. Insertions may be located at either or both termini of the protein, or may be positioned within internal regions of the amino acid sequence. Insertional variants with additional residues at either or both termini can include, for example, fusion proteins and proteins including amino acid tags or labels.

Insertion variants include T1R polypeptides wherein one or more amino acid residues are added to a biologically active fragment thereof. For example, the insertion variants of the invention include chimeric T1R receptors wherein at least one functional domain of a canine T1R receptor of the invention is present.

The invention also embraces T1R variants having additional amino acid residues that result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants that result from expression in other vector systems are also contemplated.

In another aspect, the invention provides deletion variants wherein one or more amino acid residues in a T1R polypeptide are removed. Deletions can be effected at one or both termini of the T1R polypeptide, or with removal of one or more non-terminal amino acid residues of T1R. Deletion variants, therefore, include all fragments of a T1R polypeptide.

The invention also embraces polypeptide fragments that maintain biological (e.g., ligand binding, heterodimerization, receptor activity) and/or immunological properties of a T1R polypeptide.

As used in the present invention, polypeptide fragments preferably comprise at least 10, 15, 20, 25, 30, 35, 40, 45, or 50 consecutive amino acids of SEQ ID NO:3, SEQ ID NO:6, or SEQ ID NO:9. Some polypeptide fragments display antigenic properties unique to, or specific for, a canine T1R receptor. Fragments of the invention having the desired biological and immunological properties can be prepared by any of the methods well known and routinely practiced in the art.

In still another aspect, the invention provides substitution variants of T1R polypeptides. Substitution variants include those polypeptides wherein one or more amino acid residues of a T1R polypeptide are removed and replaced with alternative residues. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

Conservative Substitutions I

| SIDE CHAIN CHARACTERISTIC | AMINO ACID |
| --- | --- |
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [BIOCHEMISTRY, Second Edition; Worth Publishers, Inc. NY, N.Y. (1975), pp. 71-77] as set out in Table 2, below.

TABLE 2

| Conservative Substitutions II | |
|---|---|
| SIDE CHAIN CHARACTERISTIC | AMINO ACID |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, below.

TABLE 3

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces T1R polypeptides that have been covalently modified to include one or more water-soluble polymer attachments such as polyethylene glycol, polyoxyethylene glycol, or polypropylene glycol. Variants that display ligand binding properties of native T1R and are expressed at higher levels, as well as variants that provide for constitutively active receptors, are particularly useful in assays of the invention; the variants are also useful in providing cellular, tissue and animal models of diseases/conditions characterized by aberrant T1R activity.

In a related embodiment, the present invention provides compositions comprising purified polypeptides of the invention. Some compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Variants that display ligand-binding properties of native T1R and are expressed at higher levels, as well as variants that provide for constitutively active receptors, are particularly useful in assays of the invention; the variants are also useful in assays of the invention and in providing cellular, tissue and animal models of diseases/conditions characterized by aberrant T1R activity.

Antibodies

Also included in the present invention are antibodies (e.g., monoclonal and polyclonal antibodies, single chain antibodies, chimeric antibodies, bifunctional/bispecific antibodies, humanized antibodies, human antibodies, caninized antibodies, canine antibodies, and complementary determining region (CDR)-grafted antibodies, including compounds which include CDR sequences which specifically recognize a polypeptide of the invention) specific for a T1R receptor of the invention or fragments thereof. Antibody fragments, including Fab, Fab', $F(ab')_2$, and $F_v$, are also provided by the invention. The term "specific for," when used to describe antibodies of the invention, indicates that the variable regions of the antibodies of the invention recognize and bind T1R polypeptides, preferably exclusively (i.e., are able to distinguish T1R polypeptides of the invention from other known polypeptides by virtue of measurable differences in binding affinity, despite the possible existence of localized sequence identity, homology, or similarity between T1R and such polypeptides). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6. Antibodies that recognize and bind fragments of the T1R polypeptides of the invention are also contemplated, provided that the antibodies are specific for T1R polypeptides. Antibodies of the invention can be produced using any method well known and routinely practiced in the art.

The invention provides an antibody that is specific for the canine T1R receptors of the invention. Antibodies that can be generated from polypeptides that have previously been described in the literature and that are capable of fortuitously cross-reacting with canine T1R receptor (e.g., due to the fortuitous existence of a similar epitope in both polypeptides) are considered "cross-reactive" antibodies. Such cross-reactive antibodies are not antibodies that are "specific" for a canine T1R receptor. The determination of whether an antibody is specific for a canine T1R receptor or is cross-reactive with another known receptor is made using any of several assays, such as Western blotting assays, that are well known in the art. For identifying cells that express a T1R receptor and also for modulating T1R-ligand binding activity, antibodies that specifically bind to an extracellular epitope of the T1R receptor may be used.

In some variations, the invention provides monoclonal antibodies. Hybridomas that produce such antibodies also are intended as aspects of the invention. In yet another variation, the invention provides a caninized antibody. Caninized antibodies are useful for in vivo therapeutic indications.

In another variation, the invention provides a cell-free composition comprising polyclonal antibodies, wherein at least one of the antibodies is an antibody of the invention specific for T1R receptor. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for T1R receptor of the invention.

It is well known that antibodies contain relatively small antigen binding domains that can be isolated chemically or by recombinant techniques. Such domains are useful T1R receptor binding molecules themselves, and also may be reintroduced into other antibodies or fused to toxins or other polypeptides. Thus, in still another embodiment, the invention provides a polypeptide comprising a fragment of a T1R-specific antibody, wherein the fragment and the polypeptide bind to the T1R receptor. By way of non-limiting example, the invention provides polypeptides that are single chain antibodies and CDR-grafted antibodies.

Non-canine antibodies may be caninized by any of the methods known in the art for humanization of antibodies, for example. In one method, the non-canine CDRs are inserted into a canine antibody or consensus antibody framework sequence. Similarly, non-human antibodies may be humanized by methods known in the art. In one embodiment, non-human CDRs are inserted into a human antibody or consensus antibody framework sequence. Further changes can then be introduced into the antibody framework to modulate affinity or immunogenicity.

Antibodies of the invention are useful for, e.g., therapeutic purposes (such as by modulating activity of T1R receptor), diagnostic purposes (such as detecting or quantitating T1R receptor activity), and also for purification of T1R receptor. Kits comprising an antibody of the invention for any of the purposes described herein are also included within the scope of the invention. In general, a kit of the invention preferably includes a control antigen for which the antibody is immunospecific.

Compositions

Mutations in the T1R gene that result in loss of normal function of the T1R gene product underlie some T1R-related disease states. The invention comprehends gene and peptide therapy, for example, to restore T1R activity to treat those disease states. Delivery of a functional T1R gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, No. 6679, pp. 25-20 (1998). For additional reviews of gene therapy technology see Friedmann, *Science,* 244: 1275-1281 (1989); Verma, *Scientific American:* 68-84 (1990); and Miller, *Nature,* 357: 455-460 (1992). Alternatively, it is contemplated that in other disease states, preventing the expression of, or inhibiting the activity of, T1R receptor will be useful in treatment. It is contemplated that antisense therapy or gene therapy could be applied to negatively regulate the expression of T1R receptor.

Another aspect of the present invention is directed to compositions, including pharmaceutical compositions, comprising any of the nucleic acid molecules or recombinant expression vectors described above and an acceptable carrier or diluent. The carrier or diluent may be pharmaceutically acceptable. Suitable carriers are described in the most recent edition of *Remington's Pharmaceutical Sciences*, A. Osol, a standard reference text in this field, which is incorporated herein by reference in its entirety. Examples of such carriers or diluents include, but are not limited to, water, saline, Ringer's solution, dextrose solution, and 5% serum albumin. Liposomes and nonaqueous vehicles such as fixed oils may also be used. The formulations may be sterilized by commonly used techniques.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating ligand-binding of a T1R receptor comprising the step of contacting the receptor with an antibody specific for the T1R polypeptide, under conditions wherein the antibody binds the receptor.

Methods of Identifying Ligands and Modulators

The invention also provides assays to identify compounds that bind and/or modulate T1R receptor. A "T1R binding partner" is a compound that directly or indirectly binds a T1R polypeptide of the invention. One assay of the invention comprises the steps of: (a) contacting T1R receptor with a compound suspected of binding T1R receptor (the test compound); and (b) measuring binding between the compound and the T1R receptor. In one variation, the composition comprises a cell expressing T1R receptor on its surface. In another variation, isolated T1R receptor or cell membranes comprising T1R receptor are employed. The binding may be measured directly, e.g., by using a labeled compound, or may be measured indirectly. Compounds identified as binding T1R receptor may be further tested in other assays including, but not limited to, T1R activity assays and/or in vivo models, in order to confirm or quantitate their activity.

Specific binding molecules, including natural ligands and synthetic compounds, can be identified or developed using isolated or recombinant T1R products, T1R variants, or preferably, cells expressing such products. Binding partners are useful for purifying T1R products and detection or quantification of T1R products in fluid and tissue samples using known immunological procedures. Binding molecules are also manifestly useful in modulating (i.e., blocking, inhibiting or stimulating) biological activities of T1R, especially those activities involved in signal transduction. Binding molecules also are useful in methods for predicting the taste perception of an organism such as a mammal by detecting a polypeptide of the invention in a biological sample of the organism. For example, an organism in which a polypeptide of the invention has been identified may perceive saccharin as bitter and/or D-fructose, β-D -fructose, or sucrose as sweet.

The DNA and amino acid sequence information provided by the present invention also makes possible identification of binding partner compounds with which a T1R polypeptide or polynucleotide will interact. Methods to identify binding partner compounds include solution assays, in vitro assays wherein T1R polypeptides are immobilized, and cell-based assays. Identification of binding partner compounds of T1R polypeptides provides candidates for therapeutic or prophylactic intervention in pathologies associated with T1R normal and aberrant biological activity.

The invention includes several assay systems for identifying T1R-binding partners. In solution assays, methods of the invention comprise the steps of (a) contacting a T1R polypeptide with one or more candidate binding partner compounds and (b) identifying the compounds that bind to the T1R polypeptide. Identification of the compounds that bind the T1R polypeptide can be achieved by isolating the T1R polypeptide/binding partner complex, and separating the binding partner compound from the T1R polypeptide. An additional step of characterizing the physical, biological, and/or biochemical properties of the binding partner compound is also comprehended in another embodiment of the invention. In one aspect, the T1R polypeptide/binding partner complex is isolated using an antibody immunospecific for either the T1R polypeptide or the candidate binding partner compound.

In still other embodiments, either the T1R polypeptide or the candidate binding partner compound comprises a label or tag that facilitates its isolation, and methods of the invention to identify binding partner compounds include a step of isolating the T1R polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized T1R polypeptide with a candidate binding partner compound and (b) detecting binding of the candidate compound to the T1R polypeptide. In an alternative embodiment, the candidate binding partner compound is immobilized and binding of T1R receptor is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into a canine-specific electronic tongue or biosensor. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

The invention also provides cell-based assays to identify binding partner compounds of a T1R polypeptide. In one embodiment, the invention provides a method comprising the steps of contacting a T1R polypeptide expressed on the surface of a cell with a candidate binding partner compound and detecting binding of the candidate binding partner compound to the T1R polypeptide. In some embodiments, the detection comprises detecting physiological event in the cell caused by the binding of the molecule.

Another aspect of the present invention is directed to methods of identifying compounds that bind to either T1R receptor or nucleic acid molecules encoding T1R receptor, comprising contacting T1R receptor, or a nucleic acid molecule encoding the same, with a compound, and determining whether the compound binds T1R receptor or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross-linking, interaction trap/two-hybrid analysis, southwestern analysis, ELISA, and the like, which are described in, for example, Current Protocols in Molecular Biology, 1999, John Wiley & Sons, NY, which is incorporated herein by reference in its entirety. The compounds to be screened include (which may include compounds which are suspected to bind T1R receptor, or a nucleic acid molecule encoding the same), but are not limited to, extracellular, intracellular, biological, or chemical origin. The methods of the invention also embrace ligands, especially neuropeptides, that are attached to a label, such as a radiolabel (e.g., $^{125}I$, $^{35}S$, $^{32}P$, $^{33}P$, $^{3}H$), a fluorescence label, a chemiluminescent label, an enzymic label, and an immunogenic label. Modulators falling within the scope of the invention include, but are not limited to, non-peptide molecules such as non-peptide mimetics, non-peptide allosteric effectors, and peptides. The T1R polypeptide or polynucleotide employed in such a test may either be free in solution, attached to a solid support, borne on a cell surface or located intracellularly, or associated with a portion of a cell. One skilled in the art can, for example, measure the formation of complexes between T1R receptor and the compound being tested. Alternatively, one skilled in the art can examine the diminution in complex formation between T1R receptor and its substrate caused by the compound being tested. In some embodiments of the invention, the recognition sites of the T1R receptor are coupled with a monitoring system, either electrical or optical. An appropriate chemical stimulus can bind to the receptor's ligand binding domain, changing the receptor conformation to a degree that the coupled electronics or optical changes can be observed on a read-out. Such a device could be developed into a canine-specific electronic tongue, for example.

In another embodiment of the invention, high throughput screening for compounds having suitable binding affinity to T1R receptor is employed. Briefly, large numbers of different small peptide test compounds are synthesized on a solid substrate. The peptide test compounds are contacted with T1R receptor and washed. Bound T1R receptor is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed T1R receptor can be used for HTS binding assays in conjunction with a ligand, such as an amino acid or carbohydrate. The identified peptide is labeled with a suitable radioisotope, including, but not limited to, $^{125}I$, $^{3}H$, $^{35}S$ or $^{32}P$, by methods that are well known to those skilled in the art. Alternatively, the peptides may be labeled by well-known methods with a suitable fluorescent derivative (Baindur et al., *Drug Dev. Res.*, 1994, 33, 373-398; Rogers, *Drug Discovery Today*, 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147-184; Sweetnam et al., *J. Natural Products*, 1993, 56, 441-455). Alternative methods include a scintillation proximity assay (SPA) or a FlashPlate format in which such separation is unnecessary (Nakayama, *Cur. Opinion Drug Disc. Dev.*, 1998, 1, 85-91; Bossé et al., *J. Biomo-*

*lecular Screening,* 1998, 3, 285-292.). Binding of fluorescent ligands can be detected in various ways, including fluorescence energy transfer (FRET), direct spectrophotofluorometric analysis of bound ligand, or fluorescence polarization (Rogers, *Drug Discovery Today,* 1997, 2, 156-160; Hill, *Cur. Opinion Drug Disc. Dev.,* 1998, 1, 92-97).

Other assays may be used to identify specific ligands of a T1R receptor, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., *Nature,* 340:245-246 (1989), and Fields et al., *Trends in Genetics,* 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a receptor, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to a T1R receptor, or fragment thereof, a fusion polynucleotide encoding both a T1R receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., *Anal. Chem.,* 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with T1R receptor. Radiolabeled competitive binding studies are described in A. H. Lin et al., *Antimicrobial Agents and Chemotherapy,* 1997, 41(10): 2127-2131, the disclosure of which is incorporated herein by reference in its entirety.

Another aspect of the present invention is directed to methods of identifying compounds that modulate (i.e., increase or decrease) activity of T1R receptor comprising contacting T1R receptor with a compound, and determining whether the compound modifies activity of T1R receptor. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist.

Agents that modulate (i.e., increase, decrease, or block) T1R receptor activity or expression also may be identified, for example, by incubating a putative modulator with a cell containing a T1R polypeptide or polynucleotide and determining the effect of the putative modulator on T1R receptor activity or expression. The selectivity of a compound that modulates the activity of T1R receptor can be evaluated by comparing its effects on T1R receptor to its effect on other T1R receptors. Selective modulators may include, for example, antibodies and other proteins, peptides, or organic molecules that specifically bind to a T1R polypeptide or a T1R receptor-encoding nucleic acid. Modulators of T1R receptor activity will be therapeutically useful in treatment of diseases and physiological conditions in which normal or aberrant T1R receptor activity is involved. Compounds identified as modulating T1R receptor activity may be further tested in other assays including, but not limited to, in vivo models, in order to confirm or quantitate their activity.

The invention also provides methods for identifying a T1R receptor modulator by: (a) contacting a T1R receptor binding partner and a composition comprising a T1R receptor in the presence and in the absence of a putative modulator compound; (b) detecting binding between the binding partner and the T1R receptor; and (c) identifying a putative modulator compound or a modulator compound in view of decreased or increased binding between the binding partner and the T1R receptor in the presence of the putative modulator, as compared to binding in the absence of the putative modulator. Compounds identified as modulators of binding between T1R receptor and a T1R binding partner may be further tested in other assays including, but not limited to, in vivo models, in order to confirm or quantitate their activity.

The invention also includes within its scope high-throughput screening (HTS) assays to identify compounds that interact with, enhance, or inhibit biological activity (i.e., affect enzymatic activity, binding activity, etc.) of a T1R polypeptide. HTS assays permit screening of large numbers of compounds in an efficient manner. Cell-based HTS systems are contemplated to investigate T1R receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the T1R polypeptide.

For example, modulators of T1R receptor activity may be identified by expressing the T1R receptor in a heterologous cultured mammalian cell line, such as HEK cells, and detecting receptor activity in the presence and absence of a test compound by monitoring changes in intracellular calcium using a calcium-specific intracellular dye. In another embodiment, this process may be automated using a high-throughput screening device.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides, or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant, or marine microorganisms or (2) extraction of plants or marine organisms. Natural product libraries include polyketides, non-ribosomal peptides, and variants (non-naturally occurring) thereof. For a review, see *Science* 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity.

T1R receptor binding partners that stimulate T1R receptor activity are useful as agonists in disease states or conditions characterized by insufficient T1R receptor signaling (e.g., as a result of insufficient activity of a T1R receptor ligand). T1R receptor binding partners that block ligand-mediated T1R receptor signaling are useful as T1R receptor antagonists to treat disease states or conditions characterized by excessive T1R receptor signaling. Thus, in another aspect, the invention provides methods for treating a disease or abnormal condition by administering to a patient in need of such treatment a substance that modulates the activity or expression of a polypeptide having a sequence of SEQ ID NO:3, SEQ ID NO:6, or SEQ ID NO:9, or exhibiting substantially the same biological activity as a polypeptide having a sequence of SEQ ID NO:3, SEQ ID NO:6, or SEQ ID NO:9.

In addition T1R receptor modulators in general, as well as T1R receptor encoding polynucleotides and polypeptides, are useful in diagnostic assays for such diseases or conditions.

Mimetics

Mimetics or mimics of compounds identified herein (sterically similar compounds formulated to mimic the key portions of the structure) may be designed for pharmaceutical use. Mimetics may be used in the same manner as the compounds identified by the present invention that modulate the T1R receptor and hence are also functional equivalents. The generation of a structural-functional equivalent may be achieved by the techniques of modeling and chemical design known to those of skill in the art. It will be understood that all such sterically similar constructs fall within the scope of the present invention.

The design of mimetics to a known pharmaceutically active compound is a known approach to the development of pharmaceuticals based on a "lead" compound. This is desirable where, for example, the active compound is difficult or expensive to synthesize, or where it is unsuitable for a particular method of administration, e.g., some peptides may be unsuitable active agents for oral compositions as they tend to be quickly degraded by proteases in the alimentary canal.

There are several steps commonly taken in the design of a mimetic. First, the particular parts of the compound that are critical and/or important in determining its T1R-modulating properties are determined. In the case of a polypeptide, this can be done by systematically varying the amino acid residues in the peptide, e.g. by substituting each residue in turn. Alanine scans of peptides are commonly used to refine such peptide motifs.

Once the active region of the compound has been identified, its structure is modeled according to its physical properties, e.g. stereochemistry, bonding, size, and/or charge, using data from a range of sources, such as, but not limited to, spectroscopic techniques, X-ray diffraction data, and NMR. Computational analysis, similarity mapping (which models the charge and/or volume of the active region, rather than the bonding between atoms), and other techniques known to those of skill in the art can be used in this modeling process.

In a variant of this approach, the three-dimensional structure of the compound that modulates a T1R receptor and the active region of the T1R receptor are modeled. This can be especially useful where either or both of these compounds change conformation upon binding. Knowledge of the structure of the ligand-binding domain the receptor also allows the design of high potency ligands and/or modulators.

A template molecule is then selected onto which chemical groups that mimic the T1R modulator can be grafted. The template molecule and the chemical groups grafted onto it can conveniently be selected so that the mimetic is easy to synthesize, is pharmacologically acceptable, and does not degrade in vivo, while retaining the biological activity of the lead compound. Alternatively, where the mimetic is peptide-based, further stability can be achieved by cyclizing the peptide, thereby increasing its rigidity. The mimetic or mimetics found by this approach can then be screened by the methods of the present invention to see whether they have the ability to modulate the T1R receptor. Further optimization or modification can then be performed to arrive at one or more final mimetics for in vivo or clinical testing.

Compositions of Binding and/or Modulating Compounds

Following identification of a compound that binds and/or or modulates a T1R receptor, the compound may be manufactured and/or used in preparation of compositions including, but not limited to, foods, drinks, and pharmaceutical compositions. The compositions are provided or administered to patients, including, but not limited to, avians, felines, canines, bovines, ovines, porcines, equines, rodents, simians, and humans.

Thus, the present invention extends, in various aspects, not only to compounds identified in accordance with the methods disclosed herein but also foods, drinks, pharmaceutical compositions, drugs, or other compositions comprising such a compound; methods comprising administration of such a composition to a patient, e.g. for treatment (which includes prophylactic treatment) of a T1R receptor-associated disorder (e.g., obesity, diabetes); uses of such a compound in the manufacture of a composition for administration to a patient; and methods of making a composition comprising admixing such a compound with a pharmaceutically acceptable excipient, vehicle or carrier, and optionally other ingredients.

Some compositions of the invention comprise a taste-modifying amount of at least one or more binding or modulating compounds. A "taste-modifying amount" is a quantity sufficient to increase or decrease the perception of a taste stimulus by a given mammal. The food and drink compositions of the invention are formulated by the addition of a binding or modulating compound to a food or drink of the mammal. Such compositions may be individualized or breed-specific. For example, canine veterinary specialty diets may thus be made more palatable.

The pharmaceutical compositions of the invention comprise a therapeutically effective amount of a compound identified according to the methods disclosed herein, or a pharmaceutically acceptable salt thereof, and a pharmaceutically acceptable carrier or excipient.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutically acceptable carriers include but are not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

The pharmaceutical compositions of the invention may further comprise a secondary compound for the treatment of a disorder unrelated to the T1R receptor, such as an antibiotic or other therapeutic agent, to improve the palatability of the pharmaceutical composition, thereby improving the ease of administration.

In one embodiment, the composition is formulated in accordance with routine procedures as a pharmaceutical composition adapted for oral (e.g., tablets, granules, syrups) or non-oral (e.g., ointments, injections) administration to the subject. Various delivery systems are known and can be used to administer a compound that modulates a T1R receptor, e.g., encapsulation in liposomes, microparticles, microcapsules, expression by recombinant cells, receptor-mediated endocytosis, construction of a therapeutic nucleic acid as part of a retroviral or other vector, etc. Methods of introduction include but are not limited to intradermal, intramuscular, intraperitoneal, intravenous, subcutaneous, intranasal, topical, and oral routes.

The compounds of the invention may be administered by any convenient route, for example by infusion or bolus injection, by absorption through epithelial or mucocutaneous linings (e.g., oral mucosa, rectal and intestinal mucosa, etc.), and may be administered together with other biologically active agents, for example in HAART therapy. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery; topical application, e.g., in conjunction with a wound dressing after surgery; by injection; by means of a catheter; by means of a suppository; or by means of an implant, said implant being of a porous, non-porous, or gelatinous material, including membranes, such as sialastic membranes, or fibers.

The composition can be administered in unit dosage form and may be prepared by any of the methods well known in the pharmaceutical art, for example, as described in Remington's Pharmaceutical Sciences (Mack Publishing Co., Easton, Pa.). The amount of the compound of the invention that modulates a T1R receptor that is effective in the treatment of a particular disorder or condition will depend on factors including but not limited to the chemical characteristics of the compounds employed, the route of administration, the age, body weight, and symptoms of a patient, the nature of the disorder or condition, and can be determined by standard clinical techniques. Typically therapy is initiated at low levels of the compound and is increased until the desired therapeutic effect is achieved. In addition, in vitro assays may optionally be employed to help identify optimal dosage ranges. Suitable dosage ranges for intravenous administration are preferably generally about 20-500 micrograms of active compound per kilogram body weight. Suitable dosage ranges for intranasal administration are preferably generally about 0.01 pg/kg body weight to 1 mg/kg body weight. Suppositories preferably generally contain active ingredient in the range of 0.5% to 10% by weight; oral formulations preferably may contain 10% to 95% active ingredient. Effective doses may be extrapolated from dose-response curves derived from in vitro or animal model test systems.

Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry-lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline.

Where the composition is administered by injection, an ampoule of sterile water for injection or saline can be provided so that the ingredients may be mixed prior to administration.

Treatment Methods

The invention provides methods of treatment of T1R receptor-associated disorders by administering to a subject or patient an effective amount of a compound that modulates the T1R receptor. In some aspects of the invention, the compounds or pharmaceutical compositions of the invention are administered to a patient having an increased risk of or having a disorder associated with the T1R receptor. The patient may be, for example, avian, feline, canine, bovine, ovine, porcine, equine, rodent, simian, or human.

Kits

A kit of the invention comprises a carrier means being compartmentalized to receive in close confinement one or more container means such as vials, tubes, and the like, each of the container means comprising an element to be used in the methods of the invention. For example, one of the container means may comprise the a polynucleotide encoding a T1R receptor of the invention, a T1R receptor of the invention, or an antibody thereto. The kit may also have one or more conventional kit components, including, but not limited to, instructions, test tubes, Eppendorf™ tubes, labels, reagents helpful for quantification of marker gene expression, etc.

EXAMPLES

The following examples are meant to be illustrative of the present invention and are not intended to limit the scope thereof.

Cloning and Characterization of the Canine T1R receptors

The discovery of canine taste receptors, T1R1, T1R2, and T1R3, was achieved by using a molecular strategy termed "overgo" (Thomas, et al., *Genome Res.,* 12:1277-1285 (2002); Vollrath, D., *DNA markers for physical mapping* In Genome Analysis: A laboratory manual, Vol. 4, ed. B. Birren, et al., pp. 187-215, 1999). Cold Spring Harbor Laboratory Press, Cold Spring Harbor, N.Y.). This strategy involves the use of the shortest DNA probes among the many kinds of probes used in bacterial artificial chromosome (BAC) library screening. These probes are comprised of two DNA sequences (e.g., 22mers) with a complementary 8 base overlap. They can be designed by computer program (available online through the Genome Sequencing Center of the Washington University School of Medicine) and are readily synthesized.

Overgo probes were designed from conserved coding regions of Tas1R1, Tas1R2, and Tas1R3 gene sequences from human, mouse, rat, cow, and pig. The overlapping sequences of the seven DVL1 overgo probes used in the present invention were as follows:

| | | |
|---|---|---|
| t1r1_1-OVa | TAAACAACTCCACGGCCCTGCTGC | (SEQ ID NO:28) |
| t1r1_1-OVb | CCCAGGGTGATGTTGGGCAGCAGG | (SEQ ID NO:29) |
| t1r1_2-OVa | GCTGTGTATGCGGTGGCCCATGGC | (SEQ ID NO:30) |
| t1r1_2-OVb | CCAGGAGCTGGTGGAGGCCATGGG | (SEQ ID NO:31) |
| t1r1_3-OVa | TGCTGACCAACCTGACTGGCAAGG | (SEQ ID NO:32) |
| t1r1_3-OVb | TCTGAGGCGACCCACACCTTGCCA | (SEQ ID NO:33) |
| t1r1_4-OVa | CCAGTTCAGCTAAACATAAATGAG | (SEQ ID NO:34) |
| t1r1_4-OVb | GCCACTGGATTTTGGTCTCATTTA | (SEQ ID NO:35) |
| t1r1_5-OVa | AGCTAACACGCTGCTGCTGCTGCT | (SEQ ID NO:36) |
| t1r1_5-OVb | AGCAGTCCCAAGCAGCAGCAGCAG | (SEQ ID NO:37) |
| t1r1_6-OVa | TGTGTCACCTTCAGCCTGCTCTTC | (SEQ ID NO:38) |
| t1r1_6-OVb | TCCAGGACACGAAGTTGAAGAGCA | (SEQ ID NO:39) |
| t1r2_1-OVa | TACTTCGGCCCCAAGTGCTACATG | (SEQ ID NO:40) |
| t1r2_1-OVb | CCGGGTAGAAGAGGATCATGTAGC | (SEQ ID NO:41) |
| t1r2_2-OVa | TGGTCACCATCGTGGACCTCTTGG | (SEQ ID NO:42) |
| t1r2_2-OVb | AGGTTGAGCACAGTGACCAAGAGG | (SEQ ID NO:43) |
| t1r2_3-OVa | ACCAACTACAACGAGGCCAAGTTC | (SEQ ID NO:44) |
| t1r2_3-OVb | TCATGCTGAGGGTGATGAACTTGG | (SEQ ID NO:45) |
| t1r2_4-OVa | TCCGAGTCCTGGGCCATCGACCCG | (SEQ ID NO:46) |
| t1r2_4-OVb | TGAGGTTGTGCAGGACCGGGTCGA | (SEQ ID NO:47) |
| t1r2_5-OVa | TACAACCTCATGCAGGCCATGCGC | (SEQ ID NO:48) |
| t1r2_5-OVb | TCTCCTCCACCGCGAAGCGCATGG | (SEQ ID NO:49) |
| t1r2_6-OVa | ATCACCATCCAGAGCGTGCCCATC | (SEQ ID NO:50) |
| t1r2_6-OVb | ACTCACTGAAGCCCGGGATGGGCA | (SEQ ID NO:51) |
| t1r2_7-OVa | ACCACCACGTCGAGGCCATGGTGC | (SEQ ID NO:52) |
| t1r2_7-OVb | AAGTGCAGCATCAGCTGCACCATG | (SEQ ID NO:53) |

-continued

```
t1r3-OV1a CTTCCACTCCTGCTGCTACGACTG   (SEQ ID NO:54)
t1r3-OV1b TGCCTCGCAGTCCACGCAGTCGTA   (SEQ ID NO:55)

t1r3-OV2a AGGTGCGCCGCGTCAAGGGCTTCC   (SEQ ID NO:56)
t1r3-OV2b TCGTAGCAGCAGGAGTGGAAGCCC   (SEQ ID NO:57)

t1r3-OV3a GTTCCTGGCATGGGGGGAGCCGGC   (SEQ ID NO:58)
t1r3-OV3b GAGCAGCACAAGCACAGCCGGCTC   (SEQ ID NO:59)

t1r3-OV4a ACAGCCCACTAGTTCAGGCCGCAG   (SEQ ID NO:60)
t1r3-OV4b CAGGCCCGGGGTCCCCCTGCGGCC   (SEQ ID NO:61)

t1r3-OV5a CCCACTGGTTCAGGCCTCGGGGGG   (SEQ ID NO:62)
t1r3-OV5b AAAGCAGGCCAGGGGCCCCCCCGA   (SEQ ID NO:63)

t1r3-OV6a AGGCGCTGGTGCACTGCCGCACAC   (SEQ ID NO:64)
t1r3-OV6b AAGCTGACCCAGGAGCGTGTGCGG   (SEQ ID NO:65)

t1r3-OV7a ACAGAGGCACTGGTGCACTGCCGC   (SEQ ID NO:66)
t1r3-OV7b TGATCCAGGAGTGCACGCGGCAGT   (SEQ ID NO:67)

t1r3-OV8a ACCAATGCCACGCTGGCCTTTCTC   (SEQ ID NO:68)
t1r3-OV8b AAGTGCCCAGGAAGCAGAGAAAGG   (SEQ ID NO:69)

t1r3-OV9a TGGTACATGCTGCCAATGCCACGC   (SEQ ID NO:70)
t1r3-OV9b AAGCAGAGGAAAGCCAGCGTGGCA   (SEQ ID NO:71)

t1r3-     TACAACCGTGCCCGTGGCCTCACC   (SEQ ID NO:72)
OV10a
t1r3-     AGGCCAGCATGGCGAAGGTGAGGC   (SEQ ID NO:73)
OV10b

t1r3-     TCATCACCTGGGTCTCCTTTGTGC   (SEQ ID NO:74)
OV11a
t1r3-     ACATTGGCCAGGAGGGGCACAAAG   (SEQ ID NO:75)
OV11b

t1r3-     TGCAGATGGGTGCCCTCCTGCTCT   (SEQ ID NO:76)
OV12a
t1r3-     AGGATGCCCAGCACACAGAGCAGG.  (SEQ ID NO:77)
OV12b
```

The 14-base single-stranded overhangs were filled in with $^{32}P$ labeled dATP and dCTP, and the overgo probes hybridized with BAC libraries.

The overgo strategy is considered to be more versatile than a PCR-based strategy by those skilled in the art of comparative physical mapping for the following reasons: (1) overgo probes are short (e.g., 36mers or 40mers), making the probability of good alignment from among many species more favorable; (2) overgo probes are more specific to the target genes compared with traditional cDNA and genomic DNA probes used by PCR; and (3) although overgo probes are short, they are not as restricted as traditional PCR probes, which cannot tolerate even a few mismatches, because they can be used in hybridization approaches with BACs or other libraries.

Screening a canine genomic BAC library. Six Tas1r1, seven Tas1r2, and twelve Tas1r3 overgo probes (SEQ ID NOS:28-77) were used in screening a canine genomic BAC library. Probes were radioactively labeled by the random hexa-nucleotide method (Feinberg & Vogelstein, *Analytical Biochemistry,* 132:6-13 (1983)). Hybridization and washing of membranes followed standard protocols (Church & Gilbert, *PNAS U.S.A.,* 81:1991-1995 (1984)). One positive BAC clone was identified for dog Tas1r1 (clone 181F20). Two positive BAC clones were identified for each of canine Tas1r2 (clone 24F22 and 189L1) and canine Tas1R3 (clones 205J13 and 245K17).

Production of a shotgun library for BACs containing canine Tas1rs and identification of small insert clones containing canine T1R5. All positive BACs containing canine Tas1r1, Tas1r2, and Tas1r3 were selected to prepare BAC DNAs using Qiagen Large Construct Kit. BAC DNA was digested by the restriction enzyme Sau3A1 and subcloned into pGEM+3Z (Promega) vector. After transformants were arrayed to a nylon membrane, two separate hybridizations were performed using pooled six Tas1r1 (SEQ ID NOs:28-39), seven (SEQ ID NOs:40-53), and twelve Tas1r3 overgo probes (SEQ ID NOS:54-77). Sequencing of positive clones and chromosome walking yielded the partial coding regions of canine Tas1r1, Tas1r2, and Tas1r3.

Identification of full-length coding regions of canine Tas1rs. A BLAST search of a dog genome database using known Tas1r sequences was performed and yielded partial canine Tas1r sequences. This sequence information was combined with the sequence information yielded from the BAC library screening to generate the following primers for screening of the positive BAC clones:

```
dgR2ex3fa:
5'CTACAACAGCCAGCTGCTCA3'     (SEQ ID NO:78)

dgR2ex3fb:
5'CTTCAGCGAGTTCCGCATAC3'     (SEQ ID NO:79)

dogR1Ex4-5f1:
5'GGTTCTGCTCTGGGAGTGAG3'     (SEQ ID NO:80)

dogR1Ex4-5f2:
5'TTGGCCATGTGGTTACAGAA3'     (SEQ ID NO:81)

dogR1Ex1ra:
5'GAGGTCCTTCTAGGCACAGG3'     (SEQ ID NO:82)

dogR1Ex1rb:
5'CAGAAGTGCCAGGGAAGGT3'      (SEQ ID NO:83)

dgex4f1:
5'ACATAATTGCCTGGGACTGG3'     (SEQ ID NO:84)

dgex4f2:
5'ACCAAAATCCRGTGGCACGG3'     (SEQ ID NO:85)

dgex4r1:
5'CCGTGCCACYGGATTTTGGT3'     (SEQ ID NO:86)

dgex4r2:
5'TCCAGTCCCAGGCAATTATG3'     (SEQ ID NO:87)

dgex5f1:
5'TCCAGTCCCAGGCAATTATGT3'    (SEQ ID NO:88)

dgex5f2:
5'CTYGAAGGGCACCAGCGAGTG3'    (SEQ ID NO:89)

dgex5r1:
5'ACAGGGCACACACTCAAAGC3'     (SEQ ID NO:90)

dgex5r2:
5'CACTCGCTGGTGCCCTTCRA3'     (SEQ ID NO:91)

dgex1r3:
5'GAGTGCAGAGGGAACAGACC3'     (SEQ ID NO:92)

dgex1r4:
5'TCACCTGTCACAGAGGGTCA3'     (SEQ ID NO:93)

dgex3f7:
5'GGACCCTCTCAGTGGCTATG3'     (SEQ ID NO:94)

dgex3f8:
5'ACGGAGAGGACAACCAGGTA3'     (SEQ ID NO:95)

dgR1Ex1f1:
5'CAGCTGCCACAACACAGAGT3'     (SEQ ID NO:96)

dgR1Ex1f2:
5'ATGTCACTCGTGGCAGCTC3'      (SEQ ID NO:97)
```

-continued dgR1Ex3f1:
5'TACAGCAGATGCCCACACTC3' (SEQ ID NO:98)

dgR1Ex3f2:
5'GAAACAGGGTGCTTTCCTGA3' (SEQ ID NO:99)

dgR1Ex6r1:
5'AGGGCTAGTGGAGCAGTTCA3' (SEQ ID NO:100)

dgR1Ex6r2:
5'AGGCCATGTGTTTCCTCAAG3' (SEQ ID NO:101)

dogEx1f1:
5'CRCCTGGTCGGCCTGCAGCT3' (SEQ ID NO:102)

dogEx1f2:
5'GATTACCTCCTSGCAGGYCT3' (SEQ ID NO:103)

dogEx1r1:
5'CCTGTCACASAGGGTCACC3' (SEQ ID NO:104)

dogEx1r2:
5'AGRCCTGCSAGGAGGTAATC3' (SEQ ID NO:105)

dogEx3f1:
5'TCCCCAGCGATAAGTACCAG3' (SEQ ID NO:106)

dogEx3f2:
5'GGGTCTGGATCTCATTGGTGGG3' (SEQ ID NO:107)

dogEx6r1:
5'CGCAAGCCAAGTTACACAGATG3' (SEQ ID NO:108)

dogEx6r2:
5'GGCGGAAAACTTGAAGATGAAG3' (SEQ ID NO:109)

dogX4r1:
5'GTGTGCCAGGAGATGTTGTG3' (SEQ ID NO:110)

dogX4r2:
5'GGGTAGTAGGAGGCGATGCT3' (SEQ ID NO:111)

dogR2X4f1:
5'GAGCGTCGCCTCCTACTRCC3' (SEQ ID NO:112)

dogR2X4F2:
5'ATCTGGAAGGTCAACTTCAC3' (SEQ ID NO:113)

dogR2X4F3:
5'TGGGACCKGAGCCAGAACC3' (SEQ ID NO:114)

dogR2x6R3:
5'CAGAGGGAGAGAAGGCATTG3' (SEQ ID NO:115)

dogR2x6R4:
5'CCCGGCGTTTGTGATCTAT3' (SEQ ID NO:116)

dogR3ex2f1:
5'AGCTTCTTCCTCATGCCTCA3' (SEQ ID NO:117)

dogR3ex2f2:
5'GGGCTACGACCTCTTTGACA3' (SEQ ID NO:118)

dogR3ex6r1:
5'AGTTGGCCTTTGAGTCAGGA3' (SEQ ID NO:119)

dogR3ex6r2:
5'GGACCACTGGTTCTGGTCAC3' (SEQ ID NO:120)

dogR3ex6f1:
5'TGACAGACTGGTGGGTGCTA3' (SEQ ID NO:121)

dogR3ex6f2:
5'CCATGCTGGCCTACTTCATC3' (SEQ ID NO:122)

dogR2ex6r1:
5'AGCAGGAGGTGTCGTTCCTA3' (SEQ ID NO:123)

dogR2ex6r2:
5'CCCAGGATGGTCAGCATAAC3' (SEQ ID NO:124)

-continued dogR2ex3f1:
5'CTACAACAGCCAGCTGCTCA3' (SEQ ID NO:125)

dogR2ex3r1:
5'CGGAAGAAGTTGTGCAGGAT3' (SEQ ID NO:126)

dogR2ex3r2:
5'CTATCATGCGCTTCCTGACA3' (SEQ ID NO:127)

dogR2ex3r3:
5'TGTGTGCCAAGTCTTCTTGC3' (SEQ ID NO:128)

dogR2ex1r1:
5'GCAATGGATGAGGAGCATTT3' (SEQ ID NO:129)

dogR2ex1r2:
5'ACCACATCCAGCCTCACACT3' (SEQ ID NO:130)

dogR2ex2f1:
5'TTCCTCCTTCCACAGGTGAG3' (SEQ ID NO:131)

dogR2ex2f2:
5'AAGCCAGGTCAGGATGTCAG3' (SEQ ID NO:132)

Results

Approximately 8 kb of genomic sequence containing the open reading frame (ORF) for canine Tas1r1, approximately 9 kb of genomic sequence containing the ORF for canine Tas1r2, and approximately 4.4 kb of genomic sequence containing the ORF for canine Tas1r3 were obtained. The genomic sequences of canine T1R1, T1R2, and T1R3 are shown in provided in SEQ ID NOs:1, 4, and 7, respectively. The letter "N" denotes gaps between exons or unknown sequences.

A multiple sequence alignment of the T1R receptors of domestic dog (T1R1, SEQ ID NO:2; T1R2, SEQ ID NO:5; and T1R3, SEQ ID NO:8) with known nucleotide sequences of receptors of the T1R family from human (T1R1, SEQ ID NO:15; T1R2, SEQ ID NO:12; T1R3, SEQ ID NO:18), cat (T1R1, SEQ ID NO:133; T1R2, SEQ ID NO:135; T1R3, SEQ ID NO:137), mouse (T1R1, SEQ ID NO:13; T1R2, SEQ ID NO:10; T1R3, SEQ ID NO:16), and rat (T1R1, SEQ ID NO:14; T1R2, SEQ ID NO:11; T1R3, SEQ ID NO:17) is provided in FIGS. 1A-L. An asterisk (*) indicates a conserved nucleotide position among the sequences.

FIGS. 2A-D show the deduced amino acid sequences of the canine T1R taste receptors (T1R1, SEQ ID NO:3; T1R2, SEQ ID NO:6; and T1R3, SEQ ID NO:9) aligned with the amino acid sequences of members of the T1R receptor family from human (T1R1, SEQ ID NO:24; T1R2, SEQ ID NO:21; T1R3, SEQ ID NO:27), cat (T1R1, SEQ ID NO:134; T1R2, SEQ ID NO:136; and T1R3, SEQ ID NO:138), rat (T1R1, SEQ ID NO:23; T1R2, SEQ ID NO:20; T1R3, SEQ ID NO:26), and mouse (T1R1, SEQ ID NO:22; T1R2, SEQ ID NO:19; T1R3, SEQ ID NO:25). An asterisk (*) indicates a conserved nucleotide position among the sequences. A colon (:) indicates an observed conserved amino acid substitution. A period (.) indicates an observed semi-conserved amino acid substitution.

The relatedness of canine T1R receptor family to the T1R family of receptors including human, cat, rat, and mouse T1R1, T1R2, and T1R3 is shown in the phylogenetic tree of FIG. 3. The T1R receptors of the rat and mouse are closely related, while the T1R receptors of human and dog diverge from rat and mouse. Interestingly, the sweet stimuli to which the rat and mouse respond are very similar, whereas those that stimulate human and those that stimulate dog differ from one another and from those for rat and mouse. For example, humans are unique in their ability to taste most high-intensity sweeteners, while dogs apparently find saccharin bitter.

Figure 4A:
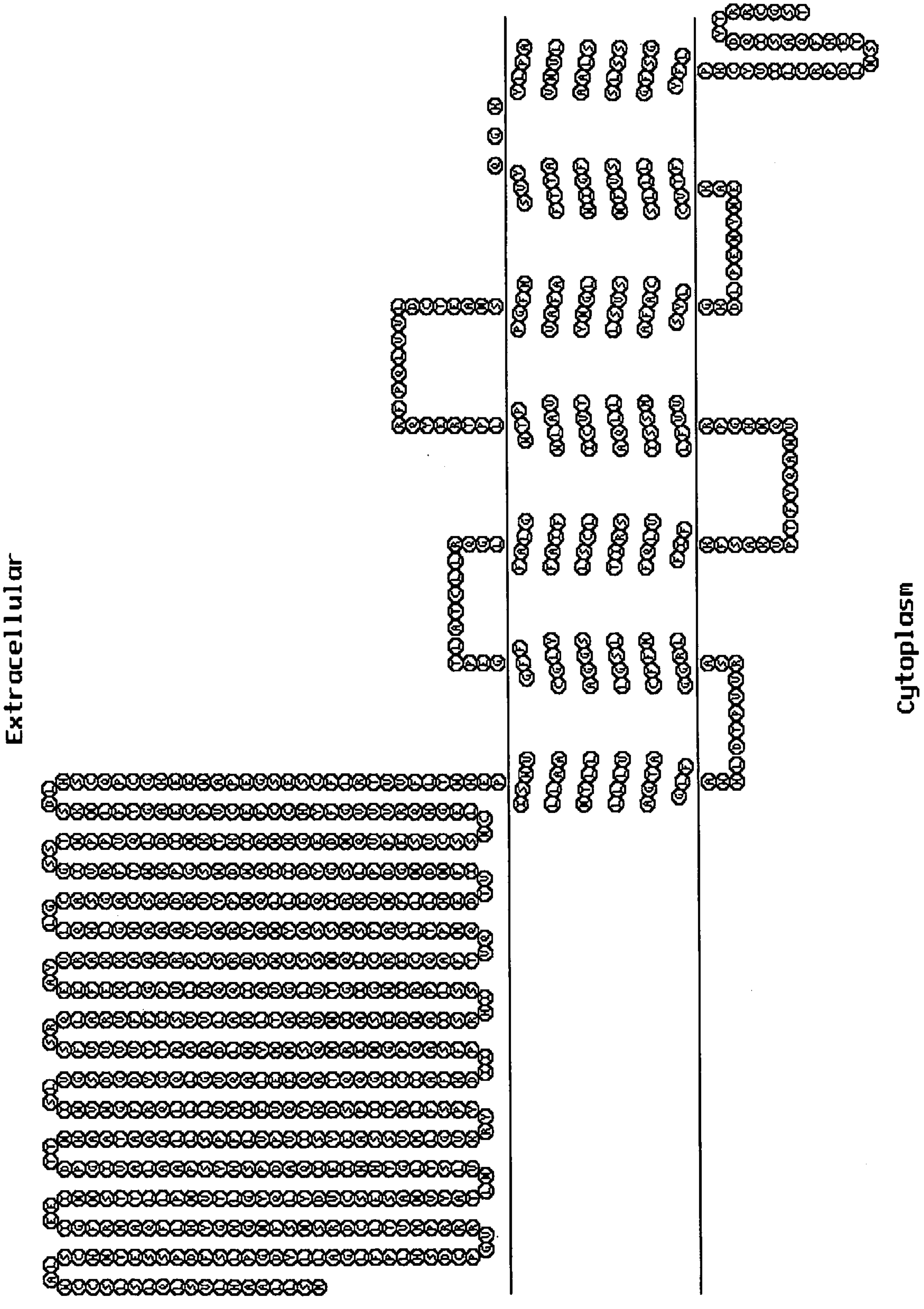
FIGS. 4A-C illustrate the predicted conformation of dog T1R receptors.
Figure 4B:
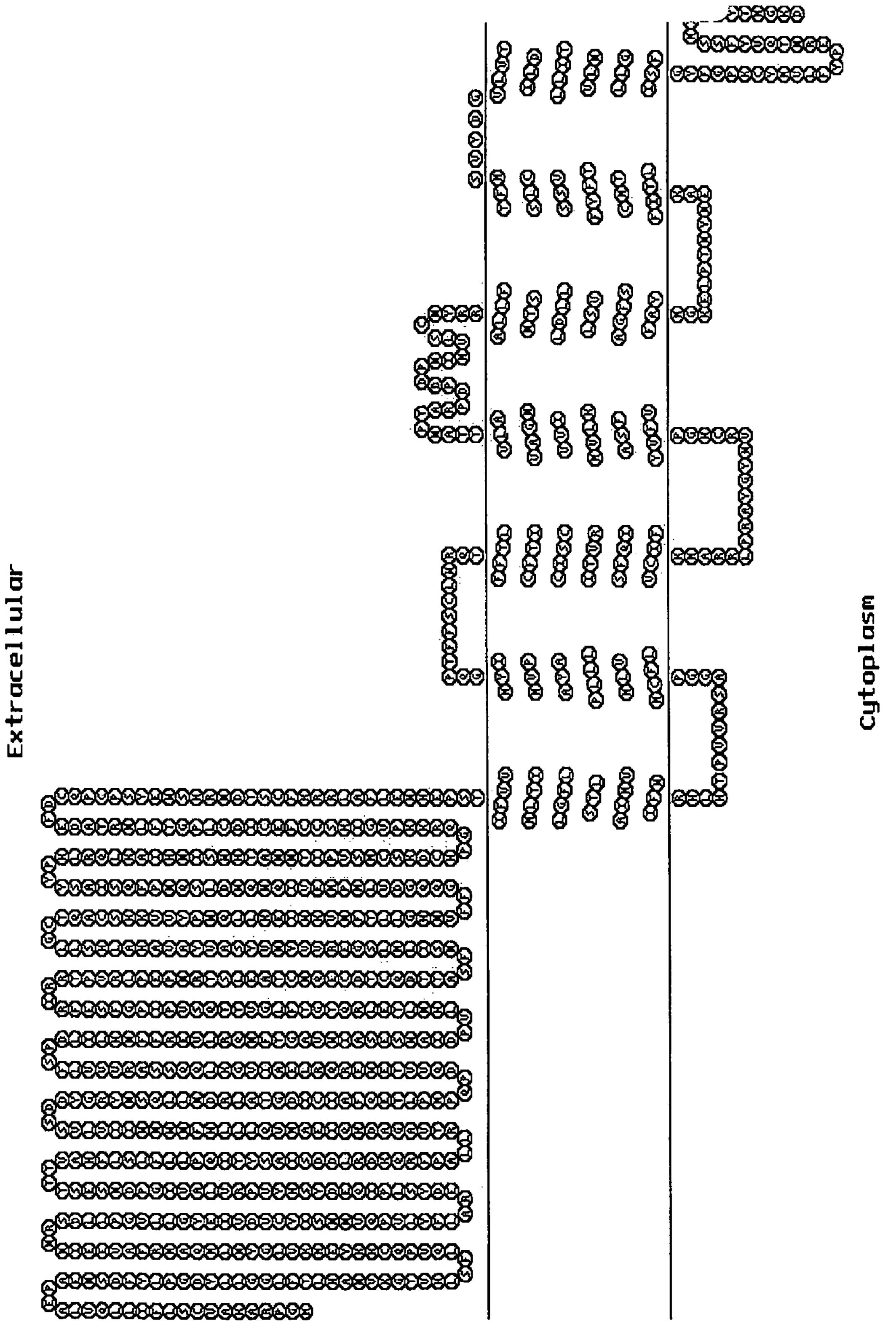
Figure 4C:
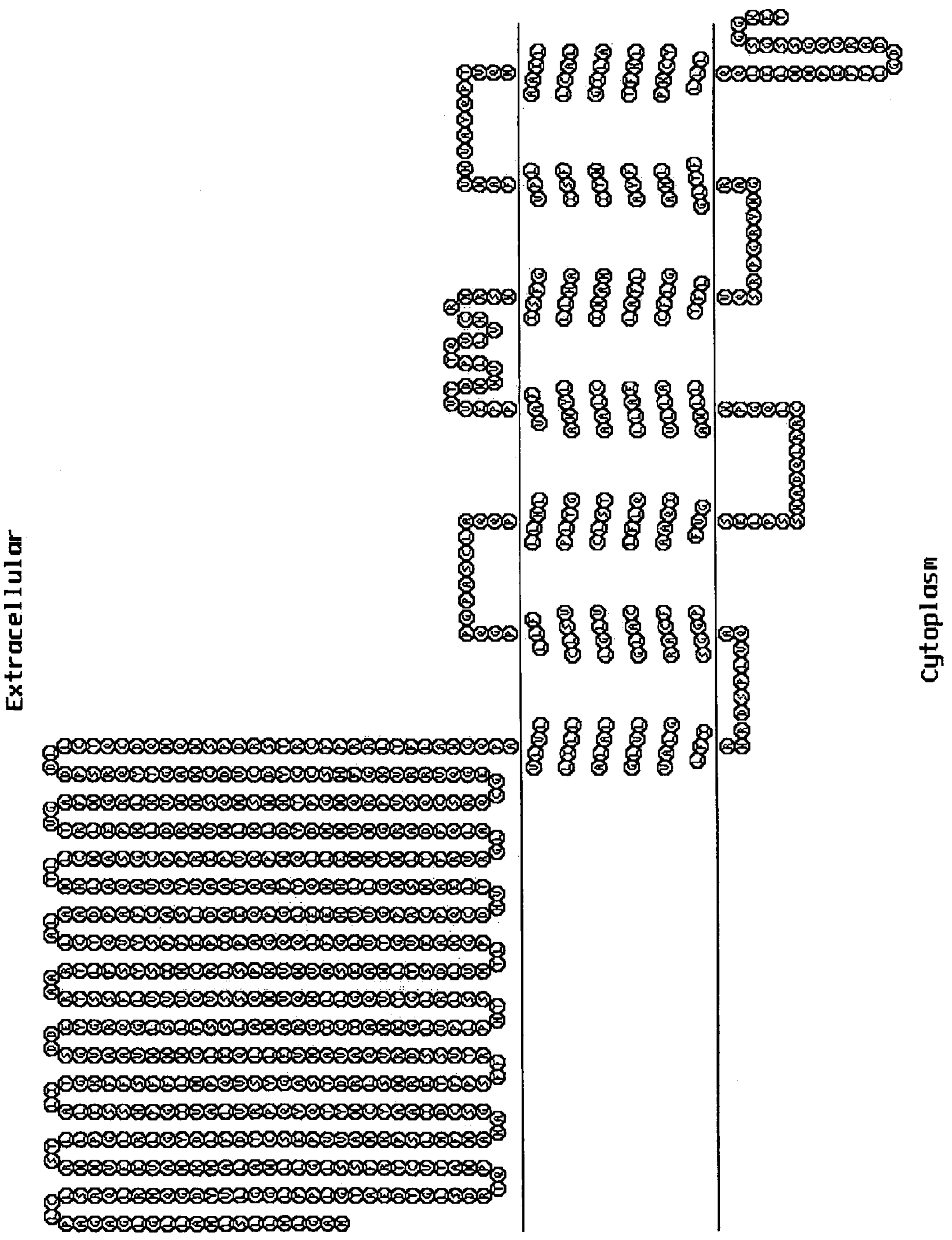

FIGS. 4A-C illustrate the predicted conformation of dog T1R receptors. FIG. 4A shows that the canine T1R1 receptor (SEQ ID NO:3) is a seven-transmembrane domain receptor. The structure of the canine T1R1 receptor was generated through use of the protein modeling programs available online through the European Bioinformatics Institute and the Sequence Analysis and Consulting Service of the University of California, San Francisco. FIG. 4B illustrates the predicted conformation of dog T1R2 receptor (SEQ ID NO:6) as a seven-transmembrane-domain receptor. FIG. 4C illustrates the predicted conformation of canine T1R3 receptor (SEQ ID NO:9), a seven-transmembrane domain structure. The dog T1R receptors T1R1, T1R2, and T1R3 are each predicted to have a seven transmembrane domain-structure, which is typical structure for G protein-coupled receptors involved in taste transduction.

Table 4 shows the percent homology among the members of the T1R family in relation to the dog T1R taste receptors. The portion of Table 4 to the left of the diagonal (in bold type) shows the percent homology based on the open reading frame of the nucleotide sequences obtained from FIG. 1 for the T1R family among human, dog, rat, and mouse. The upper portion to the right of the diagonal (in italic type) shows the percent homology of the T1R members based on the amino acid sequences of FIG. 2. Dog Tas1r1 shows 84% nucleotide sequence homology with human Tas1r1, 91% nucleotide homology with feline Tas1r1, and 78% nucleotide sequence homology with rat and mouse Tas1r1. At the amino acid level, dog T1R1 shows 80% homology with human T1R1, 91% homology with feline T1R1, 73% homology with rat T1R1, and 74% homology with mouse T1R1. Dog T1R1 shows generally low homology with the other known members of the T1R family, T1R2 and T1R3, from human, cat, rat and mouse. The same range of relatively low homology is present among the human, cat, rat, and mouse T1R1, T1R2 and T1R3 receptors from the same species. Dog Tas1r2 shows 83% nucleotide sequence homology with human Tas1r2, 71% nucleotide sequence homology with cat Tas1r2, and 79% nucleotide sequence homology with rat and mouse Tas1r2. At the amino acid level, dog T1R2 shows 76% homology with human T1R2, 62% homology with cat T1R2, and 71% with rat and mouse T1R2. Dog T1R2 shows generally low homology with the other members of the T1R family, T1R1 and T1R3, from human, cat, rat, and mouse. The same range of relatively low homology is present among the human, cat, rat, and mouse T1R2 and the T1R1 and T1R3 receptors from the same species. Dog Tas1r3 shows 78% nucleotide sequence homology with human Tas1r3, 87% homology with cat Tas1r3, 75% homology with rat, and 74% homology with mouse Tas1r3. At the amino acid sequence level, dog T1R3 shows 75% homology with human T1R3, 85% homology with cat T1R3, and 73% homology with rodent both rat and mouse T1R3.

TABLE 4

Percent Homology Among Diverse Species for T1Rs

| Species | Mouse T1R1 | Mouse T1R2 | Mouse T1R3 | Rat T1R1 | Rat T1R2 | Rat T1R3 | Human T1R1 | Human T1R2 | Human T1R3 | Cat T1R1 | Cat T1R2 | Cat T1R3 | Dog T1R1 | Dog T1R2 | Dog T1R3 |
|---|---|---|---|---|---|---|---|---|---|---|---|---|---|---|---|
| Mouse T1R1 | | *36* | *30* | *90* | *36* | *30* | *73* | *37* | *30* | *74* | *30* | *30* | *74* | *36* | *29* |
| Mouse T1R2 | **55** | | *28* | *36* | *91* | *28* | *34* | *69* | *28* | *36* | *53* | *28* | *35* | *71* | *28* |
| Mouse T1R3 | **33** | **15** | | *31* | *28* | *92* | *30* | *27* | *72* | *30* | *25* | *72* | *30* | *27* | *73* |
| Rat T1R1 | **91** | **55** | **33** | | *37* | *31* | *73* | *37* | *31* | *74* | *26* | *31* | *73* | *38* | *31* |
| Rat T1R2 | **55** | **91** | **15** | **57** | | *28* | *34* | *71* | *29* | *36* | *52* | *28* | *36* | *71* | *29* |
| Rat T1R3 | **33** | **21** | **93** | **32** | **15** | | *31* | *27* | *73* | *30* | *26* | *72* | *30* | *27* | *73* |
| Human T1R1 | **79** | **56** | **35** | **79** | **56** | **35** | | *35* | *31* | *81* | *29* | *31* | *80* | *37* | *31* |
| Human T1R2 | **57** | **78** | **17** | **56** | **78** | **17** | **57** | | *28* | *36* | *58* | *28* | *36* | *76* | *27* |
| Human T1R3 | **41** | **39** | **73** | **39** | **36** | **75** | **40** | **38** | | *29* | *23* | *73* | *30* | *28* | *75* |
| Cat T1R1 | **79** | **54** | **35** | **78** | **56** | **35** | **84** | **56** | **53** | | *28* | *30* | *91* | *38* | *30* |
| Cat T1R2 | **42** | **64** | **22** | **41** | **61** | **22** | **44** | **72** | **48** | **44** | | *29* | *30* | *62* | *25* |
| Cat T1R3 | **33** | **34** | **74** | **36** | **36** | **75** | **53** | **39** | **79** | **53** | **39** | | *30* | *28* | *85* |
| Dog T1R1 | **78** | **54** | **36** | **78** | **56** | **35** | **84** | **57** | **50** | **91** | **41** | **54** | | 38 | 30 |
| Dog T1R2 | **56** | **79** | **35** | **56** | **79** | **37** | **59** | **83** | **51** | **58** | **71** | **40** | **57** | | 28 |
| Dog T1R3 | **34** | **34** | **74** | **34** | **36** | **75** | **49** | **39** | **78** | **53** | **35** | **87** | **54** | **39** | |

Note:

Upper right cells (italics) contain deduced amino acid homology; lower left cells (bold) contain nucleotide homology.

What is claimed:

1. An isolated and purified T1R receptor polypeptide comprising the amino acid sequence of SEQ ID NO:6 or at least 30 contiguous amino acids of SEQ ID NO:6.

2. A method for identifying compounds that interact with a canine T1R receptor comprising:

contacting an isolated canine T1R receptor comprising an amino acid sequence of SEQ ID NO:6 with a test compound, and detecting interaction between said receptor and said compound.

3. The method of claim 2, wherein said receptor is bound to a solid support.

4. The method of claim 3, wherein said solid support is formulated into a canine-specific electronic tongue.

5. The method of claim 2 wherein said step of contacting said T1R receptor with said test compound occurs in the presence of a heterodimerization partner of said T1R receptor.

6. An isolated T1R receptor comprising at least one extracellular domain of a canine T1R receptor, said extracellular domain comprising amino acids 1-565, 622-634, 699-723, or 778-782 of SEQ ID NO:6.

7. An isolated T1R receptor comprising at least one transmembrane domain of a canine T1R receptor, said transmembrane domain comprising amino acids 566-587, 602-621, 635-658, 678-698, 724-744, 758-777, or 783-802 of SEQ ID NO:6.

8. An isolated T1R receptor comprising an intracellular domain of a canine T1R receptor, said intracellular domain comprising acids 588-601, 659-677, 745-757, or 803-836 of SEQ ID NO:6.

9. An isolated and purified T1R receptor comprising a T1R2 polypeptide comprising the amino acid sequence of SEQ ID NO:6 and a T1R3 polypeptide comprising the amino acid sequence of SEQ ID NO:9.

10. A method for identifying an agonist of a canine T1R receptor comprising:

contacting an isolated polypeptide comprising an amino acid sequence of SEQ ID NO:6 with a test compound, and detecting an increase in biological activity of said polypeptide in the presence of said compound relative to biological activity of said polypeptide in the absence of said compound.

11. The method of claim 10 wherein said contacting step occurs in the presence of a heterodimerization partner of said polypeptide.

12. A method for identifying an antagonist of a canine T1R receptor comprising:

contacting an isolated polypeptide comprising an amino acid sequence of SEQ ID NO:6 with a test compound, and detecting a decrease in biological activity of said polypeptide in the presence of said compound relative to biological activity of said polypeptide in the absence of said compound.

13. The method of claim 12 wherein said contacting step occurs in the presence of a heterodimerization partner of said T1R receptor.

14. The method of claim 10 wherein said polypeptide is bound to a solid support.

15. The method of claim 14 wherein said solid support is formulated into a canine-specific electronic tongue.

16. The method of claim 12 wherein said polypeptide is bound to a solid support.

17. The method of claim 16 wherein said solid support is formulated into a canine-specific electronic tongue.

18. A chimeric T1R receptor comprising at least one extracellular domain of a canine T1R receptor, said extracellular domain comprising amino acids 1-565, 622-634, 699-723, or 778-782 of SEQ ID NO:6.

19. A chimeric T1R receptor comprising at least one transmembrane domain of a canine T1R receptor, said transmembrane domain comprising amino acids 566-587, 602-621, 635-658, 678-698, 724-744, 758-777, or 783-802 of SEQ ID NO:6.

20. A chimeric T1R receptor comprising an intracellular domain of a canine T1R receptor, said intracellular domain comprising acids 588-601, 659-677, 745-757, or 803-836 of SEQ ID NO:6.

* * * * *

SEQUENCE LISTING

<160> NUMBER OF SEQ ID NOS: 138

<210> SEQ ID NO 1
<211> LENGTH: 7951
<212> TYPE: DNA
<213> ORGANISM: Canis familiaris
<220> FEATURE:
<221> NAME/KEY: misc_feature
<222> LOCATION: (1037)..(1082)
<223> OTHER INFORMATION: n is a, c, g, or t
<220> FEATURE:
<221> NAME/KEY: misc_feature
<222> LOCATION: (2757)..(2797)
<223> OTHER INFORMATION: n is a, c, g, or t
<220> FEATURE:
<221> NAME/KEY: misc_feature
<222> LOCATION: (5733)..(5779)
<223> OTHER INFORMATION: n is a, c, g, or t

<400> SEQUENCE: 1

```
agggtggggg ggctcccttt ctgagccagg tgaagaagcc mcaggcacca gagcaagaac     60

tgaagccaca accatgcaga ggaagggtca gtggctgcca cctggtttgc atctgttctt    120

tccccctgct gagttcctga gcaggaccac aggcccagaa ggccacggca agcagccagg    180

ttcctacaac tggatttcag ccccacccct ggcacaagca tgaagttggg aagcatctgg    240

gcagctgcca tctattctat ttaaacggcc aacctggtca gagggctctg ctcggccatg    300

ccaggcacag gactgtgtgg ccagcatgtc actcctggca gctcacctgg tcagcttgca    360

gctctccctc tcctgctgct gggccctcag ctgccacaac acagagtcat ctcctgattt    420

cagcctccct ggggattacc tacttgcagg tctgttccct ctgcactctg actgtcccgg    480

ggtgagacgc aggcccatgg tgaccctctg tgacaggtga gtgaggggcc tgtgcctaga    540

aggacctctg cctgcccttt ctgcctctgg ggccgcctcc tgaactatct ccagtccctc    600

cccctcctag gtcactacct tcaagccctg gctggacctt ccctggcact tctgctcagg    660

ttccacttta taatatgtta ttttgtcttc actattagag tgctttgtat tgtaatccca    720

ttccagttga tccaggattt gtgacataag taggcagcaa aggttaagca atcatggctt    780

ttccctgctt ccgtgtcctc cctattcctc tctgggtctc ccgatggtga gtgtggtttt    840

ccatgcaggg taaatggaag gcacacagca gtagatgctt tagcttagta aagattcttt    900

agattgggtg ccttgccttc atcaagtcga cagtcttggt agagaaaagc atctgctttt    960

ctcctaaaga agacaagtgg tggggcagcc ccggtggtgc cggggttwag cgyctgcctg   1020

cagcccaggg tgtgatnnnn nnnnnnnnnn nnnnnnnnnn nnnnnnnnnn nnnnnnnnnn   1080

nntgggttgc ttgggtggct cagcagttga gtgtctgcct ttggctcagg gagtgatcct   1140

cgagtcccag gatcgagtcc cacattggac tctcttcatg gagcctgctt ctccctcttc   1200

ctgtgtctct gcctctctct ctctctctct ctctctctct gtgtctctca tgaataaata   1260

aattaagtct ttttaaaaaa ttaataaacc ataaagaaac caaaaagcat gttgtgaaac   1320

acatatttgt aaagcatttg ggaatcctat gaagctttgt gtttacaaaa ccatgcaatg   1380

cttggtaaat ggtcaaacac ttagaaatga gaattttttt taaaaaagag agagggaggg   1440

atagctcagc ggtggctgag cggtgtagcg ccgcctttgg tccagggcgt gatcctggag   1500

acccaggatc gagtcccacg tcgggctccc tgcttggagc ctgcttctcc ctctgcctgt   1560

gtctctgcct ctctctttct ctctttctct ctctcaatct gtgtatctaa taaataaaat   1620

ctttaaaaaa ataaataaat cgatgggtga gtaaagcaga ttgccttcca ttgtgtgggt   1680
```

-continued

```
gggcctcatc caatcagttg aagaccttaa aagactgagg tcccctaaaa aggaaggaat   1740
tctgccttca gactcaagac tgcagcatct accattaagg gaatttctaa cctgccctgc   1800
aaacatcaga cttgccagcc ccataatcat acgagctaat tccttaaaat aacctttctc   1860
tctacatata tgtccagttg gttctgtttc tctagagaac cctgattaat acagcacgtg   1920
tctctgatac aggacttcat cagcctttca atgctaatat gcttatctgg ggaggcatgg   1980
tatgggttcc tccaacttgt tccccacccc aaacccctgc aaaggcctat taacacaact   2040
gtgtgtatgg tacagggccc acattgaggt cctggttgta ggggactgga cagatgacct   2100
cagagtttcc tctctacccc ccaaagaggg tttcggcaag gccttgccct tctcggctct   2160
cagcttggct ttctctacag gcccaacagc ttcaatggcc atggctacca cctctttcag   2220
gccatgcggt ttggcattga ggagatcaac aactccacaa cactgctgcc taatgtcacc   2280
ctggggtacc agctgtatga cgtgtgctca gagtcagcca atgtgtacgc cacactcaac   2340
gtactctcca cgctggggac acatcacata gagatccaag cagacccttc ccactattcc   2400
ccggccgccc tggcggtgat tggacctgac accaccaacc atgctgccac cgctgcagcc   2460
ctgctgagcc cgtttctggt gcctgtggta agctggtgcc ctgacagggt gtccgtctcc   2520
ccttctgtca agtccagtgt gggctagggg tggtgggcag gagctgctgg gcccccaggc   2580
cagtctgagc ccctggatct cctgggtgat cactgctcat tagtcacatt gcaggaggcc   2640
ctgccccatc gcaatctgca ctccagcatt tcttcccccc aggtgctgca tccagacccc   2700
tggcctcaat gctcctgaga aaacccattc tattgaaact gctgccgttt actcctnnnn   2760
nnnnnnnnnn nnnnnnnnnn nnnnnnnnnn nnnnnnnttc ctattgaaat gagagataca   2820
ctcctaaaac acaagtctga atatatcact tctctgccta aatatttagg ggctcccaat   2880
ggcctacaga taaagaccaa gtatcttagc ctgacagtta aggccccctt ggcctaacca   2940
catacctact tttgtgctcc ttcttctggc atccaacctc ttgggtcatt tcactcactg   3000
tgtgcagctt ttgttccctt ccttttcttc tctcagaact ccctccttgg gtttctgcct   3060
cttttccgca tgtaactcgt cagcctccta tgtccactag agctctcctt gagaaccagg   3120
gcagggacca tgtgtcccgc atccctgggt cccggtgccc agaacagggc cagcacttgg   3180
gggccctgat tgagactgat gccactgaac ttgctgaact gaacccccgc agatcagcta   3240
cgaggccagc agtgtgatgc ttggagtgaa gcggtattac ccctcgtttc tgcgcactat   3300
ccccagcgat aagtaccagg tggagatcat ggtgctactg ctgcagaggt ttgggtgggt   3360
ctggatctca ttggtgggca gcgacggcga ctatgggcag ctgggggtgc aggcactgga   3420
ggagcaggcc acccagcagg gcatctgcat tgccttcaag gacatcatac ccttctctgc   3480
ccagccgggt aatgagagga tgcagagcat gatgtaccac ctggaccgag caaggaccac   3540
tgttgtggtc gttttctcca gcaggcagct ggccagggtg ttcttcgagt ccgtggtcct   3600
ggccaagctg actgccaagg tgtggatcgc ttcagaagac tgggccatct ccagacatat   3660
tagcagcctg cccaggatct ggggcattgg cacagtgttg ggcgtggcca tccagcagaa   3720
gcttgtccct ggtctgaagg agtttgaaga ggcctacgtc cgggcaaaga aggcagccca   3780
taggccttgc tccagggact cctggtgcag cagcaaccaa ctctgcagag agtgccaagc   3840
tttcacagta cagcagatgc ccacactcgg agcattctcc atgagctctg cctacaatgc   3900
ctaccgggct gtctacgcag cagcccatgg cctccaccag ctcctgggct gtgcctctgg   3960
agcctgttcc agggaccgag tctacccctg gcaggtaagg tggccctacc cctggcaccc   4020
tgaaacaggg tgctttcctg aggaaaccag agtgatcact ctctgcccaa ctaagtgttg   4080
```

-continued

```
ggggcagagg acaaaggcca ttgaccagag ggctgatccc ctctcttagg cttcaattct   4140
ctgaacctca gcccctccca ctcaccatgc ttcatatcca ggactaaaaa tcactgtaaa   4200
ggggtccttt gttagaaact tcctctcaga agcctggttg ggagggttga ggggtttcct   4260
tggaggggaa ggagggctct gaatttccag atggcctgaa accacccaaa tagaagcata   4320
aggccccagg cacttgattc ctgatccttc caggtctggg tgggttgagg aggagcaaca   4380
tttgccatct acggcagctc cctgatccct gtgtatttca gcttctagag cagatccgca   4440
aggtgaattt ccttctacac gaggacactg tgatatttaa tgacaacggg gaccctctca   4500
gtggctatga cataattgcc tgggactgga gtggtcccaa gtggaccttc agggtcatcg   4560
gctcctccac gtggcctcca gttcagctgg acataaataa aaccaaaatc cggtggcacg   4620
gagaggacaa ccaggtaata gagacatggt cacttaccag atgactgctt tatgggcagc   4680
ctgcagccca aggatactgt tgacatagat tacacagagc aggagggaga tcccaggtac   4740
caggccaaca tgcctctatc cagccctgct ggggaagccc cacaggcagc acccagatgg   4800
cctgctgcgc tggtttataa aaccaggggt tctgctctgg gagtgagctg tgaaggcaga   4860
tgcacagaga ctatttccca ttccacctgt gagtattcct tgacttggcc atgtggttac   4920
agaacacctg tggcttcttg caggtgcctg agtctgtgtg ctccagcaac tgtcttgaag   4980
ggcaccagcg agtagttgtg ggtttctacc actgttgctt tgagtgtgtg ccctgtgagg   5040
ccggcacctt cctcaacaag agtggtgagt gatcaagtga gtgggtgaag gactgggcac   5100
tcctagggtc tgtacagcag aagaggggct ctccctcagg ccacacatgc acagaaccag   5160
ggccttgctc gcttcactgc tagttaggta taggctgaag aatacctgtc accagactga   5220
attctgagga agcagaaaga aacaacctgt taaaatcctc agacccacta tgtcttttac   5280
tagagagctc ccagccccat tcctacaggc acaattttat cctaaattca acctctttat   5340
gcaagcagag gtagctacgt tcccttgtac ccttccctgc tatctgtgtg aagtcccttc   5400
tattgcccat gctgtagcta gcacctgaac agcttggcct gaatgaagaa actgtatctg   5460
cagctgaaaa aacagcatac tatacccagt gatgcaaggc caagatcaga gagcaaatta   5520
aggcaactaa gggctcagcc cagagttgga cgccatgagc cacattcttt tccttttatg   5580
atctctatgg gcatgggaac gcatctcttc tgttctcaga gtcagagaaa ccacagagtg   5640
gcagcacagg aaggcggatt tggctaggtg gattttagca cggaagtgct ggggagagaa   5700
gaaaatgccc ttcctttggg gctggctgct ccnnnnnnnn nnnnnnnnnn nnnnnnnnnn   5760
nnnnnnnnnn nnnnnnnnnc tattgcccat gctgtagcta gcacctgaac agcttggcct   5820
gaatgaagaa actgtatctg cagctgaaaa aacagcatac tatacccagt gatgcaaggc   5880
caagatcaga gagcaaatta aggcaactaa gggctcagcc cagagttgga cgccatgagc   5940
cacattcttt tccttttatg atctctatgg gcatgggaac gcatctcttc tgttctcaga   6000
gtcagagaaa ccacagagtg gcagcacagg aaggcggatt tggctaggtg gattttagca   6060
cggaagtgct ggggagagaa gaaaatgccc ttcctttggg gctggctgct cctattggat   6120
catagcctca ctggcaggtg ggcagagcaa ccagagtaaa gccctcccta gggacctctt   6180
ggtttgcaag ccccttctgg gatcacgagc catacataac ctacccaagg gtctccagaa   6240
tctaattcac acaggcatct tgaggaaaca catggcctca ggaccccact cagggctacc   6300
cccatctcca gctcctgtgg tatctccctc gcagcacttt gcagatcaat gtggtctccc   6360
ttcctcattc ctgaactgct ccactagccc ttaggactcc cctccgcctt tccttccaga   6420
cctccacagc tgccagcctt gtgggaaaga agagtgggca cctgagggaa gtgaatcctg   6480
```

-continued

```
cttcctacgc actgtggtgt ttttgacttg gcatgagcct atctcttggg tgctgctggc   6540

agctaatacg ctgctgttgc tgctggtggc tgggactgct ggcctgtttg cctggcactt   6600

agacaccccg gtggtgaggt cagctggggg caggctgtgc ttctttatgc tgggctccct   6660

ggcagggggc agctgtgggc tctatggctt ttttggggag cccaccctgg ccacatgctt   6720

gttgcgccaa ggcctctttg ccctcggctt tgccatcttc ctgtcctgcc tgacaatccg   6780

ctccttccaa ctggtcttca tcttcaagtt ttccgccaag gtacccacct tctaccaggc   6840

ctgggtccaa aaccatggtc cccgcctctt tgtggtgatc agctccatgg cccagctgct   6900

catctgtgta acttggcttg cggtgtggac cccgttgccc accagggagt accagcgctt   6960

ccctcagctg gtggtgcttg actgcacgga ggccaactcc ccgggcttca tggtggcctt   7020

tgcctacaat ggcctgctgt ccgtcagcgc ctttgcctgc agctacctgg gtaaggacct   7080

gccggagaac tacaacgagg ccaaatgcgt caccttcagt ctgctcctca acttcgtgtc   7140

ctggattggc tttttcacca cagccagcgt ctaccagggc aaatacctgc ccgcggtcaa   7200

cgtgctggcg gcgctgagca gcctgagcag cggcttcagc ggttacttcc tccccaagtg   7260

ctatgtgatc ctgtgccgcc cagatctcaa cagcaccgag cacttccagg cctccatcca   7320

ggactacacg aggcgctgcg gctccacctg accccgcctc ccctgtcccg agggccgagg   7380

gtcaagcgag gcgcgcacgc cctgcgctgt cccggaggcc tttggactct tcagtttggg   7440

ctcggggagt gtaagctcgc cggaggccgc cccgggctcc caggctctgc caataaagcg   7500

ctgaaatgtg cgtcctggct gcgcttgctg tctggggcca ggggtggggc gcggcctcca   7560

gcaggctgag ggcgccgcgg gggcccaccg cagccggaac ccgggaccca gccccagccg   7620

cgcaaccagc cgtcgcccag cttggcgttg ctaagcaaca tcgagagccg agccaaccgc   7680

cgagcgccca gggcctggac ccctctcccc attccattgg ccgttctctg cctggccacg   7740

ccctcgaggg cggagccaga agcccggcac ctcccaggct ttcgcccctt ccggcgcgcc   7800

ctgacgtcac gtccggcggc ggcggcggcg gcggcggaga cggctgcgtc tccgtacggt   7860

cggcggggca cgtacggccc gggcagttga gcagggggc tgtggcgacg acgaggtcca   7920

gggtcggtgg ggccggcacc gggagcacag g                                 7951
```

<210> SEQ ID NO 2
<211> LENGTH: 2526
<212> TYPE: DNA
<213> ORGANISM: Canis familiaris

<400> SEQUENCE: 2

```
atgtcactcc tggcagctca cctggtcagc ttgcagctct ccctctcctg ctgctgggcc     60

ctcagctgcc acaacacaga gtcatctcct gatttcagcc tccctgggga ttacctactt    120

gcaggtctgt tccctctgca ctctgactgt cccggggtga gacgcaggcc catggtgacc    180

ctctgtgaca ggtccaacag cttcaatggc catggctacc acctctttca ggccatgcgg    240

tttggcattg aggagatcaa caactccaca acactgctgc ctaatgtcac cctggggtac    300

cagctgtatg acgtgtgctc agagtcagcc aatgtgtacg ccacactcaa cgtactctcc    360

acgctgggga cacatcacat agagatccaa gcagaccctt cccactattc cccggccgcc    420

ctggcggtga ttggacctga caccaccaac catgctgcca ccgctgcagc cctgctgagc    480

ccgtttctgg tgcctgtgat cagctacgag gccagcagtg tgatgcttgg agtgaagcgg    540

tattacccct cgtttctgcg cactatcccc agcgataagt accaggtgga gatcatggtg    600

ctactgctgc agaggtttgg gtgggtctgg atctcattgg tgggcagcga cggcgactat    660
```

```
gggcagctgg gggtgcaggc actggaggag caggccaccc agcagggcat ctgcattgcc    720
ttcaaggaca tcataccctt ctctgcccag ccgggtaatg agaggatgca gagcatgatg    780
taccacctgg accgagcaag gaccactgtt gtggtcgttt tctccagcag gcagctggcc    840
agggtgttct tcgagtccgt ggtcctggcc aagctgactg ccaaggtgtg gatcgcttca    900
gaagactggg ccatctccag acatattagc agcctgccca ggatctgggg cattggcaca    960
gtgttgggcg tggccatcca gcagaagctt gtccctggtc tgaaggagtt tgaagaggcc   1020
tacgtccggg caaagaaggc agcccatagg ccttgctcca gggactcctg gtgcagcagc   1080
aaccaactct gcagagagtg ccaagctttc acagtacagc agatgcccac actcggagca   1140
ttctccatga gctctgccta caatgcctac cgggctgtct acgcagcagc ccatggcctc   1200
caccagctcc tgggctgtgc ctctggagcc tgttccaggg accgagtcta cccctggcag   1260
cttctagagc agatccgcaa ggtgaatttc cttctacacg aggacactgt gatatttaat   1320
gacaacgggg accctctcag tggctatgac ataattgcct gggactggag tggtcccaag   1380
tggaccttca gggtcatcgg ctcctccacg tggcctccag ttcagctgga cataaataaa   1440
accaaaatcc ggtggcacgg agaggacaac caggtgcctg agtctgtgtg ctccagcaac   1500
tgtcttgaag ggcaccagcg agtagttgtg ggtttctacc actgttgctt tgagtgtgtg   1560
ccctgtgagg ccggcacctt cctcaacaag agtgacctcc acagctgcca gccttgtggg   1620
aaagaagagt gggcacctga gggaagtgaa tcctgcttcc tacgcactgt ggtgtttttg   1680
acttggcatg agcctatctc ttgggtgctg ctggcagcta atacgctgct gttgctgctg   1740
gtggctggga ctgctggcct gtttgcctgg cacttagaca ccccggtggt gaggtcagct   1800
gggggcaggc tgtgcttctt tatgctgggc tccctggcag gggcagctg tgggctctat   1860
ggcttttttg gggagcccac cctggccaca tgcttgttgc gccaaggcct ctttgccctc   1920
ggctttgcca tcttcctgtc ctgcctgaca atccgctcct tccaactggt cttcatcttc   1980
aagttttccg ccaaggtacc caccttctac caggcctggg tccaaaacca tggtccccgc   2040
ctctttgtgg tgatcagctc catggcccag ctgctcatct gtgtaacttg gcttgcggtg   2100
tggaccccgt tgcccaccag ggagtaccag cgcttccctc agctggtggt gcttgactgc   2160
acggaggcca actccccggg cttcatggtg gcctttgcct acaatggcct gctgtccgtc   2220
agcgcctttg cctgcagcta cctgggtaag gacctgccgg agaactacaa cgaggccaaa   2280
tgcgtcacct tcagtctgct cctcaacttc gtgtcctgga ttggcttttt caccacagcc   2340
agcgtctacc agggcaaata cctgcccgcg gtcaacgtgc tggcggcgct gagcagcctg   2400
agcagcggct tcagcggtta cttcctcccc aagtgctatg tgatcctgtg ccgcccagat   2460
ctcaacagca ccgagcactt ccaggcctcc atccaggact acacgaggcg ctgcggctcc   2520
acctga                                                              2526
```

```
<210> SEQ ID NO 3
<211> LENGTH: 841
<212> TYPE: PRT
<213> ORGANISM: Canis familiaris

<400> SEQUENCE: 3

Met Ser Leu Leu Ala Ala His Leu Val Ser Leu Gln Leu Ser Leu Ser
1               5                   10                  15

Cys Cys Trp Ala Leu Ser Cys His Asn Thr Glu Ser Ser Pro Asp Phe
            20                  25                  30

Ser Leu Pro Gly Asp Tyr Leu Leu Ala Gly Leu Phe Pro Leu His Ser
        35                  40                  45
```

-continued

```
Asp Cys Pro Gly Val Arg Arg Arg Pro Met Val Thr Leu Cys Asp Arg
    50                  55                  60

Ser Asn Ser Phe Asn Gly His Gly Tyr His Leu Phe Gln Ala Met Arg
65                  70                  75                  80

Phe Gly Ile Glu Glu Ile Asn Asn Ser Thr Thr Leu Leu Pro Asn Val
                85                  90                  95

Thr Leu Gly Tyr Gln Leu Tyr Asp Val Cys Ser Glu Ser Ala Asn Val
            100                 105                 110

Tyr Ala Thr Leu Asn Val Leu Ser Thr Leu Gly Thr His His Ile Glu
        115                 120                 125

Ile Gln Ala Asp Pro Ser His Tyr Ser Pro Ala Ala Leu Ala Val Ile
    130                 135                 140

Gly Pro Asp Thr Thr Asn His Ala Ala Thr Ala Ala Ala Leu Leu Ser
145                 150                 155                 160

Pro Phe Leu Val Pro Val Ile Ser Tyr Glu Ala Ser Ser Val Met Leu
                165                 170                 175

Gly Val Lys Arg Tyr Tyr Pro Ser Phe Leu Arg Thr Ile Pro Ser Asp
            180                 185                 190

Lys Tyr Gln Val Glu Ile Met Val Leu Leu Leu Gln Arg Phe Gly Trp
        195                 200                 205

Val Trp Ile Ser Leu Val Gly Ser Asp Gly Asp Tyr Gly Gln Leu Gly
    210                 215                 220

Val Gln Ala Leu Glu Glu Gln Ala Thr Gln Gln Gly Ile Cys Ile Ala
225                 230                 235                 240

Phe Lys Asp Ile Ile Pro Phe Ser Ala Gln Pro Gly Asn Glu Arg Met
                245                 250                 255

Gln Ser Met Met Tyr His Leu Asp Arg Ala Arg Thr Thr Val Val Val
            260                 265                 270

Val Phe Ser Ser Arg Gln Leu Ala Arg Val Phe Phe Glu Ser Val Val
        275                 280                 285

Leu Ala Lys Leu Thr Ala Lys Val Trp Ile Ala Ser Glu Asp Trp Ala
    290                 295                 300

Ile Ser Arg His Ile Ser Ser Leu Pro Arg Ile Trp Gly Ile Gly Thr
305                 310                 315                 320

Val Leu Gly Val Ala Ile Gln Gln Lys Leu Val Pro Gly Leu Lys Glu
                325                 330                 335

Phe Glu Glu Ala Tyr Val Arg Ala Lys Lys Ala Ala His Arg Pro Cys
            340                 345                 350

Ser Arg Asp Ser Trp Cys Ser Ser Asn Gln Leu Cys Arg Glu Cys Gln
        355                 360                 365

Ala Phe Thr Val Gln Gln Met Pro Thr Leu Gly Ala Phe Ser Met Ser
    370                 375                 380

Ser Ala Tyr Asn Ala Tyr Arg Ala Val Tyr Ala Ala Ala His Gly Leu
385                 390                 395                 400

His Gln Leu Leu Gly Cys Ala Ser Gly Ala Cys Ser Arg Asp Arg Val
                405                 410                 415

Tyr Pro Trp Gln Leu Leu Glu Gln Ile Arg Lys Val Asn Phe Leu Leu
            420                 425                 430

His Glu Asp Thr Val Ile Phe Asn Asp Asn Gly Asp Pro Leu Ser Gly
        435                 440                 445

Tyr Asp Ile Ile Ala Trp Asp Trp Ser Gly Pro Lys Trp Thr Phe Arg
    450                 455                 460

Val Ile Gly Ser Ser Thr Trp Pro Pro Val Gln Leu Asp Ile Asn Lys
```

-continued

```
465                 470                 475                 480

Thr Lys Ile Arg Trp His Gly Glu Asp Asn Gln Val Pro Glu Ser Val
                485                 490                 495

Cys Ser Ser Asn Cys Leu Glu Gly His Gln Arg Val Val Val Gly Phe
            500                 505                 510

Tyr His Cys Cys Phe Glu Cys Val Pro Cys Glu Ala Gly Thr Phe Leu
        515                 520                 525

Asn Lys Ser Asp Leu His Ser Cys Gln Pro Cys Gly Lys Glu Glu Trp
    530                 535                 540

Ala Pro Glu Gly Ser Glu Ser Cys Phe Leu Arg Thr Val Val Phe Leu
545                 550                 555                 560

Thr Trp His Glu Pro Ile Ser Trp Val Leu Leu Ala Ala Asn Thr Leu
                565                 570                 575

Leu Leu Leu Leu Val Ala Gly Thr Ala Gly Leu Phe Ala Trp His Leu
            580                 585                 590

Asp Thr Pro Val Val Arg Ser Ala Gly Gly Arg Leu Cys Phe Phe Met
        595                 600                 605

Leu Gly Ser Leu Ala Gly Gly Ser Cys Gly Leu Tyr Gly Phe Phe Gly
    610                 615                 620

Glu Pro Thr Leu Ala Thr Cys Leu Leu Arg Gln Gly Leu Phe Ala Leu
625                 630                 635                 640

Gly Phe Ala Ile Phe Leu Ser Cys Leu Thr Ile Arg Ser Phe Gln Leu
                645                 650                 655

Val Phe Ile Phe Lys Phe Ser Ala Lys Val Pro Thr Phe Tyr Gln Ala
            660                 665                 670

Trp Val Gln Asn His Gly Pro Arg Leu Phe Val Val Ile Ser Ser Met
        675                 680                 685

Ala Gln Leu Leu Ile Cys Val Thr Trp Leu Ala Val Trp Thr Pro Leu
    690                 695                 700

Pro Thr Arg Glu Tyr Gln Arg Phe Pro Gln Leu Val Val Leu Asp Cys
705                 710                 715                 720

Thr Glu Ala Asn Ser Pro Gly Phe Met Val Ala Phe Ala Tyr Asn Gly
                725                 730                 735

Leu Leu Ser Val Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Leu
        755                 760                 765

Asn Phe Val Ser Trp Ile Gly Phe Phe Thr Thr Ala Ser Val Tyr Gln
    770                 775                 780

Gly Lys Tyr Leu Pro Ala Val Asn Val Leu Ala Ala Leu Ser Ser Leu
785                 790                 795                 800

Ser Ser Gly Phe Ser Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
        835                 840
```

<210> SEQ ID NO 4
<211> LENGTH: 10959
<212> TYPE: DNA
<213> ORGANISM: Canis familiaris
<220> FEATURE:
<221> NAME/KEY: misc_feature
<222> LOCATION: (5540)..(5578)
<223> OTHER INFORMATION: n is a, c, g, or t -continued
<220> FEATURE:
<221> NAME/KEY: misc_feature
<222> LOCATION: (8208)..(8250)
<223> OTHER INFORMATION: n is a, c, g, or t

<400> SEQUENCE: 4

```
tgcaacctgg ggtggggggt ggggattaga ctctgcgtgc ctccatttcc tcatccgtga     60

aatgggtctg gcaccatccg tgcttatcat gagcattaaa cgagatggtg aacggcaagc    120

acgcagcgtg atgcctggtt cttactgcca gtggctgctg ctcctggaac acctgctatg    180

gggccaatgc tacctatgaa ttattgtgtg ccaggctcag cttgggctcc atttgccaga    240

ctactctgcc cccttggatg agtacctggg tcctttgctc ccaaatgttg gctacgtcag    300

gggcatgaga cctgtcctca atcgagtggc agaaggctat agggagtgtc caagtgagca    360

ggacatgctt tctctacttc caggtgggat tctcctagac cacccaggtc ccaccatacc    420

ctaggaaggg accatcctag ttccggcccc ttcctttccc cccagagttc gcaaatctct    480

ccacctgtgc caggtgcttt ccccgcccca cgggccacgg cggggccacc attatgtaaa    540

tgtctgtgca aatcccctga tgtcaagctg ccagctctct gatgaggcag ggccacctct    600

ggggaccccc acttcccagc catgggaccc cgggccaagg cggtctgctc cctattcatc    660

ctgctgcagg tcctggctga accggctgag aactcagact tctacctgcc tggagattac    720

ctcctgggtg gcctcttcac cctccatgcc aacgtgaagg gcaccgtcca cctcagcttc    780

ctgcaggtgc cccagtgcaa gaagtgagtc tccagtgtga ggctggatgt ggtgatgggg    840

gtggggtggg aagcctgcgc tggtcccgtg gtcctcacgg accaagtccc ggaccaaggg    900

cttgaaatgc tcctcatcca ttgcaaaacc cctcatcctg ggttatcccc actggccccc    960

agggagaacc cacacagttc atgtcactaa gatcttcggc aattgtgttc tgaaacatgg   1020

agacctggta ggcccaaagt cacatctctt aataaagagt tacaagatat ttgagcctgg   1080

aggggttgta gagaccgtca aaatcacccc cacctacttt ggcaactgag tccatgtcaa   1140

ggcctggtct agaaaccaag ggttacgcct ttggaaggca gaaacgtggt ttttctgtag   1200

caggttctca gaccggaggg gaatgtttgc ctttctctag ggctgtggtt aggtgggtgg   1260

cggtgcttcc aggacgggaa ggatttcctt cacccgtctc acggggtggt ggcatcactc   1320

aagattaggt ggaccatctt catgcaagca agggattatg aattaaagac ctagtgcaga   1380

gagggaaggc attctgagag agaaggaaaa aggaagggat aaaggtgata aagggccaac   1440

tgtaagaaat gcatgctttt tgtgatgttg gggaagatca tgtgctgatt tgagaatggt   1500

gagggtgatg gtgccgtgat ggtaccaggc acattgttga atgttctgat gcctgtgata   1560

gtggtgggga gaccagtgaa gtaacggtgg tgatggtggt gatgttgata acattgatag   1620

cagtcatact ggtgataatg caaatggtga agagtatggt gatgatgatg gtggtggtga   1680

tggtggtgat gacggcgatg atggtgatga tgatgatggt ggtaatgatg gggatggtaa   1740

tggtggtgag gatcgttgtg gtggtggtga tggtgatgaa gatgatgatg gtgatgaaga   1800

tgatggtgat gagggggatg gtggtgatgg tggtgatgag gatcatgatg gtgatgaaga   1860

tgatggtgct ggtgtgatgg tgctggcagt attggtagtg gtgggcacag acatgtggtc   1920

acagtgatgg cagtgatgat gatattgttc atagggaata gtaggtgcat gatgtgacag   1980

tgatgatagc gatggcagac attgtagtgg gtaatggtga ttgtatccgt ggacattggt   2040

aaagtggtgg tagatcatag ggatggtggt agtggtgaca atggtagtga ttgatggtag   2100

ccacaaggat cataatgcca gaggtggtca tagggatgat ggtgaaccta gagatgtggt   2160

atggcatggt gaccacgatg tgatgataaa aataccagaa tatcctggaa tggcgctttc   2220
```

-continued

```
ttggataact cctgggcttt cctctggtag gcagaggaaa caagcaggct ctccaggaaa   2280
caatcctgcc ccttcccact ctggacctgc ttcctacccc accctccatg gcttccccag   2340
gtatgaaatg aaggtgttgg gctacaacct gatgcaggcc atgcgctttg cggtggaaga   2400
gattaacaac cgcagcgacc tgctgcccgg cgtgctgctg ggctatgaga tagtggatgt   2460
ctgctacatc tccaacaacg tccagcccgt gctctacttc ttggcacggg aggactactc   2520
cctgcccatc caggaggact acagccacta cgtgccccgt gtgttggcgg tcattggccc   2580
tgacaactcc gagtccacta ctactgtggc ccatttcctc tcactcttcc tccttccaca   2640
ggtgaggccc tggctcctgg gggaaggagc tggggagggg gcagaggagg ggttgtctag   2700
agggctcgct tccccccact ggtcatgagg ggagaaggag gtgggaagcc aggtcaggat   2760
gtcagcccca accctgggag ggaagcctgg cctattcatg agaagcctag gctttggaga   2820
cagacagacc tgggcgtgca tcttggctct gagtcttggc cattttgagt cacggagcaa   2880
atctcttaac tcttctgagc ttcagcttcc ccacctataa aatgggatga tgagagttcc   2940
atcctaggac tgtctgaggc ttaaaggatt taacctctgc agacatttat aggatacagt   3000
agctggtcaa ttatgtaatg gtcgttatct aaggcacctt ccttgcacag aaatgaaaac   3060
ccagaaaatg ctcaatatta tcctgtacag ttgcctagta cagggtctgc cacatagtag   3120
gtcctcagaa aaatgccact agtattagta ctattattgt aagcgtcatc atcatcatga   3180
tcgaaaatgc ctcaaccagt tttagttggt ctaaaacttc aacacattaa agagcagcta   3240
gcgcaagaag acttggcaca cagtaggtag ctgcaaatac tgtatttttg ctgacatttt   3300
tattatgcaa agcaccaagg gtctgacaca cagtaggtgc ctagtaaatg ttaatgtact   3360
taggtgaggc gtctctttca ggactaaact cattctttca ttcccttaac aaatatttat   3420
tgagctcacc ctccagtggg agagacaggc catgtcagga agcgcatgat agggctgctg   3480
gaaagtgaga agtgccgtgc acaaaggtaa aaggcaaaca gggtgagggg ggctggacgg   3540
gtcggtggac agatggaacg gggagaggga ggctgcaact gcaagcaggg tggtcgggtg   3600
agcctcgctg gcaattggac aaaggcttga gggaggtgaa ggggtgaggg aggtacggag   3660
gtgtctggga gaagagcctt caggaagagg gggcagcgaa tgcagaggcc ggcaggtgcc   3720
tggattcgct tatggaacca gggagcagaa ctgggacccg ggagagacta ggaggagatg   3780
aagtcaggga ggtgagggcc ggggtcagtg atggagcccc ttgggggccc ctgaaggact   3840
ctgactgtcc ctgcatgact ttcggagcta ttgaagggtt ttcaagtgcc tgccgggtca   3900
cctggccgcc gccacgttca gcggagactg taggaggaag ggtgggggga tgctttggta   3960
gcctggcgag gccctagctc atgtgccggc aggggtcccc tcccgcagat cacctacagc   4020
gccatcagtg acgatctgcg ggacaagcag cgcttcccgg ccctgctgcg cacagtggcg   4080
ggcgcggacc accagatcga ggccatggtg cagctcctgc tccacttcaa ctggaactgg   4140
atcatcgtgc tagtgagcag cgacgactac ggccgctaca acagccagct gctcaacgat   4200
cgcctggcca ccggcgacat ctgcatcgcc ttccaggaga cgctgcccat gccgcagccc   4260
gaccaggtgg tgacggagtg ggagcgccag cgcctggagg ccatcgtggg caagctgcag   4320
cagagctcgg cgcgcgtcgt ggtgctgttc tcgccagacc tgatcctgca caacttcttc   4380
cgcgaggtgc tccgccagaa cttcacgggc gccgtgtgga tcgcctccga gtcctgggcc   4440
atcgacccgg ttctgcacaa cctcaccgag ctgcgccaaa ccggcacctt cctgggcgtc   4500
accacccaga gtgtgcccat cccgggcttc agcgagttcc gcatacgccg caccccggtc   4560
aggctgcctg agcccaacag gaccagcctg gaggccacct gcaaccagga gtgcgacacc   4620
```

-continued

```
tgccaggaca ccaccgcgtc cttcaacagc atcctcatgc tctccggcga gcgcgtggtc   4680
tacaacgtgt actcggctgt ctacgccgtg gcccatgcat tacacagcct tctgggctgc   4740
acccaggcct gctccaagga ggtggtctac ccctggcagg tgaggcccac cccgtggaag   4800
ggcaggcata gagtggttgt catggagacg ctgggtgcac ctgctgggct ctagccttcc   4860
catctcatgc tgggttctgg gcaaactggc gggagaggtc atgggacatg ccctgccctc   4920
cagacacata gaaccagaaa tccttcatgg tgacaaaact ccttttttttt tttttttaaa   4980
tgtaatcatc gccatccaag gtggcctgtc ctggtaggag atttgggtga aattccctgg   5040
aagggagcct ggcaggccgt gggggcccca ggtcccctgc catttctctg gataagaggc   5100
ctcgggggcc cacttgtgta ctccctcctc tctctgaggc cctacttgag gtttacgcac   5160
ctcctctcgt tccaggtttg tgttgtctgg attccaagct ggaatttaaa actgtgtttt   5220
tctgacttgc acttatacac acgcacaccc aatcaggaaa ccctcatggg ggtgagaggt   5280
tttactgagg agcagaggag cagaggggat tcacatcaga gacgcacacc tcatacctaa   5340
taacccggca tctctgtgct tgaatggctc cttggctttt tcgtggttta aggttcaggc   5400
actcctccaa cccttgccta tattctgtct ttattctctg cttcctcccc tttttctgga   5460
tccccgatcc ccaaatacct gtacacttcc ttcccagagc aacctagctc tttaaaaaaa   5520
aaaaaaaaac cctccttccn nnnnnnnnnn nnnnnnnnnn nnnnnnnnnn nnnnnnnntg   5580
aatgtttatt gaatgaatta atgaacagag gagcacttac tgtgtgctaa ccccttatgt   5640
gatttgccat ctacccgcag acacgctgtg agtagacact gttgcttgat gattgttctc   5700
ccacattagg tctagagaag tgacgatcac ccagctgggg agtggccagg gcagtggtgg   5760
gggggggcg tgggggtggt aatgaggcac aagggcaggg gcagtgggga tggagaggcc   5820
tcaggtgact aggatacttg aggatggagg ttgggaggtc acactgcccg tggtgttggg   5880
gggctgggga tgcactcggg ggcacgctcg ggaaatccag gctggcagag ggcagagggc   5940
tttggcggtc ccagggaaac tgttcatcag gttatggaat catagagggt ggaagttgca   6000
aggtcttaga atctccaggt ccaatatttt tgttttacaa atgggggtgg ggatggcgcc   6060
cttgtggcat ttgccacgtg cttgccatct cggcatctca ggtacagtcc ctctgtccgt   6120
cagtcggggg gagagcttgg tacttaggtt tgaatcccag ctttgccacc actagctctg   6180
caaccttggg caggttattt aatgcatccg ggccttgggt ttctcatgtg ctaagcagaa   6240
ggaacgctaa gcaccgtgct gagctctgga ggggactgac cgcgctgtgt gtccatgacc   6300
cggtgcagat agaagctccg tgtcttcctc cccccctct tccatgtctg acaccagtgt   6360
ctggacagtg ataatccagg cctcctcccc gtcaggagag ttgcagggag gatcctttct   6420
gacccctctg tcagagccct ggaatctggg gttgctgagc ccagcctggc caggtcagtg   6480
cggggatggg cctggccacc aggacctggc tccttaaggc ctccaccatc ctcacccctg   6540
ccagaggcca accacctgcg aggagccttc ctcctctcag ctcccgagac cattgccccc   6600
agtcgcagca tcatgtgcaa attccagaga cttccagagc ctgactctgt ggtcagggtg   6660
ggaagaaggc gagagcccaa atcccttggc taactgtgtg tcggtccctg aagggaggtc   6720
ccccaagata cagcccaata gactctctca tttatggtgg gaaaatctag gagctagatt   6780
gatgaaatat ctaagttgga agttccctca aggggtcagc acagaggttc agtgacttac   6840
ccaaagtcac acagcaaatt gaggaaagag ctcagattgg aattcaggcc agaggatgcc   6900
cagtccaaag catgttccag tttgtaccag cctctgcatg ctcagagcaa caggggacga   6960
tgacatgggg agagactgga gactggcctc taactggggg gaggcaggaa gccccagag   7020
```

-continued ggacaggggc aggtgcagct gaccagggca ggtgagggag gcagtggact cgagctcagc 7080
tatgggtccc cgaggggtgg ccgagtgact tccagggaga aggaataaga tcaacacttc 7140
ggcgggaggt gagtacttac tcgtgttgag gcaccgtgct aagttcccaa cataggtaaa 7200
ctctcatttg ttgcctccga gcccaggaga cagggttttt gttgtcctgc tttgctgaag 7260
aggaaactgg ggctcacaga ggtcaggcga caggtgcaag gcctcatagc aggtggcaga 7320
gctggtgtct aaacccagag tatccgaccc cggagctgga gctctcagcc cccacctccc 7380
gggtagcccc cttctcagtc ctcttgcccc cttgtcccca tgtggaagtc aggctagggg 7440
gatgggaaaa tttcccccgg gtctggcccc agctctgatg ccagcctttc cctttggccc 7500
ttctagctcc ttaaggaaat ctggaaggtc aacttcaccc ttctgggcca caatgtcttt 7560
tttgggcagc aaggggacgt gctcatgccc atggaggtca tccagtggca gtgggacctg 7620
agccagaacc ctttccagag catcgcctcc tactacccca agctgcggca gctcaaggcc 7680
atccacaaca tctcctggca caccgccaac aacacggtca gctctctgag ggctggggct 7740
gggccccggc tcaccctggg gtggcgaggg ccctctggac ccgagatccg tcactgacag 7800
cgggtggggg gggtgtctgt gcagtggggg gggggcgtct aggccctgtc cctcccgttg 7860
ataaggccta gggtttctgg ctccccgaga cccaggggct caggggctgt gcccagtgaa 7920
cgtgtgctgg acacgcgtgt gctgaggact cagctctcac gtcaaccatt gctggtgctc 7980
cccgtacggt agctgtaccc tcaactgcgt ctggcacctg tcattccaaa gctcctctgt 8040
tttaccctct tagatgcata acaagctgtc ggagtggtgg tggtggtgtg tggggacaga 8100
cagggaccca gcctcgtagg aggggagggg gagggggagg ggatacagaa gctccaagag 8160
ccttcctcat ctggatcctc tccccgcccc atcccccttt atcctcannn nnnnnnnnnn 8220
nnnnnnnnnn nnnnnnnnnn nnnnnnnnnn ccgagatctc caggatcacg ccctgggcca 8280
aaggcaggcg ccaaactgct gcgccaccca gggatccccc agacgtccag ttctaatggc 8340
aactcctgct ccttccccat cccagatggg ggccaggctt ccctccccag agcatcctgc 8400
tggttggtct caggggctct tgtcctcctc cctccagatc cccgtgtcca tgtgttccaa 8460
ggactgccat cctggccaaa ggaagaagcc tgtgggcatc cactcctgct gcttcgagtg 8520
tattgactgc cttcctggca ccttcctcaa ccgaactgca ggtgggactt gcagacccgc 8580
acccctgctc cccaccctca gccctgccct gctctgagag cagggtctct ggagtctccc 8640
ccacaggatg taagtgtcca aaggccaggg tccatgcctg attccagtgt atctccctag 8700
gaattggtgt agagaaaaat cttcaatgct cgctgctagg gagggtggga gaaggaacag 8760
ccctccacca ggcaaggctg tcactggtcc ccactccacg cacatgtagc tgagggctca 8820
ggggtgtcag accagagaat gtccattgga tggatggctg gatggatgga tgagtgggtg 8880
aatgaatgaa taaatgaatg tctctgtcca tagaagaaat gtttctggca gacggggaca 8940
ggatctggtt tatctctctg acctcccagt gcctaatgta gtgcagagcg tatcacgttt 9000
gctcagtgaa ttttgattga gtgacatcct tgatcagaag agctcatacc tcccccctata 9060
gatcacaaac gccgggaagg tgcggacaat gccttctctc cctctgtttt agtgttgagc 9120
accgttcaca gctggggctt aaattatttt ttttcgtgac ttcctcatca gagtacttac 9180
cgtgggccca gcatagccca gagcccagag taggtgccca acaaaaaattt gttgcatgat 9240
ttcacaggct gttcccctac ccagttggtc ggttcctgac ggcagggggc tggctaggtt 9300
tcgcccacgt ctctgtcctc ccacctcagg tgcccatcac ccactgtgga gggtgtttga 9360
aaaaaaaaat gtgttgaagg aattctttgg accaatgtgt gagtgtctat gccaccagag 9420
ggtaaggtct cgggagcaag gaattacagt tgttaggatc cgagtcaagg gaacctcggt 9480
tcaaaccctg cctctgtaac gaccacctgg ctgagcctcg ggttactcat ctgtgaaatg 9540
gggttgcagg gaggagctga tgggccagtg ggtgtaagag gggcagtgag tggtggtggc 9600
taggccggta ggcgttgccc tcagctcgcc ccccaccccc gaggcctggc ccggggcggg 9660
tgcagaggat gggggtgctg ccaagtgggc gaggctgacg ggagctgccg tgggctcttg 9720
cagacgaatt tgactgccag ccttgcccaa gttacgagtg gtcccatagg aacgacacct 9780
cctgcttcaa gcggcggctg gccttcctcg aatggcacga gccctccacc atctttgtgg 9840
ttatgctgac catcctgggc ttcctcagca ccctggccat catggtgatc ttctggaggc 9900
acctccacac gcccgtggtt cgctcggccg ggggccccat gtgcttcctg atgctggtgc 9960
cgctgctgct ggcgtacgcc atggtcccca tgtacatagg gcagcccacg ttcttctcgt 10020
gcctctggcg ccagaccttc ttcaccctct gcttcaccat ctgcatctcc tgcatcaccg 10080
tgcgctcttt ccagatcgtc tgcatcttca agatggccag gcgcctcccg cgcgcctacg 10140
gctactgggt gcgctgccac gggccctacg tcttcgtggc gtccttcatg gtgctcaagg 10200
tggtcatcgt ggcaggcaac gtgctggcca cgaccgccaa ccctactgcc cgccccgacc 10260
ccgatgaccc caatatcatg gtcctgtcct gcaactaccg cagggcgctg ctgttcaaca 10320
ccagcctgga cctgctcctg tccgtggcgg gcttcagctt cgcctacatg ggcaaggagc 10380
tgcccaccaa ctacaacgag gccaagttca tcaccctctg catgaccttc tacttcacct 10440
cctccgtctc cctctgcacc ttcatgtccg tctatgatgg ggtcctggtc accatcctgg 10500
acctcttgat caccgtgctc aaccttctgg gcatcagctt tggctacttt ggtcccaaat 10560
gctacatggt cctcttctac ccagagcgca acacgcaggt ctacttcagc agcatgattc 10620
agggctacac catggggaag gactagcacc gcccactagg gctgcccagg gggcccaagg 10680
gctcagctgg gggcgggggg agacgcagac gggatgggga ggtggagctg ggtgcaggtc 10740
gcagtttccc ggtagctgtt tggcttgcta ggccctgccg cccattctag gaaaacctgc 10800
ccagggtggg gaccctactg gtgtccccga cagagatgga tttgagcagc ctacagtctc 10860
catctggtgg tcacagcgga tgcaggctcg ttcccctccc tcctgttcgc ggggagcgaa 10920
ggctgggctg caggggctgg ggctgggacg ggctggtgt 10959

<210> SEQ ID NO 5
<211> LENGTH: 2510
<212> TYPE: DNA
<213> ORGANISM: Canis familiaris

<400> SEQUENCE: 5
atgggacccc gggccaaggc ggtctgctcc ctattcatcc tgctgcaggt cctggctgaa 60
ccggctgaga actcagactt ctacctgcct ggagattacc tcctgggtgg cctcttcacc 120
ctccatgcca acgtgaaggg caccgtccac ctcagcttcc tgcaggtgcc ccagtgcaag 180
aagtatgaaa tgaaggtgtt gggctacaac ctgatgcagg ccatgcgctt tgcggtggaa 240
gagattaaca accgcagcga cctgctgccc ggcgtgctgc tgggctatga gatagtggat 300
gtctgctaca tctccaacaa cgtccagccc gtgctctact tcttggcacg ggaggactac 360
tccctgccca tccaggagga ctacagccac tacgtgcccc gtgtgttggc ggtcattggc 420
cctgacaact ccgagtccac tactactgtg gcccatttcc tctcactctt cctccttcca 480
cagatcacct acagcgccat cagtgacgat ctgcgggaca agcagcactt cccggccctg 540
ctgcgcacag tggcgggcgc ggaccaccag atcgaggcca tggtgcagct cctgctccac 600

```
ttcaactgga actggatcat cgtgctagtg agcagcgacg actacggccg ctacaacagc    660

cagctgctca acgatcgcct ggccaccggc gacatctgca tcgccttcca ggagacgctg    720

cccatgccgc agcccgacca ggtggtgacg gagtgggagc gccagcgcct ggaggccatc    780

gtgggcaagc tgcagcagag ctcggcgcgc gtcgtggtgc tgttctcgcc agacctgatc    840

ctgcacaact tcttccgcga ggtgctccgc cagaacttca cgggcgccgt gtggatcgcc    900

tccgagtcct gggccatcga cccggttctg cacaacctca ccgagctgcg ccaaaccggc    960

accttcctgg gcgtcaccac ccagagtgtg cccatcccgg gcttcagcga gttccgcata   1020

cgccgcaccc cggtcaggct gcctgagccc aacaggacca gcctggaggc cacctgcaac   1080

caggagtgcg acacctgcca ggacaccacc gcgtccttca acagcatcct catgctctcc   1140

ggcgagcgcg tggtctacaa cgtgtactcg gctgtctacg ccgtggccca tgcattacac   1200

agccttctgg gctgcaccca ggcctgctcc aaggaggtgg tctacccctg gcagctcctt   1260

aaggaaatct ggaaggtcaa cttcaccctt ctgggccaca atgtcttttt tgggcagcaa   1320

ggggacgtgc tcatgcccat ggaggtcatc cagtggcagt gggacctgag ccagaaccct   1380

ttccagagca tcgcctccta ctaccccaag ctgcggcagc tcaaggccat ccacaacatc   1440

tcctggcaca ccgccaacaa cacgatcccc gtgtccatgt gttccaagga ctgccatcct   1500

ggccaaagga agaagcctgt gggcatccac tcctgctgct tcgagtgtat tgactgcctt   1560

cctggcacct tcctcaaccg aactgaagac gaatttgact gccagccttg cccaagttac   1620

gagtggtccc ataggaacga cacctcctgc ttcaagcggc ggctggcctt cctcgaatgg   1680

cacgagccct ccaccatctt tgtggttatg ctgaccatcc tgggcttcct cagcaccctg   1740

gccatcatgg tgatcttctg gaggcacctc cacacgcccg tggttcgctc ggccgggggc   1800

cccatgtgct tcctgatgct ggtgccgctg ctgctggcgt acgccatggt ccccatgtac   1860

atagggcagc ccacgttctt ctcgtgcctc tggcgccaga ccttcttcac cctctgcttc   1920

accatctgca tctcctgcat caccgtgcgc tctttccaga tcgtctgcat cttcaagatg   1980

gccaggcgcc tcccgcgcgc ctacggctac tgggtgcgct gccacgggcc ctacgtcttc   2040

gtggcgtcct tcatggtgct caaggtggtc atcgtggcag gcaacgtgct ggccacgacc   2100

gccaacccta ctgcccgccc cgaccccgat gaccccaata tcatggtcct gtcctgcaac   2160

taccgcaggg cgctgctgtt caacaccgcc tggacctgct cctgtccgtg gcgggcttca   2220

gcttcgccta catgggcaag gagctgccca ccaactacaa cgaggccaag ttcatcaccc   2280

tctgcatgac cttctacttc acctcctccg tctccctctg caccttcatg tccgtctatg   2340

atggggtcct ggtcaccatc ctggacctct tgatcaccgt gctcaacctt ctgggcatca   2400

gctttggcta ctttggtccc aaatgctaca tggtcctctt ctacccagag cgcaacacgc   2460

aggtctactt cagcagcatg attcagggct acaccatggg gaaggactag              2510
```

<210> SEQ ID NO 6
<211> LENGTH: 836
<212> TYPE: PRT
<213> ORGANISM: Canis familiaris

<400> SEQUENCE: 6

```
Met Gly Pro Arg Ala Lys Ala Val Cys Ser Leu Phe Ile Leu Leu Gln
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Thr Leu His Ala Asn Val Lys Gly Thr
```

-continued

```
        35                  40                  45

Val His Leu Ser Phe Leu Gln Val Pro Gln Cys Lys Lys Tyr Glu Met
    50                  55                  60

Lys Val Leu Gly Tyr Asn Leu Met Gln Ala Met Arg Phe Ala Val Glu
65                  70                  75                  80

Glu Ile Asn Asn Arg Ser Asp Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala Arg Glu Asp Tyr Ser Leu Pro Ile Gln Glu Asp Tyr
        115                 120                 125

Ser His Tyr Val Pro Arg Val Leu Ala Val Ile Gly Pro Asp Asn Ser
    130                 135                 140

Glu Ser Thr Thr Thr Val Ala His Phe Leu Ser Leu Phe Leu Leu Pro
145                 150                 155                 160

Gln Ile Thr Tyr Ser Ala Ile Ser Asp Asp Leu Arg Asp Lys Gln His
                165                 170                 175

Phe Pro Ala Leu Leu Arg Thr Val Ala Gly Ala Asp His Gln Ile Glu
            180                 185                 190

Ala Met Val Gln Leu Leu Leu His Phe Asn Trp Asn Trp Ile Ile Val
        195                 200                 205

Leu Val Ser Ser Asp Asp Tyr Gly Arg Tyr Asn Ser Gln Leu Leu Asn
    210                 215                 220

Asp Arg Leu Ala Thr Gly Asp Ile Cys Ile Ala Phe Gln Glu Thr Leu
225                 230                 235                 240

Pro Met Pro Gln Pro Asp Gln Val Val Thr Glu Trp Glu Arg Gln Arg
                245                 250                 255

Leu Glu Ala Ile Val Gly Lys Leu Gln Gln Ser Ser Ala Arg Val Val
            260                 265                 270

Val Leu Phe Ser Pro Asp Leu Ile Leu His Asn Phe Phe Arg Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg Gln Thr Gly
305                 310                 315                 320

Thr Phe Leu Gly Val Thr Thr Gln Ser Val Pro Ile Pro Gly Phe Ser
                325                 330                 335

Glu Phe Arg Ile Arg Arg Thr Pro Val Arg Leu Pro Glu Pro Asn Arg
            340                 345                 350

Thr Ser Leu Glu Ala Thr Cys Asn Gln Glu Cys Asp Thr Cys Gln Asp
        355                 360                 365

Thr Thr Ala Ser Phe Asn Ser Ile Leu Met Leu Ser Gly Glu Arg Val
    370                 375                 380

Val Tyr Asn Val Tyr Ser Ala Val Tyr Ala Val Ala His Ala Leu His
385                 390                 395                 400

Ser Leu Leu Gly Cys Thr Gln Ala Cys Ser Lys Glu Val Val Tyr Pro
                405                 410                 415

Trp Gln Leu Leu Lys Glu Ile Trp Lys Val Asn Phe Thr Leu Leu Gly
            420                 425                 430

His Asn Val Phe Phe Gly Gln Gln Gly Asp Val Leu Met Pro Met Glu
        435                 440                 445

Val Ile Gln Trp Gln Trp Asp Leu Ser Gln Asn Pro Phe Gln Ser Ile
    450                 455                 460
```

Ala Ser Tyr Tyr Pro Lys Leu Arg Gln Leu Lys Ala Ile His Asn Ile
465 470 475 480

Ser Trp His Thr Ala Asn Asn Thr Ile Pro Val Ser Met Cys Ser Lys
485 490 495

Asp Cys His Pro Gly Gln Arg Lys Lys Pro Val Gly Ile His Ser Cys
500 505 510

Cys Phe Glu Cys Ile Asp Cys Leu Pro Gly Thr Phe Leu Asn Arg Thr
515 520 525

Ala Asp Glu Phe Asp Cys Gln Pro Cys Pro Ser Tyr Glu Trp Ser His
530 535 540

Arg Asn Asp Thr Ser Cys Phe Lys Arg Arg Leu Ala Phe Leu Glu Trp
545 550 555 560

His Glu Pro Ser Thr Ile Phe Val Val Met Leu Thr Ile Leu Gly Phe
565 570 575

Leu Ser Thr Leu Ala Ile Met Val Ile Phe Trp Arg His Leu His Thr
580 585 590

Pro Val Val Arg Ser Ala Gly Gly Pro Met Cys Phe Leu Met Leu Val
595 600 605

Pro Leu Leu Leu Ala Tyr Ala Met Val Pro Met Tyr Ile Gly Gln Pro
610 615 620

Thr Phe Phe Ser Cys Leu Trp Arg Gln Thr Phe Phe Thr Leu Cys Phe
625 630 635 640

Thr Ile Cys Ile Ser Cys Ile Thr Val Arg Ser Phe Gln Ile Val Cys
645 650 655

Ile Phe Lys Met Ala Arg Arg Leu Pro Arg Ala Tyr Gly Tyr Trp Val
660 665 670

Arg Cys His Gly Pro Tyr Val Phe Val Ala Ser Phe Met Val Leu Lys
675 680 685

Val Val Ile Val Ala Gly Asn Val Leu Ala Thr Thr Ala Asn Pro Thr
690 695 700

Ala Arg Pro Asp Pro Asp Asp Pro Asn Ile Met Val Leu Ser Cys Asn
705 710 715 720

Tyr Arg Arg Ala Leu Leu Phe Asn Thr Ser Leu Asp Leu Leu Leu Ser
725 730 735

Val Ala Gly Phe Ser Phe Ala Tyr Met Gly Lys Glu Leu Pro Thr Asn
740 745 750

Tyr Asn Glu Ala Lys Phe Ile Thr Leu Cys Met Thr Phe Tyr Phe Thr
755 760 765

Ser Ser Val Ser Leu Cys Thr Phe Met Ser Val Tyr Asp Gly Val Leu
770 775 780

Val Thr Ile Leu Asp Leu Leu Ile Thr Val Leu Asn Leu Leu Gly Ile
785 790 795 800

Ser Phe Gly Tyr Phe Gly Pro Lys Cys Tyr Met Val Leu Phe Tyr Pro
805 810 815

Glu Arg Asn Thr Gln Val Tyr Phe Ser Ser Met Ile Gln Gly Tyr Thr
820 825 830

Met Gly Lys Asp
835

<210> SEQ ID NO 7
<211> LENGTH: 4347
<212> TYPE: DNA
<213> ORGANISM: Canis familiaris

<400> SEQUENCE: 7

-continued

```
tacctactcc tcaggtcact tgcacctccc tcaggcagct ggagacccca ggaccctctg      60
gcagagaagt cctgagtgtc cttcctcctt tccaggagtg gggtggggct tgggcacagg     120
catgtaacaa gatgtggtca gtggtcagtc agagcccgac tgcccaggtc actgtcaatc     180
agagagcctc gtggtggcat caggataaac gagtccggga tccctgggtg gtacagtggt     240
ttggcgcctg cctttggccc ggggcacgat cctggagacc cgggatcaaa tcccacatcg     300
ggctctcggt gcatggagcc tgcttctccc tctgcctgtg tctctgcctc tctctctgtg     360
tgactatcat aaataaataa aaattttaaa aatgtttaaa aaaaaaaaag gataaacgag     420
tccaagaagc gcagacctgc aaggcctagg aaagtgaggg tgtccccagg ggcccctgga     480
catgactggt aaggacaggt gataattttg ctaagcaaat cctctgccct cccctgcccc     540
cactcatcat attgggggcc cccactcggt tctctcattt gccgtccctg ctggaagctg     600
ccacctgcca tggcaggcct gatgctcctg agcctcatgg ctctcttggg ccttggagca     660
ggcgccccat tgtgcttatc ccggcagctc aggatgcaag ggactatgt gctgggcggg     720
ctcttccccc tgggcacagc tgaggacaca ggtctcagtg acaggacaca gcccaatgcc     780
actgtgtgca ccaggtaggg atgccggggc tgggaagcaa agggtgacgg ggtgggggc     840
tcagctctgg ggtgctccca agggaggacg tggggtcagc cccccacaac ccttgtggcc     900
caggttctcg tccctcggcc tgctctgggc gctggccatg aagatggcgg tggaggaggt     960
caacaacagg tccacgctgc tgccaggact gcgcctgggc tacgacctct ttgacacatg    1020
ttcggagcct gtggtggcca tgaagcccag cctcatgttc atggccaaag cgggcagctg    1080
cgacatcgcc gcctactgca actacacgca gtaccagccc cgtgtgctgg cagtcattgg    1140
gccacactca tctgagctcg ccctcatcac cggcaagttc ttcagcttct tcctcatgcc    1200
tcaggtgtgc tccccctcct ctcctgggtc ccctgccccc actggccctg cccacaggag    1260
cccccacatc aggaggtgcc tcccggctgc cacaggtcag ctacggggcc agcaccgacc    1320
ggctgagcaa ccgggagacg ttcccatcct tcttccgcac ggtgtccagc gaccgcgtac    1380
aggcagtggc catggtggag ctgctgcagg agcttggctg gaactgggtg gctgcagtgg    1440
gcagcgatga cgagtatggc cggcagggcc tgagcctctt ctccagcctg gccaatgcca    1500
ggggcatctg tattgcgcat gagggcctgg tgccattgcc gcacacgagt agcctgcggc    1560
tgggcactgt ccagggccta ctgcaccagg taaaccagag cagcgtgcag gtggtggtgc    1620
ttttctcttc cactcgtgct gcccgcaccc tcttcagcta cagcatccac tgcaggctct    1680
cgcccaaggt ttgggtggcc agtgaggcct ggctgacctc ggacctggtc atgacgctgc    1740
ctggcatggc tgaggtgggc accgtgcttg gctttctgca gcagggcgcc ccaatacccg    1800
agttcccatc ctatgtgcag acctgcctgg ccctggctgc tgaccctgcc ttttgcgcct    1860
cactggatgc agagcagccg ggcctggaag agcacgtggt ggggccccgc tgtccccagt    1920
gtgaccacgt cactctggag gctatgtctg cagggctgct gcaccaccag accttcgcgg    1980
cctacgcagc cgtgtatggc gtggcccagg ccctccacaa cacactgctc tgcaatgcct    2040
caggctgccc cccacgggag ccagtgcggc cctggcaggt aaggccagga ggccccgcac    2100
ttctgaggag cagtgtcagt ggggagtctg ggccggggac agctactggc ctggccccac    2160
ccacctgctc caatctgcct accagctcct agaaaacatg tacaacttga ccttccgtgt    2220
gcgcggctta gcactgcagt tcgatgccag gggggaacgtg aatatggatt atgacctgaa    2280
actgtgggtg tggcgggacc tgaagcccga gttgcgcacc gtaggtgcct tcaacggccg    2340
cctgaaggtc tggcactccc agatgtcctg gcacacacct gggaaccagg tgagcaccag    2400
```

-continued gtggcacggc cctaactgca cagcagcttt cccttcagcc ccatacgagc tctggctctg 2460
ctgggggggg ggggtgaggt gggggagcac cccaaagact gggcgggcgc actcagcaca 2520
gcacagcctg agccccaagg cctttgtggc agcggcccgt gtcccagtgc tcccggcagt 2580
gcggggaggg ccaggtgcgc cgtgtgaagg gcttccactc ctgctgctat gactgcgtgg 2640
actgcaaggc gggcacctat cagcgcagcc caggtgagca cctctccaag gcccatacac 2700
acgggacagg tgggggcagg gacccccagg tctcatgtcc tgactcaaag gccaactttg 2760
aggccagagc aagtgggtgg gagcctgaac tctcccccaa gtgccccatc ttcctcccac 2820
atgacagatg acctcctctg cacccagtgt gaccagaacc agtggtcccc agaccggagc 2880
acacgctgct tcccccgcag gctcactttc ctggcatggg ggcagccggc tgtgctggtg 2940
ctgcttatac tgctggctct ggcgctgggc ctggtgctgg tggccctggg gctctttatt 3000
aggcaccggg acagcccact ggttcaggcc tcaggggggc cacgggcctg ctttggcttg 3060
gcctgcctgg gccttgtctg cctcagtgtc cttctgttcc ctggccagcc gggccctgcc 3120
agctgcctgg cccagcagcc actgcttcac cttccactca ctggctgtct gagcacactt 3180
ttcctgcaag cggcccagat atttgtgggt tcagagctgc catcaagctg ggcagatcag 3240
ctgcgtaggt gcctgcaggg gccctgggcc tggttgctgg tgctgcttgc tttgctggcg 3300
gaagcggcat tatgtgcctg gtacctggtg gcctttccac cagaggtggt gacagactgg 3360
tgggtgctac ccacgcaagt gctggtgcac tgccgaatgc gctcctggat cagctttggc 3420
ctattgcatg ccatcaatgc catgctggcc ttcctctgct tcctgggcac gttcttggtg 3480
cagagccggc caggccgcta caatggcgcc cggggtctca cttttgccat gctggcctac 3540
ttcatcacct ggatctcctt tgtccctctc tttgccaatg tgcatgtggc ctaccagccc 3600
actgtgcaga tggccgccat cctcctctgt gccctgggca tcctggccac cttccacctg 3660
cccaagtgct acctgctgct gcagcagctg gagctcaaca acccggagtt cttcctagga 3720
gatgatgcca gaggacaggg cagcagtggt agtgggggga aggagactta gggcaaaaac 3780
aagtgacccc tgacccagtg accccagacc tagctgagat acccacaaat cacatttcta 3840
tgaagcaacc accaacctgg accccagctg ctgagaccac ccctttctag atcctaactg 3900
taggctaact agctgacctt gatggaacag tgaccgttag gcctgtagca tccatgaagg 3960
gcttcagcac ccacctgagg ccccagaaaa gctttgtccc tgtcctagcc aaggcctggc 4020
caaggcctac ccatgtgatc cagccctact gaacaaaagg tccacgaaaa ggatccttga 4080
ggctcctggc gttcatgcca agagctcaag acacctacca gccaggtcac ttaaaggcca 4140
aactgggcat tacttgcctg gccaggccca gcctggagcc tccagccagc accctctcca 4200
agcatcacag ggatgggaga ttggtaagag ggctggagat gtcgtgaccc ctctgcaggg 4260
gtctatgact gaccacagga ccagatgggg caggaatggt gagcagggaa gagggctagt 4320
gggagggtac atacccaacc tccttct 4347

<210> SEQ ID NO 8
<211> LENGTH: 2496
<212> TYPE: DNA
<213> ORGANISM: Canis familiaris

<400> SEQUENCE: 8
atggcaggcc tgatgctcct gagcctcatg gctctcttgg gccttggagc aggcgcccca 60
ttgtgcttat cccggcagct caggatgcaa ggggactatg tgctgggcgg gctcttcccc 120
ctgggcacag ctgaggacac aggtctcagt gacaggacac agcccaatgc cactgtgtgc 180

-continued

```
accaggttct cgtccctcgg cctgctctgg gcgctggcca tgaagatggc ggtggaggag    240
gtcaacaaca ggtccacgct gctgccagga ctgcgcctgg gctacgacct ctttgacaca    300
tgttcggagc ctgtggtggc catgaagccc agcctcatgt tcatggccaa agcgggcagc    360
tgcgacatcg ccgcctactg caactacacg cagtaccagc cccgtgtgct ggcagtcatt    420
gggccacact catctgagct cgccctcatc accggcaagt tcttcagctt cttcctcatg    480
cctcaggtca gctacggggc cagcaccgac cggctgagca accgggagac gttcccatcc    540
ttcttccgca cggtgtccag cgaccgcgta caggcagtgg ccatggtgga gctgctgcag    600
gagcttggct ggaactgggt ggctgcagtg ggcagcgatg acgagtatgg ccggcagggc    660
ctgagcctct tctccagcct ggccaatgcc aggggcatct gtattgcgca tgagggcctg    720
gtgccattgc cgcacacgag tagcctgcgg ctgggcactg tccagggcct actgcaccag    780
gtaaaccaga gcagcgtgca ggtggtggtg cttttctctt ccactcgtgc tgcccgcacc    840
ctcttcagct acagcatcca ctgcaggctc tcgcccaagg tttgggtggc cagtgaggcc    900
tggctgacct cggacctggt catgacgctg cctggcatgg ctgaggtggg caccgtgctt    960
ggctttctgc agcagggcgc cccaataccc gagttcccat cctatgtgca gacctgcctg   1020
gccctggctg ctgaccctgc cttttgcgcc tcactggatg cagagcagcc gggcctggaa   1080
gagcacgtgg tggggccccg ctgtccccag tgtgaccacg tcactctgga gctatgtctg   1140
cagggctgct gcaccaccag accttcgcgg cctacgcagc cgtgtatggc gtggcccagg   1200
ccctccacaa cacactgctc tgcaatgcct caggctgccc cccacgggag ccagtgcggc   1260
cctggcagct cctagaaaac atgtacaact tgaccttccg tgtgcgcggc ttagcactgc   1320
agttcgatgc caggggggaac gtgaatatgg attatgacct gaaactgtgg gtgtggcggg   1380
acctgaagcc cgagttgcgc accgtaggtg ccttcaacgg ccgcctgaag gtctggcact   1440
cccagatgtc ctggcacaca cctgggaacc agcggcccgt gtcccagtgc tcccggcagt   1500
gcggggaggg ccaggtgcgc cgtgtgaagg gcttccactc ctgctgctat gactgcgtgg   1560
actgcaaggc gggcacctat cagcgcagcc cagatgacct cctctgcacc cagtgtgacc   1620
agaaccagtg gtccccagac cggagcacac gctgcttccc ccgcaggctc actttcctgg   1680
catgggggca gccggctgtg ctggtgctgc ttatactgct ggctctggcg ctgggcctgg   1740
tgctggtggc cctggggctc tttattaggc accgggacag cccactggtt caggcctcag   1800
gggggccacg ggcctgcttt ggcttggcct gcctgggcct tgtctgcctc agtgtccttc   1860
tgttccctgg ccagccgggc cctgccagct gcctggccca gcagccactg cttcaccttc   1920
cactcactgg ctgtctgagc acacttttcc tgcaagcggc ccagatattt gtgggttcag   1980
agctgccatc aagctgggca gatcagctgc gtaggtgcct gcaggggccc tgggcctggt   2040
tgctggtgct gcttgctttg ctggcggaag cggcattatg tgcctggtac ctggtggcct   2100
ttccaccaga ggtggtgaca gactggtggg tgctacccac gcaagtgctg gtgcactgcc   2160
gaatgcgctc ctggatcagc tttggcctag tgcatgccat caatgccatg ctggccttcc   2220
tctgcttcct gggcacgttc ttggtgcaga gccggccagg ccgctacaat ggcgcccggg   2280
gtctcacttt tgccatgctg gcctacttca tcacctggat ctcctttgtc cctctctttg   2340
ccaatgtgca tgtggcctac cagcccactg tgcagatggc cgccatcctc ctctgtgccc   2400
tgggcatcct ggccaccttc cacctgccca agtgctacct gctgctgcag cagctggagc   2460
tcaacaaccc ggagttcttc ctaggagatg atgcca                             2496
```

<210> SEQ ID NO 9

<211> LENGTH: 845
<212> TYPE: PRT
<213> ORGANISM: Canis familiaris

<400> SEQUENCE: 9

```
Met Ala Gly Leu Met Leu Leu Ser Leu Met Ala Leu Leu Gly Leu Gly
1               5                   10                  15

Ala Gly Ala Pro Leu Cys Leu Ser Arg Gln Leu Arg Met Gln Gly Asp
            20                  25                  30

Tyr Val Leu Gly Gly Leu Phe Pro Leu Gly Thr Ala Glu Asp Thr Gly
        35                  40                  45

Leu Ser Asp Arg Thr Gln Pro Asn Ala Thr Val Cys Thr Arg Phe Ser
    50                  55                  60

Ser Leu Gly Leu Leu Trp Ala Leu Ala Met Lys Met Ala Val Glu Glu
65                  70                  75                  80

Val Asn Asn Arg Ser Thr Leu Leu Pro Gly Leu Arg Leu Gly Tyr Asp
                85                  90                  95

Leu Phe Asp Thr Cys Ser Glu Pro Val Val Ala Met Lys Pro Ser Leu
            100                 105                 110

Met Phe Met Ala Lys Ala Gly Ser Cys Asp Ile Ala Ala Tyr Cys Asn
        115                 120                 125

Tyr Thr Gln Tyr Gln Pro Arg Val Leu Ala Val Ile Gly Pro His Ser
    130                 135                 140

Ser Glu Leu Ala Leu Ile Thr Gly Lys Phe Phe Ser Phe Phe Leu Met
145                 150                 155                 160

Pro Gln Val Ser Tyr Gly Ala Ser Thr Asp Arg Leu Ser Asn Arg Glu
                165                 170                 175

Thr Phe Pro Ser Phe Phe Arg Thr Val Ser Ser Asp Arg Val Gln Ala
            180                 185                 190

Val Ala Met Val Glu Leu Leu Gln Glu Leu Gly Trp Asn Trp Val Ala
        195                 200                 205

Ala Val Gly Ser Asp Asp Glu Tyr Gly Arg Gln Gly Leu Ser Leu Phe
    210                 215                 220

Ser Ser Leu Ala Asn Ala Arg Gly Ile Cys Ile Ala His Glu Gly Leu
225                 230                 235                 240

Val Pro Leu Pro His Thr Ser Ser Leu Arg Leu Gly Thr Val Gln Gly
                245                 250                 255

Leu Leu His Gln Val Asn Gln Ser Ser Val Gln Val Val Val Leu Phe
            260                 265                 270

Ser Ser Thr Arg Ala Ala Arg Thr Leu Phe Ser Tyr Ser Ile His Cys
        275                 280                 285

Arg Leu Ser Pro Lys Val Trp Val Ala Ser Glu Ala Trp Leu Thr Ser
    290                 295                 300

Asp Leu Val Met Thr Leu Pro Gly Met Ala Glu Val Gly Thr Val Leu
305                 310                 315                 320

Gly Phe Leu Gln Gln Gly Ala Pro Ile Pro Glu Phe Pro Ser Tyr Val
                325                 330                 335

Gln Thr Cys Leu Ala Leu Ala Ala Asp Pro Ala Phe Cys Ala Ser Leu
            340                 345                 350

Asp Ala Glu Gln Pro Gly Leu Glu Glu His Val Val Gly Pro Arg Cys
        355                 360                 365

Pro Gln Cys Asp His Val Thr Leu Glu Ala Met Ser Ala Gly Leu Leu
    370                 375                 380

His His Gln Thr Phe Ala Ala Tyr Ala Ala Val Tyr Gly Val Ala Gln
385                 390                 395                 400
```

-continued

```
Ala Leu His Asn Thr Leu Leu Cys Asn Ala Ser Gly Cys Pro Pro Arg
                405                 410                 415

Glu Pro Val Arg Pro Trp Gln Leu Leu Glu Asn Met Tyr Asn Leu Thr
            420                 425                 430

Phe Arg Val Arg Gly Leu Ala Leu Gln Phe Asp Ala Arg Gly Asn Val
        435                 440                 445

Asn Met Asp Tyr Asp Leu Lys Leu Trp Val Trp Arg Asp Leu Lys Pro
    450                 455                 460

Glu Leu Arg Thr Val Gly Ala Phe Asn Gly Arg Leu Lys Val Trp His
465                 470                 475                 480

Ser Gln Met Ser Trp His Thr Pro Gly Asn Gln Arg Pro Val Ser Gln
                485                 490                 495

Cys Ser Arg Gln Cys Gly Glu Gly Gln Val Arg Arg Val Lys Gly Phe
            500                 505                 510

His Ser Cys Cys Tyr Asp Cys Val Asp Cys Lys Ala Gly Thr Tyr Gln
        515                 520                 525

Arg Ser Pro Asp Asp Leu Leu Cys Thr Gln Cys Asp Gln Asn Gln Trp
    530                 535                 540

Ser Pro Asp Arg Ser Thr Arg Cys Phe Pro Arg Arg Leu Thr Phe Leu
545                 550                 555                 560

Ala Trp Gly Gln Pro Ala Val Leu Val Leu Leu Ile Leu Leu Ala Leu
                565                 570                 575

Ala Leu Gly Leu Val Leu Val Ala Leu Gly Leu Phe Ile Arg His Arg
            580                 585                 590

Asp Ser Pro Leu Val Gln Ala Ser Gly Gly Pro Arg Ala Cys Phe Gly
        595                 600                 605

Leu Ala Cys Leu Gly Leu Val Cys Leu Ser Val Leu Leu Phe Pro Gly
    610                 615                 620

Gln Pro Gly Pro Ala Ser Cys Leu Ala Gln Gln Pro Leu Leu His Leu
625                 630                 635                 640

Pro Leu Thr Gly Cys Leu Ser Thr Leu Phe Leu Gln Ala Ala Gln Ile
                645                 650                 655

Phe Val Gly Ser Glu Leu Pro Ser Ser Trp Ala Asp Gln Leu Arg Arg
            660                 665                 670

Cys Leu Gln Gly Pro Trp Ala Trp Leu Leu Val Leu Leu Ala Leu Leu
        675                 680                 685

Ala Glu Ala Ala Leu Cys Ala Trp Tyr Leu Val Ala Phe Pro Pro Glu
    690                 695                 700

Val Val Thr Asp Trp Trp Val Leu Pro Thr Gln Val Leu Val His Cys
705                 710                 715                 720

Arg Met Arg Ser Trp Ile Ser Phe Gly Leu Val His Ala Ile Asn Ala
                725                 730                 735

Met Leu Ala Phe Leu Cys Phe Leu Gly Thr Phe Leu Val Gln Ser Arg
            740                 745                 750

Pro Gly Arg Tyr Asn Gly Ala Arg Gly Leu Thr Phe Ala Met Leu Ala
        755                 760                 765

Tyr Phe Ile Thr Trp Ile Ser Phe Val Pro Leu Phe Ala Asn Val His
    770                 775                 780

Val Ala Tyr Gln Pro Thr Val Gln Met Ala Ala Ile Leu Leu Cys Ala
785                 790                 795                 800

Leu Gly Ile Leu Ala Thr Phe His Leu Pro Lys Cys Tyr Leu Leu Leu
                805                 810                 815

Gln Gln Leu Glu Leu Asn Asn Pro Glu Phe Phe Leu Gly Asp Asp Ala
```

```
            820                 825                 830

Arg Gly Gln Gly Ser Ser Gly Ser Gly Gly Lys Glu Thr
        835                 840                 845
```

<210> SEQ ID NO 10
<211> LENGTH: 2532
<212> TYPE: DNA
<213> ORGANISM: Mus musculus

<400> SEQUENCE: 10

```
atgggacccc aggcgaggac actccatttg ctgtttctcc tgctgcatgc tctgcctaag      60

ccagtcatgc tggtagggaa ctccgacttt cacctggctg ggactacct cctgggtggc     120

ctctttaccc tccatgccaa cgtgaagagc gtctctcacc tcagctacct gcaggtgccc    180

aagtgcaatg agtacaacat gaaggtcttg ggctacaacc tcatgcaggc catgcgattc    240

gccgtggagg aaatcaacaa ctgtagctct ctgctgcccg gcgtgctgct cggctacgag    300

atggtggatg tctgctacct ctccaacaat atccagcctg ggctctactt cctgtcacag    360

atagatgact tcctgcccat cctcaaagac tacagccagt acaggcccca agtggtggcc    420

gtcattggcc cagacaactc tgagtccgcc atcaccgtgt ccaacattct ctcctacttc    480

ctcgtgccac aggtcacata tagcgccatc accgacaagc tgcgagacaa gcggcgcttc    540

cctgccatgc tgcgcactgt gcccagcgcc acccaccaca tcgaggccat ggtgcaactg    600

atggttcact tccagtggaa ctggatcgtg gtgctggtga gcgatgacga ttatggccga    660

gagaacagcc acctgctgag ccagcgtctg accaacactg gcgatatctg cattgccttc    720

caggaggttc tgcctgtacc agaacccaac caggccgtga ggcctgagga gcaggaccaa    780

ctggacaaca tcctggacaa gctgcggcgg acctcggcgc gtgtggtggt gatattctcg    840

ccagagctga gcctgcacaa cttcttccgc gaggtgctgc gctggaactt cacaggcttt    900

gtgtggattg cctctgagtc ctgggccatc gaccctgttc tacacaacct cacagagctg    960

cgccacacgg gcactttcct gggcgtcacc atccagaggg tgtccatccc tggcttcagc   1020

cagttccgag tgcgccacga caagccagag tatcccatgc ctaacgagac cagcctgagg   1080

actacctgta accaggactg tgacgcctgc atgaacatca ccgagtcctt taacaacgtt   1140

ctcatgcttt cgggggagcg tgtggtctac agtgtgtact cggccgtcta cgcggtagcc   1200

cacaccctcc acagactcct ccactgcaac caggtccgct gcaccaagca aatcgtctat   1260

ccatggcagc tactcaggga gatctggcat gtcaacttca cgctcctggg caaccagctc   1320

ttcttcgacg aacaagggga catgccgatg ctcctggaca tcatccagtg gcaatggggc   1380

ctgagccaga accccttcca aagcatcgcc tcctactccc ccaccgagac gaggctgacc   1440

tacattagca atgtgtcctg gtacaccccc aacaacacgg tccccatatc catgtgttct   1500

aagagttgcc agcctgggca aatgaaaaaa cccataggcc tccacccgtg ctgcttcgag   1560

tgtgtggact gtccgccggg cacctacctc aaccgatcag tagatgagtt taactgtctg   1620

tcctgcccgg gttccatgtg gtcttacaag aacaacatcg cttgcttcaa gcggcggctg   1680

gccttcctgg agtggcacga agtgcccact atcgtggtga ccatcctggc cgccctgggc   1740

ttcatcagta cgctggccat tctgctcatc ttctggagac atttccagac gcccatggtg   1800

cgctcggcgg gcggccccat gtgcttcctg atgctggtgc ccctgctgct ggcgttcggg   1860

atggtccccg tgtatgtggg cccccccacg gtcttctcct gtttctgccg ccaggctttc   1920

ttcaccgttt gcttctccgt ctgcctctcc tgcatcacgg tgcgctcctt ccagattgtg   1980

tgcgtcttca agatggccag acgcctgcca agcgcctacg gtttctggat gcgttaccac   2040
```

```
gggccctacg tctttgtggc cttcatcacg gccgtcaagg tggccctggt ggcaggcaac   2100

atgctggcca ccaccatcaa ccccattggc cggaccgacc ccgatgaccc caatatcata   2160

atcctctcct gccaccctaa ctaccgcaac gggctactct tcaacaccag catggacttg   2220

ctgctgtccg tgctgggttt cagcttcgcg tacgtgggca aggaactgcc caccaactac   2280

aacgaagcca agttcatcac cctcagcatg accttctcct tcacctcctc catctccctc   2340

tgcacgttca tgtctgtcca cgatggcgtg ctggtcacca tcatggatct cctggtcact   2400

gtgctcaact ttctggccat cggcttgggg tactttggcc ccaagtgtta catgatcctt   2460

ttctacccgg agcgcaacac ttcagcttat ttcaatagca tgattcaggg ctacacgatg   2520

aggaagagct ag                                                       2532
```

```
<210> SEQ ID NO 11
<211> LENGTH: 2529
<212> TYPE: DNA
<213> ORGANISM: Rattus rattus

<400> SEQUENCE: 11

atgggtcccc aggcaaggac actctgcttg ctgtctctcc tgctgcatgt tctgcctaag     60

ccaggcaagc tggtagagaa ctctgacttc cacctggccg gggactacct cctgggtggc    120

ctctttaccc tccatgccaa cgtgaagagc atctcccacc tcagctacct gcaggtgccc    180

aagtgcaatg agttcaccat gaaggtgttg ggctacaacc tcatgcaggc catgcgtttc    240

gctgtggagg agatcaacaa ctgtagctcc ctgctacccg gcgtgctgct cggctacgag    300

atggtggatg tctgttacct ctccaacaat atccaccctg ggctctactt cctggcacag    360

gacgacgacc tcctgcccat cctcaaagac tacagccagt acatgcccca cgtggtggct    420

gtcattggcc ccgacaactc tgagtccgcc attaccgtgt ccaacattct ctctcatttc    480

ctcatcccac agatcacata cagcgccatc tccgacaagc tgcgggacaa gcggcacttc    540

cctagcatgc tacgcacagt gcccagcgcc acccaccaca tcgaggccat ggtgcagctg    600

atggttcact tccaatggaa ctggattgtg gtgctggtga gcgacgacga ttacggccgc    660

gagaacagcc acctgttgag ccagcgtctg accaaaacga gcgacatctg cattgccttc    720

caggaggttc tgcccatacc tgagtccagc caggtcatga ggtccgagga gcagagacaa    780

ctggacaaca tcctggacaa gctgcggcgg acctcggcgc gcgtcgtggt ggtgttctcg    840

cccgagctga gcctgtatag cttctttcac gaggtgctcc gctggaactt cacgggtttt    900

gtgtggatcg cctctgagtc ctgggctatc gacccagttc tgcataacct cacggagctg    960

cgccacacgg gtacttttct gggcgtcacc atccagaggg tgtccatccc tggcttcagt   1020

cagttccgag tgcgccgtga caagccaggg tatcccgtgc ctaacacgac caacctgcgg   1080

acgacctgca accaggactg tgacgcctgc ttgaacacca ccaagtcctt caacaacatc   1140

cttatacttt cgggggagcg cgtggtctac agcgtgtact cggcagttta cgcggtggcc   1200

catgccctcc acagactcct cggctgtaac cgggtccgct gcaccaagca aaaggtctac   1260

ccgtggcagc tactcaggga gatctggcac gtcaacttca cgctcctggg taaccggctc   1320

ttctttgacc aacaagggga catgccgatg ctcttggaca tcatccagtg gcagtgggac   1380

ctgagccaga atcccttcca aagcatcgcc tcctattctc ccaccagcaa gaggctaacc   1440

tacattaaca atgtgtcctg gtacaccccc aacaacacgg tccctgtctc catgtgttcc   1500

aagagctgcc agccagggca aatgaaaaag tctgtgggcc tccacccttg ttgcttcgag   1560

tgcttggatt gtatgccagg cacctacctc aaccgctcag cagatgagtt taactgtctg   1620
```

```
tcctgcccgg gttccatgtg gtcctacaag aacgacatca cttgcttcca gcggcggcct   1680

accttcctgg agtggcacga agtgcccacc atcgtggtgg ccatactggc tgccctgggc   1740

ttcttcagta cactggccat tcttttcatc ttctggagac atttccagac acccatggtg   1800

cgctcggccg gtggccccat gtgcttcctg atgctcgtgc ccctgctgct ggcgtttggg   1860

atggtgcccg tgtatgtggg gcccccacg gtcttctcat gcttctgccg acaggctttc   1920

ttcaccgtct gcttctccat ctgcctatcc tgcatcaccg tgcgctcctt ccagatcgtg   1980

tgtgtcttca agatggccag acgcctgcca agtgcctaca gtttttggat gcgttaccac   2040

gggccctatg tcttcgtggc cttcatcacg gccatcaagg tggccctggt ggtgggcaac   2100

atgctggcca ccaccatcaa ccccattggc cggaccgacc cggatgaccc caacatcatg   2160

atcctctcgt gccaccctaa ctaccgcaac gggctactgt tcaacaccag catggacttg   2220

ctgctgtctg tgctgggttt cagcttcgct tacatgggca aggagctgcc caccaactac   2280

aacgaagcca agttcatcac tctcagcatg accttctcct tcacctcctc catctccctc   2340

tgcaccttca tgtctgtgca cgacggcgtg ctggtcacca tcatggacct cctggtcact   2400

gtgctcaact tcctggccat cggcttggga tactttggcc ccaagtgtta catgatcctt   2460

ttctacccgg agcgcaacac ctcagcctat ttcaatagca tgatccaggg ctacaccatg   2520

aggaagagc                                                          2529
```

```
<210> SEQ ID NO 12
<211> LENGTH: 2520
<212> TYPE: DNA
<213> ORGANISM: Homo sapiens

<400> SEQUENCE: 12

atggggccca gggcaaagac catctgctcc ctgttcttcc tcctatgggt cctggctgag     60

ccggctgaga actcggactt ctacctgcct ggggattacc tcctgggtgg cctcttctcc    120

ctccatgcca acatgaaggg cattgttcac cttaacttcc tgcaggtgcc catgtgcaag    180

gagtatgaag tgaaggtgat aggctacaac ctcatgcagg ccatgcgctt cgcggtggag    240

gagatcaaca atgacagcag cctgctgcct ggtgtgctgc tgggctatga gatcgtggat    300

gtgtgctaca tctccaacaa tgtccagccg gtgctctact tcctggcaca cgaggacaac    360

ctccttccca tccaagagga ctacagtaac tacatttccc gtgtggtggc tgtcattggc    420

cctgacaact ccgagtctgt catgactgtg gccaacttcc tctccctatt tctccttcca    480

cagatcacct acagcgccat cagcgatgag ctgcgagaca aggtgcgctt cccggctttg    540

ctgcgtacca cacccagcgc cgaccaccac gtcgaggcca tggtgcagct gatgctgcac    600

ttccgctgga actggatcat tgtgctggtg agcagcgaca cctatggccg cgacaatggc    660

cagctgcttg gcgagcgcgt ggcccggcgc gacatctgca tcgccttcca ggagacgctg    720

cccacactgc agcccaacca gaacatgacg tcagaggagc gccagcgcct ggtgaccatt    780

gtggacaagc tgcagcagag cacagcgcgc gtcgtggtcg tgttctcgcc cgacctgacc    840

ctgtaccact tcttcaatga ggtgctgcgc cagaacttca cgggcgccgt gtggatcgcc    900

tccgagtcct gggccatcga cccggtcctg cacaacctca cggagctggg ccacttgggc    960

accttcctgg gcatcaccat ccagagcgtg cccatcccgg gcttcagtga gttccgcgag   1020

tggggcccac aggctgggcc gccacccctc agcaggacca gccagagcta tacctgcaac   1080

caggagtgcg acaactgcct gaacgccacc ttgtccttca acaccattct caggctctct   1140

ggggagcgtg tcgtctacag cgtgtactct gcggtctatg ctgtggccca tgccctgcac   1200
```

```
agcctcctcg gctgtgacaa aagcacctgc accaagaggg tggtctaccc ctggcagctg   1260

cttgaggaga tctggaaggt caacttcact ctcctggacc accaaatctt cttcgacccg   1320

caaggggacg tggctctgca cttggagatt gtccagtggc aatgggaccg gagccagaat   1380

cccttccaga gcgtcgcctc ctactacccc ctgcagcgac agctgaagaa catccaagac   1440

atctcctggc acaccgtcaa caacacgatc cctatgtcca tgtgttccaa gaggtgccag   1500

tcagggcaaa agaagaagcc tgtgggcatc cacgtctgct gcttcgagtg catcgactgc   1560

cttcccggca ccttcctcaa ccacactgaa gatgaatatg aatgccaggc ctgcccgaat   1620

aacgagtggt cctaccagag tgagacctcc tgcttcaagc ggcagctggt cttcctggaa   1680

tggcatgagg cacccaccat cgctgtggcc ctgctggccg ccctgggctt cctcagcacc   1740

ctggccatcc tggtgatatt ctggaggcac ttccagacac ccatagttcg ctcggctggg   1800

ggccccatgt gcttcctgat gctgacactg ctgctggtgg catacatggt ggtcccggtg   1860

tacgtggggc cgcccaaggt ctccacctgc ctctgccgcc aggccctctt tcccctctgc   1920

ttcacaattt gcatctcctg tatcgccgtg cgttctttcc agatcgtctg cgccttcaag   1980

atggccagcc gcttcccacg cgcctacagc tactgggtcc gctaccaggg gccctacgtc   2040

tctatggcat ttatcacggt actcaaaatg gtcattgtgg taattggcat gctggccacg   2100

ggcctcagtc ccaccacccg tactgacccc gatgacccca agatcacaat tgtctcctgt   2160

aaccccaact accgcaacag cctgctgttc aacaccagcc tggacctgct gctctcagtg   2220

gtgggtttca gcttcgccta catgggcaaa gagctgccca ccaactacaa cgaggccaag   2280

ttcatcaccc tcagcatgac cttctatttc acctcatccg tctccctctg caccttcatg   2340

tctgcctaca gcggggtgct ggtcaccatc gtggacctct tggtcactgt gctcaacctc   2400

ctggccatca gcctgggcta cttcggcccc aagtgctaca tgatcctctt ctacccggag   2460

cgcaacacgc ccgcctactt caacagcatg atccagggct acaccatgag gagggactag   2520
```

<210> SEQ ID NO 13
<211> LENGTH: 2529
<212> TYPE: DNA
<213> ORGANISM: Mus musculus

<400> SEQUENCE: 13

```
atgcttttct gggcagctca cctgctgctc agcctgcagc tggccgttgc ttactgctgg     60

gctttcagct gccaaaggac agaatcctct ccaggtttca gcctccctgg ggacttcctc    120

ctggcaggcc tgttctccct ccatgctgac tgtctgcagg tgagacacag acctctggtg    180

acaagttgtg acaggtctga cagcttcaac ggccatggct atcacctctt ccaagccatg    240

cggttcaccg ttgaggagat aaacaactcc acagctctgc ttcccaacat caccctgggg    300

tatgaactgt atgacgtgtg ctcagagtct tccaatgtct atgccaccct gagggtgctc    360

gcccagcaag ggacaggcca cctagagatg cagagagatc ttcgcaacca ctcctccaag    420

gtggtggcac tcattgggcc tgataacact gaccacgctg tcaccactgc tgccctgctg    480

agccctttc tgatgcccct ggtcagctat gaggcgagca gcgtgatcct cagtgggaag     540

cgcaagttcc cgtccttctt gcgcaccatc cccagcgata agtaccaggt ggaagtcata    600

gtgcggctgc tgcagagctt cggctgggtc tggatctcgc tcgttggcag ctatggtgac    660

tacgggcagc tgggcgtaca ggcgctggag gagctggcca ctccacgggg catctgcgtc    720

gccttcaagg acgtggtgcc tctctccgcc caggcgggtg acccaaggat gcagcgcatg    780

atgctgcgtc tggctcgagc caggaccacc gtggtcgtgg tcttctctaa ccggcacctg    840
```

gctggagtgt tcttcaggtc tgtggtgctg gccaacctga ctggcaaagt gtggatcgcc 900
tccgaagact gggccatctc cacgtacatc accaatgtgc ccgggatcca gggcattggg 960
acggtgctgg gggtggccat ccagcagaga caagtccctg gcctgaagga gtttgaagag 1020
tcctatgtcc aggcagtgat gggtgctccc agaacttgcc cagaggggtc ctggtgcggc 1080
actaaccagc tgtgcaggga gtgtcacgct ttcacgacat ggaacatgcc cgagcttgga 1140
gccttctcca tgagcgctgc ctacaatgtg tatgaggctg tgtatgctgt ggcccacggc 1200
ctccaccagc tcctgggatg tacctctggg acctgtgcca gaggcccagt ctacccctgg 1260
cagcttcttc agcagatcta caaggtgaat ttccttctac ataagaagac tgtagcattc 1320
gatgacaagg gggaccctct aggttattat gacatcatcg cctgggactg gaatggacct 1380
gaatggacct ttgaggtcat tggttctgcc tcactgtctc cagttcatct agacataaat 1440
aagacaaaaa tccagtggca cgggaagaac aatcaggtgc ctgtgtcagt gtgtaccagg 1500
gactgtctcg aagggcacca caggttggtc atgggttccc accactgctg cttcgagtgc 1560
atgccctgtg aagctgggac atttctcaac acgagtgagc ttcacacctg ccagccttgt 1620
ggaacagaag aatgggcccc tgaggggagc tcagcctgct tctcacgcac cgtggagttc 1680
ttggggtggc atgaacccat ctctttggtg ctattagcag ctaacacgct attgctgctg 1740
ctgctgattg ggactgctgg cctgtttgcc tggcgtcttc acacgcctgt tgtgaggtca 1800
gctgggggta ggctgtgctt cctcatgctg ggttccttgg tagctgggag ttgcagcctc 1860
tacagcttct tcgggaagcc cacggtgccc gcgtgcttgc tgcgtcagcc cctcttttct 1920
ctcgggtttg ccattttcct ctcctgtctg acaatccgct ccttccaact ggtcatcatc 1980
ttcaagtttt ctaccaaggt acccacattc taccacactt gggcccaaaa ccatggtgcc 2040
ggaatattcg tcattgtcag ctccacggtc catttgttcc tctgtctcac gtggcttgca 2100
atgtggaccc cacggcccac cagggagtac cagcgcttcc cccatctggt gattcttgag 2160
tgcacagagg tcaactctgt gggcttcctg gtggctttcg cacacaacat cctcctctcc 2220
atcagcacct ttgtctgcag ctacctgggt aaggaactgc cggagaacta taacgaagcc 2280
aaatgtgtca ccttcagcct gctcctccac ttcgtatcct ggatcgcttt cttcaccatg 2340
tccagcattt accagggcag ctacctaccc gcggtcaatg tgctggcagg gctggccact 2400
ctgagtggcg gcttcagcgg ctatttcctc cctaaatgct acgtgattct ctgccgtcca 2460
gaactcaaca acacagaaca ctttcaggcc tccatccagg actacacgag gcgctgcggc 2520
actacctga 2529

<210> SEQ ID NO 14
<211> LENGTH: 2520
<212> TYPE: DNA
<213> ORGANISM: Rattus rattus

<400> SEQUENCE: 14
atgctcttct gggctgctca cctgctgctc agcctgcagt tggtctactg ctgggctttc 60
agctgccaaa ggacagagtc ctctccaggc ttcagccttc ctggggactt cctccttgca 120
ggtctgttct ccctccatgg tgactgtctg caggtgagac acagacctct ggtgacaagt 180
tgtgacaggc ccgacagctt caacggccat ggctaccacc tcttccaagc catgcggttc 240
actgttgagg agataaacaa ctcctcggcc ctgcttccca acatcaccct ggggtatgag 300
ctgtacgacg tgtgctcaga atctgccaat gtgtatgcca ccctgagggt gcttgccctg 360
caagggcccc gccacataga gatacagaaa gaccttcgca accactcctc caaggtggtg 420

-continued

```
gccttcatcg ggcctgacaa cactgaccac gctgtcacta ccgctgcctt gctgggtcct    480

ttcctgatgc ccctggtcag ctatgaggca agcagcgtgg tactcagtgc caagcgcaag    540

ttcccgtctt tccttcgtac cgtccccagt gaccggcacc aggtggaggt catggtgcag    600

ctgctgcaga gttttgggtg ggtgtggatc tcgctcattg gcagctacgg tgattacggg    660

cagctgggtg tgcaggcgct ggaggagctg gccgtgcccc ggggcatctg cgtcgccttc    720

aaggacatcg tgcctttctc tgcccgggtg ggtgacccga ggatgcagag catgatgcag    780

catctggctc aggccaggac caccgtggtt gtggtcttct ctaaccggca cctggctaga    840

gtgttcttca ggtccgtggt gctggccaac ctgactggca aagtgtgggt cgcctcagaa    900

gactgggcca tctccacgta catcaccagc gtgactggga tccaaggcat tgggacggtg    960

ctcggtgtgg ccgtccagca gagacaagtc cctgggctga aggagtttga ggagtcttat   1020

gtcagggctg taacagctgc tcccagcgct tgcccggagg ggtcctggtg cagcactaac   1080

cagctgtgcc gggagtgcca cacgttcacg actcgtaaca tgcccacgct tggagccttc   1140

tccatgagtg ccgcctacag agtgtatgag gctgtgtacg ctgtggccca cggcctccac   1200

cagctcctgg gatgtacttc tgagatctgt tccagaggcc cagtctaccc ctggcagctt   1260

cttcagcaga tctacaaggt gaattttctt ctacatgaga atactgtggc atttgatgac   1320

aacggggaca ctctaggtta ctacgacatc atcgcctggg actggaatgg acctgaatgg   1380

acctttgaga tcattggctc tgcctcactg tctccagttc atctggacat aaataagaca   1440

aaaatccagt ggcacgggaa gaacaatcag gtgcctgtgt cagtgtgtac cacggactgt   1500

ctggcagggc accacagggt ggttgtgggt tcccaccact gctgcttcga gtgcatgccc   1560

tgtgaagctg ggacatttct caacacgagt gagcttcaca tctgccagcc ttgtggaaca   1620

gaagaatggg cacccaagga gagcactact tgcttcccac gcacggtgga gttcttggct   1680

tggcatgaac ccatctcttt ggtgctaata gcagctaaca cgctattgct gctgctgctg   1740

gttgggactg ctggcctgtt tgcctggcat tttcacacac ctgtagtgag gtcagctggg   1800

ggtaggctgt gcttcctcat gctgggttcc ctggtggccg gaagttgcag cttctatagc   1860

ttcttcgggg agcccacggt gcccgcgtgc ttgctgcgtc agcccctctt ttctctcggg   1920

tttgccatct tcctctcctg cctgacaatc cgctccttcc aactggtcat catcttcaag   1980

ttttctacca aggtgcccac attctaccgt acctgggccc aaaaccatgg tgcaggtcta   2040

ttcgtcattg tcagctccac ggtccatttg ctcatctgtc tcacatggct tgtaatgtgg   2100

accccacgac ccaccaggga ataccagcgc ttcccccatc tggtgattct cgagtgcaca   2160

gaggtcaact ctgtaggctt cctgttggct ttcacccaca acattctcct ctccatcagt   2220

accttcgtct gcagctacct gggtaaggaa ctgccagaga actataatga agccaaatgt   2280

gtcaccttca gcctgctcct caacttcgta tcctggatcg ccttcttcac catggccagc   2340

atttaccagg gcagctacct gcctgcggtc aatgtgctgg cagggctgac cacactgagc   2400

ggcggcttca gcggttactt cctccccaag tgctatgtga ttctctgccg tccagaactc   2460

aacaatacag aacactttca ggcctccatc caggactaca cgaggcgctg cggcactacc   2520
```

<210> SEQ ID NO 15
<211> LENGTH: 2526
<212> TYPE: DNA
<213> ORGANISM: Homo sapiens

<400> SEQUENCE: 15

```
atgctgctct gcacggctcg cctggtcggc ctgcagcttc tcatttcctg ctgctgggcc     60
```

```
tttgcctgcc atagcacgga gtcttctcct gacttcaccc tccccggaga ttacctcctg    120
gcaggcctgt tccctctcca ttctggctgt ctgcaggtga ggcacagacc cgaggtgacc    180
ctgtgtgaca ggtcttgtag cttcaatgag catggctacc acctcttcca ggctatgcgg    240
cttggggttg aggagataaa caactccacg gccctgctgc ccaacatcac cctggggtac    300
cagctgtatg atgtgtgttc tgactctgcc aatgtgtatg ccacgctgag agtgctctcc    360
ctgccagggc aacaccacat agagctccaa ggagaccttc tccactattc ccctacggtg    420
ctggcagtga ttgggcctga cagcaccaac cgtgctgcca ccacagccgc cctgctgagc    480
cctttcctgg tgcccatgat tagctatgcg gccagcagcg agacgctcag cgtgaagcgg    540
cagtatccct ctttcctgcg caccatcccc aatgacaagt accaggtgga gaccatggtg    600
ctgctgctgc agaagttcgg gtggacctgg atctctctgg ttggcagcag tgacgactat    660
gggcagctag ggtgcaggc actggagaac caggccactg gtcaggggat ctgcattgct    720
ttcaaggaca tcatgccctt ctctgcccag gtgggcgatg agaggatgca gtgcctcatg    780
cgccacctgg cccaggccgg ggccaccgtc gtggttgttt tttccagccg gcagttggcc    840
agggtgtttt tcgagtccgt ggtgctgacc aacctgactg gcaaggtgtg ggtcgcctca    900
gaagcctggg ccctctccag gcacatcact ggggtgcccg ggatccagcg cattgggatg    960
gtgctgggcg tggccatcca gaagagggct gtccctggcc tgaaggcgtt tgaagaagcc   1020
tatgcccggg cagacaagaa ggcccctagg ccttgccaca agggctcctg gtgcagcagc   1080
aatcagctct gcagagaatg ccaagctttc atggcacaca cgatgcccaa gctcaaagcc   1140
ttctccatga gttctgccta caacgcatac cgggctgtgt atgcggtggc ccatggcctc   1200
caccagctcc tgggctgtgc ctctggagct tgttccaggg gccgagtcta cccctggcag   1260
cttttggagc agatccacaa ggtgcatttc cttctacaca aggacactgt ggcgtttaat   1320
gacaacagag atcccctcag tagctataac ataattgcct gggactggaa tggacccaag   1380
tggaccttca cggtcctcgg ttcctccaca tggtctccag ttcagctaaa cataaatgag   1440
accaaaatcc agtggcacgg aaaggacaac caggtgccta agtctgtgtg ttccagcgac   1500
tgtcttgaag ggcaccagcg agtggttacg ggtttccatc actgctgctt tgagtgtgtg   1560
ccctgtgggg ctgggacctt cctcaacaag agtgacctct acagatgcca gccttgtggg   1620
aaagaagagt gggcacctga gggaagccag acctgcttcc cgcgcactgt ggtgtttttg   1680
gctttgcgtg agcacacctc ttgggtgctg ctggcagcta acacgctgct gctgctgctg   1740
ctgcttggga ctgctggcct gtttgcctgg cacctagaca cccctgtggt gaggtcagca   1800
gggggccgcc tgtgctttct tatgctgggc tccctggcag caggtagtgg cagcctctat   1860
ggcttctttg gggaacccac aaggcctgcg tgcttgctac gccaggccct ctttgccctt   1920
ggtttcacca tcttcctgtc ctgcctgaca gttcgctcat tccaactaat catcatcttc   1980
aagttttcca ccaaggtacc tacattctac cacgcctggg tccaaaacca cggtgctggc   2040
ctgtttgtga tgatcagctc agcggcccag ctgcttatct gtctaacttg gctggtggtg   2100
tggaccccac tgcctgctag ggaataccag cgcttccccc atctggtgat gcttgagtgc   2160
acagagacca actccctggg cttcatactg gccttcctct acaatggcct cctctccatc   2220
agtgcctttg cctgcagcta cctgggtaag gacttgccag agaactacaa cgaggccaaa   2280
tgtgtcacct tcagcctgct cttcaacttc gtgtcctgga tcgccttctt caccacggcc   2340
agcgtctacg acggcaagta cctgcctgcg gccaacatga tggctgggct gagcagcctg   2400
agcagcggct tcggtgggta ttttctgcct aagtgctacg tgatcctctg ccgcccagac   2460
```

ctcaacagca cagagcactt ccaggcctcc attcaggact acacgaggcg ctgcggctcc 2520
acctga 2526

<210> SEQ ID NO 16
<211> LENGTH: 2577
<212> TYPE: DNA
<213> ORGANISM: Mus musculus

<400> SEQUENCE: 16
atgccagctt tggctatcat gggtctcagc ctggctgctt tcctggagct tgggatgggg 60
gcctctttgt gtctgtcaca gcaattcaag gcacaagggg actacatact gggcgggcta 120
tttcccctgg gctcaaccga ggaggccact ctcaaccaga gaacacaacc caacagcatc 180
ccgtgcaaca ggttctcacc ccttggtttg ttcctggcca tggccatgtg ctttgcaggg 240
gaggagatca atagccagag cagcctgctg cctggcgtgc tgctgggcta tgacctattt 300
gacacatgct ccgagccagt ggtcaccatg aaatccagtc tcatgttcct ggccaaggtg 360
ggcagtcaaa gcattgctgc ctactgcaac tacacacagt accaaccccg tgtgctggct 420
gtcatcggcc cccactcatc agagcttgcc ctcattacag gcaagttctt cagcttcttc 480
ctcatgccac aggtcagcta tagtgccagc atggatcggc taagtgaccg ggaaacgttt 540
ccatccttct tccgcacagt gcccagtgac cgggtgcagc tgcaggcagt tgtgactctg 600
ttgcagaact tcagctggaa ctgggtggcc gccttaggga gtgatgatga ctatggccgg 660
gaaggtctga gcatcttttc tagtctggcc aatgcacgag gtatctgcat cgcacatgag 720
ggcctggtgc cacaacatga cactagtggc caacagttgg gcaaggtgct ggatgtacta 780
cgccaagtga accaaagtaa agtacaagtg gtggtgctgt ttgcctctgc ccgtgctgtc 840
tactcccttt ttagttacag catccatcat ggcctctcac ccaaggtatg ggtggccagt 900
gagtcttggc tgacatctga cctggtcatg acacttccca atattgcccg tgtgggcact 960
gtgcttgggt ttttgcagcg gggtgcccta ctgcctgaat ttcccatta tgtggagact 1020 caccttgccc tggccgctga cccagcattc tgtgcctcac tgaatgcgga gttggatctg 1080
gaggaacatg tgatggggca acgctgtcca cggtgtgacg acatcatgct gcagaaccta 1140
tcatctgggc tgttgcagaa cctatcagct gggcaattgc accaccaaat atttgcaacc 1200
tatgcagctg tgtacagtgt ggctcaagcc cttcacaaca ccctacagtg caatgtctca 1260
cattgccacg tatcagaaca tgttctaccc tggcagctcc tggagaacat gtacaatatg 1320
agtttccatg ctcgagactt gacactacag tttgatgctg aagggaatgt agacatggaa 1380
tatgacctga agatgtgggt gtggcagagc cctacacctg tattacatac tgtgggcacc 1440
ttcaacggca cccttcagct gcagcagtct aaaatgtact ggccaggcaa ccaggtgcca 1500
gtctcccagt gttcccgcca gtgcaaagat ggccaggttc gccgagtaaa gggctttcat 1560
tcctgctgct atgactgcgt ggactgcaag gcgggcagct accggaagca tccagatgac 1620
ttcacctgta ctccatgtaa ccaggaccag tggtccccag agaaaagcac agcctgctta 1680
cctcgcaggc ccaagtttct ggcttggggg gagccagttg tgctgtcact cctcctgctg 1740
ctttgcctgg tgctgggtct agcactggct gctctggggc tctctgtcca ccactgggac 1800
agccctcttg tccaggcctc aggtggctca cagttctgct ttggcctgat ctgcctaggc 1860
ctcttctgcc tcagtgtcct tctgttccca gggcggccaa gctctgccag ctgccttgca 1920
caacaaccaa tggctcacct ccctctcaca ggctgcctga gcacactctt cctgcaagca 1980
gctgagacct ttgtggagtc tgagctgcca ctgagctggg caaactggct atgcagctac 2040

-continued cttcggggac tctgggcctg gctagtggta ctgttggcca cttttgtgga ggcagcacta 2100
tgtgcctggt atttgatcgc tttcccacca gaggtggtga cagactggtc agtgctgccc 2160
acagaggtac tggagcactg ccacgtgcgt tcctgggtca gcctgggctt ggtgcacatc 2220
accaatgcaa tgttagcttt cctctgcttt ctgggcactt tcctggtaca gagccagcct 2280
ggccgctaca accgtgcccg tggtctcacc ttcgccatgc tagcttattt catcacctgg 2340
gtctcttttg tgcccctcct ggccaatgtg caggtggcct accagccagc tgtgcagatg 2400
ggtgctatcc tagtctgtgc cctgggcatc ctggtcacct tccacctgcc caagtgctat 2460
gtgcttcttt ggctgccaaa gctcaacacc caggagttct tcctgggaag gaatgccaag 2520
aaagcagcag atgagaacag tggcggtggt gaggcagctc agggacacaa tgaatga 2577

<210> SEQ ID NO 17
<211> LENGTH: 2577
<212> TYPE: DNA
<213> ORGANISM: Rattus rattus

<400> SEQUENCE: 17
atgccgggtt tggctatctt gggcctcagt ctggctgctt tcctggagct tgggatgggg 60
tcctctttgt gtctgtcaca gcaattcaag gcacaagggg actatatatt gggtggacta 120
tttcccctgg gcacaactga ggaggccact ctcaaccaga gaacacagcc caacggcatc 180
ctatgtacca ggttctcgcc ccttggtttg ttcctggcca tggctatgaa gatggctgta 240
gaggagatca acaatggatc tgccttgctc cctgggctgc gactgggcta tgacctgttt 300
gacacatgct cagagccagt ggtcaccatg aagcccagcc tcatgttcat ggccaaggtg 360
ggaagtcaaa gcattgctgc ctactgcaac tacacacagt accaaccccg tgtgctggct 420
gtcattggtc cccactcatc agagcttgcc ctcattacag gcaagttctt cagcttcttc 480
ctcatgccac aggtcagcta tagtgccagc atggatcggc taagtgaccg ggaaacattt 540
ccatccttct tccgcacagt gcccagtgac cgggtgcagc tgcaggccgt tgtgacactg 600
ttgcagaatt tcagctggaa ctgggtggct gccttaggta gtgatgatga ctatggccgg 660
gaaggtctga gcatcttttc tggtctggcc aactcacgag gtatctgcat tgcacacgag 720
ggcctggtgc cacaacatga cactagtggc caacaattgg gcaaggtggt ggatgtgcta 780
cgccaagtga accaaagcaa agtacaggtg gtggtgctgt ttgcatctgc ccgtgctgtc 840
tactcccttt ttagctacag catccttcat gacctctcac ccaaggtatg ggtggccagt 900
gagtcctggc tgacctctga cctggtcatg acacttccca atattgcccg tgtgggcact 960
gttcttgggt ttctgcagcg cggtgcccta ctgcctgaat ttcccatta tgtggagact 1020 cgccttgccc tagctgctga cccaacattc tgtgcctccc tgaaagctga gttggatctg 1080
gaggagcgcg tgatggggcc acgctgttca caatgtgact acatcatgct acagaacctg 1140
tcatctgggc tgatgcagaa cctatcagct gggcagttgc accaccaaat atttgcaacc 1200
tatgcagctg tgtacagtgt ggctcaggcc cttcacaaca ccctgcagtg caatgtctca 1260
cattgccaca catcagagcc tgttcaaccc tggcagctcc tggagaacat gtacaatatg 1320
agtttccgtg ctcgagactt gacactgcag tttgatgcca aagggagtgt agacatggaa 1380
tatgacctga agatgtgggt gtggcagagc cctacacctg tactacatac tgtaggcacc 1440
ttcaacggca cccttcagct gcagcactcg aaaatgtatt ggccaggcaa ccaggtgcca 1500
gtctcccagt gctcccggca gtgcaaagat ggccaggtgc gcagagtaaa gggctttcat 1560
tcctgctgct atgactgtgt ggactgcaag gcagggagct accggaagca tccagatgac 1620

-continued ttcacctgta ctccatgtgg caaggatcag tggtccccag aaaaaagcac aacctgctta 1680
cctcgcaggc ccaagtttct ggcttggggg gagccagctg tgctgtcact tctcctgctg 1740
ctttgcctgg tgctgggcct gacactggct gccctggggc tctttgtcca ctactgggac 1800
agccctcttg ttcaggcctc aggtgggtca ctgttctgct ttggcctgat ctgcctaggc 1860
ctcttctgcc tcagtgtcct tctgttccca ggacgaccac gctctgccag ctgccttgcc 1920
caacaaccaa tggctcacct ccctctcaca ggctgcctga gcacactctt cctgcaagca 1980
gccgagatct ttgtggagtc tgagctgcca ctgagttggg caaactggct ctgcagctac 2040
cttcggggcc cctgggcttg gctggtggta ctgctggcca ctcttgtgga ggctgcacta 2100
tgtgcctggt acttgatggc tttccctcca gaggtggtga cagattggca ggtgctgccc 2160
acggaggtac tggaacactg ccgcatgcgt tcctgggtca gcctgggctt ggtgcacatc 2220
accaatgcag tgttagcttt cctctgcttt ctgggcactt tcctggtaca gagccagcct 2280
ggtcgctata accgtgcccg tggcctcacc ttcgccatgc tagcttattt catcatctgg 2340
gtctcttttg tgcccctcct ggctaatgtg caggtggcct accagccagc tgtgcagatg 2400
ggtgctatct tattctgtgc cctgggcatc ctggccacct tccacctgcc caaatgctat 2460
gtacttctgt ggctgccaga gctcaacacc caggagttct tcctgggaag gagccccaag 2520
gaagcatcag atgggaatag tggtagtagt gaggcaactc ggggacacag tgaatga 2577

<210> SEQ ID NO 18
<211> LENGTH: 2559
<212> TYPE: DNA
<213> ORGANISM: Homo sapiens

<400> SEQUENCE: 18
atgctgggcc ctgctgtcct gggcctcagc ctctgggctc tcctgcaccc tgggacgggg 60
gccccattgt gcctgtcaca gcaacttagg atgaaggggg actacgtgct gggggggctg 120 ttcccccctgg gcgaggccga ggaggctggc ctccgcagcc ggacacggcc cagcagccct 180
gtgtgcacca ggttctcctc aaacggcctg ctctgggcac tggccatgaa aatggccgtg 240
gaggagatca acaacaagtc ggatctgctg cccgggctgc gcctgggcta cgacctcttt 300
gatacgtgct cggagcctgt ggtggccatg aagcccagcc tcatgttcct ggccaaggca 360
ggcagccgcg acatcgccgc ctactgcaac tacacgcagt accagccccg tgtgctggct 420
gtcatcgggc cccactcgtc agagctcgcc atggtcaccg gcaagttctt cagcttcttc 480
ctcatgcccc aggtcagcta cggtgctagc atggagctgc tgagcgcccg ggagaccttc 540
ccctccttct tccgcaccgt gcccagcgac cgtgtgcagc tgacggccgc cgcggagctg 600
ctgcaggagt tcggctggaa ctgggtggcc gccctgggca gcgacgacga gtacggccgg 660
cagggcctga gcatcttctc ggccctggcc gcggcacgcg gcatctgcat cgcgcacgag 720
ggcctggtgc cgctgccccg tgccgatgac tcgcggctgg ggaaggtgca ggacgtcctg 780
caccaggtga accagagcag cgtgcaggtg gtgctgctgt tcgcctccgt gcacgccgcc 840
cacgccctct tcaactacag catcagcagc aggctctcgc ccaaggtgtg ggtggccagc 900
gaggcctggc tgacctctga cctggtcatg gggctgcccg gcatggccca gatgggcacg 960
gtgcttggct tcctccagag gggtgcccag ctgcacgagt tcccccagta cgtgaagacg 1020
cacctggccc tggccaccga cccggccttc tgctctgccc tgggcgagag ggagcagggt 1080
ctggaggagg acgtggtggg ccagcgctgc ccgcagtgtg actgcatcac gctgcagaac 1140
gtgagcgcag ggctaaatca ccaccagacg ttctctgtct acgcagctgt gtatagcgtg 1200

```
gcccaggccc tgcacaacac tcttcagtgc aacgcctcag gctgccccgc gcaggacccc   1260

gtgaagccct ggcagctcct ggagaacatg tacaacctga ccttccacgt gggcgggctg   1320

ccgctgcggt tcgacagcag cggaaacgtg gacatggagt acgacctgaa gctgtgggtg   1380

tggcagggct cagtgcccag gctccacgac gtgggcaggt tcaacggcag cctcaggaca   1440

gagcgcctga agatccgctg gcacacgtct gacaaccaga agcccgtgtc ccggtgctcg   1500

cggcagtgcc aggagggcca ggtgcgccgg gtcaaggggt tccactcctg ctgctacgac   1560

tgtgtggact gcgaggcggg cagctaccgg caaaacccag acgacatcgc ctgcaccttt   1620

tgtggccagg atgagtggtc cccggagcga agcacacgct gcttccgccg caggtctcgg   1680

ttcctggcat ggggcgagcc ggctgtgctg ctgctgctcc tgctgctgag cctggcgctg   1740

ggccttgtgc tggctgcttt ggggctgttc gttcaccatc gggacagccc actggttcag   1800

gcctcggggg ggcccctggc ctgctttggc ctggtgtgcc tgggcctggt ctgcctcagc   1860

gtcctcctgt tccctggcca gcccagccct gcccgatgcc tggcccagca gcccttgtcc   1920

cacctcccgc tcacgggctg cctgagcaca ctcttcctgc aggcggccga gatcttcgtg   1980

gagtcagaac tgcctctgag ctgggcagac cggctgagtg gctgcctgcg ggggccctgg   2040

gcctggctgg tggtgctgct ggccatgctg gtggaggtcg cactgtgcac ctggtacctg   2100

gtggccttcc cgccggaggt ggtgacggac tggcacatgc tgcccacgga ggcgctggtg   2160

cactgccgca cacgctcctg ggtcagcttc ggcctagcgc acgccaccaa tgccacgctg   2220

gcctttctct gcttcctggg cactttcctg gtgcggagcc agccgggccg ctacaaccgt   2280

gcccgtggcc tcacctttgc catgctggcc tacttcatca cctgggtctc ctttgtgccc   2340

ctcctggcca atgtgcaggt ggtcctcagg cccgccgtgc agatgggcgc cctcctgctc   2400

tgtgtcctgg gcatcctggc tgccttccac ctgcccaggt gttacctgct catgcggcag   2460

ccagggctca acacccccga gttcttcctg ggagggggcc ctggggatgc ccaaggccag   2520

aatgacggga acacaggaaa tcaggggaaa catgagtga                          2559
```

<210> SEQ ID NO 19
<211> LENGTH: 843
<212> TYPE: PRT
<213> ORGANISM: Mus musculus

<400> SEQUENCE: 19

```
Met Gly Pro Gln Ala Arg Thr Leu His Leu Leu Phe Leu Leu Leu His
1               5                   10                  15

Ala Leu Pro Lys Pro Val Met Leu Val Gly Asn Ser Asp Phe His Leu
            20                  25                  30

Ala Gly Asp Tyr Leu Leu Gly Gly Leu Phe Thr Leu His Ala Asn Val
        35                  40                  45

Lys Ser Val Ser His Leu Ser Tyr Leu Gln Val Pro Lys Cys Asn Glu
    50                  55                  60

Tyr Asn Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile Gln
            100                 105                 110

Pro Gly Leu Tyr Phe Leu Ser Gln Ile Asp Asp Phe Leu Pro Ile Leu
        115                 120                 125

Lys Asp Tyr Ser Gln Tyr Arg Pro Gln Val Val Ala Val Ile Gly Pro
```

-continued

```
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Arg Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Asp Tyr Gly Arg Glu Asn Ser His
    210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
        275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Glu Tyr Pro
            340                 345                 350

Met Pro Asn Glu Thr Ser Leu Arg Thr Thr Cys Asn Gln Asp Cys Asp
        355                 360                 365

Ala Cys Met Asn Ile Thr Glu Ser Phe Asn Asn Val Leu Met Leu Ser
    370                 375                 380

Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                405                 410                 415

Gln Ile Val Tyr Pro Trp Gln Leu Leu Arg Glu Ile Trp His Val Asn
            420                 425                 430

Phe Thr Leu Leu Gly Asn Gln Leu Phe Phe Asp Glu Gln Gly Asp Met
        435                 440                 445

Pro Met Leu Leu Asp Ile Ile Gln Trp Gln Trp Gly Leu Ser Gln Asn
    450                 455                 460

Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
                485                 490                 495

Ser Met Cys Ser Lys Ser Cys Gln Pro Gly Gln Met Lys Lys Pro Ile
            500                 505                 510

Gly Leu His Pro Cys Cys Phe Glu Cys Val Asp Cys Pro Pro Gly Thr
        515                 520                 525

Tyr Leu Asn Arg Ser Val Asp Glu Phe Asn Cys Leu Ser Cys Pro Gly
    530                 535                 540

Ser Met Trp Ser Tyr Lys Asn Asn Ile Ala Cys Phe Lys Arg Arg Leu
545                 550                 555                 560
```

Ala Phe Leu Glu Trp His Glu Val Pro Thr Ile Val Val Thr Ile Leu
565 570 575

Ala Ala Leu Gly Phe Ile Ser Thr Leu Ala Ile Leu Leu Ile Phe Trp
580 585 590

Arg His Phe Gln Thr Pro Met Val Arg Ser Ala Gly Gly Pro Met Cys
595 600 605

Phe Leu Met Leu Val Pro Leu Leu Leu Ala Phe Gly Met Val Pro Val
610 615 620

Tyr Val Gly Pro Pro Thr Val Phe Ser Cys Phe Cys Arg Gln Ala Phe
625 630 635 640

Phe Thr Val Cys Phe Ser Val Cys Leu Ser Cys Ile Thr Val Arg Ser
645 650 655

Phe Gln Ile Val Cys Val Phe Lys Met Ala Arg Arg Leu Pro Ser Ala
660 665 670

Tyr Gly Phe Trp Met Arg Tyr His Gly Pro Tyr Val Phe Val Ala Phe
675 680 685

Ile Thr Ala Val Lys Val Ala Leu Val Ala Gly Asn Met Leu Ala Thr
690 695 700

Thr Ile Asn Pro Ile Gly Arg Thr Asp Pro Asp Asp Pro Asn Ile Ile
705 710 715 720

Ile Leu Ser Cys His Pro Asn Tyr Arg Asn Gly Leu Leu Phe Asn Thr
725 730 735

Ser Met Asp Leu Leu Leu Ser Val Leu Gly Phe Ser Phe Ala Tyr Val
740 745 750

Gly Lys Glu Leu Pro Thr Asn Tyr Asn Glu Ala Lys Phe Ile Thr Leu
755 760 765

Ser Met Thr Phe Ser Phe Thr Ser Ser Ile Ser Leu Cys Thr Phe Met
770 775 780

Ser Val His Asp Gly Val Leu Val Thr Ile Met Asp Leu Leu Val Thr
785 790 795 800

Val Leu Asn Phe Leu Ala Ile Gly Leu Gly Tyr Phe Gly Pro Lys Cys
805 810 815

Tyr Met Ile Leu Phe Tyr Pro Glu Arg Asn Thr Ser Ala Tyr Phe Asn
820 825 830

Ser Met Ile Gln Gly Tyr Thr Met Arg Lys Ser
835 840

<210> SEQ ID NO 20
<211> LENGTH: 843
<212> TYPE: PRT
<213> ORGANISM: Rattus rattus

<400> SEQUENCE: 20

Met Gly Pro Gln Ala Arg Thr Leu Cys Leu Leu Ser Leu Leu Leu His
1 5 10 15

Val Leu Pro Lys Pro Gly Lys Leu Val Glu Asn Ser Asp Phe His Leu
20 25 30

Ala Gly Asp Tyr Leu Leu Gly Gly Leu Phe Thr Leu His Ala Asn Val
35 40 45

Lys Ser Ile Ser His Leu Ser Tyr Leu Gln Val Pro Lys Cys Asn Glu
50 55 60

Phe Thr Met Lys Val Leu Gly Tyr Asn Leu Met Gln Ala Met Arg Phe
65 70 75 80

Ala Val Glu Glu Ile Asn Asn Cys Ser Ser Leu Leu Pro Gly Val Leu
85 90 95

-continued

```
Leu Gly Tyr Glu Met Val Asp Val Cys Tyr Leu Ser Asn Asn Ile His
            100                 105                 110

Pro Gly Leu Tyr Phe Leu Ala Gln Asp Asp Asp Leu Leu Pro Ile Leu
        115                 120                 125

Lys Asp Tyr Ser Gln Tyr Met Pro His Val Val Ala Val Ile Gly Pro
    130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
    370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
    450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525
```

```
Tyr Leu Asn Arg Ser Ala Asp Glu Phe Asn Cys Leu Ser Cys Pro Gly
    530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
    690                 695                 700

Thr Ile Asn Pro Ile Gly Arg Thr Asp Pro Asp Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840
```

<210> SEQ ID NO 21
<211> LENGTH: 839
<212> TYPE: PRT
<213> ORGANISM: Homo sapiens

<400> SEQUENCE: 21

```
Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60
```

-continued

```
Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
```

```
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Val Ile Gly Met Leu Ala Thr Gly Leu Ser Pro
    690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835


<210> SEQ ID NO 22
<211> LENGTH: 842
<212> TYPE: PRT
<213> ORGANISM: Mus musculus

<400> SEQUENCE: 22

Met Leu Phe Trp Ala Ala His Leu Leu Leu Ser Leu Gln Leu Ala Val
1               5                   10                  15

Ala Tyr Cys Trp Ala Phe Ser Cys Gln Arg Thr Glu Ser Ser Pro Gly
```

-continued

```
            20                  25                  30

Phe Ser Leu Pro Gly Asp Phe Leu Leu Ala Gly Leu Phe Ser Leu His
        35                  40                  45

Ala Asp Cys Leu Gln Val Arg His Arg Pro Leu Val Thr Ser Cys Asp
    50                  55                  60

Arg Ser Asp Ser Phe Asn Gly His Gly Tyr His Leu Phe Gln Ala Met
65                  70                  75                  80

Arg Phe Thr Val Glu Glu Ile Asn Asn Ser Thr Ala Leu Leu Pro Asn
                85                  90                  95

Ile Thr Leu Gly Tyr Glu Leu Tyr Asp Val Cys Ser Glu Ser Ser Asn
            100                 105                 110

Val Tyr Ala Thr Leu Arg Val Leu Ala Gln Gln Gly Thr Gly His Leu
        115                 120                 125

Glu Met Gln Arg Asp Leu Arg Asn His Ser Ser Lys Val Val Ala Leu
    130                 135                 140

Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
            180                 185                 190

Asp Lys Tyr Gln Val Glu Val Ile Val Arg Leu Leu Gln Ser Phe Gly
        195                 200                 205

Trp Val Trp Ile Ser Leu Val Gly Ser Tyr Gly Asp Tyr Gly Gln Leu
    210                 215                 220

Gly Val Gln Ala Leu Glu Glu Leu Ala Thr Pro Arg Gly Ile Cys Val
225                 230                 235                 240

Ala Phe Lys Asp Val Val Pro Leu Ser Ala Gln Ala Gly Asp Pro Arg
                245                 250                 255

Met Gln Arg Met Met Leu Arg Leu Ala Arg Ala Arg Thr Thr Val Val
            260                 265                 270

Val Val Phe Ser Asn Arg His Leu Ala Gly Val Phe Phe Arg Ser Val
        275                 280                 285

Val Leu Ala Asn Leu Thr Gly Lys Val Trp Ile Ala Ser Glu Asp Trp
    290                 295                 300

Ala Ile Ser Thr Tyr Ile Thr Asn Val Pro Gly Ile Gln Gly Ile Gly
305                 310                 315                 320

Thr Val Leu Gly Val Ala Ile Gln Gln Arg Gln Val Pro Gly Leu Lys
                325                 330                 335

Glu Phe Glu Glu Ser Tyr Val Gln Ala Val Met Gly Ala Pro Arg Thr
            340                 345                 350

Cys Pro Glu Gly Ser Trp Cys Gly Thr Asn Gln Leu Cys Arg Glu Cys
        355                 360                 365

His Ala Phe Thr Thr Trp Asn Met Pro Glu Leu Gly Ala Phe Ser Met
    370                 375                 380

Ser Ala Ala Tyr Asn Val Tyr Glu Ala Val Tyr Ala Val Ala His Gly
385                 390                 395                 400

Leu His Gln Leu Leu Gly Cys Thr Ser Gly Thr Cys Ala Arg Gly Pro
                405                 410                 415

Val Tyr Pro Trp Gln Leu Leu Gln Gln Ile Tyr Lys Val Asn Phe Leu
            420                 425                 430

Leu His Lys Lys Thr Val Ala Phe Asp Asp Lys Gly Asp Pro Leu Gly
        435                 440                 445
```

```
Tyr Tyr Asp Ile Ile Ala Trp Asp Trp Asn Gly Pro Glu Trp Thr Phe
    450                 455                 460

Glu Val Ile Gly Ser Ala Ser Leu Ser Pro Val His Leu Asp Ile Asn
465                 470                 475                 480

Lys Thr Lys Ile Gln Trp His Gly Lys Asn Asn Gln Val Pro Val Ser
                485                 490                 495

Val Cys Thr Arg Asp Cys Leu Glu Gly His His Arg Leu Val Met Gly
            500                 505                 510

Ser His His Cys Cys Phe Glu Cys Met Pro Cys Glu Ala Gly Thr Phe
        515                 520                 525

Leu Asn Thr Ser Glu Leu His Thr Cys Gln Pro Cys Gly Thr Glu Glu
    530                 535                 540

Trp Ala Pro Glu Gly Ser Ser Ala Cys Phe Ser Arg Thr Val Glu Phe
545                 550                 555                 560

Leu Gly Trp His Glu Pro Ile Ser Leu Val Leu Leu Ala Ala Asn Thr
                565                 570                 575

Leu Leu Leu Leu Leu Leu Ile Gly Thr Ala Gly Leu Phe Ala Trp Arg
            580                 585                 590

Leu His Thr Pro Val Val Arg Ser Ala Gly Gly Arg Leu Cys Phe Leu
        595                 600                 605

Met Leu Gly Ser Leu Val Ala Gly Ser Cys Ser Leu Tyr Ser Phe Phe
    610                 615                 620

Gly Lys Pro Thr Val Pro Ala Cys Leu Leu Arg Gln Pro Leu Phe Ser
625                 630                 635                 640

Leu Gly Phe Ala Ile Phe Leu Ser Cys Leu Thr Ile Arg Ser Phe Gln
                645                 650                 655

Leu Val Ile Ile Phe Lys Phe Ser Thr Lys Val Pro Thr Phe Tyr His
            660                 665                 670

Thr Trp Ala Gln Asn His Gly Ala Gly Ile Phe Val Ile Val Ser Ser
        675                 680                 685

Thr Val His Leu Phe Leu Cys Leu Thr Trp Leu Ala Met Trp Thr Pro
    690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
            740                 745                 750

Leu Pro Glu Asn Tyr Asn Glu Ala Lys Cys Val Thr Phe Ser Leu Leu
        755                 760                 765

Leu His Phe Val Ser Trp Ile Ala Phe Phe Thr Met Ser Ser Ile Tyr
    770                 775                 780

Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
            820                 825                 830

Gln Asp Tyr Thr Arg Arg Cys Gly Thr Thr
        835                 840
```

<210> SEQ ID NO 23
<211> LENGTH: 840
<212> TYPE: PRT
<213> ORGANISM: Rattus rattus

<400> SEQUENCE: 23

```
Met Leu Phe Trp Ala Ala His Leu Leu Leu Ser Leu Gln Leu Val Tyr
1               5                   10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
    130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415
```

-continued

```
Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Val Gly Ser His
            500                 505                 510

His Cys Cys Phe Glu Cys Val Pro Cys Glu Ala Gly Thr Phe Leu Asn
        515                 520                 525

Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
    610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
    770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
                805                 810                 815

Arg Pro Glu Leu Asn Asn Thr Glu His Phe Gln Ala Ser Ile Gln Asp
            820                 825                 830

Tyr Thr Arg Arg Cys Gly Thr Thr
```

```
        835                 840


<210> SEQ ID NO 24
<211> LENGTH: 841
<212> TYPE: PRT
<213> ORGANISM: Homo sapiens

<400> SEQUENCE: 24

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
```

-continued

```
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
    450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
        595                 600                 605

Leu Gly Ser Leu Ala Ala Gly Ser Gly Ser Leu Tyr Gly Phe Phe Gly
    610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
    690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
    770                 775                 780

Gly Lys Tyr Leu Pro Ala Ala Asn Met Met Ala Gly Leu Ser Ser Leu
785                 790                 795                 800
```

```
Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
        835                 840


<210> SEQ ID NO 25
<211> LENGTH: 858
<212> TYPE: PRT
<213> ORGANISM: Mus musculus

<400> SEQUENCE: 25

Met Pro Ala Leu Ala Ile Met Gly Leu Ser Leu Ala Ala Phe Leu Glu
1               5                   10                  15

Leu Gly Met Gly Ala Ser Leu Cys Leu Ser Gln Gln Phe Lys Ala Gln
            20                  25                  30

Gly Asp Tyr Ile Leu Gly Gly Leu Phe Pro Leu Gly Ser Thr Glu Glu
        35                  40                  45

Ala Thr Leu Asn Gln Arg Thr Gln Pro Asn Ser Ile Pro Cys Asn Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335
```

-continued

```
Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
    370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
        595                 600                 605

Gly Ser Gln Phe Cys Phe Gly Leu Ile Cys Leu Gly Leu Phe Cys Leu
    610                 615                 620

Ser Val Leu Leu Phe Pro Gly Arg Pro Ser Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Thr Phe Val Glu Ser Glu Leu Pro Leu Ser
            660                 665                 670

Trp Ala Asn Trp Leu Cys Ser Tyr Leu Arg Gly Leu Trp Ala Trp Leu
        675                 680                 685

Val Val Leu Leu Ala Thr Phe Val Glu Ala Ala Leu Cys Ala Trp Tyr
    690                 695                 700

Leu Ile Ala Phe Pro Pro Glu Val Val Thr Asp Trp Ser Val Leu Pro
705                 710                 715                 720

Thr Glu Val Leu Glu His Cys His Val Arg Ser Trp Val Ser Leu Gly
                725                 730                 735

Leu Val His Ile Thr Asn Ala Met Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765
```

-continued

```
Leu Thr Phe Ala Met Leu Ala Tyr Phe Ile Thr Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Val Cys Ala Leu Gly Ile Leu Val Thr Phe His Leu
                805                 810                 815

Pro Lys Cys Tyr Val Leu Leu Trp Leu Pro Lys Leu Asn Thr Gln Glu
            820                 825                 830

Phe Phe Leu Gly Arg Asn Ala Lys Lys Ala Ala Asp Glu Asn Ser Gly
        835                 840                 845

Gly Gly Glu Ala Ala Gln Gly His Asn Glu
    850                 855


<210> SEQ ID NO 26
<211> LENGTH: 858
<212> TYPE: PRT
<213> ORGANISM: Rattus rattus

<400> SEQUENCE: 26

Met Pro Gly Leu Ala Ile Leu Gly Leu Ser Leu Ala Ala Phe Leu Glu
1               5                   10                  15

Leu Gly Met Gly Ser Ser Leu Cys Leu Ser Gln Gln Phe Lys Ala Gln
            20                  25                  30

Gly Asp Tyr Ile Leu Gly Gly Leu Phe Pro Leu Gly Thr Thr Glu Glu
        35                  40                  45

Ala Thr Leu Asn Gln Arg Thr Gln Pro Asn Gly Ile Leu Cys Thr Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Pro
            100                 105                 110

Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
                245                 250                 255

Val Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285
```

-continued

```
Leu His Asp Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
            340                 345                 350

Ser Leu Lys Ala Glu Leu Asp Leu Glu Glu Arg Val Met Gly Pro Arg
        355                 360                 365

Cys Ser Gln Cys Asp Tyr Ile Met Leu Gln Asn Leu Ser Ser Gly Leu
    370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
            420                 425                 430

Leu Leu Glu Asn Met Tyr Asn Met Ser Phe Arg Ala Arg Asp Leu Thr
        435                 440                 445

Leu Gln Phe Asp Ala Lys Gly Ser Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
            580                 585                 590

Gly Leu Phe Val His Tyr Trp Asp Ser Pro Leu Val Gln Ala Ser Gly
        595                 600                 605

Gly Ser Leu Phe Cys Phe Gly Leu Ile Cys Leu Gly Leu Phe Cys Leu
    610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
        675                 680                 685

Val Val Leu Leu Ala Thr Leu Val Glu Ala Ala Leu Cys Ala Trp Tyr
    690                 695                 700

Leu Met Ala Phe Pro Pro Glu Val Val Thr Asp Trp Gln Val Leu Pro
```

```
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
        835                 840                 845

Ser Ser Glu Ala Thr Arg Gly His Ser Glu
    850                 855


<210> SEQ ID NO 27
<211> LENGTH: 852
<212> TYPE: PRT
<213> ORGANISM: Homo sapiens

<400> SEQUENCE: 27

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
```

-continued

```
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540

Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655
```

-continued

```
Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
    690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
    770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850


<210> SEQ ID NO 28
<211> LENGTH: 24
<212> TYPE: DNA
<213> ORGANISM: Artificial Sequence
<220> FEATURE:
<223> OTHER INFORMATION: Overgo probe

<400> SEQUENCE: 28

taaacaactc cacggccctg ctgc                                            24


<210> SEQ ID NO 29
<211> LENGTH: 24
<212> TYPE: DNA
<213> ORGANISM: Artificial Sequence
<220> FEATURE:
<223> OTHER INFORMATION: Overgo probe

<400> SEQUENCE: 29

cccagggtga tgttgggcag cagg                                            24


<210> SEQ ID NO 30
<211> LENGTH: 24
<212> TYPE: DNA
<213> ORGANISM: Artificial Sequence
<220> FEATURE:
<223> OTHER INFORMATION: Overgo probe

<400> SEQUENCE: 30

gctgtgtatg cggtggccca tggc                                            24


<210> SEQ ID NO 31
<211> LENGTH: 24
<212> TYPE: DNA
<213> ORGANISM: Artificial Sequence
```

<220> FEATURE:
<223> OTHER INFORMATION: Overgo probe

<400> SEQUENCE: 31
ccaggagctg gtggaggcca tggg 24

<210> SEQ ID NO 32
<211> LENGTH: 24
<212> TYPE: DNA
<213> ORGANISM: Artificial Sequence
<220> FEATURE:
<223> OTHER INFORMATION: Overgo probe

<400> SEQUENCE: 32
tgctgaccaa cctgactggc aagg 24

<210> SEQ ID NO 33
<211> LENGTH: 24
<212> TYPE: DNA
<213> ORGANISM: Artificial Sequence
<220> FEATURE:
<223> OTHER INFORMATION: Overgo probe

<400> SEQUENCE: 33
tctgaggcga cccacacctt gcca 24

<210> SEQ ID NO 34
<211> LENGTH: 24
<212> TYPE: DNA
<213> ORGANISM: Artificial Sequence
<220> FEATURE:
<223> OTHER INFORMATION: Overgo probe

<400> SEQUENCE: 34
ccagttcagc taaacataaa tgag 24

<210> SEQ ID NO 35
<211> LENGTH: 24
<212> TYPE: DNA
<213> ORGANISM: Artificial Sequence
<220> FEATURE:
<223> OTHER INFORMATION: Overgo probe

<400> SEQUENCE: 35
gccactggat tttggtctca ttta 24

<210> SEQ ID NO 36
<211> LENGTH: 24
<212> TYPE: DNA
<213> ORGANISM: Artificial Sequence
<220> FEATURE:
<223> OTHER INFORMATION: Overgo probe

<400> SEQUENCE: 36
agctaacacg ctgctgctgc tgct 24

<210> SEQ ID NO 37
<211> LENGTH: 24
<212> TYPE: DNA
<213> ORGANISM: Artificial Sequence
<220> FEATURE:
<223> OTHER INFORMATION: Overgo probe

<400> SEQUENCE: 37
agcagtccca agcagcagca gcag 24

<210> SEQ ID NO 38
<211> LENGTH: 24
<212> TYPE: DNA
<213> ORGANISM: Artificial Sequence
<220> FEATURE:
<223> OTHER INFORMATION: Overgo probe

<400> SEQUENCE: 38
tgtgtcacct tcagcctgct cttc 24

<210> SEQ ID NO 39
<211> LENGTH: 24
<212> TYPE: DNA
<213> ORGANISM: Artificial Sequence
<220> FEATURE:
<223> OTHER INFORMATION: Overgo probe

<400> SEQUENCE: 39
tccaggacac gaagttgaag agca 24

<210> SEQ ID NO 40
<211> LENGTH: 24
<212> TYPE: DNA
<213> ORGANISM: Artificial Sequence
<220> FEATURE:
<223> OTHER INFORMATION: Overgo probe

<400> SEQUENCE: 40
tacttcggcc ccaagtgcta catg 24

<210> SEQ ID NO 41
<211> LENGTH: 24
<212> TYPE: DNA
<213> ORGANISM: Artificial Sequence
<220> FEATURE:
<223> OTHER INFORMATION: Overgo probe

<400> SEQUENCE: 41
ccgggtagaa gaggatcatg tagc 24

<210> SEQ ID NO 42
<211> LENGTH: 24
<212> TYPE: DNA
<213> ORGANISM: Artificial Sequence
<220> FEATURE:
<223> OTHER INFORMATION: Overgo probe

<400> SEQUENCE: 42
tggtcaccat cgtggacctc ttgg 24

<210> SEQ ID NO 43
<211> LENGTH: 24
<212> TYPE: DNA
<213> ORGANISM: Artificial Sequence
<220> FEATURE:
<223> OTHER INFORMATION: Overgo probe

<400> SEQUENCE: 43
aggttgagca cagtgaccaa gagg 24

<210> SEQ ID NO 44
<211> LENGTH: 24
<212> TYPE: DNA
<213> ORGANISM: Artificial Sequence
<220> FEATURE:
<223> OTHER INFORMATION: Overgo probe

<400> SEQUENCE: 44
accaactaca acgaggccaa gttc 24

<210> SEQ ID NO 45
<211> LENGTH: 24
<212> TYPE: DNA
<213> ORGANISM: Artificial Sequence
<220> FEATURE:
<223> OTHER INFORMATION: Overgo probe

<400> SEQUENCE: 45
tcatgctgag ggtgatgaac ttgg 24

<210> SEQ ID NO 46
<211> LENGTH: 24
<212> TYPE: DNA
<213> ORGANISM: Artificial Sequence
<220> FEATURE:
<223> OTHER INFORMATION: Overgo probe

<400> SEQUENCE: 46
tccgagtcct gggccatcga cccg 24

<210> SEQ ID NO 47
<211> LENGTH: 24
<212> TYPE: DNA
<213> ORGANISM: Artificial Sequence
<220> FEATURE:
<223> OTHER INFORMATION: Overgo probe

<400> SEQUENCE: 47
tgaggttgtg caggaccggg tcga 24

<210> SEQ ID NO 48
<211> LENGTH: 24
<212> TYPE: DNA
<213> ORGANISM: Artificial Sequence
<220> FEATURE:
<223> OTHER INFORMATION: Overgo probe

<400> SEQUENCE: 48
tacaacctca tgcaggccat gcgc 24

<210> SEQ ID NO 49
<211> LENGTH: 24
<212> TYPE: DNA
<213> ORGANISM: Artificial Sequence
<220> FEATURE:
<223> OTHER INFORMATION: Overgo probe

<400> SEQUENCE: 49
tctcctccac cgcgaagcgc atgg 24

<210> SEQ ID NO 50
<211> LENGTH: 24
<212> TYPE: DNA
<213> ORGANISM: Artificial Sequence
<220> FEATURE:
<223> OTHER INFORMATION: Overgo probe

<400> SEQUENCE: 50
atcaccatcc agagcgtgcc catc 24

<210> SEQ ID NO 51
<211> LENGTH: 24
<212> TYPE: DNA
<213> ORGANISM: Artificial Sequence
<220> FEATURE:
<223> OTHER INFORMATION: Overgo probe

<400> SEQUENCE: 51
actcactgaa gcccgggatg ggca 24

<210> SEQ ID NO 52
<211> LENGTH: 24
<212> TYPE: DNA
<213> ORGANISM: Artificial Sequence
<220> FEATURE:
<223> OTHER INFORMATION: Overgo probe

<400> SEQUENCE: 52
accaccacgt cgaggccatg gtgc 24

<210> SEQ ID NO 53
<211> LENGTH: 24
<212> TYPE: DNA
<213> ORGANISM: Artificial Sequence
<220> FEATURE:
<223> OTHER INFORMATION: Overgo probe

<400> SEQUENCE: 53
aagtgcagca tcagctgcac catg 24

<210> SEQ ID NO 54
<211> LENGTH: 24
<212> TYPE: DNA
<213> ORGANISM: Artificial Sequence
<220> FEATURE:
<223> OTHER INFORMATION: Overgo probe

<400> SEQUENCE: 54
cttccactcc tgctgctacg actg 24

<210> SEQ ID NO 55
<211> LENGTH: 24
<212> TYPE: DNA
<213> ORGANISM: Artificial Sequence
<220> FEATURE:
<223> OTHER INFORMATION: Overgo probe

<400> SEQUENCE: 55
tgcctcgcag tccacgcagt cgta 24

<210> SEQ ID NO 56
<211> LENGTH: 24
<212> TYPE: DNA
<213> ORGANISM: Artificial Sequence
<220> FEATURE:
<223> OTHER INFORMATION: Overgo probe

<400> SEQUENCE: 56
aggtgcgccg cgtcaagggc ttcc 24

<210> SEQ ID NO 57
<211> LENGTH: 24
<212> TYPE: DNA
<213> ORGANISM: Artificial Sequence
<220> FEATURE:
<223> OTHER INFORMATION: Overgo probe

<400> SEQUENCE: 57
tcgtagcagc aggagtggaa gccc 24

-continued

<210> SEQ ID NO 58
<211> LENGTH: 24
<212> TYPE: DNA
<213> ORGANISM: Artificial Sequence
<220> FEATURE:
<223> OTHER INFORMATION: Overgo probe

<400> SEQUENCE: 58
gttcctggca tggggggagc cggc 24

<210> SEQ ID NO 59
<211> LENGTH: 24
<212> TYPE: DNA
<213> ORGANISM: Artificial Sequence
<220> FEATURE:
<223> OTHER INFORMATION: Overgo probe

<400> SEQUENCE: 59
gagcagcaca agcacagccg gctc 24

<210> SEQ ID NO 60
<211> LENGTH: 24
<212> TYPE: DNA
<213> ORGANISM: Artificial Sequence
<220> FEATURE:
<223> OTHER INFORMATION: Overgo probe

<400> SEQUENCE: 60
acagcccact agttcaggcc gcag 24

<210> SEQ ID NO 61
<211> LENGTH: 24
<212> TYPE: DNA
<213> ORGANISM: Artificial Sequence
<220> FEATURE:
<223> OTHER INFORMATION: Overgo probe

<400> SEQUENCE: 61
caggcccggg gtccccctgc ggcc 24

<210> SEQ ID NO 62
<211> LENGTH: 24
<212> TYPE: DNA
<213> ORGANISM: Artificial Sequence
<220> FEATURE:
<223> OTHER INFORMATION: Overgo probe

<400> SEQUENCE: 62
cccactggtt caggcctcgg gggg 24

<210> SEQ ID NO 63
<211> LENGTH: 24
<212> TYPE: DNA
<213> ORGANISM: Artificial Sequence
<220> FEATURE:
<223> OTHER INFORMATION: Overgo probe

<400> SEQUENCE: 63
aaagcaggcc aggggccccc ccga 24

<210> SEQ ID NO 64
<211> LENGTH: 24
<212> TYPE: DNA
<213> ORGANISM: Artificial Sequence
<220> FEATURE:
<223> OTHER INFORMATION: Overgo probe

<400> SEQUENCE: 64
aggcgctggt gcactgccgc acac 24

<210> SEQ ID NO 65
<211> LENGTH: 24
<212> TYPE: DNA
<213> ORGANISM: Artificial Sequence
<220> FEATURE:
<223> OTHER INFORMATION: Overgo probe

<400> SEQUENCE: 65
aagctgaccc aggagcgtgt gcgg 24

<210> SEQ ID NO 66
<211> LENGTH: 24
<212> TYPE: DNA
<213> ORGANISM: Artificial Sequence
<220> FEATURE:
<223> OTHER INFORMATION: Overgo probe

<400> SEQUENCE: 66
acagaggcac tggtgcactg ccgc 24

<210> SEQ ID NO 67
<211> LENGTH: 24
<212> TYPE: DNA
<213> ORGANISM: Artificial Sequence
<220> FEATURE:
<223> OTHER INFORMATION: Overgo probe

<400> SEQUENCE: 67
tgatccagga gtgcacgcgg cagt 24

<210> SEQ ID NO 68
<211> LENGTH: 24
<212> TYPE: DNA
<213> ORGANISM: Artificial Sequence
<220> FEATURE:
<223> OTHER INFORMATION: Overgo probe

<400> SEQUENCE: 68
accaatgcca cgctggcctt tctc 24

<210> SEQ ID NO 69
<211> LENGTH: 24
<212> TYPE: DNA
<213> ORGANISM: Artificial Sequence
<220> FEATURE:
<223> OTHER INFORMATION: Overgo probe

<400> SEQUENCE: 69
aagtgcccag gaagcagaga aagg 24

<210> SEQ ID NO 70
<211> LENGTH: 24
<212> TYPE: DNA
<213> ORGANISM: Artificial Sequence
<220> FEATURE:
<223> OTHER INFORMATION: Overgo probe

<400> SEQUENCE: 70
tggtacatgc tgccaatgcc acgc 24

<210> SEQ ID NO 71
<211> LENGTH: 24
<212> TYPE: DNA
<213> ORGANISM: Artificial Sequence
<220> FEATURE:
<223> OTHER INFORMATION: Overgo probe

<400> SEQUENCE: 71
aagcagagga aagccagcgt ggca 24

<210> SEQ ID NO 72
<211> LENGTH: 24
<212> TYPE: DNA
<213> ORGANISM: Artificial Sequence
<220> FEATURE:
<223> OTHER INFORMATION: Overgo probe

<400> SEQUENCE: 72
tacaaccgtg cccgtggcct cacc 24

<210> SEQ ID NO 73
<211> LENGTH: 24
<212> TYPE: DNA
<213> ORGANISM: Artificial Sequence
<220> FEATURE:
<223> OTHER INFORMATION: Overgo probe

<400> SEQUENCE: 73
aggccagcat ggcgaaggtg aggc 24

<210> SEQ ID NO 74
<211> LENGTH: 24
<212> TYPE: DNA
<213> ORGANISM: Artificial Sequence
<220> FEATURE:
<223> OTHER INFORMATION: Overgo probe

<400> SEQUENCE: 74
tcatcacctg ggtctccttt gtgc 24

<210> SEQ ID NO 75
<211> LENGTH: 24
<212> TYPE: DNA
<213> ORGANISM: Artificial Sequence
<220> FEATURE:
<223> OTHER INFORMATION: Overgo probe

<400> SEQUENCE: 75
acattggcca ggaggggcac aaag 24

<210> SEQ ID NO 76
<211> LENGTH: 24
<212> TYPE: DNA
<213> ORGANISM: Artificial Sequence
<220> FEATURE:
<223> OTHER INFORMATION: Overgo probe

<400> SEQUENCE: 76
tgcagatggg tgccctcctg ctct 24

<210> SEQ ID NO 77
<211> LENGTH: 24
<212> TYPE: DNA
<213> ORGANISM: Artificial Sequence
<220> FEATURE:
<223> OTHER INFORMATION: Overgo probe

<400> SEQUENCE: 77
aggatgccca gcacacagag cagg 24

-continued

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ctacaacagc cagctgctca 20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
cttcagcgag ttccgcatac 20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ggttctgctc tgggagtgag 20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ttggccatgt ggttacagaa 20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
gaggtccttc taggcacagg 20

<210> SEQ ID NO 83
<211> LENGTH: 19
<212> TYPE: DNA
<213> ORGANISM: Artificial Sequence
<220> FEATURE:
<223> OTHER INFORMATION: Primer

<400> SEQUENCE: 83
cagaagtgcc agggaaggt 19

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
acataattgc ctgggactgg 20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
accaaaatcc rgtggcacgg 20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
ccgtgccacy ggattttggt 20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
tccagtccca ggcaattatg 20

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
tccagtccca ggcaattatg t 21

<210> SEQ ID NO 89
<211> LENGTH: 21
<212> TYPE: DNA
<213> ORGANISM: Artificial Sequence
<220> FEATURE:
<223> OTHER INFORMATION: Primer

<400> SEQUENCE: 89
ctygaagggc accagcgagt g 21

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
acagggcaca cactcaaagc 20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
cactcgctgg tgcccttcra 20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
gagtgcagag ggaacagacc 20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
tcacctgtca cagagggtca 20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ggaccctctc agtggctatg 20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
acggagagga caaccaggta 20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
cagctgccac aacacagagt 20

<210> SEQ ID NO 97
<211> LENGTH: 19
<212> TYPE: DNA
<213> ORGANISM: Artificial Sequence
<220> FEATURE:
<223> OTHER INFORMATION: Primer

<400> SEQUENCE: 97
atgtcactcg tggcagctc 19

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
tacagcagat gcccacactc 20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
gaaacagggt gctttcctga 20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
agggctagtg gagcagttca 20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
aggccatgtg tttcctcaag 20

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
crcctggtcg gcctgcagct 20

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
gattacctcc tsgcaggyct 20

<210> SEQ ID NO 104
<211> LENGTH: 19
<212> TYPE: DNA
<213> ORGANISM: Artificial Sequence
<220> FEATURE:
<223> OTHER INFORMATION: Primer

<400> SEQUENCE: 104
cctgtcacas agggtcacc 19

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
agrcctgcsa ggaggtaatc 20

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
tccccagcga taagtaccag 20

<210> SEQ ID NO 107
<211> LENGTH: 22
<212> TYPE: DNA
<213> ORGANISM: Artificial Sequence
<220> FEATURE:
<223> OTHER INFORMATION: Primer

<400> SEQUENCE: 107
gggtctggat ctcattggtg gg 22

<210> SEQ ID NO 108
<211> LENGTH: 22
<212> TYPE: DNA
<213> ORGANISM: Artificial Sequence
<220> FEATURE:
<223> OTHER INFORMATION: Primer

<400> SEQUENCE: 108
cgcaagccaa gttacacaga tg 22

<210> SEQ ID NO 109
<211> LENGTH: 22
<212> TYPE: DNA
<213> ORGANISM: Artificial Sequence
<220> FEATURE:
<223> OTHER INFORMATION: Primer

<400> SEQUENCE: 109
ggcggaaaac ttgaagatga ag 22

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
gtgtgccagg agatgttgtg 20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
gggtagtagg aggcgatgct 20

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
gagcgtcgcc tcctactrcc 20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
atctggaagg tcaacttcac 20

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
tgggacckga gccagaacc 19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
cagagggaga gaaggcattg 20

<210> SEQ ID NO 116
<211> LENGTH: 19
<212> TYPE: DNA
<213> ORGANISM: Artificial Sequence
<220> FEATURE:
<223> OTHER INFORMATION: Primer

<400> SEQUENCE: 116
cccggcgttt gtgatctat 19

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
agcttcttcc tcatgcctca 20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
gggctacgac ctctttgaca 20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
agttggcctt tgagtcagga 20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
ggaccactgg ttctggtcac 20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
tgacagactg gtgggtgcta 20

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ccatgctggc ctacttcatc 20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
agcaggaggt gtcgttccta 20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
cccaggatgg tcagcataac 20

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
ctacaacagc cagctgctca 20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
cggaagaagt tgtgcaggat 20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
ctatcatgcg cttcctgaca 20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
tgtgtgccaa gtcttcttgc 20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
gcaatggatg aggagcattt 20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
accacatcca gcctcacact 20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
ttcctccttc cacaggtgag 20

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
aagccaggtc aggatgtcag 20

<210> SEQ ID NO 133
<211> LENGTH: 2526
<212> TYPE: DNA
<213> ORGANISM: Felis catus

<400> SEQUENCE: 133
atgtcactcc cggcggctca cctggtcggc ctgcagctct ccctctcctg ctgctgggct 60
ctcagctgcc acagcacaga gacgtctgcc gacttcagcc tccctgggga ttacctcctc 120
gcaggtctgt tccctctgca ctctgactgt ccgggcgtga ggcaccggcc cacggtgacc 180
ctctgtgaca ggcccgacag cttcaacggt cacggctacc acctcttcca ggccatgcgg 240
tttggcatcg aggagataaa caactccacg gccctcctgc cgaacgtcac cctgggatac 300
cagctgtacg acgtgtgctc ggagtctgcc aacgtgtatg ccacactaaa cgtgctctcc 360
ctgctgggga cacatcacgt agagatccga gcagaccctt cccactattc gcctgccgcc 420
ctggctgtca ttgggcctga caccaccaac cacgcagcca ccactgcagc cctgctgagc 480
cccttcctgg tgcccctgat cagctacgag gccagcagcg tgacgctcgg agtgaagcgg 540
cattacccct cgtttctgcg caccatcccc agcgacaagc accaggtgga ggccatggtg 600
ctgctgctgc agagcttcgg gtgggtctgg atctcggtgg tcggcagcga cggcgactac 660
gggcagctgg gggtgcaggc gctggaggag caggccaccc agcagggcat ctgcgttgcc 720
ttcaaggaca tcatcccctt ctctgcccgg ccgggcgacg agaggatgca gagcatcatg 780
caccacctgg cccgagcgag gaccaccgtt gtggtcgttt tctccagcag gcagctggcc 840
agggtgttct ttgagtcggt ggtgctggcc aacctgactg ccaaggtgtg gatcgcctca 900
gaagactggg ccatctctag acacatcagc aatgtgcccg ggatccaggg cattggcacg 960
gtgctgggtg tggccatcca gcagaggctt gtccctggcc tgaaggagtt tgaagaggcc 1020
tatgtccagg cagataaggg ggcccctggg ccttgctcca ggacctccga gtgcagcagc 1080
aaccagctct gtagagagtg tcgggctttc acggcagagc agatgcccac gctcggggca 1140
ttctccatga gctctgctta taacgcctac cgggcagtct acgcagtggc ccatggcctc 1200
caccagctcc tgggctgtgc ctctggagcc tgttccaggg accgagtcta cccctggcag 1260
cttctggagc agatccgcaa ggtgaatttc ctcctacaca aggacaccgt gaggtttaat 1320
gacaacgggg accctctcag tggctacgac ataattgcct gggactggag tggccccaag 1380
tggaacttca gggtcattgg ctcctccatg tggcctccag ttcagctgga cataaataaa 1440
accaaaatcc ggtggcacgg gaaggacaac caggtgccaa agtctgtgtg ctccagcgac 1500
tgcctcgaag ggcaccagcg agtgatttcg ggtttctacc actgttgctt tgagtgtgtg 1560
ccctgtgagg ccgggagctt cctcaacaag agcgacctcc acagctgcca gccttgtggg 1620

```
aaagaaaagt gggcacccgc gggaagtgaa acctgctttc cacgcaccgt ggtgtttttg   1680

acttggcacg agaccatctc ttgggtgctg ctggcagcta atacgttgct gctgctgctg   1740

gtgactggga ctgctggcct gtttgcctgg cacttagaca cccctgtggt gaagtccgct   1800

gggggccgac tgtgcttctt catgctaggc tccctggcag gggcagctg tgggctctac   1860

ggcttttttg gggagcccac gctgcccaca tgcttgttgc gccaaagcct ccttgccctg   1920

ggttttgcca tcttcctgtc ctgcctgacc atccgctcct tccaactggt cttcatcttc   1980

aagttttctg ccaaggtacc caccttctac cgtgcctggg tccaaaacca cggtcctggc   2040

ctatttgtgg tgatcagctc aatggcccag ctgctcatct gtctaacttg gctggcggtg   2100

tggaccccac tgcccaccag ggagtaccag cgcttccctc agctggtggt gcttgattgc   2160

acagaggcca actcaccggg cttcatgttg gctttcgcct acaatggcct cctgtccgtc   2220

agcgcctttg cctgcagcta cctgggcaag gacctgccag agaactacaa cgaggccaaa   2280

tgtgtcactt ttagtctgct gctcaacttc gtgtcctgga ttgccttctt caccacggcc   2340

agcgtctacc agggcaagta cttgcccgcg gtcaacgtgc tggcggcgct gagcagcctg   2400

agtggcggct tcagcggtta tttcctcccc aagtgctacg tgatcctgtg ccgcccaaaa   2460

tttaacagca cacagcactt ccaggcctcc atccaggagt acacgaggcg ctgcggctcc   2520

acctga                                                              2526
```

```
<210> SEQ ID NO 134
<211> LENGTH: 841
<212> TYPE: PRT
<213> ORGANISM: Felis catus

<400> SEQUENCE: 134

Met Ser Leu Pro Ala Ala His Leu Val Gly Leu Gln Leu Ser Leu Ser
1               5                   10                  15

Cys Cys Trp Ala Leu Ser Cys His Ser Thr Glu Thr Ser Ala Asp Phe
            20                  25                  30

Ser Leu Pro Gly Asp Tyr Leu Leu Ala Gly Leu Phe Pro Leu His Ser
        35                  40                  45

Asp Cys Pro Gly Val Arg His Arg Pro Thr Val Thr Leu Cys Asp Arg
    50                  55                  60

Pro Asp Ser Phe Asn Gly His Gly Tyr His Leu Phe Gln Ala Met Arg
65                  70                  75                  80

Phe Gly Ile Glu Glu Ile Asn Asn Ser Thr Ala Leu Leu Pro Asn Val
                85                  90                  95

Thr Leu Gly Tyr Gln Leu Tyr Asp Val Cys Ser Glu Ser Ala Asn Val
            100                 105                 110

Tyr Ala Thr Leu Asn Val Leu Ser Leu Leu Gly Thr His His Val Glu
        115                 120                 125

Ile Arg Ala Asp Pro Ser His Tyr Ser Pro Ala Ala Leu Ala Val Ile
    130                 135                 140

Gly Pro Asp Thr Thr Asn His Ala Ala Thr Thr Ala Ala Leu Leu Ser
145                 150                 155                 160

Pro Phe Leu Val Pro Leu Ile Ser Tyr Glu Ala Ser Ser Val Thr Leu
                165                 170                 175

Gly Val Lys Arg His Tyr Pro Ser Phe Leu Arg Thr Ile Pro Ser Asp
            180                 185                 190

Lys His Gln Val Glu Ala Met Val Leu Leu Leu Gln Ser Phe Gly Trp
        195                 200                 205
```

-continued

```
Val Trp Ile Ser Val Val Gly Ser Asp Gly Asp Tyr Gly Gln Leu Gly
    210                 215                 220

Val Gln Ala Leu Glu Glu Gln Ala Thr Gln Gln Gly Ile Cys Val Ala
225                 230                 235                 240

Phe Lys Asp Ile Ile Pro Phe Ser Ala Arg Pro Gly Asp Glu Arg Met
                245                 250                 255

Gln Ser Ile Met His His Leu Ala Arg Ala Arg Thr Thr Val Val Val
            260                 265                 270

Val Phe Ser Ser Arg Gln Leu Ala Arg Val Phe Phe Glu Ser Val Val
        275                 280                 285

Leu Ala Asn Leu Thr Ala Lys Val Trp Ile Ala Ser Glu Asp Trp Ala
    290                 295                 300

Ile Ser Arg His Ile Ser Asn Val Pro Gly Ile Gln Gly Ile Gly Thr
305                 310                 315                 320

Val Leu Gly Val Ala Ile Gln Gln Arg Leu Val Pro Gly Leu Lys Glu
                325                 330                 335

Phe Glu Glu Ala Tyr Val Gln Ala Asp Lys Gly Ala Pro Gly Pro Cys
            340                 345                 350

Ser Arg Thr Ser Glu Cys Ser Ser Asn Gln Leu Cys Arg Glu Cys Arg
        355                 360                 365

Ala Phe Thr Ala Glu Gln Met Pro Thr Leu Gly Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Asp Arg Val
                405                 410                 415

Tyr Pro Trp Gln Leu Leu Glu Gln Ile Arg Lys Val Asn Phe Leu Leu
            420                 425                 430

His Lys Asp Thr Val Arg Phe Asn Asp Asn Gly Asp Pro Leu Ser Gly
        435                 440                 445

Tyr Asp Ile Ile Ala Trp Asp Trp Ser Gly Pro Lys Trp Asn Phe Arg
    450                 455                 460

Val Ile Gly Ser Ser Met Trp Pro Pro Val Gln Leu Asp Ile Asn Lys
465                 470                 475                 480

Thr Lys Ile Arg Trp His Gly Lys Asp Asn Gln Val Pro Lys Ser Val
                485                 490                 495

Cys Ser Ser Asp Cys Leu Glu Gly His Gln Arg Val Ile Ser Gly Phe
            500                 505                 510

Tyr His Cys Cys Phe Glu Cys Val Pro Cys Glu Ala Gly Ser Phe Leu
        515                 520                 525

Asn Lys Ser Asp Leu His Ser Cys Gln Pro Cys Gly Lys Glu Lys Trp
    530                 535                 540

Ala Pro Ala Gly Ser Glu Thr Cys Phe Pro Arg Thr Val Val Phe Leu
545                 550                 555                 560

Thr Trp His Glu Thr Ile Ser Trp Val Leu Leu Ala Ala Asn Thr Leu
                565                 570                 575

Leu Leu Leu Leu Val Thr Gly Thr Ala Gly Leu Phe Ala Trp His Leu
            580                 585                 590

Asp Thr Pro Val Val Lys Ser Ala Gly Gly Arg Leu Cys Phe Phe Met
        595                 600                 605

Leu Gly Ser Leu Ala Gly Gly Ser Cys Gly Leu Tyr Gly Phe Phe Gly
    610                 615                 620

Glu Pro Thr Leu Pro Thr Cys Leu Leu Arg Gln Ser Leu Leu Ala Leu
625                 630                 635                 640
```

-continued

```
Gly Phe Ala Ile Phe Leu Ser Cys Leu Thr Ile Arg Ser Phe Gln Leu
                645                 650                 655

Val Phe Ile Phe Lys Phe Ser Ala Lys Val Pro Thr Phe Tyr Arg Ala
            660                 665                 670

Trp Val Gln Asn His Gly Pro Gly Leu Phe Val Val Ile Ser Ser Met
        675                 680                 685

Ala Gln Leu Leu Ile Cys Leu Thr Trp Leu Ala Val Trp Thr Pro Leu
    690                 695                 700

Pro Thr Arg Glu Tyr Gln Arg Phe Pro Gln Leu Val Val Leu Asp Cys
705                 710                 715                 720

Thr Glu Ala Asn Ser Pro Gly Phe Met Leu Ala Phe Ala Tyr Asn Gly
                725                 730                 735

Leu Leu Ser Val Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Leu
        755                 760                 765

Asn Phe Val Ser Trp Ile Ala Phe Phe Thr Thr Ala Ser Val Tyr Gln
    770                 775                 780

Gly Lys Tyr Leu Pro Ala Val Asn Val Leu Ala Ala Leu Ser Ser Leu
785                 790                 795                 800

Ser Gly Gly Phe Ser Gly Tyr Phe Leu Pro Lys Cys Tyr Val Ile Leu
                805                 810                 815

Cys Arg Pro Lys Phe Asn Ser Thr Gln His Phe Gln Ala Ser Ile Gln
            820                 825                 830

Glu Tyr Thr Arg Arg Cys Gly Ser Thr
        835                 840
```

<210> SEQ ID NO 135
<211> LENGTH: 1176
<212> TYPE: DNA
<213> ORGANISM: Felis catus

<400> SEQUENCE: 135

```
atgggacccc gggccaggga agtctgctgc ttcatcatcc tgccgcggct cctggctgag     60

ccggctgaga actcagactt ctacttggct ggggattact tcctcggcgg cctcttcacc    120

ctccatgcca acgtgaaggg catcgtccac ctcaacctcc tgcaggtgcc ccagtgcaag    180

gagtatgaaa taaaggtgtt gggctacgat ctcatgcagg ccatgtgctt tgcaggggag    240

gagatcaata gccagagcag cctgctgcct ggcgtgctgc tgggctacaa aatggtggat    300

gtcagctaca tctccaacaa tgtccagccc gtgctccact tcccggcaaa ggaggactgt    360

tccttgccca tccaggagga ctacagccac tgtgtgcccc gtgtggtggc tgtcattggt    420

cctggcaact ctgagtccac tgtgactgtg gcccgcttcc tctctctctt cctccttcca    480

cagatcacct acagcgccat cagtgacgag ctacgggaca agcagcgctt cccggccctt    540

ctgcccacag cgccgggcgc cgatcaccag atcgaggcca tggtgcagct gatgttgtac    600

ttccgccgga actggatcat cgcgctggtg agcagcggcg actgcggccg cgacgacagc    660

cagctgctca gcgatcgccc ggccggcggc gacacctgca tcgccttccg ggagacgctg    720

cccatgcccc agcccaacca ggcggtgacg cagtgggagc gccggcgcct gaaggccatc    780

gtggacgagc agcagcggca gagctctgcg cgcgtcgtgg tcctgctgtc gccaaagctg    840

gtcctgcaca acttcttccg cgaggtgctc cgccagaacc tcacgggcgt cgtgcggatc    900

gcctccgagt cctgggccat cgacccggtc ctgcacgaca ggcccacgcg ctgcacagcc    960
```

-continued

```
tcctgggctg cacccagacc agcagctccg ggtcgtctat ccctggcagg tgaggcccca   1020

cccacggaga gtcggggcca cacacgcagg cgccgccaca gccctgagtg gttgccatgg   1080

agaccactgc cctgctctag cgtccccctc tctggccggg tcctgggcaa actggcggga   1140

gaggccaggg gacgtaccct gtccccagac acataa                             1176


<210> SEQ ID NO 136
<211> LENGTH: 391
<212> TYPE: PRT
<213> ORGANISM: Felis catus

<400> SEQUENCE: 136

Met Gly Pro Arg Ala Arg Glu Val Cys Cys Phe Ile Ile Leu Pro Arg
1               5                   10                  15

Leu Leu Ala Glu Pro Ala Glu Asn Ser Asp Phe Tyr Leu Ala Gly Asp
            20                  25                  30

Tyr Phe Leu Gly Gly Leu Phe Thr Leu His Ala Asn Val Lys Gly Ile
        35                  40                  45

Val His Leu Asn Leu Leu Gln Val Pro Gln Cys Lys Glu Tyr Glu Ile
    50                  55                  60

Lys Val Leu Gly Tyr Asp Leu Met Gln Ala Met Cys Phe Ala Gly Glu
65                  70                  75                  80

Glu Ile Asn Ser Gln Ser Ser Leu Leu Pro Gly Val Leu Leu Gly Tyr
                85                  90                  95

Lys Met Val Asp Val Ser Tyr Ile Ser Asn Asn Val Gln Pro Val Leu
            100                 105                 110

His Phe Pro Ala Lys Glu Asp Cys Ser Leu Pro Ile Gln Glu Asp Tyr
        115                 120                 125

Ser His Cys Val Pro Arg Val Val Ala Val Ile Gly Pro Gly Asn Ser
    130                 135                 140

Glu Ser Thr Val Thr Val Ala Arg Phe Leu Ser Leu Phe Leu Leu Pro
145                 150                 155                 160

Gln Ile Thr Tyr Ser Ala Ile Ser Asp Glu Leu Arg Asp Lys Gln Arg
                165                 170                 175

Phe Pro Ala Leu Leu Pro Thr Ala Pro Gly Ala Asp His Gln Ile Glu
            180                 185                 190

Ala Met Val Gln Leu Met Leu Tyr Phe Arg Arg Asn Trp Ile Ile Ala
        195                 200                 205

Leu Val Ser Ser Gly Asp Cys Gly Arg Asp Asp Ser Gln Leu Leu Ser
    210                 215                 220

Asp Arg Pro Ala Gly Gly Asp Thr Cys Ile Ala Phe Arg Glu Thr Leu
225                 230                 235                 240

Pro Met Pro Gln Pro Asn Gln Ala Val Thr Gln Trp Glu Arg Arg Arg
                245                 250                 255

Leu Lys Ala Ile Val Asp Glu Gln Gln Arg Gln Ser Ser Ala Arg Val
            260                 265                 270

Val Val Leu Leu Ser Pro Lys Leu Val Leu His Asn Phe Phe Arg Glu
        275                 280                 285

Val Leu Arg Gln Asn Leu Thr Gly Val Val Arg Ile Ala Ser Glu Ser
    290                 295                 300

Trp Ala Ile Asp Pro Val Leu His Asp Arg Pro Thr Arg Cys Thr Ala
305                 310                 315                 320

Ser Trp Ala Ala Pro Arg Pro Ala Ala Pro Gly Arg Leu Ser Leu Ala
                325                 330                 335
```

```
Gly Glu Ala Pro Pro Thr Glu Ser Arg Gly His Thr Arg Arg Arg Arg
            340                 345                 350

His Ser Pro Glu Trp Leu Pro Trp Arg Pro Leu Pro Cys Ser Ser Val
        355                 360                 365

Pro Leu Ser Gly Arg Val Leu Gly Lys Leu Ala Gly Glu Ala Arg Gly
    370                 375                 380

Arg Thr Leu Ser Pro Asp Thr
385                 390


<210> SEQ ID NO 137
<211> LENGTH: 2569
<212> TYPE: DNA
<213> ORGANISM: Felis catus

<400> SEQUENCE: 137

atgcccggcc tcgctctcct gggcctcacg gctctcctgg gcctcacggc tctcttggac      60

cacggggagg gcgcaacgtc ctgcttgtca cagcagctca ggatgcaggg ggactatgtg     120

ctgggtgggc tcttccctct gggctctgcc gagggtacag gtcttggcga cgggctgcag     180

cccaatgcca ccgtgtgcac caggttctcg tctctgggcc tgctctgggc gctggccgtg     240

aagatggcgg tggaggagat caacaacggg tcggccctgc tgcccgggct gcacctgggc     300

tatgacctct ttgacacgtg ttcagagccc atggtggcca tgaagcccag cctcgtgttc     360

atggccaaag caggcagctg cagcattgcc gcctactgca attacacaca gtaccagccc     420

cgcgtgctgg ccgtcatcgg gccccactcg tctgagctcg ccctcgtcac cggcaagttc     480

ttcagcttct tccttgtgcc tcaggtcagc tacggcgcca gcaccgaccg gctgagcaac     540

cgggagacgt tcccatcctt cttccgcacg gtgtccagcg accgcgtaca ggcagcggcc     600

atggtggagc tgctggagga gctcggctgg aactgggtgg cggcggtggg tagtgacgac     660

gagtatggcc ggcagggcct gagcctcttc tccggcctgg ccagcgccag ggcatctgc      720

atcgcgcatg agggcctggt gccactgccg ccaggcagcc tgcggctggg cgccctacag     780

ggcctgctgc gccaggtgaa ccagagcagc gtgcaggtgg tggtgctgtt ctcctccgcc     840

cacgcggccc gcaccctctt cagctacagc atccgctgca agctctcacc caaggtgtgg     900

gtggccagcg aggcctggct gacctcagac ctggtcatga cgctgcccgg catgcctggg     960

gtgggcaccg tgctgggctt cctgcagcag ggcgccccga tgccggagtt cccatcctac    1020

gtgcggaccc gcctggccct ggccgctgac cctgccttct gcgcctcgct ggacgctgaa    1080

cagccaggcc tggaggagca cgtggtgggg ccacgctgcc cccaatgtga ccacgtcacg    1140

ctagagaacc tatctgcggg gctgctgcac caccagacct tcgctgccta cgcggctgtg    1200

tatggcgtgg cccaagccct tcacaacaca ctgcgctgca atgcctcggg ctgccccagg    1260

cgggagcctg tgcggccctg gcagctccta gagaacatgt acaacgtgag cttccgtgct    1320

cgcggcctgg cactgcagtt cgacgccagc gggaacgtga acgtggatta cgacctgaaa    1380

ctgtgggtgt ggcaggaccc gacgcccgag ctgcgcaccg taggcacctt caagggccgc    1440

ctggagctct ggcgctctca gatgtgctgg cacacgccgg ggaagcagca gcccgtgtcc    1500

cagtgctccc ggcagtgcaa ggaaggccag gtgcgccgcg tgaagggctt ccactcttgc    1560

tgttacaact gcgtggactg caaggcgggc agttatcagc gcaacccaga tgacctcctc    1620

tgcacccagt gtgaccagga ccagtggtcc ccagaccgga gcacacgctg cttcgcccgc    1680

aagcccatgt tcctggcatg gggggagcca gctgtgctgc tactgctcgc gctgctggct    1740

ctggcgctgg gcctggcgct ggcagccctg ggctcttcc  tctggcactc ggacagcccg    1800
```

-continued

```
ctggttcagg cctcaggtgg gccacgggcc tgctttggcc tggcttgcct gggcctggtc   1860

tgcctcagtg tcctcctgtt ccctggccag ccaggccctg ccagctgcct ggcccagcag   1920

ccactgttcc acctcccact cactggctgc ctgagcacgt ttttcctgca agcggccgag   1980

atatttgtgg ggtcggagct gccaccaagc tgggctgaga agatgcgtgg ccgcctgcgg   2040

gggccctggg cctggctggt ggtgctgctt gctatgctgg cagaagccgc attgtgtgcc   2100

tggtacctgg tagccttccc gccagaggtg gtgacggact ggcgggtact gcccacagag   2160

gcgctggtgc actgccacgt gcactcctgg atcagcttcg gcctggtgca tgccactaac   2220

gccatgctgg ccttcctctg cttcctgggc actttcctgg tgcagagccg gccaggccgc   2280

tacaatggtg cccgcggcct cacctttgcc atgctggcct acttcatcac ctggatctcc   2340

tttgtgcccc tctttgccaa tgtgcacgtg gcctaccagc ctgccgtgca gatgggcacc   2400

atcctcctct gtgccctggg tatcctagcc accttccacc tgcccaagtg ctacctgctg   2460

ctgcagcggc cggagctcaa cacccctgag ttcttcctgg aagacaatgc cagagcacag   2520

ggcagcagtt gggggcaggg gaggggagaa tcggggcaaa aacaagtga               2569


<210> SEQ ID NO 138
<211> LENGTH: 865
<212> TYPE: PRT
<213> ORGANISM: Felis catus

<400> SEQUENCE: 138

Met Pro Gly Leu Ala Leu Leu Gly Leu Thr Ala Leu Leu Gly Leu Thr
1               5                   10                  15

Ala Leu Leu Asp His Gly Glu Gly Ala Thr Ser Cys Leu Ser Gln Gln
            20                  25                  30

Leu Arg Met Gln Gly Asp Tyr Val Leu Gly Gly Leu Phe Pro Leu Gly
        35                  40                  45

Ser Ala Glu Gly Thr Gly Leu Gly Asp Gly Leu Gln Pro Asn Ala Thr
    50                  55                  60

Val Cys Thr Arg Phe Ser Ser Leu Gly Leu Leu Trp Ala Leu Ala Val
65                  70                  75                  80

Lys Met Ala Val Glu Glu Ile Asn Asn Gly Ser Ala Leu Leu Pro Gly
                85                  90                  95

Leu His Leu Gly Tyr Asp Leu Phe Asp Thr Cys Ser Glu Pro Met Val
            100                 105                 110

Ala Met Lys Pro Ser Leu Val Phe Met Ala Lys Ala Gly Ser Cys Ser
        115                 120                 125

Ile Ala Ala Tyr Cys Asn Tyr Thr Gln Tyr Gln Pro Arg Val Leu Ala
    130                 135                 140

Val Ile Gly Pro His Ser Ser Glu Leu Ala Leu Val Thr Gly Lys Phe
145                 150                 155                 160

Phe Ser Phe Phe Leu Val Pro Gln Val Ser Tyr Gly Ala Ser Thr Asp
                165                 170                 175

Arg Leu Ser Asn Arg Glu Ile Phe Pro Ser Phe Phe Arg Thr Val Pro
            180                 185                 190

Ser Asp Gln Val Gln Val Ala Ala Met Val Glu Leu Leu Glu Glu Leu
        195                 200                 205

Gly Trp Asn Trp Val Ala Ala Val Gly Ser Asp Asp Glu Tyr Gly Arg
    210                 215                 220

Gln Gly Leu Ser Leu Phe Ser Gly Leu Ala Ser Ala Arg Gly Ile Cys
225                 230                 235                 240
```

-continued

```
Ile Ala His Glu Gly Leu Val Pro Leu Pro Pro Gly Ser Leu Arg Leu
                245                 250                 255

Gly Ala Leu Gln Gly Leu Leu Arg Gln Val Asn Gln Ser Ser Val Gln
            260                 265                 270

Val Val Val Leu Phe Ser Ser Ala His Ala Ala Arg Thr Leu Phe Ser
        275                 280                 285

Tyr Ser Ile Arg Cys Lys Leu Ser Pro Lys Val Trp Val Ala Ser Glu
    290                 295                 300

Ala Trp Leu Thr Ser Asp Leu Val Met Thr Leu Pro Gly Met Pro Gly
305                 310                 315                 320

Val Gly Thr Val Leu Gly Phe Leu Gln Gln Gly Ala Pro Met Pro Glu
                325                 330                 335

Phe Pro Ser Tyr Val Arg Thr Arg Leu Ala Leu Ala Ala Asp Pro Ala
            340                 345                 350

Phe Cys Ala Ser Leu Asp Ala Glu Gln Pro Gly Leu Glu Glu His Val
        355                 360                 365

Val Gly Pro Arg Cys Pro Gln Cys Asp His Val Thr Leu Glu Asn Leu
    370                 375                 380

Ser Ala Gly Leu Leu His His Gln Thr Phe Ala Ala Tyr Ala Ala Val
385                 390                 395                 400

Tyr Gly Val Ala Gln Ala Leu His Asn Thr Leu Arg Cys Asn Ala Ser
                405                 410                 415

Gly Cys Pro Arg Arg Glu Pro Val Arg Pro Trp Gln Leu Leu Glu Asn
            420                 425                 430

Met Tyr Asn Val Ser Phe Arg Ala Arg Gly Leu Ala Leu Gln Phe Asp
        435                 440                 445

Ala Ser Gly Asn Val Asn Val Asp Tyr Asp Leu Lys Leu Trp Val Trp
    450                 455                 460

Gln Asp Pro Thr Pro Glu Leu Arg Thr Val Gly Thr Phe Lys Gly Arg
465                 470                 475                 480

Leu Glu Leu Trp Arg Ser Gln Met Cys Trp His Thr Pro Gly Lys Gln
                485                 490                 495

Gln Pro Val Ser Gln Cys Ser Arg Gln Cys Lys Glu Gly Gln Val Arg
            500                 505                 510

Arg Val Lys Gly Phe His Ser Cys Cys Tyr Asn Cys Val Asp Cys Lys
        515                 520                 525

Ala Gly Ser Tyr Gln Arg Asn Pro Asp Asp Leu Leu Cys Thr Gln Cys
    530                 535                 540

Asp Gln Asp Gln Trp Ser Pro Asp Arg Ser Thr Arg Cys Phe Ala Arg
545                 550                 555                 560

Lys Pro Met Phe Leu Ala Trp Gly Glu Pro Ala Val Leu Leu Leu Leu
                565                 570                 575

Ala Leu Leu Ala Leu Ala Leu Gly Leu Ala Leu Ala Ala Leu Gly Leu
            580                 585                 590

Phe Leu Trp His Ser Asp Ser Pro Leu Val Gln Ala Ser Gly Gly Pro
        595                 600                 605

Arg Ala Cys Phe Gly Leu Ala Cys Leu Gly Leu Val Cys Leu Ser Val
    610                 615                 620

Leu Leu Phe Pro Gly Gln Pro Gly Pro Ala Ser Cys Leu Ala Gln Gln
625                 630                 635                 640

Pro Leu Phe His Leu Pro Leu Thr Gly Cys Leu Ser Thr Phe Phe Leu
                645                 650                 655

Gln Ala Ala Glu Ile Phe Val Gly Ser Glu Leu Pro Pro Ser Trp Ala
            660                 665                 670
```

-continued

```
Glu Lys Met Arg Gly Arg Leu Arg Gly Pro Trp Ala Trp Leu Val Val
        675                 680                 685

Leu Leu Ala Met Leu Ala Glu Ala Ala Leu Cys Ala Trp Tyr Leu Val
    690                 695                 700

Ala Phe Pro Pro Glu Val Val Thr Asp Trp Arg Val Leu Pro Thr Glu
705                 710                 715                 720

Ala Leu Val His Cys His Val His Ser Trp Ile Ser Phe Gly Leu Val
                725                 730                 735

His Ala Thr Asn Ala Met Leu Ala Phe Leu Cys Phe Leu Gly Thr Phe
            740                 745                 750

Leu Val Gln Ser Arg Pro Gly Arg Tyr Asn Gly Ala Arg Gly Leu Thr
        755                 760                 765

Phe Ala Met Leu Ala Tyr Phe Ile Thr Trp Ile Ser Phe Val Pro Leu
    770                 775                 780

Phe Ala Asn Val His Val Ala Tyr Gln Pro Ala Val Gln Met Gly Thr
785                 790                 795                 800

Ile Leu Leu Cys Ala Leu Gly Ile Leu Ala Thr Phe His Leu Pro Lys
                805                 810                 815

Cys Tyr Leu Leu Leu Gln Arg Pro Glu Leu Asn Thr Pro Glu Phe Phe
            820                 825                 830

Leu Glu Asp Asn Ala Arg Ala Gln Gly Ser Ser Trp Gly Gln Gly Arg
        835                 840                 845

Gly Glu Ser Gly Gln Lys Gln Val Thr Pro Asp Pro Val Thr Ser Pro
    850                 855                 860

Gln
865
```